US012281167B2

United States Patent

(12) United States Patent
Siegel et al.

(10) Patent No.: US 12,281,167 B2
(45) Date of Patent: *Apr. 22, 2025

(54) HUMANIZED ANTI-GDNF FAMILY ALPHA-RECEPTOR 4 (GRF-ALPHA-4) ANTIBODIES AND CHIMERIC ANTIGEN RECEPTORS (CARs)

(71) Applicants: The Trustees of the University of Pennsylvania, Philadelphia, PA (US); University of FLorida Research Foundation, Incorporated, Gainesville, FL (US)

(72) Inventors: Donald L. Siegel, Lansdale, PA (US); Vijay Bhoj, Philadelphia, PA (US); Christoph Rader, Jupiter, FL (US); Rebecca Goydel, La Jolla, CA (US)

(73) Assignees: The Trustees of the University of Pennsylvania, Philadelphia, PA (US); University of Florida Research Foundation, Incorporated, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/475,958

(22) Filed: Sep. 27, 2023

(65) Prior Publication Data

US 2024/0067737 A1 Feb. 29, 2024

Related U.S. Application Data

(63) Continuation of application No. 17/037,203, filed on Sep. 29, 2020, now Pat. No. 11,802,159.

(Continued)

(51) Int. Cl.

*C07K 16/28* (2006.01)
*A61K 39/00* (2006.01)

(Continued)

(52) U.S. Cl.

CPC ...... *C07K 16/2863* (2013.01); *A61K 39/4611* (2023.05); *A61K 39/4631* (2023.05);

(Continued)

(58) Field of Classification Search

CPC ............ C07K 16/2863; C07K 14/7051; C07K 14/70517; C07K 14/70578;

(Continued)

(56) References Cited

U.S. PATENT DOCUMENTS

| | | | |
|---|---|---|---|
| 2017/0096488 | A1 | 4/2017 | Croll |
| 2017/0334967 | A1 | 11/2017 | Siegel |

FOREIGN PATENT DOCUMENTS

| | | | |
|---|---|---|---|
| WO | 2001062795 | | 8/2001 |
| WO | 2016025880 | A1 | 2/2016 |

(Continued)

OTHER PUBLICATIONS

Rabia, L.A. et al (2018) Understanding and overcoming trade-offs between antibody affinity, specificity, stability and solubility Biochem Eng J 137; 365-374 (Year: 2018).*

(Continued)

*Primary Examiner* — Scarlett Y Goon
*Assistant Examiner* — Audrey L Buttice
(74) *Attorney, Agent, or Firm* — Saul Ewing LLP; Kathryn Doyle; Alireza Behrooz

(57) ABSTRACT

The present invention relates to compositions and methods for treating diseases, disorders or conditions associated with the expression of the glycosyl-phosphatidylinositol (GPI)-linked GDNF family protein α-receptor 4 (GFRα4).

17 Claims, 31 Drawing Sheets

Specification includes a Sequence Listing.

Related U.S. Application Data

(60) Provisional application No. 62/907,909, filed on Sep. 30, 2019.

(51) Int. Cl.
*A61P 35/00* (2006.01)
*C07K 14/705* (2006.01)
*C07K 14/725* (2006.01)

(52) U.S. Cl.
CPC .................. *A61K 39/46432* (2023.05); *A61K 39/464412* (2023.05); *A61P 35/00* (2018.01); *C07K 14/7051* (2013.01); *C07K 14/70517* (2013.01); *C07K 14/70578* (2013.01); *A61K 2039/505* (2013.01); *A61K 2239/28* (2023.05); *A61K 2239/31* (2023.05); *A61K 2239/38* (2023.05); *A61K 2239/48* (2023.05); *C07K 2317/24* (2013.01); *C07K 2317/622* (2013.01); *C07K 2319/02* (2013.01); *C07K 2319/03* (2013.01)

(58) Field of Classification Search
CPC .......... C07K 2317/24; C07K 2317/622; C07K 2317/73; C07K 2319/02; C07K 2319/03; A61K 35/17; A61K 2039/505; A61K 2239/31; A61K 2239/38; A61K 2239/48; A61K 2239/28; A61K 39/4611; A61K 39/4631; A61K 39/46432; A61K 39/464412; A61K 38/00; A61P 35/00
See application file for complete search history.

(56) References Cited

FOREIGN PATENT DOCUMENTS

| | | | | |
|---|---|---|---|---|
| WO | WO-2016025884 A1 * | 2/2016 | ............. | A61K 35/17 |
| WO | 2019165156 A1 | 8/2019 | | |

OTHER PUBLICATIONS

Rojas, G. (2022) Understanding and Modulating Antibody Fine Specificity: Lessons from Combinatorial Biology Antibodies 11(48); 1-22 (Year: 2022).*
Chiu, M.L., et al (2019) Antibody structure and function: The basis for engineering therapeutics Antibodies 8(55); 1-80 (Year: 2019).*
Naran, K., et al (2018) Principles of Immunotherapy: Implications for treatment strategies in cancer and infectious diseases Frontiers in Microbiology 9(3158); 1-23 (Year: 2018).*
DeKosky et al., “Large-scale sequence and strucural comparisons of human naive and antigen-experienced antibody repertoires.” (2016) Proc Natl Acad Sci 113:E2636-E2645.
Zhang and Ho, “Humanization of rabbit monocolonal antibodies via grafting combined Kabat/IMGT/Paratome complementarity-determining regions: Rationale and examples.” (2017) MABS, 9:419-429.

* cited by examiner

Top row: Rabbit P4-10 HC (Kabat CDRs)
Bottom row: Rabbit P4-10 HC (IMGT CDRs)

Top row: Rabbit P4-10 LC (Kabat CDRs)
Bottom row: Rabbit P4-10 LC (IMGT CDRs)

| | CDR1 / CDR2 | |
|---|---|---|
| Rabbit P4-10 HC (Kabat CDRs) | -QSVKESEGGLFKPTDTLTLTCTVSGFSLSRHALT-WVRQAPGNGLEWIGAIDNAGTTYYASWAKSRSTITRNTDLNTVTLKMTSLTASDTATYFCAR | SEQ ID NO: 127 |
| Rabbit P4-10 HC (IMGT CDRs) | -QSVKESEGGLFKPTDTLTLTCTVSGFSLSRHALT-WVRQAPGNGLEWIGAIDNAGTTYYASWAKSRSTITRNTDLNTVTLKMTSLTASDTATYFCAR | |
| (1) IGHV4-38-2*02 54% | QVQLQESGPGLVKPSETLSLTCAVSGYSISSGYYWGWIRQPPGKGLEWIGSIYHSGSTYYNPSLKSRVTISVDTSKNQFSLKLSSVTAADTAVYYCAR | SEQ ID NO: 128 |
| (2) IGHV3-48*03 51% | EVQLVESGGGLVQPGGSLRLSCAASGFTFSSYEMNWVRQAPGKGLEWVSYISSSGSTIYYADSVKGRFTISRDNAKNSLYLQMNSLRAEDTAVYYCAR | SEQ ID NO: 129 |

Figure 3A

| | CDR1 / CDR2 / CDR3 | |
|---|---|---|
| Rabbit P4-10 LC (Kabat CDRs) | QFVLTQSPSVSAALGASAKLTCTLSSAHKTYTIDWYQQQQGEAPRYLMQVKSDGSYTKGTGVPDRFSGSSSGADRYLIIPSVQADDEAGYVCGADDNGGY | SEQ ID NO: 130 |
| Rabbit P4-10 LC (IMGT CDRs) | QFVLTQSPSVSAALGASAKLTCTLSSAHKTYTIDWYQQQQGEAPRYLMQVKSDGSYTKGTGVPDRFSGSSSGADRYLIIPSVQADDEAGYVCGADDNGGYV | SEQ ID NO: 131 |
| (1) Human IGLV4-69*01 69% | QLVLTQSPSASASLGASVKLTCTLSSGHSSYAIAWHQQQPEKGPRYLMKLNSDGSHSKGDGIPDRFSGSSSGAERYLTISSLQSEDEADYYCQTWGTGI | SEQ ID NO: 132 |
| (2) Human IGLV1-44*01 43% | QSVLTQPPSASGTPGQRVTISCSGSSSNIGSNTVNWYQQLPGTAPKLLIYSN----NQRPSGVPDRFSGSKSGTSASLAISGLQSEDEADYYCAAWDDSLNG | SEQ ID NO: 133 |
| (3) Human IGLV2-14*01 42% | QSALTQPASVSGSPGQSITISCTGTSSDVGGYNYVSWYQQHPGKAPKLMIYEV----SNRPSGVSNRFSGSKSGNTASLTISGLQAEDEADYYCSSYTSSSTL | SEQ ID NO: 134 |
| (4) Human IGLV4-3*01 70% | --VLTQPPSASALLGASIKLTCTLSSEHSTYTIEWYQQRPGRSPQYIMKVKSDGSHSKGDGIPDRFMGSSSGADRYLTFSNLQSDDEAEYHCGESHTIDGQVG* | SEQ ID NO: 135 |

Figure 3B

CDR1 CDR2

| Sequence | SEQ ID NO |
|---|---|
| -QSVKESEGGLFKPTDTLTLTCTVSGFSLS**RHALT**-WVRQAPGNGLEWIG**AIDNAGTTYYASWAKS**RSTITRNTDLHTVTLKMTSLTASDTATYFCAR | SEQ ID NO: 127 |
| -QSVKESEGGLFKPTDTLTLTCTVS**GFSLSRHA**LT-WVRQAPGNGLEWIGA**IDNAGTT**YYASWAKSRSTITRNTDLHTVTLKMTSLTASDTATYFCAR | |
| QVQLQESGPGLVKPSETLSLTCAVS**GYSISSGYY**WGWIRQPPGKGLEWIGS**IYHSGST**YYNPSLKSRVTISVDTSKNQFSLKLSSVTAADTAVYYCAR | SEQ ID NO: 128 |
| QVQLQESGPGLVKPSETLSLTCAVSGYSIS**R-HALT**WIRQPPGKGLEWIG**AIDNAGTTYYASWAKS**RVTISVDTSKNQFSLKLSSVTAADTAVYYCAR | SEQ ID NO: 136 |
| QVQLQESGPGLVKPSETLSLTCAVSGFSLS**R-HALT**WIRQPPGKGLEWIG**AIDNAGTTYYASWAKS**RVTISVDTSKNQFSLKLSSVTAADTAVYYCAR | SEQ ID NO: 137 |
| QQSVKESGPGLVKPSETLSLTCAVSGFSLS**R-HALT**WIRQPPGKGLEWIG**AIDNAGTTYYASWAKS**RVTISVDTSKNQFSLKLSSVTAADTAVYYCAR | SEQ ID NO: 138 |
| QQSVKESGPGLVKPSETLSLTCAVSGFSLS**R-HALT**WVRQPPGKGLEWIG**AIDNAGTTYYASWAKS**RVTISRNTDLHTVSLKLSSVTAADTAVYFCAR | SEQ ID NO: 139 |
| EVQLVESGGGLVQPGGSLRLSCAASGFTFS**SYEMN**WVRQAPGKGLEWVS**YISSSGSTIYYADSVKG**RFTISRDNAKNSLYLQMNSLRAEDTAVYYCAR | SEQ ID NO: 140 |
| EVQLVESGGGLVQPGGSLRLSCAASGFTFS**RHALT**WVRQAPGKGLEWVS**AIDNAGTTYYASWAKS**-RFTISRDNAKNSLYLQMNSLRAEDTAVYYCAR | SEQ ID NO: 141 |
| EQSVKESGGGLVQPGGSLRLSCAASGFTLS**RHALT**WVRQAPGKGLEWIG**AIDNAGTTYYASWAKS**-RFTISRNTDLHTVYLQMNSLRAEDTAVYFCAR | SEQ ID NO: 142 |

Rows:

Rabbit P4-10 HC (Kabat CDRs)
Rabbit P4-10 HC (IMGT CDRs)

(1) **IGHV4-38-2*02** 54%

H1 85%
H1m3 83%
H1m2 79%
H1m1 69%

(2) **IGHV3-48*03** 51%

| | CDR1 | | CDR2 | | CDR3 | |
|---|---|---|---|---|---|---|
| QFVLTQSPSVSAALGASAKLTC | **TLSSAHKTYTID** | WYQQQQGEAPRYLMQ | **VKSDGSYTKGT** | GVPDRFSGSSSGADRYLIIPSVQADDEAGYVC | **GADDNGGY** | SEQ ID NO: 130 |
| QFVLTQSPSVSAALGASAKLTCTLS | **SAHKTYT** | IDWYQQQQGEAPRYLMQ | **VKSDGSY** | TKGTGVPDRFSGSSSGADRYLIIPSVQADDEAGYVC | **GADDNGGYV** | SEQ ID NO: 131 |
| QLVLTQSPSASASLGASVKLTCTLS | **SGHSSYA** | IAWHQQQPEKGPRYLMK | **LNSDGSH** | SKGDGIPDRFSGSSSGAERYLTISSLQSEDEADYYC | **QTWGTGI** | SEQ ID NO: 132 |
| QLVLTQSPSASASLGASVKLTCTLS | **SAHKTYT** | IAWHQQQPEKGPRYLMK | **VKSDGSY** | SKGDGIPDRFSGSSSGAERYLTISSLQSEDEADYYC | **GADDNGGYV** | SEQ ID NO: 143 |
| QFVLTQSPSASASLGASVKLTCTLS | **SAHKTYT** | IDWHQQQPEKGPRYLMQ | **VKSDGSY** | TKGTGIPDRFSGSSSGAERYLTISSLQSEDEADYYC | **GADDNGGYV** | SEQ ID NO: 144 |
| QLVLTQSPSASASLGASVKLTCTLS | **SAHKTYT** | IAWHQQQPEKGPRYLMQ | **VKSDGSY** | TKGTGVPDRFSGSSSGADRYLTISSLQSEDEADYYC | **GADDNGGYV** | SEQ ID NO: 145 |
| QLVLTQSPSASASLGASVKLTCTLS | **SAHKTYT** | IDWYQQQPEKGPRYLMQ | **VKSDGSY** | TKGTGVPDRFSGSSSGADRYLTISSLQSEDEADYYC | **GADDNGGYV** | SEQ ID NO: 146 |
| QFVLTQSPSASASLGASVKLTCTLS | **SAHKTYT** | IDWYQQQPEKGPRYLMQ | **VKSDGSY** | TKGTGVPDRFSGSSSGADRYLTISSLQSEDEADYYC | **GADDNGGYV** | SEQ ID NO: 147 |

Rows:

Rabbit P4-10 LC (Kabat CDRs)
Rabbit P4-10 LC (IMGT CDRs)

**(1) Human IGLV4-69*01** (69%)

QSVLTQPPSASGTPGQRVTISCSGSSSNIGSNTVNWYQQLPGTAPKLLIYSN----NQRPSGVPDRFSGSKSGTSASLAISGLQSEDEADYYCAAWDDSLNG SEQ ID NO: 133

QSVLTQPPSASGTPGQRVTISCSGSSAHK-TYTVNWYQQLPGTAPKLLIYVKSDGSYQRPSGVPDRFSGSKSGTSASLAISGLQSEDEADYYCGADDNGGYV SEQ ID NO: 148
QSVLTQPPSASGTPGQRVTISCTLSSAHK-TYTLDWYQQLPGTAPKLLIYVKSDGSYTKGTGVPDRFSGSKSGTSASLAISGLQSEDEADYYCGADDNGGYV SEQ ID NO: 149
QFVLTQPPSASGTPGQRVTISCTLSSAHK-TYTLDWYQQLPGTAPKLLIYVKSDGSYTKGTGVPDRFSGSSSGADASLAISGLQSEDEADYYCGADDNGGYV SEQ ID NO: 150
QFVLTQPPSASGTPGQRVTISCTLSSAHK-TYTLDWYQQLPGTAPKLLIYVKSDGSYTKGTGVPDRFSGSSSGADRYLAISGLQSEDEADYYCGADDNGGYV SEQ ID NO: 151

Rows:

(2) Human IGLV1-44*01 (43%)

QSALTQPASVSGSPGQSITISCTGTSSDVGGYNYVSWYQQHPGKAPKLMIYEV----SNRPSGVSNRFSGSKSGNTASLTISGLQAEDEADYYCSSYTSSSTL SEQ ID NO: 134

QSALTQPASVSGSPGQSITISCTGTSAH-K-TYTVSWYQQHPGKAPKLMIYVKSDGSYNRPSGVSNRFSGSKSGNTASLTISGLQAEDEADYYCGADDNGGYV SEQ ID NO: 152
QSALTQPASVSGSPGQSITISCTGTSAH-K-TYTIDWYQQHPGKAPKLMIYVKSDGSYRKGTGVSNRFSGSKSGNTASLTISGLQAEDEADYYCGADDNGGYV SEQ ID NO: 153

QSALTQPASVSGSPGQSITISCTGTSAH-K-TYTVSWYQQHPGKAPKLMIYVKSDGSYRKGTGVENRFSGSSSGADRYLTISGLQAEDEADYYCGADDNGGYV SEQ ID NO: 154
QSALTQPASVSGSPGQSITISCTGTSAH-K-TYTVSWYQQHPGKAPKYLMQVKSDGSYRKGTGVENRFSGSSSGADRYLTISGLQAEDEADYYCGADDNGGYV SEQ ID NO: 155

QFVLTQPASVSGSPGQSITISCTLSSAH-K-TYTIDWYQQHPGKAPKLMIEVKSDGSYRKGTGVSNRFSGSSSGADRYLTISGLQAEDEADYYCGADDNGGYV SEQ ID NO: 156
QFVLTQPASVSGSPGQSITISCTLSSAH-K-TYTIDWYQQHPGKAPKYLMQVKSDGSYRKGTGVENRFSGSSSGADRYLTISGLQAEDEADYVCGADDNGGYV SEQ ID NO: 157

Rows:

**(3) Human IGLV2-14*01** (42%)

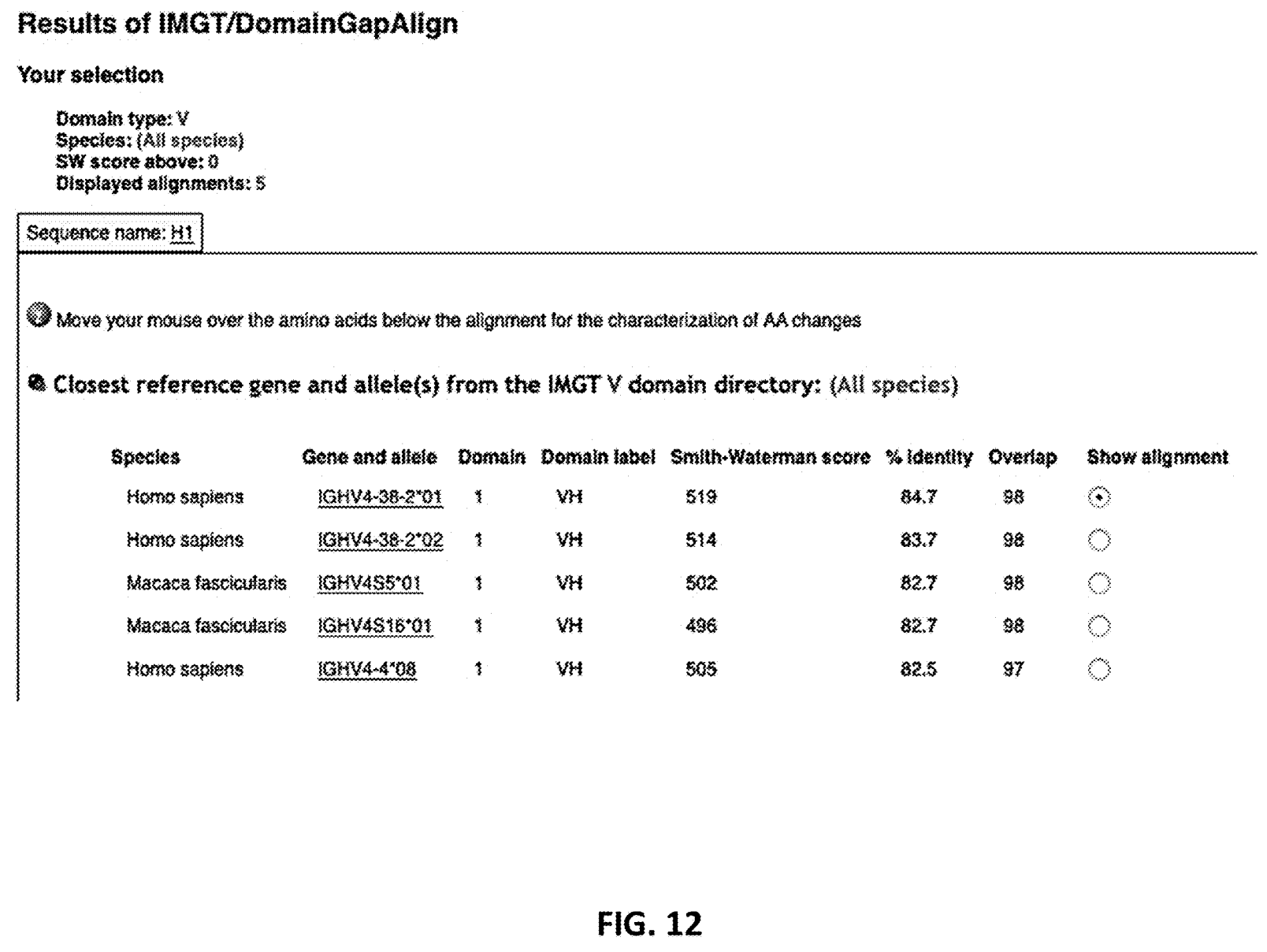

Results of IMGT/DomainGapAlign

Your selection

Domain type: V
Species: (All species)
SW score above: 0
Displayed alignments: 5

Sequence name: H1

Move your mouse over the amino acids below the alignment for the characterization of AA changes

Closest reference gene and allele(s) from the IMGT V domain directory: (All species)

| Species | Gene and allele | Domain | Domain label | Smith-Waterman score | % Identity | Overlap | Show alignment |
|---|---|---|---|---|---|---|---|
| Homo sapiens | IGHV4-38-2*01 | 1 | VH | 519 | 84.7 | 98 | ◉ |
| Homo sapiens | IGHV4-38-2*02 | 1 | VH | 514 | 83.7 | 98 | ○ |
| Macaca fascicularis | IGHV4S5*01 | 1 | VH | 502 | 82.7 | 98 | ○ |
| Macaca fascicularis | IGHV4S16*01 | 1 | VH | 496 | 82.7 | 98 | ○ |
| Homo sapiens | IGHV4-4*08 | 1 | VH | 505 | 82.5 | 97 | ○ |

FIG. 12

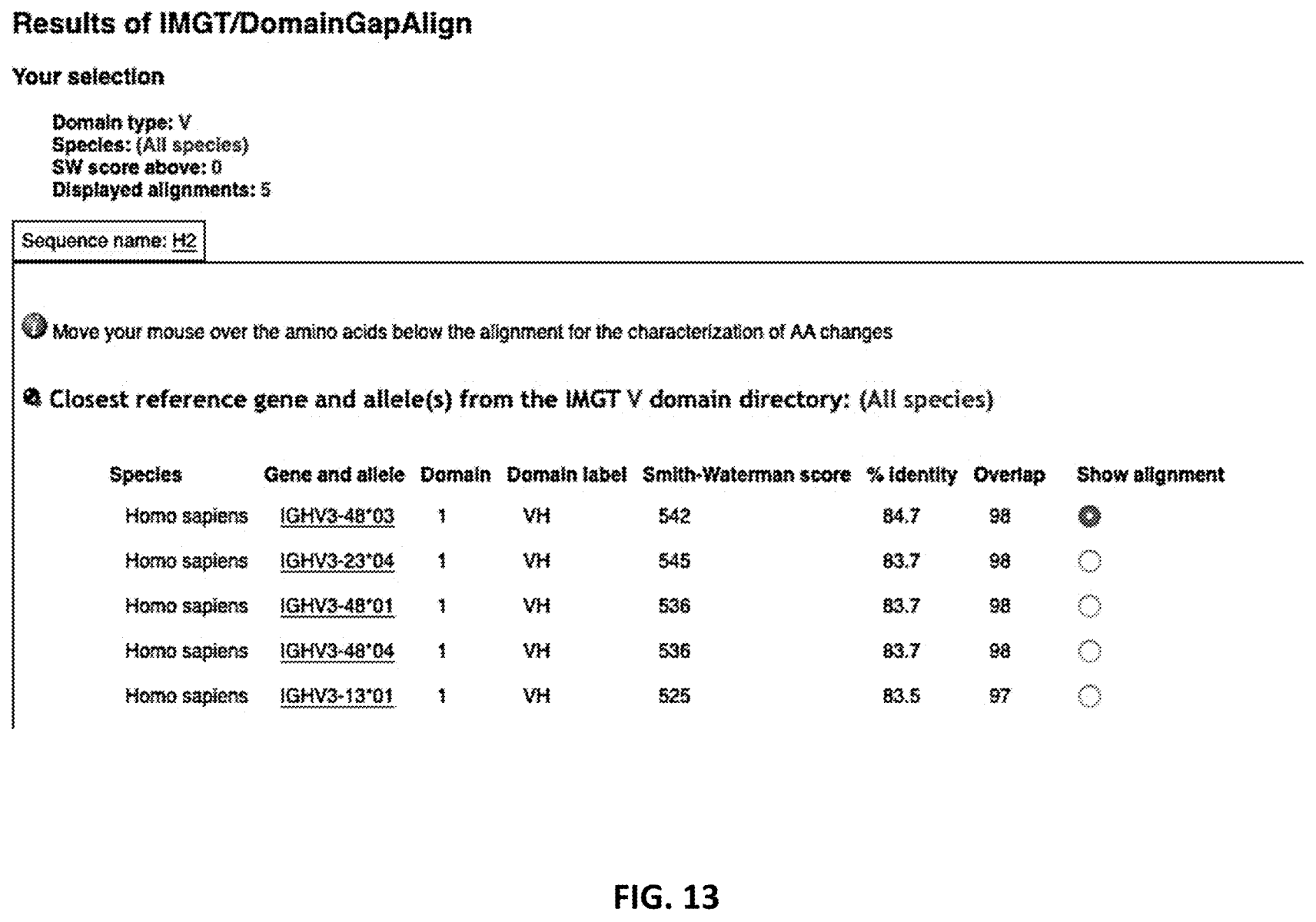

Results of IMGT/DomainGapAlign

Your selection

Domain type: V
Species: (All species)
SW score above: 0
Displayed alignments: 5

Sequence name: H2

Move your mouse over the amino acids below the alignment for the characterization of AA changes

Closest reference gene and allele(s) from the IMGT V domain directory: (All species)

| Species | Gene and allele | Domain | Domain label | Smith-Waterman score | % Identity | Overlap | Show alignment |
|---|---|---|---|---|---|---|---|
| Homo sapiens | IGHV3-48*03 | 1 | VH | 542 | 84.7 | 98 | ● |
| Homo sapiens | IGHV3-23*04 | 1 | VH | 545 | 83.7 | 98 | ○ |
| Homo sapiens | IGHV3-48*01 | 1 | VH | 536 | 83.7 | 98 | ○ |
| Homo sapiens | IGHV3-48*04 | 1 | VH | 536 | 83.7 | 98 | ○ |
| Homo sapiens | IGHV3-13*01 | 1 | VH | 525 | 83.5 | 97 | ○ |

FIG. 13

Results of IMGT/DomainGapAlign

Your selection

Domain type: V
Species: (All species)
SW score above: 0
Displayed alignments: 5

Sequence name: L1m3

Move your mouse over the amino acids below the alignment for the characterization of AA changes

Closest reference gene and allele(s) from the IMGT V domain directory: (All species)

| Species | Gene and allele | Domain | Domain label | Smith-Waterman score | % Identity | Overlap | Show alignment |
|---|---|---|---|---|---|---|---|
| Homo sapiens | IGLV4-69*01 | 1 | V-LAMBDA | 532 | 84.8 | 92 | |
| Homo sapiens | IGLV4-69*02 | 1 | V-LAMBDA | 532 | 84.8 | 92 | |
| Oryctolagus cuniculus | IGLV4S4*01 | 1 | V-LAMBDA | 520 | 84.8 | 92 | |
| Oryctolagus cuniculus | IGLV4S3*01 | 1 | V-LAMBDA | 509 | 83.7 | 92 | |
| Macaca mulatta | IGLV4S2*01 | 1 | V-LAMBDA | 499 | 81.5 | 92 | |

FIG. 14

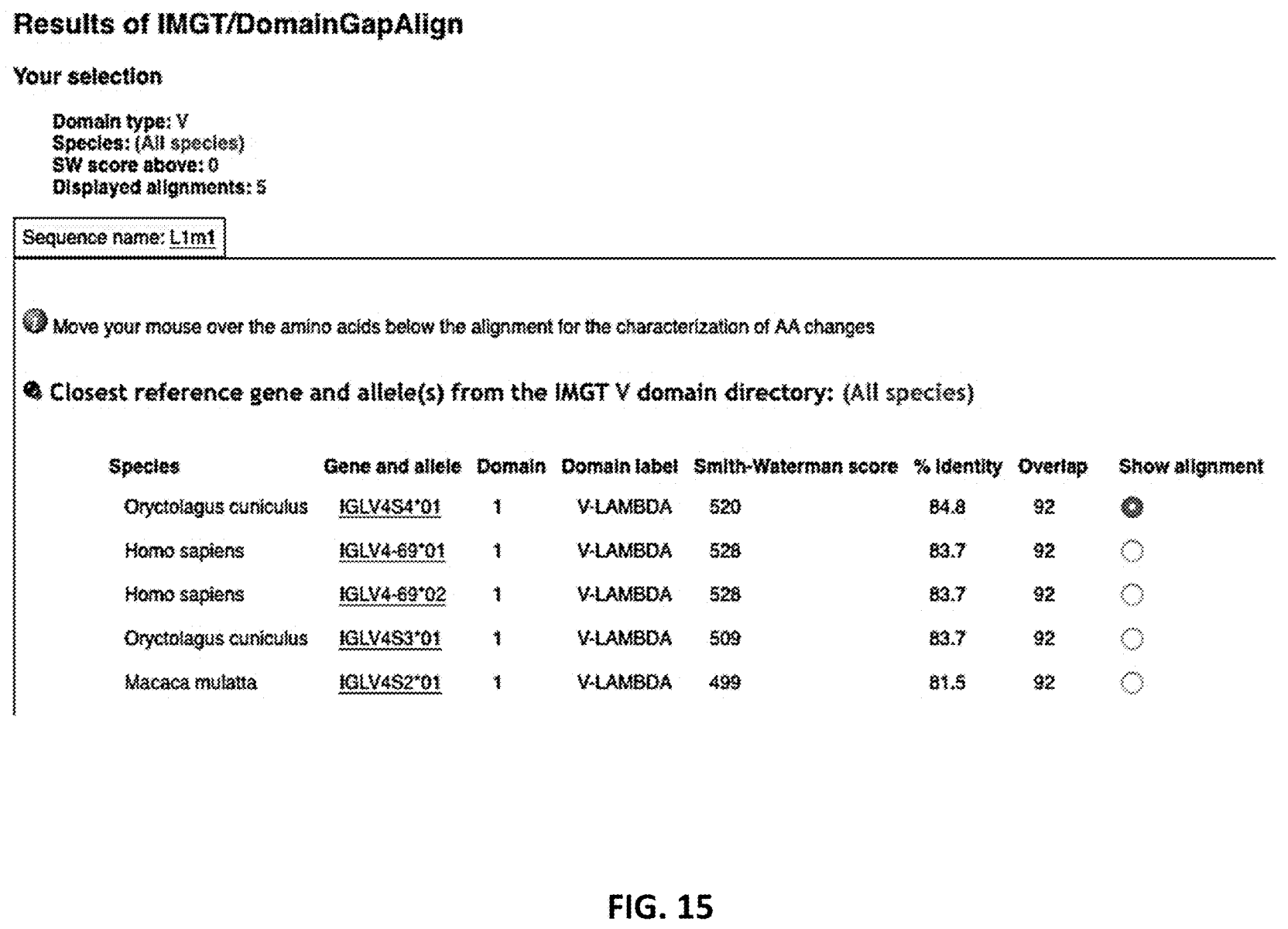

Results of IMGT/DomainGapAlign

Your selection

Domain type: V
Species: (All species)
SW score above: 0
Displayed alignments: 5

Sequence name: L1m1

Move your mouse over the amino acids below the alignment for the characterization of AA changes

Closest reference gene and allele(s) from the IMGT V domain directory: (All species)

| Species | Gene and allele | Domain | Domain label | Smith-Waterman score | % identity | Overlap | Show alignment |
|---|---|---|---|---|---|---|---|
| Oryctolagus cuniculus | IGLV4S4*01 | 1 | V-LAMBDA | 520 | 84.8 | 92 | |
| Homo sapiens | IGLV4-69*01 | 1 | V-LAMBDA | 528 | 83.7 | 92 | |
| Homo sapiens | IGLV4-69*02 | 1 | V-LAMBDA | 528 | 83.7 | 92 | |
| Oryctolagus cuniculus | IGLV4S3*01 | 1 | V-LAMBDA | 509 | 83.7 | 92 | |
| Macaca mulatta | IGLV4S2*01 | 1 | V-LAMBDA | 499 | 81.5 | 92 | |

FIG. 15

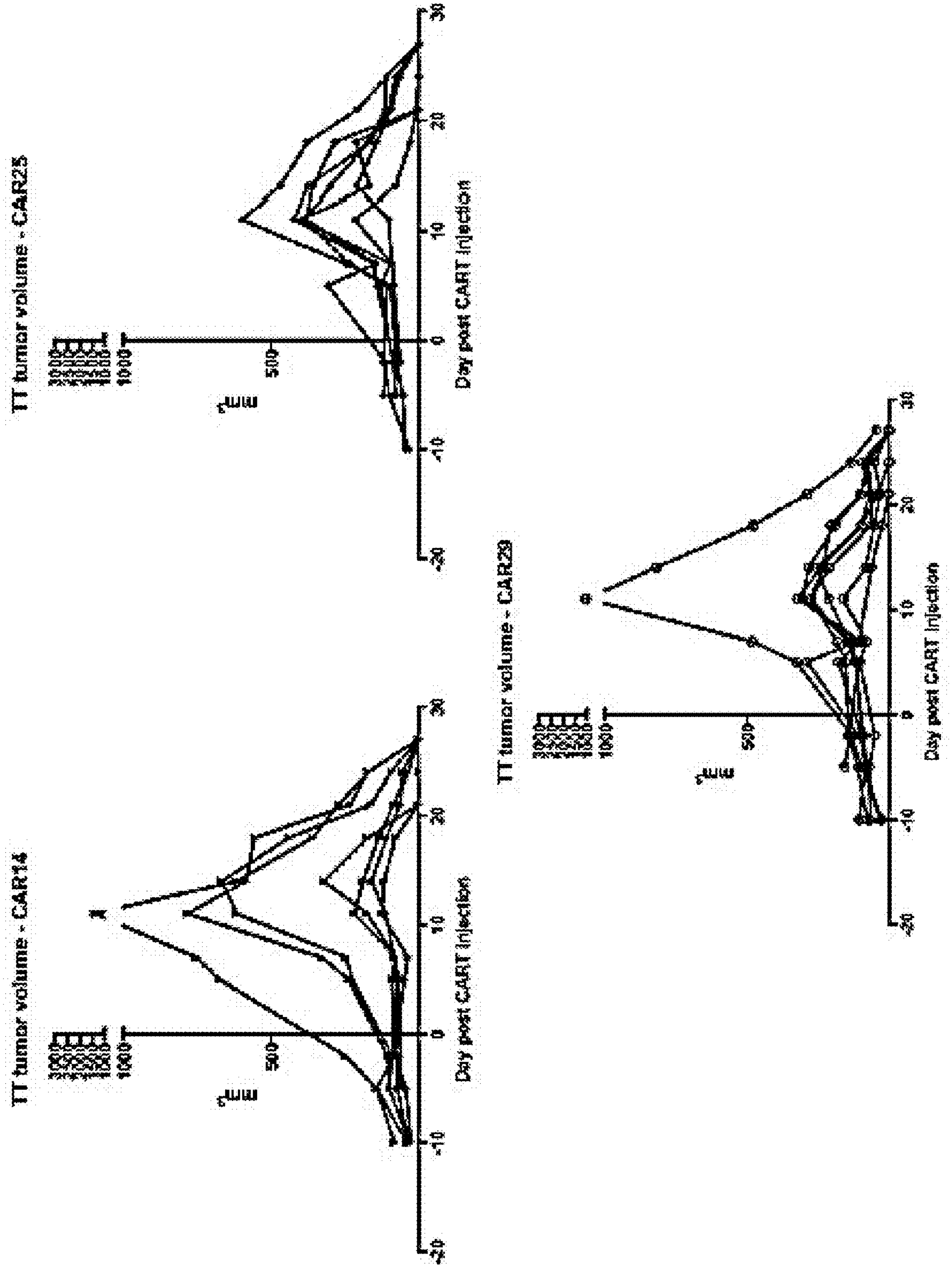
FIG. 26, Continued

HUMANIZED ANTI-GDNF FAMILY ALPHA-RECEPTOR 4 (GRF-ALPHA-4) ANTIBODIES AND CHIMERIC ANTIGEN RECEPTORS (CARs)

CROSS-REFERENCE TO RELATED APPLICATION

The present application is a continuation of U.S. patent application Ser. No. 17/037,203, filed Sep. 29, 2020 and is entitled to priority under U.S.C. § 119(e) to U.S. Provisional Patent Application No. 62/907,909 filed Sep. 30, 2019, all of which are hereby incorporated by reference in their entireties herein.

REFERENCE TO SEQUENCE LISTING

The instant application contains a Sequence Listing which has been submitted in XML format via Patent Center and is hereby incorporated by reference in its entirety. Said XML file, created on Sep. 25, 2023, is named "046483-7262US2 Sequence Listing ST_26.xml" and is 364,544 bytes in size.

BACKGROUND OF THE INVENTION

Thyroid cancer is one of the few cancers that has increased in incidence over recent years with the incidence of new cases rising on average 5.5% each year from 2002-2011. It is the most common endocrine cancer with an expected incidence of ~60,000 new cases this year and about 2,000 deaths. Papillary and follicular thyroid carcinomas comprise 80-90% of all thyroid cancers while medullary and anaplastic comprise 5-10% and 1-2% respectively. While thyroid cancer has a good prognosis overall, this is not necessarily the case for the medullary and anaplastic forms if they are not treated early before they spread beyond the thyroid gland.

Medullary Thyroid Cancer (MTC) is a type of thyroid cancer that develops from the parafollicular cells of the thyroid that are not related with the main function of the thyroid gland, i.e. production and secretion of thyroid hormone. Rather, these cells are involved in the production of calcitonin, a calcium-regulatory hormone apparently unimportant to humans for maintaining calcium homeostasis. Approximately 25% of MTC is genetic in nature caused by a mutation in the proto-oncogene receptor tyrosine kinase RET. MTC can also coexist with tumors of the parathyroid gland and adrenal gland (pheochromocytoma) in a syndrome known as multiple endocrine neoplasia type 2 (MEN2). Calcitonin doubling time (CDT) can be used as a prognostic marker; e.g. when the CDT is <6 months, 5-year survival is <25%. Surgery and radiation therapy are used for MTC, though risk of recurrence remains high due to the fact that 50% of patients have metastasis to regional lymph nodes at the time of diagnosis. Tyrosine kinase inhibitors such as vandetanib (Caprelsa) and cabozantinib (Cometriq) were approved by the FDA in April, 2011 and November, 2012, respectively, for treatment of late-stage metastatic MTC, though only 10-30% of patients show clear evidence of response.

The GDNF family of neurotrophic factors includes four members: glial cell line-derived neurotrophic factor (GDNF), neurturin, artemin, and persephin (PSPN). GDNF family ligands signal through receptors consisting of a GPI-linked GFRα subunit and the transmembrane receptor tyrosine kinase RET. In order to activate the transmembrane receptor tyrosine kinase RET, each of the GDNF family neurotrophic factors binds preferentially to one of the glycosyl-phosphatidylinositol (GPI)-linked GDNF family α-receptors (GFRα1-4) (Airaksinen et al., *Mol Cell Neurosci.;* 13(5):313-25, 1999). GDNF signals via GFRα1, neurturin via GFRα2, artemin via GFRα3; however, the mammalian GFRα receptor for persephin (PSPN) and the biological role of GFRα4 has so far remained unclear. In adult humans, GFRα4 is restricted to normal and malignant thyroid medullary cells (Lindahl et al., *J. Biol. Chem.* 276:9344-51, 2001), although it may be expressed elsewhere during fetal development. GFRα1, GFRα2, and GFRα3 appear to be expressed in non-thyroid tissues of the human body that may include brain.

Thus, the relative specific expressions of GFRα4 on the cell surface of malignant parafollicular cells of the thyroid tissues make it an attractive target for MTC tumor diagnosis and therapy. Although generic anti-GFRα4 antibodies were previously identified (WO2001062795A1), humanized GFRα4-specific antibodies and fragments thereof, remain unexplored.

There is a need in the art for the development of therapies to treat medullary thyroid carcinoma. The present invention addresses this need.

SUMMARY OF THE INVENTION

Provided is an isolated binding polypeptide comprising a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds a glial cell derived neurotrophic factor (GDNF) family receptor alpha-4 (GFRα4). In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region comprising an amino acid sequence having at least 95-99% identity to the amino acid sequence of any of the heavy chain variable regions set forth in SEQ ID NOs: 7-10. In some embodiments, the binding polypeptide comprises a heavy chain variable region comprising at least 1, 2, or 3 modifications but not more than 20 modifications of the amino acid sequence of any of the heavy chain variable regions set forth in SEQ ID NOs: 7-10. In further embodiments, the binding polypeptide comprises a heavy chain variable region comprising an amino acid sequence of any of the heavy chain variable regions set forth in SEQ ID NOs: 7-10. In yet further embodiments, the binding polypeptide comprises a heavy chain variable region consisting of an amino acid sequence of any of the heavy chain variable regions set forth in SEQ ID NOs: 7-10.

In some embodiments, the binding polypeptide comprises a light chain variable region comprising an amino acid sequence having at least 95-99% identity to the amino acid sequence of any of the light chain variable regions set forth in SEQ ID NOs: 28-42. In some embodiments, the binding polypeptide comprises a light chain variable region comprising at least 1, 2, or 3 modifications but not more than 20 modifications of the amino acid sequence of any of the light chain variable regions set forth in SEQ ID NOs: 28-42. In further embodiments, the binding polypeptide comprises a light chain variable region comprising an amino acid sequence of any of the light chain variable regions set forth in SEQ ID NOs: 28-42. In yet further embodiments, the binding polypeptide comprises a light chain variable region consisting of an amino acid sequence of any of the light chain variable regions set forth in SEQ ID NOs: 28-42.

Provided is an isolated binding polypeptide comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

Provided is a single-chain variable fragment (scFv) comprising a heavy chain variable region that comprises three heavy chain complementarity determining regions (HCDRs), wherein HCDR1 comprises the amino acid sequence RHALT (SEQ ID NO:162), HCDR2 comprises the amino acid sequence AIDNAGTTYYASWAKS (SEQ ID NO:163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is a single-chain variable fragment (scFv) comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

Also provided is a single chain variable fragment comprising any one of the amino acid sequences set forth in SEQ ID NOs: 74-102. Also provided is a is a single chain variable fragment consisting of any one of the amino acid sequences set forth in SEQ ID NOs: 74-102.

Provided is an isolated nucleic acid encoding the binding polypeptide or scFv of any preceding embodiment.

Provided is an isolated nucleic acid encoding a binding polypeptide comprising a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region encoded by a nucleotide sequence having at least 95-99% identity to the nucleotide sequence of any of the heavy chain variable regions set forth in SEQ ID NOs: 2-5. In further embodiments, the binding polypeptide comprises a heavy chain variable region encoded by a nucleotide sequence comprising any of the heavy chain variable region sequences provided in SEQ ID NOs: 2-5. In yet further embodiments, the binding polypeptide comprises a heavy chain variable region encoded by a nucleotide sequence consisting of any of the heavy chain variable region sequences provided in SEQ ID NOs: 2-5.

In some embodiments, the binding polypeptide comprises a light chain variable region encoded by a nucleotide sequence having at least 95-99% identity to the nucleotide sequence of any of the light chain variable regions provided in SEQ ID NOs: 12-26. In further embodiments, the binding polypeptide comprises a light chain variable region encoded by a nucleotide sequence comprising any of the light chain variable region sequences provided in SEQ ID NOs: 12-26. In yet further embodiments, the binding polypeptide comprises a light chain variable region encoded by a nucleotide sequence consisting of any of the light chain variable region sequences provided in SEQ ID NOs: 12-26.

Provided is an isolated nucleic acid encoding a binding polypeptide comprising: a heavy chain variable region encoded by any of the nucleotide sequences set forth in SEQ ID NO: 2-5; and a light chain variable region encoded by any of the nucleotide sequences set forth in SEQ ID NO: 12-26.

Provided is an isolated nucleic acid encoding a single-chain variable fragment (scFv) comprising a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is isolated nucleic acid encoding a single-chain variable fragment (scFv) comprising: a heavy chain variable region comprising any of the nucleotide sequences set forth in SEQ ID NO: 2-5; and a light chain variable region comprising any of the nucleotide sequences set forth in SEQ ID NO: 12-26. Also provided is an isolated nucleic acid encoding a single-chain variable fragment (scFv) comprising any one of the nucleotide sequences set forth in SEQ ID NOs: 43-72. Also provided is an isolated nucleic acid encoding a single-chain variable fragment (scFv) consisting of any one of the nucleotide sequences set forth in SEQ ID NOs: 43-72.

Provided is a vector comprising the isolated nucleic acid of any one of the preceding embodiments. In further embodiments, the vector is an expression vector. In yet further embodiments, the vector is selected from the group consisting of a DNA vector, an RNA vector, a plasmid, a lentiviral vector, an adenoviral vector, an adeno-associated viral vector, and a retroviral vector.

Provided is a host cell comprising the vector of any one of the preceding embodiments. In further embodiments, the host cell is of eukaryotic or prokaryotic origin. In some embodiments, the host cell is of mammalian origin. In some embodiments, the host cell is of bacterial origin.

Provided is a pharmaceutical composition comprising the binding polypeptide or scFv of any one of the preceding embodiments. Also provided is a pharmaceutical composition comprising the antibody or an antigen-binding fragment of any one of the preceding embodiments.

Provided is a chimeric chimeric antigen receptor (CAR) comprising an antigen binding domain, a transmembrane domain, and an intracellular domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody.

In some embodiments, the antibody or antigen-binding fragment is a humanized antibody or a fragment thereof. In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42. In some embodiments, the antigen binding domain comprises a light chain variable region comprising at least 1, 2, or 3 modifications but not more than 20 modifications of the amino acid sequence of any of the light chain variable regions set forth in SEQ ID NOs: 28-42. In further embodiments, the antigen binding domain comprises a light chain variable region comprising an amino acid sequence of any of the light chain variable regions set forth in SEQ ID NOs: 28-42. In yet further embodiments, the antigen binding domain comprises a light chain variable region consisting of an amino acid sequence of any of the light chain variable regions set forth in SEQ ID NOs: 28-42.

Provided is a chimeric antigen receptor (CAR) comprising an antigen binding domain, a transmembrane domain, and an intracellular domain, wherein the antigen binding domain comprises: a heavy chain variable region comprising any of the amino acid sequences set forth in SEQ ID NO: 7-10; and a light chain variable region comprising any of the amino acid sequences set forth in SEQ ID NO: 28-42.

Provided is a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcyRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

Provided is a chimeric antigen receptor (CAR) comprising an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

Provided is a chimeric antigen receptor (CAR) comprising an antigen binding domain comprising: a heavy chain variable region comprising any of the amino acid sequences set forth in SEQ ID NO: 7-10; and a light chain variable region comprising any of the amino acid sequences set forth in SEQ ID NO: 28-42; a CD8 transmembrane domain; a 4-1BB costimulatory domain; and a CD3ζ intracellular signaling domain.

Provided is a chimeric antigen receptor (CAR) comprising any one of the amino acid sequences set forth in SEQ ID NOs: 107-110. Also provided is a chimeric antigen receptor (CAR) consisting of any one of the amino acid sequences set forth in SEQ ID NOs: 107-110.

Provided is a nucleic acid encoding for the CAR of any one of the preceding embodiments.

Provided is a nucleic acid encoding a chimeric antigen receptor (CAR) comprising an antigen binding domain, a transmembrane domain, and an intracellular domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region encoded by a nucleotide sequence having at least 95-99% identity to the nucleotide sequence of any of the heavy chain variable regions set forth in SEQ ID NOs: 2-5. In some embodiments, the antigen binding domain comprises a heavy chain variable region encoded by a nucleotide sequence comprising any of the heavy chain variable region sequences set forth in SEQ ID NOs: 2-5. In further embodiments, the antigen binding domain comprises a heavy chain variable region encoded by a nucleotide sequence consisting of any of the heavy chain variable region sequences set forth in SEQ ID NOs: 2-5.

In some embodiments, the antigen binding domain comprises a light chain variable region encoded by a nucleotide sequence having at least 95-99% identity to the nucleotide sequence of any of the light chain variable regions set forth in SEQ ID NOs: 12-26. In some embodiments, the antigen binding domain comprises a light chain variable region encoded by a nucleotide sequence comprising any of the light chain variable region sequences set forth in SEQ ID NOs: 12-26. In further embodiments, the antigen binding domain comprises a light chain variable region encoded by a nucleotide sequence consisting of any of the light chain variable region sequences set forth in SEQ ID NOs: 12-26.

Provided is a nucleic acid encoding a chimeric antigen receptor (CAR) comprising an antigen binding domain, a transmembrane domain, and an intracellular domain, wherein the antigen binding domain comprises a heavy chain variable region encoded by any of the nucleotide sequences set forth in SEQ ID NO: 2-5; and a light chain variable region encoded by any of the nucleotide sequences set forth in SEQ ID NO: 12-26.

Provided is a nucleic acid encoding a chimeric antigen receptor (CAR) comprising an antigen binding domain, a transmembrane domain, and an intracellular signaling domain, wherein the antigen binding domain is encoded by any one of the nucleotide sequences set forth in SEQ ID NOs: 103-106.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In some embodiments, the costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

Provided is a nucleic acid encoding a chimeric antigen receptor (CAR) comprising an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

Provided is a nucleic acid encoding a chimeric antigen receptor (CAR) comprising an antigen binding domain comprising: a heavy chain variable region encoded by any of the nucleotide sequences set forth in SEQ ID NO: 2-5; and a light chain variable region encoded by any of the nucleotide sequences set forth in SEQ ID NO: 12-26; a CD8 transmembrane domain; a 4-1BB costimulatory domain; and a CD3ζ intracellular signaling domain.

Also provided is a nucleic acid encoding a chimeric antigen receptor (CAR) comprising any one of the nucleotide sequences set forth in SEQ ID NOs: 111-114.

Provided is a nucleic acid encoding a chimeric antigen receptor (CAR) consisting of any one of the nucleotide sequences set forth in SEQ ID NOs: 111-114.

Provided is a vector comprising the nucleic acid of any one of the preceding embodiments. In some embodiments, the vector is an expression vector. In some embodiments, the vector is selected from the group consisting of a DNA vector, an RNA vector, a plasmid, a lentiviral vector, an adenoviral vector, an adeno-associated viral vector, and a retroviral vector. In some embodiments, the vector further comprises an EF-1 a promoter. In some embodiments, the vector further comprises a woodchuck hepatitis virus post-transcriptional regulatory element (WPRE). In further embodiments, the vector further comprises a rev response element (RRE). In further embodiments, the vector further comprises a cPPT sequence. In yet further embodiments, the vector is a self-inactivating vector.

Also provided is a cell comprising the CAR of any one of the preceding embodiments, the nucleic acid of any one of the preceding embodiments, or the vector of any one of the preceding embodiments. In some embodiments, the cell is selected from the group consisting of a T cell, a natural killer (NK) cell, a cytotoxic T lymphocyte (CTL), and a regulatory T cell.

Also provided is the CAR of any one of the preceding embodiments, the nucleic acid of any one of the preceding embodiments, the vector of any one of the preceding embodiments, or the cell of any one of the preceding embodiments, for use in the treatment of a disease associated with expression of a thyroid cell antigen.

Provided is a modified immune cell or precursor cell thereof, comprising a chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42.

Provided is the cell of any one of the preceding embodiments, wherein the antigen binding domain comprises a light chain variable region comprising at least 1, 2, or 3 modifications but not more than 20 modifications of the amino acid sequence of any of the light chain variable regions set forth in SEQ ID NOs: 28-42. Provided is the cell of any one of the preceding embodiments, wherein the antigen binding domain comprises a light chain variable region comprising an amino acid sequence of any of the light chain variable regions set forth in SEQ ID NOs: 28-42. In some embodiments, the antigen binding domain comprises a light chain variable region consisting of an amino acid sequence of any of the light chain variable regions set forth in SEQ ID NOs: 28-42.

Provided is a modified immune cell or precursor cell thereof, comprising a chimeric antigen receptor (CAR) comprising an antigen binding domain, a transmembrane domain, and an intracellular domain, wherein the antigen binding domain comprises a heavy chain variable region comprising any of the amino acid sequences set forth in SEQ ID NO: 7-10; and a light chain variable region comprising any of the amino acid sequences set forth in SEQ ID NO: 28-42.

Also provided is a modified immune cell or precursor cell thereof, comprising a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102. In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcyRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

Provided is a modified immune cell or precursor cell thereof, comprising a chimeric antigen receptor (CAR) comprising an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO:164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

Provided is a modified immune cell or precursor cell thereof, comprising chimeric antigen receptor (CAR) comprising an antigen binding domain comprising a heavy chain variable region comprising any of the amino acid sequences set forth in SEQ ID NO: 7-10; a light chain variable region comprising any of the amino acid sequences set forth in SEQ ID NO: 28-42; a CD8 transmembrane domain; a 4-1BB costimulatory domain; and a CD3ζ intracellular signaling domain.

Provided is a modified immune cell or precursor cell thereof, comprising a chimeric antigen receptor (CAR) comprising any one of the amino acid sequences set forth in SEQ ID NOs: 107-110.

Provided is a modified immune cell or precursor cell thereof, comprising a chimeric antigen receptor (CAR) consisting of any one of the amino acid sequences set forth in SEQ ID NOs: 107-110.

In some embodiments, the modified cell is a modified immune cell. In some embodiments, the modified cell is a modified T cell. In some embodiments, the modified cell is an autologous cell. In further embodiments, the modified cell is an autologous cell obtained from a human subject.

Provided is a pharmaceutical composition comprising a therapeutically effective amount of the modified cell of any one of the preceding embodiments.

Provided is a method of treating a disease in a subject in need thereof, comprising administering to the subject an effective amount of the cell of any one of the preceding embodiments, or the pharmaceutical composition of any one of the preceding embodiments. In some embodiments, the disease is associated with expression of a thyroid cell antigen. In further embodiments, the disease is associated with expression of GFRα4. In yet further embodiments, the disease is a cancer. In yet further embodiments, the cancer is medullary thyroid carcinoma (MTC) or a metastasis resulting from MTC.

Provided is a method of treating a disease associated with expression of a thyroid cell antigen in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is a method of treating a GFRα4-associated disease in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

Provided is a method of treating medullary thyroid cancer (MTC) in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A shows the heavy chain (SEQ ID NO: 6), and FIG. 1B shows the light chain (SEQ ID NO: 27). Framework regions are indicated by dotted underlines, complementarity-determining regions (CDRs) using either Kabat or IMGT analysis are indicated in bold letters with solid underlines.

FIGS. 3A-3B illustrate an alignment of rabbit P4-10 anti-GFRα4 antibody variable regions with additional human variable region genes selected on the basis of pairing frequency found in vivo. FIG. 3A shows the alignment of the heavy chains. FIG. 3B shows the alignment of the light chains. CDR regions are indicated in underlined bold letters. Percent identity to human germline genes are indicated after the germline gene name.

FIG. 4 illustrates the design of humanized versions of rabbit P4-10 heavy chain variable regions. For each human VH germline gene IGHV4-38-2*02 (1) and IGHV3-48*03 (2), P4-10 CDR1 and CDR2 have replaced the corresponding human CDRs to create humanized versions of P4-10 heavy chain. Amino acid residues in white against a black background represent amino acids back-mutated to those in the original rabbit chain. Percent identity to human germline genes are indicated after the name of each candidate.

FIGS. 5A-5C illustrate the design of humanized versions of rabbit P4-10 light chain variable regions. For each human VL germline gene IGLV4-69*01 (FIG. 5A), IGLV1-44*01 (FIG. 5B), and IGLV2-14*01 (FIG. 5C), P4-10 CDR1, CDR2, and CDR3 have replaced the corresponding human CDRs to create humanized versions of the P4-10 light chain. Amino acid residues in white against a black background represent amino acids back-mutated to those in the original rabbit chain. Percent identity to human germline genes are indicated after the name of each candidate.

FIG. 12 are the results of a search for species, heavy chain germline genes, and percent amino acid identities for "top hits" for P4-10 humanized heavy chain H1.

FIG. 13 are the results of a search for species, heavy chain germline genes, and percent amino acid identities for "top hits" for P4-10 humanized heavy chain H2.

FIG. 14 are the results of a search for species, light chain germline genes, and percent amino acid identities for "top hits" for P4-10 humanized light chain L1m3.

FIG. 15 are the results of a search for species, light chain germline genes, and percent amino acid identities for "top hits" for P4-10 humanized light chain L1m1.

FIG. 24A: Blood samples collected on Day 23 from mice treated as in shown in FIG. 23 were stained with anti-CD19 and anti-GFRα4 P4-10 antibodies to assess expression of CD19 and GFRα4b in residual Nalm6 cells post treatment with CAR-Ts (5 representative mice from each group). FIG. 24B: Control samples of wild-type Nalm6 cells and Nalm6-GFRα4 target cells spiked into mouse blood were stained with also anti-CD19 and anti-GFRα4 P4-10 antibodies (in duplicate).

DETAILED DESCRIPTION

Definitions

Figure 1A:
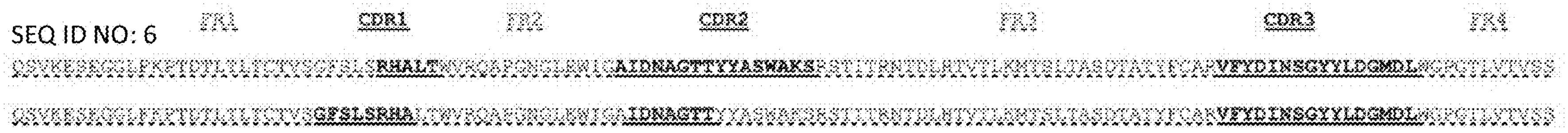
FIGS. 1A-1B are a series of illustrations showing amino acid sequences for rabbit P4-10 anti-GFRα4 antibody variable regions.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and $F(ab')_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigen determining variable regions of an intact antibody. Examples of antibody fragments include, but are not limited to, Fab, Fab', $F(ab')_2$, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind GFRα4 using the functional assays described herein.

"Co-stimulatory ligand", as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "dysregulated" when used in the context of the level of expression or activity of GFRα4 refers to the level of expression or activity that is different from the expression level or activity of GFRα4 in an otherwise identical healthy animal, organism, tissue, cell or component thereof. The term "dysregulated" also refers to the altered regulation of the level of expression and activity of GFRα4 compared to the regulation in an otherwise identical healthy animal, organism, tissue, cell or component thereof.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" and "chimeric" forms of non-human (e.g., murine) antibodies are immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized and chimeric antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized and chimeric antibodies can comprise residues which are found neither in the recipient antibody nor in the imported CDR or framework sequences. These modifications are made to further refine and optimize antibody performance. In general, the humanized and chimeric antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized and chimeric antibody optimally also will comprise at least a portion of an immunoglobulin constant region (Fc), typically that of a human immunoglobulin. The World Health Organization (WHO) International Nonproprietary Name (INN) Expert Group has defined requirements for non-human derived antibodies to be considered "humanized". According to guidelines, comparison of a candidate antibody to human sequences should be done through the International Immunogenetics Information System® (IMGT®) DomainGapAlign tool (www.imgt.org). This tool interrogates the IMGT® database of antibody germline variable region genes where the alignment score is made only against germline sequence variable region exons, thus omitting part of CDR3 and the J region from the analysis. For an antibody to be "humanized", in addition to being "closer to human than to other species", the top "hit" should be human and the identity to human sequences must be at least 85%, otherwise the antibody would be designated as "chimeric". For further details, see Jones et al., Nature, 321:

522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

As used herein, the terms "GDNF family receptor alpha 4" and "GFRα4", are used interchangeably, and include variants, isoforms and species homologs of human GFRα4. Isoforms of GFRα4 include GFRα4a and GFRα4b. Accordingly, human antibodies of this disclosure may, in certain cases, cross-react with GFRα4 from species other than human. In certain embodiments, the antibodies may be completely specific for one or more human GFRα4 proteins and may not exhibit species or other types of non-human cross-reactivity. The complete amino acid sequence of an exemplary human GFRα4 has Genbank/NCBI accession number: NM_022139.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/ regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human GFRα4.

"Single chain antibodies" refer to antibodies formed by recombinant DNA techniques in which immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell and/or on a tumor cell.

A "stimulatory ligand," as used herein, means a ligand that when present on an antigen presenting cell (e.g., an aAPC, a dendritic cell, a B-cell, and the like) or a tumor cell, can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides isolated antibodies that bind specifically to GFRα4. In certain embodiments, the antibodies of the invention comprise particular structural features such as CDR regions comprising particular amino acid sequences. The invention also provides methods of making such antibodies.

In one embodiment, peptides containing amino acids of human GFRα4 isoform "a" and GFRα4 isoform "b" were obtained from R&D Systems (Minneapolis, MN) and LakePhama, Inc (Belmont, CA), respectively, and used to screen a phage display library in order to isolate single-chain variable fragments (scFv) against GFRα4. In a particular embodiment, the isolated scFv targets GFRα4 isoform "a" (SEQ ID NO: 118). In another embodiment, the isolated scFv targets GFRα4 isoform "b" (SEQ ID NO: 119).

In one embodiment, the scFv antibodies of the invention can be used for diagnosing the presence of GFRα4 in a biological sample. In one embodiment, the scFv antibodies of the invention can be used for diagnosing the presence of GFRα4 in a tumor cell.

In one embodiment, the scFv antibodies of the invention can be used for therapy against a disease, disorder or condition associated with normal or dysregulated expression of GFRα4. The level of expression of GFRα4 on the surface of medullary cancer cells may be considered the same as on normal thyroid C-cells. That said, should a different cell type (e.g. adrenal cells, neuronal cells) exhibit a pathology that is the result of dysregulated GFRα4, the present invention may be useful in targeting these cells to relieve the pathology.

In one embodiment, the scFv antibodies of the invention can be used for cancer therapy against cancers associated with normal or dysregulated expression of GFRα4. In another embodiment, the scFv antibodies of the invention can be used for cancer therapy against thyroid cancers. In yet another embodiment, the scFv antibodies of the invention can be used for cancer therapy against Medullary Thyroid Cancer (MTC).

The present invention relates generally to the treatment of a patient having a cancer associated with the expression of GFRα4, or at risk of having a cancer associated with the expression of GFRα4, using cellular infusion. In one embodiment, lymphocyte infusion, preferably autologous lymphocyte infusion is used in the treatment. In another embodiment, the cancer associated with expression of GFRα4 is a thyroid cancer. In yet another embodiment, the cancer associated with expression of GFRα4 is MTC.

The present invention may also be useful to prevent disease in patients identified as at-risk.

In one embodiment, peripheral blood mononuclear cells (PBMCs) are collected from a patient in need of treatment and T cells therefrom are engineered and expanded using the methods described herein and then infused back into the patient. In another embodiment, autologous or heterologous NK cells or NK cell lines are engineered and expanded using the methods described herein and then infused back into the patient. The invention should not be limited to a particular cell or cell type. Rather, any cell or cell type can be engineered and expanded using the methods described herein and then infused back into the patient.

In one embodiment, the scFv antibodies of the invention can be cloned into vectors that allow expression in cis with cellular cytotoxins. The combination of the scFv antibodies with cellular cytotoxins can be used for transarterial infusion into patients in need thereof.

The antibodies of the invention can be incorporated into an immunoconjugate, a chimeric antigen receptor (CAR), a pharmaceutical composition, and the like. In one embodiment, the immunoconjugates of the invention may be therapeutic agents, for example, cytotoxins or radioactive isotopes. Accordingly, the present invention provides compositions and methods for treating, among other diseases, cancer or any malignancy or autoimmune disease in which expression of GFRα4 is expressed on the cell surface.

The present invention also relates generally to the use of T cells engineered to express a Chimeric Antigen Receptor (CAR). CARs combine an antigen recognition domain of a specific antibody with an intracellular signaling molecule. For example, the intracellular signaling molecule can include but is not limited to CD3-zeta chain, 4-1BB and CD28 signaling modules and combinations thereof. Preferably, the antigen recognition domain binds to GFRα4. In some instances, the antigen recognition domain comprises an anti-GFRα4. Accordingly, the invention provides an anti-GFRα4-CAR engineered into a T cell and methods of their use for adoptive therapy.

In one embodiment, the invention includes autologous cells that are transfected with a vector comprising an anti-GFRα4 CAR transgene. Preferably, the vector is a retroviral vector. More preferably, the vector is a self-inactivating lentiviral vector as described elsewhere herein.

In certain embodiments, the vector further comprises an EF-1α promoter. In certain embodiments, the vector further comprises a rev response element (RRE). In certain embodiments, the vector further comprises a woodchuck hepatitis virus posttranscriptional regulatory element (WPRE). In certain embodiments, the vector further comprises a cPPT sequence.

In certain embodiments, the expression construct is a viral vector selected from the group consisting of a retroviral vector, a lentiviral vector, an adenoviral vector, and an adeno-associated viral vector.

In certain embodiments, the expression construct is a lentiviral vector. In certain embodiments, the lentiviral vector is a self-inactivating lentiviral vector.

In one embodiment, the anti-GFRα 4-CAR T cells of the invention can be generated by introducing a lentiviral vector comprising a GFRα4 binding domain, a glycine-serine linker and transmembrane domain, and a CD3zeta signaling domain into the cells. In another embodiment, the anti-GFRα 4-CAR T cells of the invention can be generated by introducing a lentiviral vector comprising a GFRα4 binding domain, CD8a hinge and transmembrane domain, and a CD3zeta signaling domain into the cells. In some instances, the vector further comprises the signaling domain of 4-1BB, CD28, or a combination of both. This is because the present invention is partly based on the discovery that CAR-mediated T-cell responses can be further enhanced with the addition of costimulatory domains. For example, inclusion of the CD28 signaling domain significantly increased antitumor activity and in vivo persistence of CAR T cells compared to an otherwise identical CAR T cell not engineered to express CD28.

In one embodiment, the CAR-modified T cells of the invention are expected to replicate in vivo resulting in long-term persistence that can lead to sustained tumor control.

Binding Polypeptides and Antibodies

The binding polypeptides and antibodies of the invention are characterized by particular functional features or properties of the antibodies. For example, the binding polypeptides and antibodies specifically bind to human GFRα4. Preferably, the binding polypeptides and antibodies of the invention bind to GFRα4 with high affinity. Preferably, the binding polypeptides and antibodies of the invention specifically recognize naturally expressed hGFRα4 protein on a cell and do not cross-react to other surface molecules.

Provided is an isolated binding polypeptide comprising:

a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds a glial cell derived neurotrophic factor (GDNF) family receptor alpha-4 (GFRα4). In further embodiments, the binding polypeptide binds GFRα4a and GFRα4b.

In some embodiments, the binding polypeptide comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or an antigen-binding fragment thereof.

In some embodiments, the binding polypeptide comprises a heavy chain variable region comprising an amino acid sequence with 95-99% identity to the amino acid sequence of any of the heavy chain variable regions set forth in SEQ ID NOs: 7-10. In some embodiments, the binding polypeptide comprises a heavy chain variable region comprising at least 1, 2, or 3 modifications but not more than 20 modifications of the amino acid sequence of any of the heavy chain variable regions set forth in SEQ ID NOs: 7-10. In further embodiments, the binding polypeptide comprises a heavy chain variable region comprising an amino acid sequence of any of the heavy chain variable regions set forth in SEQ ID NOs: 7-10. In yet further embodiments, the binding polypeptide comprises a heavy chain variable region consisting of an amino acid sequence of any of the heavy chain variable regions set forth in SEQ ID NOs: 7-10.

In some embodiments, the binding polypeptide comprises a light chain variable region comprising an amino acid sequence with 95-99% identity to the amino acid sequence of any of the light chain variable regions set forth in SEQ ID NOs: 28-42. In some embodiments, the binding polypeptide comprises a light chain variable region comprising at least 1, 2, or 3 modifications but not more than 20 modifications of the amino acid sequence of any of the light chain variable regions set forth in SEQ ID NOs: 28-42. In further embodiments, the binding polypeptide comprises a light chain variable region comprising an amino acid sequence of any of the light chain variable regions set forth in SEQ ID NOs: 28-42. In yet further embodiments, the binding polypeptide comprises a light chain variable region consisting of an amino acid sequence of any of the light chain variable regions set forth in SEQ ID NOs: 28-42.

Given that each of these antibodies binds to GFRα4, the $V_H$ and $V_L$ sequences can be "mixed and matched" to create other anti-GFRα4 binding molecules of the invention. GFRα4 binding of such "mixed and matched" antibodies can be tested using the binding assays described herein, in the art, for example, in the Examples section (e.g., ELISAs). Preferably, when VH and VL chains are mixed and matched, a VH sequence from a particular VH/VL pairing is replaced with a structurally similar VH sequence. Likewise, preferably a VL sequence from a particular VH/VL pairing is replaced with a structurally similar VL sequence. It will be readily apparent to the ordinary skilled artisan that novel VH and VL sequences can be created by substituting one or more VH and/or VL CDR region sequences with structurally similar sequences from the CDR sequences disclosed herein.

In another embodiment, the invention includes antibodies that bind to the same epitope on human GFRα4 as any of the GFRα4 antibodies of the invention (i.e., antibodies that have the ability to cross-compete for binding to GFRα4 with any of the antibodies of the invention). In a preferred embodiment, the reference antibody for cross-competition studies can be one of the antibodies described herein (e.g., P4-10). For example, Biacore analysis, ELISA assays or flow cytometry may be used to demonstrate cross-competition with the antibodies of the current invention. The ability of a test antibody to inhibit the binding of, for example, P4-10, to human GFRα4 demonstrates that the test antibody can compete with P4-10 for binding to human GFRα4 and thus is considered to bind to the same epitope on human GFRα4 as P4-10.

An antibody of the invention is prepared using an antibody having one or more of the VH and/or VL sequences disclosed herein as a starting material to engineer a modified antibody, which modified antibody may have altered properties as compared with the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

Humanized Antibodies

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-GFRα4 antibodies directed against the human GFRα4 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and Duchosal et al., *Nature,* 355:258 (1992).

Human antibodies can also be derived from phage-display libraries (Hoogenboom et al., *J. Mol. Biol.,* 227:381 (1991); Marks et al., *J. Mol. Biol.,* 222:581-597 (1991); Vaughan et al., *Nature Biotech.,* 14:309 (1996)). Phage display technology (McCafferty et al., *Nature,* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., *J. Mol. Biol.,* 222:581-597 (1991), or Griffith et al., *EMBO J.,* 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al., *Methods Enzymol.,* 121:140-167 (1986).

Alternatively, in some embodiments, a non-human antibody is humanized, where specific sequences or regions of the antibody are modified to increase similarity to an antibody naturally produced in a human. For instance, in the present invention, the GFRα4 antibody comprises a rabbit scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, *Protein Engineering,* 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., *J. Immunol.,* 169:1119-25 (2002), Caldas et al., *Protein Eng.,* 13(5):353-60 (2000), Morea et al., *Methods,* 20(3):267-79 (2000), Baca et al., *J. Biol. Chem.,* 272(16):10678-84 (1997), Roguska et al., *Protein Eng.,* 9(10):895-904 (1996), Couto et al., *Cancer Res.,* 55 (23 Supp):5973s-5977s (1995), Couto et al., *Cancer Res.,* 55(8):1717-22 (1995), Sandhu J S, *Gene,* 150(2):409-10 (1994), and Pedersen et al., *J. Mol. Biol.,* 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature,* 332:323, each of which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, *Molecular Immunology,* 28(4/5):489-498; Studnicka et al., *Protein Engineering,* 7(6):805-814 (1994); and Roguska et al., *PNAS,* 91:969-973 (1994)) or chain shuffling (U.S. Pat. No. 5,565,332), the contents of which are incorporated herein by reference herein in their entirety.

In some instances, a human scFv may also be derived from a yeast display library. The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:2296 (1993); Chothia et al., *J. Mol. Biol.,* 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the rabbit scFv of the present invention, the ability to bind human GFRα4. However, using certain methods of humanization, the affinity and/or specificity of binding of the antibody for human GFRα4 may be increased using methods of "directed evolution," as described by Wu et al., *J. Mol. Biol.,* 294:151 (1999), the contents of which are incorporated herein by reference herein in their entirety.

Antigen Binding Moiety

The choice of moiety depends upon the type and number of ligands that define the surface of a target cell. For example, the antigen binding domain may be chosen to recognize a ligand that acts as a cell surface marker on target cells associated with a particular disease state.

In the context of the present invention, "tumor antigen" refers to antigens that are common to specific thyroid disorders. In certain aspects, the thyroid antigens of the present invention are derived from, cancers including but not limited to thyroid cancer, papillary thyroid cancer, follicular thyroid cancer, medullary thyroid cancer, anaplastic thyroid cancer and the like. Preferably, the cancer is a medullary thyroid carcinoma (MTC).

In one embodiment, the tumor antigen of the present invention comprises one or more antigenic cancer epitopes immunologically recognized by tumor infiltrating lymphocytes (TIL) derived from a cancer tumor of a mammal.

The antigen binding domain can be any domain that binds to the antigen including but not limited to monoclonal antibodies, polyclonal antibodies, synthetic antibodies, human antibodies, humanized antibodies, non-human antibodies and fragments thereof. Thus, in one embodiment, the antigen binding domain portion comprises a rabbit antibody or a fragment thereof.

CAR Composition

The present invention encompasses a recombinant DNA construct comprising sequences of the antigen binding domain of the invention that specifically binds to human GFRα4, wherein the sequence of the antigen binding domain is operably linked to the nucleic acid sequence of a transmembrane domain and of an intracellular domain. The intracellular domain or otherwise the intracellular domain comprises a costimulatory signaling region and/or an intracellular signaling domain, e.g., a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

The present invention therefore encompasses a recombinant DNA construct comprising sequences of a fully human CAR, wherein the sequence comprises the nucleic acid sequence of a GFRα4 binding domain operably linked to the nucleic acid sequence of an intracellular domain. An exemplary intracellular domain that can be used in the CAR includes but is not limited to the intracellular domain of CD3-zeta, CD28, 4-1BB, CD27, and the like. In some instances, the CAR can comprise any combination of CD3-zeta, CD28, 4-1BB, CD27, and the like.

Between the extracellular domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the intracellular domain in the polypeptide chain. A spacer domain may comprise up to 300 amino acids, preferably 10 to 100 amino acids and most preferably 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as cloned molecules. In one embodiment, the CAR of the invention comprises a target-specific binding element otherwise referred to as an antigen binding moiety as described elsewhere herein. Examples of cell surface markers that may act as ligands for the antigen moiety domain in the CAR of the invention include those associated with viral, bacterial and parasitic infections, autoimmune disease and cancer cells.

In one embodiment, the CAR-mediated T-cell response can be directed to an antigen of interest by way of engineering a desired antigen into the CAR.

In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof.

In one embodiment, the antigen binding moiety of the CAR includes a nucleic acid sequence encoding an antibody or antibody fragment as described elsewhere herein.

In a preferred embodiment, the antigen binding moiety portion of the CAR targets GFRα4, preferably human GFRα4.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Intracellular Domain

The intracellular domain of the CAR of the invention is responsible for activation of at least one of the normal effector functions of the immune cell in which the CAR has been placed in. In some embodiments, the intracellular domain comprises a costimulatory domain and an intracellular signaling domain. The term “effector function” refers to a specialized function of a cell. Effector function of a T cell, for example, may be cytolytic activity or helper activity including the secretion of cytokines. Thus the term “intracellular signaling domain” refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the intracellular domain of the CAR can be designed to comprise the CD3-zeta signaling domain by itself or combined with any other desired intracellular domain(s) useful in the context of the CAR of the invention. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., Molecular Cloning: A Laboratory Manual, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the EF1alpha promoter. An additional example includes the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., Molecular Cloning: A Laboratory Manual, volumes 1-3 ($3^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., *Cell* 66:807-815, 1991; Henderson et al., *Immun.* 73:316-321, 1991; Bierer et al., *Curr. Opin. Immun.* 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof, and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-7, 1L-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately predominantly of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one embodiment, the invention pertains to a method of inhibiting growth of a GFRα4-expressing tumor cell, comprising contacting the tumor cell with at least one antibody or a fragment thereof of the invention such that growth of the tumor cell is inhibited.

Without wishing to be bound by any particular theory, the anti-tumor immunity response elicited by the GFRα4 antibody of this invention may be an active or a passive immune response. The GFRα4 antibody of the invention may be used in some type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

The procedure for ex vivo expansion of hematopoietic stem and progenitor cells is described in U.S. Pat. No. 5,199,942, incorporated herein by reference, can be applied to the cells of the present invention. Other suitable methods are known in the art; therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

The GFRα4 antibody of the present invention may be administered either alone, or as a pharmaceutical composition in combination with diluents and/or with other components such as IL-2 or other cytokines or cell populations.

In one embodiment, the invention pertains to a method of inhibiting growth of a GFRα4-expressing tumor cell, comprising contacting the tumor cell with an anti-GFRα4 CAR T cell of the present invention such that growth of the tumor cell is inhibited.

In another aspect, the invention pertains to a method of treating cancer in a subject. The method comprises administering to the subject an antibody or a fragment of the invention or an anti-GFRα4 CAR T cell of the present invention such that the cancer is treated in the subject. Particularly preferred cancers for treatment are thyroid cancer, papillary thyroid cancer, follicular thyroid cancer, medullary thyroid cancer and anaplastic thyroid cancer. More specifically, the cancer for treatment is a medullary thyroid cancer.

Provided is a chimeric antigen receptor (CAR) comprising an antigen binding domain, a transmembrane domain, and an intracellular domain, wherein the antigen binding domain comprises:

- a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and
- a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

The present invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control (unless using mRNA electroporation introduction of CAR). In various embodiments, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

Without wishing to be bound by any particular theory, the anti-tumor immunity response elicited by the CAR-modified T cells may be an active or a passive immune response. In another embodiment, the CAR transduced T cells exhibit specific proinflammatory cytokine secretion and potent cytolytic activity in response to human cancer cells expressing GFRα4, resist soluble GFRα4 inhibition, mediate bystander killing and mediate regression of an established human tumor. For example, antigen-less tumor cells within a heterogeneous field of GFRα4-expressing tumor may be susceptible to indirect destruction by GFRα4-redirected T cells that has previously reacted against adjacent antigen-positive cancer cells.

The CAR-modified T cells of the invention may be a type of vaccine for ex vivo immunization and/or in vivo therapy in a mammal. Preferably, the mammal is a human.

Ex vivo procedures are well known in the art as discussed more fully above. Briefly, cells are isolated from a mammal (preferably a human) and genetically modified (i.e., transduced or transfected in vitro) with a vector expressing a CAR disclosed elsewhere herein, or by electroporating the CAR mRNA disclosed elsewhere herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with the normal or dysregulated expression of GFRα4. In certain embodiments, the cells of the invention are used in the treatment of patients at risk for developing diseases, disorders and conditions associated with expression of GFRα4. Thus, the present invention provides methods for the treatment or prevention of diseases, disorders and conditions associated with expression of GFRα4 comprising administering to a subject in need thereof, a therapeutically effective amount of the CAR-modified T cells of the invention.

Provided is a method of treating a disease associated with expression of a thyroid cell antigen in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises:

- a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

The CAR-modified T cells of the present invention may be administered either alone, or as a pharmaceutical composition in combination with diluents and/or with other components such as IL-2 or other cytokines or cell populations.

Pharmaceutical Compositions

Pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., *Cell* 66:807-815, 1991; Henderson et al., *Immun.* 73:316-321, 1991; Bierer et al., *Curr. Opin. Immun.* 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

Rabbit P4-10 heavy chain variable region and humanized heavy chain variants that are used in the invention Rabbit P4-10 heavy chain variable region (SEQ ID NO: 1)

CAGTCCGTGAAGGAGAGCGAGGGCGGCCTGTTCAAGCCCACCGACACCCTGACCCT

GACCTGCACAGTGAGCGGCTTCAGCCTGTCCAGACACGCCCTGACATGGGTGAGAC

AGGCCCCTGGCAACGGCCTGGAATGGATCGGCGCCATCGACAACGCCGGCACCACC

TACTACGCCAGCTGGGCCAAGTCCAGGTCCACCATCACCAGGAACACCGACCTCCA

CACCGTGACCCTGAAGATGACAAGCCTGACCGCCTCCGACACCGCCACCTACTTCTG

CGCCAGGGTGTTCTACGACATCAACAGCGGCTACTACCTGGATGGCATGGACCTGTG

GGGACCTGGCACACTGGTGACCGTGAGCAGC

Rabbit P4-10 heavy chain variable region (SEQ ID NO: 6)

QSVKESEGGLFKPTDTLTLTCTVSGFSLSRHALTWVRQAPGNGLEWIGAIDNAGTTYYA

SWAKSRSTITRNTDLHTVTLKMTSLTASDTATYFCARVFYDINSGYYLDGMDLWGPGT

LVTVSS

H1

(SEQ ID NO: 2)

CAAGTTCAGCTGCAAGAAAGCGGACCCGGTTTAGTCAAGCCCAGCGAGACTTTATCT

TTAACATGCGCCGTGAGCGGCTACTCCATCTCTCGTCACGCTTTAACATGGATTAGG

CAGCCCCCCGGTAAGGGTTTAGAATGGATCGGCGCCATCGACAACGCTGGCACCAC

CTACTACGCCTCTTGGGCTAAGTCTCGTGTGACAATCAGCGTGGACACCTCCAAGAA

CCAGTTTTCTTTAAAGCTGAGCAGCGTGACCGCTGCCGACACCGCTGTGTACTATTG

CGCTCGTGTCTTCTACGACATCAACAGCGGCTACTATTTAGATGGCATGGATTTATG

GGGACCCGGTACTTTAGTGACCGTGAGCTCC

H1

(SEQ ID NO: 7)

QVQLQESGPGLVKPSETLSLTCAVSGYSISRHALTWIRQPPGKGLEWIGAIDNAGTTYYA

SWAKSRVTISVDTSKNQFSLKLSSVTAADTAVYYCARVFYDINSGYYLDGMDLWGPGT

LVTVSS

H1m1

(SEQ ID NO: 3)

CAGCAGAGCGTGAAGGAGAGCGGCCCCGGTCTGGTGAAGCCCAGCGAGACTTTATC

TTTAACATGCGCCGTGAGCGGCTTCTCTTTATCTCGTCACGCTTTAACTTGGGTGAGA

CAGCCTCCCGGTAAAGGTTTAGAGTGGATCGGCGCCATCGACAACGCCGGCACAAC

CTACTACGCCAGCTGGGCCAAGTCTCGTGTGACCATCTCTCGTAACACCGATTTACA

CACCGTGTCTTTAAAGCTGAGCTCCGTGACCGCTGCCGATACCGCCGTGTACTTCTG

CGCTAGGGTGTTCTACGACATCAACAGCGGCTACTATTTAGATGGCATGGATCTGTG

GGGCCCCGGCACACTGGTCACAGTGTCCAGC

H1m1

(SEQ ID NO: 8)

QQSVKESGPGLVKPSETLSLTCAVSGFSLSRHALTWVRQPPGKGLEWIGAIDNAGTTYY

ASWAKSRVTISRNTDLHTVSLKLSSVTAADTAVYFCARVFYDINSGYYLDGMDLWGPG

TLVTVSS

H2

(SEQ ID NO: 4)

GAGGTGCAGCTGGTGGAAAGCGGCGGAGGACTGGTGCAGCCCGGTGGCTCTTTAAG

ACTGAGCTGTGCTGCCAGCGGCTTCACATTCTCTCGTCACGCTTTAACTTGGGTGAG

ACAAGCTCCCGGAAAGGGTTTAGAATGGGTGAGCGCCATCGACAACGCCGGAACCA

-continued

CCTACTACGCCAGCTGGGCCAAGTCTCGTTTCACCATCTCTCGTGATAACGCCAAGA

ACAGCCTCTATTTACAGATGAACTCTTTAAGGGCCGAGGACACCGCCGTGTACT

ACTGCGCTAGGGTGTTCTACGACATCAACAGCGGCTACTATCTGGACGGCATGGATT

TATGGGGCCCCGGTACACTGGTCACCGTGAGCAGC

H2

(SEQ ID NO: 9)

EVQLVESGGGLVQPGGSLRLSCAASGFTFSRHALTWVRQAPGKGLEWVSAIDNAGTTY

YASWAKSRFTISRDNAKNSLYLQMNSLRAEDTAVYYCARVFYDINSGYYLDGMDLWG

PGTLVTVSS

H2m1

(SEQ ID NO: 5)

CAGAGCGTCAAGGAGTCCGGAGGAGGACTGGTGCAGCCCGGTGGCTCTTTAAGGCT

GAGCTGTGCCGCCTCTGGCTTTACTTTATCTCGTCACGCTTTAACATGGGTGAGACA

AGCTCCCGGTAAGGGACTGGAGTGGATCGGCGCCATCGACAACGCCGGCACCACCT

ACTACGCCTCTTGGGCCAAGTCTCGTTTCACCATCTCTCGTAACACCGATTTACACAC

CGTGTATTTACAGATGAACTCTTTAAGGGCCGAGGACACAGCCGTCTATTTCTGCGC

TCGTGTGTTCTACGACATCAATAGCGGCTACTACCTCGACGGAATGGATCTGTGGGG

CCCCGGTACTTTAGTGACAGTCAGCAGC

H2m1

(SEQ ID NO: 10)

QSVKESGGGLVQPGGSLRLSCAASGFTLSRHALTWVRQAPGKGLEWIGAIDNAGTTYY

ASWAKSRFTISRNTDLHTVYLQMNSLRAEDTAVYFCARVFYDINSGYYLDGMDLWGP

GTLVTVSS

Rabbit P4-10 light chain variable region and humanized light chain variants that are usedin the invention Rabbit P4-10 light chain variable region (SEQ ID NO: 11)

CAGTTCGTGCTGACACAGAGCCCTAGCGTGAGCGCCGCCCTGGGAGCCTCCGCTAA

ACTGACCTGCACCCTGAGCAGCGCCCACAAGACCTACACCATCGACTGGTACCAAC

AGCAGCAGGGCGAGGCCCCCAGGTATCTGATGCAGGTGAAGTCCGACGGCAGCTAC

ACCAAAGGCACCGGCGTGCCTGACAGGTTCAGCGGCAGCTCCAGCGGAGCCGACAG

GTACCTGATCATCCCCTCCGTGCAGGCCGACGACGAGGCTGGCTACGTGTGTGGCGC

CGACGACAATGGCGGCTACGTGTTCGGAGGCGGCACCCAGCTGACCGTGACA

Rabbit P4-10 light chain variable region (SEQ ID NO: 27)

QFVLTQSPSVSAALGASAKLTCTLSSAHKTYTIDWYQQQQGEAPRYLMQVKSDGSYTK

GTGVPDRFSGSSSGADRYLIIPSVQADDEAGYVCGADDNGGYVFGGGTQLTVT

L1

(SEQ ID NO: 12)

CAGCTGGTGCTGACCCAGAGCCCCAGCGCTTCCGCCTCTTTAGGAGCCAGCGTGAAG

CTGACTTGTACTTTAAGCAGCGCCCACAAGACCTACACAATCGCTTGGCACCAGCAG

CAGCCCGAAAAGGGCCCCAGATATCTGATGAAGGTCAAGTCCGACGGCAGCTACTC

CAAGGGCGACGGCATCCCCGATCGTTTCAGCGGTTCTTCCAGCGGCGCCGAGAGGT

ATTTAACCATCAGCTCTTTACAGAGCGAGGACGAGGCCGACTACTACTGCGGCGCTG

ACGACAACGGCGGCTACGTCTTTGGCGGCGGCACAAAACTGACCGTGCTG

-continued

L1
(SEQ ID NO: 28)
QLVLTQSPSASASLGASVKLTCTLSSAHKTYTIAWHQQQPEKGPRYLMKVKSDGSYSK

GDGIPDRFSGSSSGAERYLTISSLQSEDEADYYCGADDNGGYVFGGGTKLTVL

L1m1
(SEQ ID NO: 13)
CAGTTTGTGCTGACCCAGAGCCCTAGCGCTTCCGCCTCTTTAGGAGCCAGCGTGAAG

CTGACTTGTACTTTATCCTCCGCCCACAAGACCTACACCATCGACTGGTACCAGCAG

CAGCCCGAAAAGGGCCCTCGTTATCTGATGCAAGTTAAGTCCGACGGCAGCTACAC

CAAGGGAACCGGCGTGCCCGACAGATTCTCCGGTAGCAGCAGCGGCGCCGACAGAT

ATTTAACCATCAGCTCTTTACAGTCCGAGGACGAGGCCGACTACTACTGCGGCGCCG

ACGACAATGGCGGCTACGTCTTCGGAGGCGGCACACAGCTGACCGTGACT

L1m1
(SEQ ID NO: 29)
QFVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVT

L1m2
(SEQ ID NO: 14)
CAGTTTGTGCTGACCCAGAGCCCTAGCGCTTCCGCCTCTTTAGGAGCCAGCGTGAAG

CTGACTTGTACTTTATCCTCCGCCCACAAGACCTACACCATCGACTGGCACCAGCAG

CAGCCCGAAAAGGGCCCTCGTTATCTGATGCAAGTTAAGTCCGACGGCAGCTACAC

CAAGGGAACCGGCATCCCCGACAGATTCTCCGGTAGCAGCAGCGGCGCCGAGAGAT

ATTTAACCATCAGCTCTTTACAGTCCGAGGACGAGGCCGACTACTACTGCGGCGCCG

ACGACAATGGCGGCTACGTCTTCGGAGGCGGCACACAGCTGACCGTGCTG

L1m2
(SEQ ID NO: 30)
QFVLTQSPSASASLGASVKLTCTLSSAHKTYTIDWHQQQPEKGPRYLMQVKSDGSYTK

GTGIPDRFSGSSSGAERYLTISSLQSEDEADYYCGADDNGGYVFGGGTQLTVL

L1m3
(SEQ ID NO: 15)
CAGCTGGTGCTCACCCAAAGCCCTAGCGCCTCTGCCTCTTTAGGCGCTTCCGTGAAG

CTGACTTGTACTTTAAGCTCCGCCCATAAGACCTACACCATCGACTGGTACCAGCAG

CAGCCCGAGAAGGGCCCTCGTTATTTAATGCAAGTTAAGTCCGATGGCAGCTATACC

AAGGGCACCGGCGTGCCCGACAGATTCAGCGGCAGCTCCAGCGGAGCCGATCGTTA

TTTAACCATCAGCTCTTTACAGAGCGAGGACGAGGCTGACTACTACTGCGGCGCCGA

CGATAACGGCGGCTACGTGTTCGGCGGCGGCACCCAACTGACAGTGCTG

L1m3
(SEQ ID NO: 31)
QLVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVL

L1m4
(SEQ ID NO: 16)
CAGTTGGTGCTCACCCAAAGCCCTAGCGCCTCTGCCTCTTTAGGCGCTTCCGTGAAG

CTGACTTGTACTTTAAGCTCCGCCCATAAGACCTACACCATCGCCTGGCATCAGCAG

CAGCCCGAGAAGGGCCCTCGTTATTTAATGCAAGTTAAGTCCGATGGCAGCTATACC

AAGGGCACCGGCGTGCCCGACAGATTCAGCGGCAGCTCCAGCGGAGCCGATCGTTA

TTTAACCATCAGCTCTTTACAGAGCGAGGACGAGGCTGACTACTACTGCGGCGCCGA

CGATAACGGCGGCTACGTGTTCGGCGGCGGCACCCAACTGACAGTGCTC

Lim4
(SEQ ID NO: 32)
QLVLTQSPSASASLGASVKLTCTLSSAHKTYTIAWHQQQPEKGPRYLMQVKSDGSYTK

GTGVPDRFSGSSSGADRYLTISSLQSEDEADYYCGADDNGGYVFGGGTQLTVL

L2
(SEQ ID NO: 17)
CAGAGCGTGCTGACACAGCCTCCTAGCGCCAGCGGCACACCCGGTCAGAGAGTGAC

CATCAGCTGCTCCGGCAGCAGCGCCCACAAGACCTACACCGTGAACTGGTACCAGC

AGCTGCCCGGCACAGCCCCTAAGCTGCTGATCTACGTGAAATCCGACGGCAGCTAC

CAGAGGCCTAGCGGAGTGCCCGATCGTTTCAGCGGCAGCAAAAGCGGCACAAGCGC

CTCTTTAGCTATCAGCGGTTTACAGAGCGAGGACGAGGCCGACTATTACTGCGGCGC

CGACGATAACGGCGGCTACGTGTTCGGCGGCGGAACCAAGCTGACAGTGCTG

L2
(SEQ ID NO: 33)
QSVLTQPPSASGTPGQRVTISCSGSSAHKTYTVNWYQQLPGTAPKLLIYVKSDGSYQRPS

GVPDRFSGSKSGTSASLAISGLQSEDEADYYCGADDNGGYVFGGGTKLTVL

L2m1
(SEQ ID NO: 18)
CAGTTCGTGCTGACACAGCCTCCCAGCGCCTCTGGCACACCCGGTCAGAGGGTGACC

ATCTCTTGTACTTTATCCTCCGCCCACAAGACCTACACCATTGACTGGTACCAGCAG

CTGCCCGGTACCGCCCCTAAGCTGCTGATTTACGTGAAATCCGACGGCAGCTACACC

AAGGGAACCGGCGTGCCCGATCGTTTTTCCGGCAGCTCCAGCGGCGCCGATAGGTA

TTTAGCCATCAGCGGTTTACAGTCCGAGGATGAGGCCGACTACTACTGCGGCGCCGA

TGACAACGGCGGCTACGTGTTCGGCGGAGGAACCCAGCTCACCGTGACC

L2m1
(SEQ ID NO: 34)
QFVLTQPPSASGTPGQRVTISCTLSSAHKTYTIDWYQQLPGTAPKLLIYVKSDGSYTKGT

GVPDRFSGSSSGADRYLAISGLQSEDEADYYCGADDNGGYVFGGGTQLTVT

L2m2
(SEQ ID NO: 19)
CAGTTCGTGCTGACACAGCCTCCCAGCGCCTCTGGCACACCCGGTCAGAGGGTGACC

ATCTCTTGTACTTTATCCTCCGCCCACAAGACCTACACCATTGACTGGTACCAGCAG

CTGCCCGGTACCGCCCCTAAGCTGCTGATTTACGTGAAATCCGACGGCAGCTACACC

AAGGGAACCGGCGTGCCCGATCGTTTTTCCGGCAGCTCCAGCGGCGCCGATGCCAG

CTTAGCCATCAGCGGTTTACAGTCCGAGGATGAGGCCGACTACTACTGCGGCGCCG

ATGACAACGGCGGCTACGTGTTCGGCGGAGGAACCCAGCTCACCGTGCTG

L2m2
(SEQ ID NO: 35)
QFVLTQPPSASGTPGQRVTISCTLSSAHKTYTIDWYQQLPGTAPKLLIYVKSDGSYTKGT

GVPDRFSGSSSGADASLAISGLQSEDEADYYCGADDNGGYVFGGGTQLTVL

L2m3
(SEQ ID NO: 20)
CAGAGCGTGCTGACACAGCCTCCCAGCGCCTCTGGCACACCCGGTCAGAGGGTGAC

CATCTCTTGTACTTTATCCTCCGCCCACAAGACCTACACCATTGACTGGTACCAGCA

GCTGCCCGGTACCGCCCCTAAGCTGCTGATTTACGTGAAATCCGACGGCAGCTACAC

CAAGGGAACCGGCGTGCCCGATCGTTTTTCCGGCAGCAAGAGCGGCACCAGCGCCA

GCTTAGCCATCAGCGGTTTACAGTCCGAGGATGAGGCCGACTACTACTGCGGCGCC

GATGACAACGGCGGCTACGTGTTCGGCGGAGGAACCCAGCTCACCGTGCTG

-continued

L2m3

(SEQ ID NO: 36)
QSVLTQPPSASGTPGQRVTISCTLSSAHKTYTIDWYQQLPGTAPKLLIYVKSDGSYTKGT
GVPDRFSGSKSGTSASLAISGLQSEDEADYYCGADDNGGYVFGGGTQLTVL

L3

(SEQ ID NO: 21)
CAGTCCGCTTTAACACAGCCCGCTTCTGTGTCCGGAAGCCCCGGTCAGAGCATCACC
ATCAGCTGCACCGGCACCAGCGCTCACAAGACCTACACCGTGAGCTGGTACCAGCA
GCACCCCGGTAAGGCCCCCAAACTGATGATCTACGTGAAGAGCGACGGCAGCTACA
ACAGACCCAGCGGCGTGAGCAATCGTTTCAGCGGCAGCAAGAGCGGCAACACCGCT
TCTTTAACCATCAGCGGTTTACAAGCTGAAGACGAGGCTGACTACTACTGCGGCGCC
GACGATAACGGCGGCTACGTGTTTGGCGGCGGCACCAAACTGACCGTGCTG

L3

(SEQ ID NO: 37)
QSALTQPASVSGSPGQSITISCTGTSAHKTYTVSWYQQHPGKAPKLMIYVKSDGSYNRPS
GVSNRFSGSKSGNTASLTISGLQAEDEADYYCGADDNGGYVFGGGTKLTVL

L3m1

(SEQ ID NO: 22)
CAGTTCGTGCTGACCCAGCCCGCTTCTGTGAGCGGTTCTCCCGGTCAGAGCATCACC
ATCAGCTGCACTTTAAGCAGCGCCCACAAGACCTACACCATCGACTGGTACCAGCA
GCACCCCGGCAAGGCCCCCAAGTATTTAATGCAAGTTAAGTCCGACGGCAGCTACA
CCAAGGGCACCGGCGTGCCCAACAGATTCTCCGGCAGCAGCTCCGGCGCCGACAGA
TACTTAACCATCAGCGGTTTACAAGCTGAGGATGAGGCCGACTATGTGTGCGGCGCC
GACGACAATGGCGGCTACGTGTTCGGCGGCGGCACACAGCTGACCGTGACT

L3m1

(SEQ ID NO: 38)
QFVLTQPASVSGSPGQSITISCTLSSAHKTYTIDWYQQHPGKAPKYLMQVKSDGSYTKG
TGVPNRFSGSSSGADRYLTISGLQAEDEADYVCGADDNGGYVFGGGTQLTVT

L3m2

(SEQ ID NO: 23)
CAGTTCGTGCTGACCCAGCCCGCTTCTGTGAGCGGTTCTCCCGGTCAGAGCATCACC
ATCAGCTGCACTTTAAGCAGCGCCCACAAGACCTACACCATCGACTGGTACCAGCA
GCACCCCGGCAAGGCCCCCAAGCTGATGATCCAAGTTAAGTCCGACGGCAGCTACA
CCAAGGGCACCGGCGTGAGCAACAGATTCTCCGGCAGCAGCTCCGGCGCCGACAGA
TACTTAACCATCAGCGGTTTACAAGCTGAGGATGAGGCCGACTATTACTGCGGCGCC
GACGACAATGGCGGCTACGTGTTCGGCGGCGGCACACAGCTGACCGTGCTG

L3m2

(SEQ ID NO: 39)
QFVLTQPASVSGSPGQSITISCTLSSAHKTYTIDWYQQHPGKAPKLMIQVKSDGSYTKGT
GVSNRFSGSSSGADRYLTISGLQAEDEADYYCGADDNGGYVFGGGTQLTVL

L3m3

(SEQ ID NO: 24)
CAGAGCGCCCTGACCCAGCCCGCTTCTGTGAGCGGTTCTCCCGGTCAGAGCATCACC
ATCAGCTGCACTGGCACCAGCGCCCACAAGACCTACACCATCGACTGGTACCAGCA
GCACCCCGGCAAGGCCCCCAAGCTGATGATCTATGTTAAGTCCGACGGCAGCTACA
CCAAGGGCACCGGCGTGAGCAACAGATTCTCCGGCAGCAAGTCCGGCAACACCGCC
AGCTTAACCATCAGCGGTTTACAAGCTGAGGATGAGGCCGACTATTACTGCGGCGCC
GACGACAATGGCGGCTACGTGTTCGGCGGCGGCACACAGCTGACCGTGCTG

-continued

L3m3

(SEQ ID NO: 40)
QSALTQPASVSGSPGQSITISCTGTSAHKTYTIDWYQQHPGKAPKLMIYVKSDGSYTKGT

GVSNRFSGSKSGNTASLTISGLQAEDEADYYCGADDNGGYVFGGGTQLTVL

L3m4

(SEQ ID NO: 25)
CAGAGCGCTCTGACCCAGCCCGCTTCTGTGAGCGGTTCTCCCGGTCAGAGCATCACC

ATCAGCTGCACTGGCACAAGCGCCCACAAGACCTACACCGTGAGCTGGTACCAGCA

GCACCCCGGCAAGGCCCCCAAGTATTTAATGCAAGTTAAGTCCGACGGCAGCTACA

CCAAGGGCACCGGCGTGCCCAACAGATTCTCCGGCAGCAGCTCCGGCGCCGACAGA

TACTTAACCATCAGCGGTTTACAAGCTGAGGATGAGGCCGACTATTACTGCGGCGCC

GACGACAATGGCGGCTACGTGTTCGGCGGCGGCACCCAACTGACAGTGCTG

L3m4

(SEQ ID NO: 41)
QSALTQPASVSGSPGQSITISCTGTSAHKTYTVSWYQQHPGKAPKYLMQVKSDGSYTKG

TGVPNRFSGSSSGADRYLTISGLQAEDEADYYCGADDNGGYVFGGGTQLTVL

L3m5

(SEQ ID NO: 26)
CAGTCTGCTCTGACCCAGCCCGCTTCTGTGAGCGGTTCTCCCGGTCAGAGCATCACC

ATCAGCTGCACTGGCACAAGCGCCCACAAGACCTACACCGTGAGTTGGTACCAGCA

GCACCCCGGCAAGGCCCCCAAGTTGATGATCTACGTTAAGTCCGACGGCAGCTACA

CCAAGGGCACCGGCGTGCCCAACAGATTCTCCGGCAGCAGCTCCGGCGCCGACAGA

TACTTAACCATCAGCGGTTTACAAGCTGAGGATGAGGCCGACTATTATTGCGGCGCC

GACGACAATGGCGGCTACGTGTTCGGCGGCGGCACCCAACTGACAGTGCTC

L3m5

(SEQ ID NO: 42)
QSALTQPASVSGSPGQSITISCTGTSAHKTYTVSWYQQHPGKAPKLMIYVKSDGSYTKG

TGVPNRFSGSSSGADRYLTISGLQAEDEADYYCGADDNGGYVFGGGTQLTVL scFv constructs of original P4-10 and humanized variants for
bacterial expression
0.410HC.410LC (SEQ ID NO: 43)
CAGTTCGTGCTGACCCAGAGCCCTAGCGTGAGCGCTGCTCTGGGAGCCAGCGCCAA

GCTCACTTGTACTTTAAGCTCCGCCCACAAAACCTACACCATCGACTGGTACCAGCA

GCAGCAAGGTGAGGCCCCCAGATATTTAATGCAAGTTAAGTCCGATGGCAGCTACA

CCAAGGGCACCGGAGTGCCCGATAGGTTCAGCGGCAGCTCCAGCGGCGCCGATAGG

TATTTAATCATCCCCAGCGTGCAAGCTGATGATGAGGCCGGCTACGTGTGTGGCGCC

GACGACAACGGCGGCTACGTGTTCGGAGGCGGAACCCAGCTGACAGTGACCGGAGG

CGGAAGCTCCAGAAGCTCCAGCAGCGGAGGAGGAGGAAGCGGAGGAGGCGGACAG

TCCGTCAAGGAGAGCGAGGGCGGTTTATTTAAGCCCACCGACACTTTAACTTTAACT

TGTACAGTGAGCGGCTTCTCTTTATCCAGACACGCTTTAACATGGGTGAGGCAAGCT

CCCGGTAATGGTTTAGAGTGGATCGGCGCCATCGACAACGCCGGCACCACCTACTA

CGCCAGCTGGGCCAAGTCTCGTTCCACCATCACAAGAAACACCGATTTACACACCGT

GACTTTAAAGATGACCTCTTTAACCGCCTCCGACACCGCCACATACTTCTGCGCTCG

TGTGTTCTACGACATCAATTCCGGCTACTATTTAGACGGCATGGATTTATGGGGCCC

CGGTACTTTAGTGACCGTCTCCAGC

-continued 0.410HC.410LC (SEQ ID NO: 73)

QFVLTQSPSVSAALGASAKLTCTLSSAHKTYTIDWYQQQQGEAPRYLMQVKSDGSYTK

GTGVPDRFSGSSSGADRYLIIPSVQADDEAGYVCGADDNGGYVFGGGTQLTVTGGGSS

RSSSSGGGGSGGGGQSVKESEGGLFKPTDTLTLTCTVSGFSLSRHALTWVRQAPGNGLE

WIGAIDNAGTTYYASWAKSRSTITRNTDLHTVTLKMTSLTASDTATYFCARVFYDINSG

YYLDGMDLWGPGTLVTVSS

1.H1.L3

(SEQ ID NO: 44)

CAGTCCGCTTTAACACAGCCCGCTTCTGTGTCCGGAAGCCCCGGTCAGAGCATCACC

ATCAGCTGCACCGGCACCAGCGCTCACAAGACCTACACCGTGAGCTGGTACCAGCA

GCACCCCGGTAAGGCCCCCAAACTGATGATCTACGTGAAGAGCGACGGCAGCTACA

ACAGACCCAGCGGCGTGAGCAATCGTTTCAGCGGCAGCAAGAGCGGCAACACCGCT

TCTTTAACCATCAGCGGTTTACAAGCTGAAGACGAGGCTGACTACTACTGCGGCGCC

GACGATAACGGCGGCTACGTGTTTGGCGGCGGCACCAAACTGACCGTGCTGGGAGG

CGGCTCCAGCAGAAGCTCCTCCAGCGGAGGAGGAGGAAGCGGAGGCGGAGGACAA

GTTCAGCTGCAAGAAAGCGGACCCGGTTTAGTCAAGCCCAGCGAGACTTTATCTTTA

ACATGCGCCGTGAGCGGCTACTCCATCTCTCGTCACGCTTTAACATGGATTAGGCAG

CCCCCCGGTAAGGGTTTAGAATGGATCGGCGCCATCGACAACGCTGGCACCACCTA

CTACGCCTCTTGGGCTAAGTCTCGTGTGACAATCAGCGTGGACACCTCCAAGAACCA

GTTTTCTTTAAAGCTGAGCAGCGTGACCGCTGCCGACACCGCTGTGTACTATTGCGC

TCGTGTCTTCTACGACATCAACAGCGGCTACTATTTAGATGGCATGGATTTATGGGG

ACCCGGTACTTTAGTGACCGTGAGCTCC

1.H1.L3

(SEQ ID NO: 74)

QSALTQPASVSGSPGQSITISCTGTSAHKTYTVSWYQQHPGKAPKLMIYVKSDGSYNRPS

GVSNRFSGSKSGNTASLTISGLQAEDEADYYCGADDNGGYVFGGGTKLTVLGGGSSRSS

SSGGGGSGGGGQVQLQESGPGLVKPSETLSLTCAVSGYSISRHALTWIRQPPGKGLEWIG

AIDNAGTTYYASWAKSRVTISVDTSKNQFSLKLSSVTAADTAVYYCARVFYDINSGYYL

DGMDLWGPGTLVTVSS

2.H1.L3m1

(SEQ ID NO: 45)

CAGTTCGTGCTGACCCAGCCCGCTTCTGTGAGCGGTTCTCCCGGTCAGAGCATCACC

ATCAGCTGCACTTTAAGCAGCGCCCACAAGACCTACACCATCGACTGGTACCAGCA

GCACCCCGGCAAGGCCCCCAAGTATTTAATGCAAGTTAAGTCCGACGGCAGCTACA

CCAAGGGCACCGGCGTGCCCAACAGATTCTCCGGCAGCAGCTCCGGCGCCGACAGA

TACTTAACCATCAGCGGTTTACAAGCTGAGGATGAGGCCGACTATGTGTGCGGCGCC

GACGACAATGGCGGCTACGTGTTCGGCGGCGGCACACAGCTGACCGTGACTGGTGG

AGGCTCCAGCAGATCCAGCTCCAGCGGCGGAGGAGGCAGCGGAGGCGGAGGACAA

GTGCAGCTCCAAGAATCCGGCCCCGGTCTCGTGAAGCCCAGCGAGACTTTATCTTTA

ACTTGTGCCGTGAGCGGCTACAGCATCTCTCGTCACGCTCTGACTTGGATTCGTCAA

CCTCCCGGAAAGGGTTTAGAGTGGATCGGCGCCATCGACAACGCCGGCACCACCTA

CTACGCCAGCTGGGCCAAATCTCGTGTGACCATTAGCGTGGACACCAGCAAGAACC

AGTTCTCTTTAAAACTGAGCAGCGTGACAGCTGCCGACACCGCCGTGTACTACTGCG

-continued

CTCGTGTGTTCTACGACATCAACAGCGGCTACTATTTAGACGGCATGGATTTATGGG

GCCCCGGTACTTTAGTGACCGTCAGCTCC

2.H1.L3m1

(SEQ ID NO: 75)

QFVLTQPASVSGSPGQSITISCTLSSAHKTYTIDWYQQHPGKAPKYLMQVKSDGSYTKG

TGVPNRFSGSSSGADRYLTISGLQAEDEADYVCGADDNGGYVFGGGTQLTVTGGGSSR

SSSSGGGGSGGGGQVQLQESGPGLVKPSETLSLTCAVSGYSISRHALTWIRQPPGKGLE

WIGAIDNAGTTYYASWAKSRVTISVDTSKNQFSLKLSSVTAADTAVYYCARVFYDINSG

YYLDGMDLWGPGTLVTVSSASTKGPSVTS

3.H1m1.L3

(SEQ ID NO: 46)

CAGTCCGCTTTAACCCAGCCCGCCTCTGTGTCCGGAAGCCCCGGCCAGAGCATCACC

ATCAGCTGCACCGGCACCTCCGCCCACAAGACCTACACCGTGAGCTGGTATCAGCA

GCACCCCGGCAAGGCCCCCAAGCTCATGATCTACGTGAAGAGCGACGGCTCCTACA

ATCGTCCCAGCGGAGTGAGCAATCGTTTCAGCGGCTCCAAGTCCGGCAACACCGCCT

CTTTAACCATTAGCGGTTTACAAGCTGAGGACGAGGCTGATTACTACTGCGGCGCCG

ACGATAACGGAGGCTACGTGTTCGGCGGCGGAACAAAGCTGACCGTGCTGGGCGGA

GGCTCCAGCAGAAGCAGCTCCAGCGGAGGCGGAGGAAGCGGAGGAGGAGGACAGC

AGAGCGTGAAGGAGAGCGGCCCCGGTCTGGTGAAGCCCAGCGAGACTTTATCTTTA

ACATGCGCCGTGAGCGGCTTCTCTTTATCTCGTCACGCTTTAACTTGGGTGAGACAG

CCTCCCGGTAAAGGTTTAGAGTGGATCGGCGCCATCGACAACGCCGGCACAACCTA

CTACGCCAGCTGGGCCAAGTCTCGTGTGACCATCTCTCGTAACACCGATTTACACAC

CGTGTCTTTAAAGCTGAGCTCCGTGACCGCTGCCGATACCGCCGTGTACTTCTGCGC

TAGGGTGTTCTACGACATCAACAGCGGCTACTATTTAGATGGCATGGATCTGTGGGG

CCCCGGCACACTGGTCACAGTGTCCAGC

3.H1m1.L3

(SEQ ID NO: 76)

QSALTQPASVSGSPGQSITISCTGTSAHKTYTVSWYQQHPGKAPKLMIYVKSDGSYNRPS

GVSNRFSGSKSGNTASLTISGLQAEDEADYYCGADDNGGYVFGGGTKLTVLGGGSSRSS

SSGGGGSGGGGQQSVKESGPGLVKPSETLSLTCAVSGFSLSRHALTWVRQPPGKGLEWI

GAIDNAGTTYYASWAKSRVTISRNTDLHTVSLKLSSVTAADTAVYFCARVFYDINSGYY

LDGMDLWGPGTLVTVSS

4.H1m1.L3m1

(SEQ ID NO: 47)

CAGTTCGTGCTGACCCAGCCCGCTTCCGTGAGCGGTTCTCCCGGACAGAGCATCACC

ATTAGCTGCACTTTAAGCAGCGCCCACAAGACCTACACCATCGACTGGTACCAGCA

GCATCCCGGCAAGGCCCCCAAGTACCTCATGCAAGTTAAGAGCGACGGAAGCTATA

CCAAGGGCACCGGAGTGCCCAACAGATTCAGCGGCAGCAGCTCCGGAGCCGATCGT

TATTTAACAATCAGCGGACTGCAAGCTGAGGACGAGGCCGACTACGTGTGTGGCGC

CGACGACAATGGCGGCTACGTGTTTGGAGGCGGAACCCAGCTGACCGTGACTGGAG

GCGGCAGCAGCAGAAGCAGCAGCAGCGGAGGAGGTGGCAGCGGCGGAGGCGGACA

GCAGAGCGTGAAGGAGAGCGGACCCGGTTTAGTGAAGCCTAGCGAGACTTTATCTT

TAACATGCGCCGTGTCCGGCTTCTCTTTAAGCAGACACGCTCTGACTTGGGTGAGGC

AGCCTCCCGGTAAGGGTTTAGAGTGGATCGGCGCCATCGACAACGCCGGCACCACC

TACTACGCCAGCTGGGCCAAGTCCAGAGTGACCATCTCCAGAAACACCGACCTCCA

-continued

CACAGTGTCTTTAAAGCTGTCCTCCGTCACAGCTGCCGACACCGCCGTGTACTTCTG

CGCTCGTGTGTTCTACGACATCAACAGCGGCTATTATTTAGACGGCATGGATTTATG

GGGCCCCGGTACTTTAGTGACCGTGAGCAGC

4.H1m1.L3m1

(SEQ ID NO: 77)

QFVLTQPASVSGSPGQSITISCTLSSAHKTYTIDWYQQHPGKAPKYLMQVKSDGSYTKG

TGVPNRFSGSSSGADRYLTISGLQAEDEADYVCGADDNGGYVFGGGTQLTVTGGGSSR

SSSSGGGGSGGGGQQSVKESGPGLVKPSETLSLTCAVSGFSLSRHALTWVRQPPGKGLE

WIGAIDNAGTTYYASWAKSRVTISRNTDLHTVSLKLSSVTAADTAVYFCARVFYDINSG

YYLDGMDLWGPGTLVTVSS

5.H2.L2

(SEQ ID NO: 48)

CAGAGCGTGCTGACACAGCCTCCTAGCGCCAGCGGCACACCCGGTCAGAGAGTGAC

CATCAGCTGCTCCGGCAGCAGCGCCCACAAGACCTACACCGTGAACTGGTACCAGC

AGCTGCCCGGCACAGCCCCTAAGCTGCTGATCTACGTGAAATCCGACGGCAGCTAC

CAGAGGCCTAGCGGAGTGCCCGATCGTTTCAGCGGCAGCAAAAGCGGCACAAGCGC

CTCTTTAGCTATCAGCGGTTTACAGAGCGAGGACGAGGCCGACTATTACTGCGGCGC

CGACGATAACGGCGGCTACGTGTTCGGCGGCGGAACCAAGCTGACAGTGCTGGGCG

GCGGAAGCAGCAGAAGCAGCAGCTCTGGAGGAGGAGGAAGCGGAGGTGGAGGCGA

GGTGCAGCTGGTGGAAAGCGGCGGAGGACTGGTGCAGCCCGGTGGCTCTTTAAGAC

TGAGCTGTGCTGCCAGCGGCTTCACATTCTCTCGTCACGCTTTAACTTGGGTGAGAC

AAGCTCCCGGAAAGGGTTTAGAATGGGTGAGCGCCATCGACAACGCCGGAACCACC

TACTACGCCAGCTGGGCCAAGTCTCGTTTCACCATCTCTCGTGATAACGCCAAGAAC

AGCCTCTATTTACAGATGAACTCTTTAAGGGCCGAGGACACCGCCGTGTACTACTGC

GCTAGGGTGTTCTACGACATCAACAGCGGCTACTATCTGGACGGCATGGATTTATGG

GGCCCCGGTACACTGGTCACCGTGAGCAGC

5.H2.L2

(SEQ ID NO: 78)

QSVLTQPPSASGTPGQRVTISCSGSSAHKTYTVNWYQQLPGTAPKLLIYVKSDGSYQRPS

GVPDRFSGSKSGTSASLAISGLQSEDEADYYCGADDNGGYVFGGGTKLTVLGGGSSRSS

SSGGGGSGGGGEVQLVESGGGLVQPGGSLRLSCAASGFTFSRHALTWVRQAPGKGLEW

VSAIDNAGTTYYASWAKSRFTISRDNAKNSLYLQMNSLRAEDTAVYYCARVFYDINSG

YYLDGMDLWGPGTLVTVSS

6.H2.L2m1

(SEQ ID NO: 49)

CAGTTCGTGCTGACACAGCCTCCCAGCGCCTCTGGCACACCCGGTCAGAGGGTGACC

ATCTCTTGTACTTTATCCTCCGCCCACAAGACCTACACCATTGACTGGTACCAGCAG

CTGCCCGGTACCGCCCCTAAGCTGCTGATTTACGTGAAATCCGACGGCAGCTACACC

AAGGGAACCGGCGTGCCCGATCGTTTTTCCGGCAGCTCCAGCGGCGCCGATAGGTA

TTTAGCCATCAGCGGTTTACAGTCCGAGGATGAGGCCGACTACTACTGCGGCGCCGA

TGACAACGGCGGCTACGTGTTCGGCGGAGGAACCCAGCTCACCGTGACCGGAGGAG

GCTCCTCTCGTAGCTCCAGCTCCGGAGGAGGAGGAAGCGGAGGCGGCGGAGAAGTG

CAACTGGTGGAGTCCGGCGGCGGACTGGTGCAGCCCGGTGGCTCTTTAAGACTGAG

CTGTGCCGCCTCCGGCTTCACCTTTAGCAGACACGCCCTCACTTGGGTCAGACAAGC

-continued

TCCCGGTAAGGGTTTAGAGTGGGTGAGCGCCATCGACAACGCCGGCACAACCTACT

ACGCCTCTTGGGCCAAGTCTCGTTTCACCATCAGCAGAGACAACGCCAAGAACTCTT

TATATTTACAGATGAACTCTTTAAGGGCCGAGGACACCGCCGTGTACTACTGCGCTC

GTGTGTTCTACGACATCAACAGCGGCTATTATTTAGATGGCATGGATTTATGGGGCC

CCGGTACTTTAGTGACAGTGTCCTCC

6.H2.L2m1

(SEQ ID NO: 79)

QFVLTQPPSASGTPGQRVTISCTLSSAHKTYTIDWYQQLPGTAPKLLIYVKSDGSYTKGT

GVPDRFSGSSSGADRYLAISGLQSEDEADYYCGADDNGGYVFGGGTQLTVTGGGSSRSS

SSGGGGSGGGGEVQLVESGGGLVQPGGSLRLSCAASGFTFSRHALTWVRQAPGKGLEW

VSAIDNAGTTYYASWAKSRFTISRDNAKNSLYLQMNSLRAEDTAVYYCARVFYDINSG

YYLDGMDLWGPGTLVTVSS

7.H2m1.L2

(SEQ ID NO: 50)

CAGAGCGTGCTGACCCAGCCTCCTAGCGCCTCTGGCACACCCGGTCAGAGGGTGAC

CATCAGCTGCTCCGGCTCCTCCGCCCACAAGACCTACACCGTGAACTGGTACCAGCA

GCTGCCCGGTACCGCTCCCAAGCTGCTGATTTACGTGAAAAGCGACGGCAGCTACC

AGAGACCTAGCGGCGTGCCCGATCGTTTCTCCGGTTCTAAGAGCGGCACCAGCGCCT

CTTTAGCCATTAGCGGCCTCCAGAGCGAGGACGAGGCCGATTACTACTGCGGAGCC

GACGACAATGGCGGCTACGTGTTCGGCGGCGGAACAAAGCTGACCGTTTTAGGTGG

CGGAAGCAGCAGAAGCAGCAGCTCTGGCGGCGGCGGTAGCGGCGGTGGCGGAGAG

CAGAGCGTCAAGGAGTCCGGAGGAGGACTGGTGCAGCCCGGTGGCTCTTTAAGGCT

GAGCTGTGCCGCCTCTGGCTTTACTTTATCTCGTCACGCTTTAACATGGGTGAGACA

AGCTCCCGGTAAGGGACTGGAGTGGATCGGCGCCATCGACAACGCCGGCACCACCT

ACTACGCCTCTTGGGCCAAGTCTCGTTTCACCATCTCTCGTAACACCGATTTACACAC

CGTGTATTTACAGATGAACTCTTTAAGGGCCGAGGACACAGCCGTCTATTTCTGCGC

TCGTGTGTTCTACGACATCAATAGCGGCTACTACCTCGACGGAATGGATCTGTGGGG

CCCCGGTACTTTAGTGACAGTCAGCAGC

7.H2m1.L2

(SEQ ID NO: 80)

QSVLTQPPSASGTPGQRVTISCSGSSAHKTYTVNWYQQLPGTAPKLLIYVKSDGSYQRPS

GVPDRFSGSKSGTSASLAISGLQSEDEADYYCGADDNGGYVFGGGTKLTVLGGGSSRSS

SSGGGGSGGGGEQSVKESGGGLVQPGGSLRLSCAASGFTLSRHALTWVRQAPGKGLEW

IGAIDNAGTTYYASWAKSRFTISRNTDLHTVYLQMNSLRAEDTAVYFCARVFYDINSGY

YLDGMDLWGPGTLVTVSS

8.H2m1.L2m1

(SEQ ID NO: 51)

CAGTTTGTTTTAACCCAGCCTCCTAGCGCCTCTGGAACACCCGGCCAAAGGGTCACC

ATCAGCTGCACTTTATCCTCCGCCCACAAGACCTACACCATCGACTGGTACCAGCAG

CTGCCCGGAACCGCCCCTAAGCTGCTGATCTACGTGAAGAGCGACGGCAGCTACAC

CAAGGGCACCGGCGTGCCCGATAGGTTCAGCGGCAGCAGCAGCGGCGCCGATAGAT

ATTTAGCCATTTCCGGTTTACAGAGCGAGGACGAGGCCGATTACTACTGTGGCGCTG

ACGACAACGGAGGCTACGTGTTCGGAGGCGGCACCCAGCTGACCGTGACTGGTGGC

GGTTCTAGCAGAAGCAGCAGCTCCGGAGGCGGAGGCTCTGGCGGCGGTGGCGAGCA

GTCCGTGAAGGAAAGCGGCGGCGGACTGGTGCAGCCCGGTGGATCTTTAAGACTGA

-continued

GCTGCGCCGCCTCTGGCTTCACTTTATCCAGACATGCTTTAACATGGGTGAGACAAG

CTCCCGGCAAGGGACTGGAGTGGATCGGCGCCATCGACAACGCCGGCACCACCTAC

TACGCCAGCTGGGCCAAATCTCGTTTCACCATCTCTCGTAACACCGATTTACACACC

GTGTATTTACAGATGAATTCTTTAAGGGCCGAGGACACCGCCGTGTACTTCTGCGCT

CGTGTGTTCTACGACATCAACAGCGGCTACTATTTAGACGGCATGGATTTATGGGGA

CCCGGTACACTCGTGACCGTGTCCAGC

8.H2m1.L2m1

(SEQ ID NO: 81)

QFVLTQPPSASGTPGQRVTISCTLSSAHKTYTIDWYQQLPGTAPKLLIYVKSDGSYTKGT

GVPDRFSGSSSGADRYLAISGLQSEDEADYYCGADDNGGYVFGGGTQLTVTGGGSSRSS

SSGGGGSGGGGEQSVKESGGGLVQPGGSLRLSCAASGFTLSRHALTWVRQAPGKGLEW

IGAIDNAGTTYYASWAKSRFTISRNTDLHTVYLQMNSLRAEDTAVYFCARVFYDINSGY

YLDGMDLWGPGTLVTVSS

9.H2.L1

(SEQ ID NO: 52)

CAGCTGGTGCTGACCCAGAGCCCCAGCGCTTCCGCCTCTTTAGGAGCCAGCGTGAAG

CTGACTTGTACTTTAAGCAGCGCCCACAAGACCTACACAATCGCTTGGCACCAGCAG

CAGCCCGAAAAGGGCCCCAGATATCTGATGAAGGTCAAGTCCGACGGCAGCTACTC

CAAGGGCGACGGCATCCCCGATCGTTTCAGCGGTTCTTCCAGCGGCGCCGAGAGGT

ATTTAACCATCAGCTCTTTACAGAGCGAGGACGAGGCCGACTACTACTGCGGCGCTG

ACGACAACGGCGGCTACGTCTTTGGCGGCGGCACAAAACTGACCGTGCTGGGCGGC

GGAAGCAGCAGAAGCTCCAGCTCTGGAGGAGGAGGTTCTGGAGGTGGAGGAGAGG

TGCAGCTGGTGGAGAGCGGCGGAGGACTGGTGCAGCCCGGTGGATCTTTAAGACTG

AGCTGTGCCGCCAGCGGCTTCACCTTCTCTCGTCACGCTCTGACATGGGTGAGGCAA

GCCCCCGGTAAGGGTTTAGAATGGGTGAGCGCCATCGACAATGCCGGAACCACCTA

TTACGCCTCTTGGGCCAAGTCTCGTTTCACCATCTCTCGTGACAATGCCAAGAACTCT

TTATATTTACAGATGAACTCTTTAAGAGCTGAGGACACCGCCGTCTACTACTGCGCC

AGAGTGTTCTACGACATCAACAGCGGCTACTACCTCGACGGCATGGATTTATGGGGC

CCCGGTACTTTAGTGACCGTGAGCAGC

9.H2.L1

(SEQ ID NO: 82)

QLVLTQSPSASASLGASVKLTCTLSSAHKTYTIAWHQQQPEKGPRYLMKVKSDGSYSK

GDGIPDRFSGSSSGAERYLTISSLQSEDEADYYCGADDNGGYVFGGGTKLTVLGGGSSR

SSSSGGGGSGGGGEVQLVESGGGLVQPGGSLRLSCAASGFTFSRHALTWVRQAPGKGL

EWVSAIDNAGTTYYASWAKSRFTISRDNAKNSLYLQMNSLRAEDTAVYYCARVFYDIN

SGYYLDGMDLWGPGTLVTVSS

10.H2.L1m1

(SEQ ID NO: 53)

CAGTTTGTGCTGACCCAGAGCCCTAGCGCTTCCGCCTCTTTAGGAGCCAGCGTGAAG

CTGACTTGTACTTTATCCTCCGCCCACAAGACCTACACCATCGACTGGTACCAGCAG

CAGCCCGAAAAGGGCCCTCGTTATCTGATGCAAGTTAAGTCCGACGGCAGCTACAC

CAAGGGAACCGGCGTGCCCGACAGATTCTCCGGTAGCAGCAGCGGCGCCGACAGAT

ATTTAACCATCAGCTCTTTACAGTCCGAGGACGAGGCCGACTACTACTGCGGCGCCG

ACGACAATGGCGGCTACGTCTTCGGAGGCGGCACACAGCTGACCGTGACTGGTGGA

-continued

GGCTCCTCCAGAAGCAGCTCTAGCGGAGGAGGAGGAAGCGGCGGAGGAGGCGAAG

TGCAGCTGGTGGAGTCCGGAGGAGGACTGGTGCAGCCCGGAGGTTCTTTAAGACTG

AGCTGCGCCGCCTCCGGCTTCACCTTTTCTCGTCACGCTTTAACATGGGTGAGACAA

GCTCCCGGCAAGGGACTGGAATGGGTCAGCGCCATCGATAACGCCGGCACCACCTA

TTACGCCAGCTGGGCTAAGTCTCGTTTCACCATCAGCAGAGACAACGCCAAGAACTC

TTTATATTTACAGATGAATTCTTTAAGAGCCGAGGACACCGCCGTGTATTACTGCGC

TCGTGTCTTCTACGACATCAACTCCGGCTACTATTTAGACGGCATGGATTTATGGGG

CCCCGGTACTTTAGTCACCGTGAGCTCC

10.H2.L1m1

(SEQ ID NO: 83)

QFVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVTGGGSSR

SSSSGGGGSGGGGEVQLVESGGGLVQPGGSLRLSCAASGFTFSRHALTWVRQAPGKGL

EWVSAIDNAGTTYYASWAKSRFTISRDNAKNSLYLQMNSLRAEDTAVYYCARVFYDIN

SGYYLDGMDLWGPGTLVTVSS

11.H2m1.L1

(SEQ ID NO: 54)

CAGCTGGTGCTGACACAGAGCCCCTCCGCCTCCGCCTCTTTAGGCGCTTCCGTGAAG

CTGACTTGTACTTTATCCAGCGCCCACAAGACCTACACCATCGCTTGGCACCAGCAG

CAGCCCGAGAAAGGCCCTCGTTACCTCATGAAAGTGAAGTCCGACGGCAGCTACTC

CAAGGGCGACGGCATCCCCGATCGTTTTAGCGGCAGCAGCTCCGGCGCCGAGAGGT

ATTTAACCATCAGCTCTTTACAGAGCGAAGACGAGGCCGACTATTACTGCGGCGCCG

ATGACAACGGAGGCTACGTGTTCGGCGGAGGCACCAAACTGACCGTGCTGGGCGGC

GGAAGCAGCAGAAGCTCCAGCAGCGGAGGAGGAGGTTCTGGAGGAGGCGGAGAGC

AGAGCGTGAAAGAGTCCGGCGGAGGTTTAGTGCAGCCCGGTGGTTCTTTAAGACTG

AGCTGCGCCGCCAGCGGCTTCACACTGTCCAGACACGCTTTAACATGGGTGAGACA

AGCTCCCGGTAAGGGACTGGAGTGGATCGGCGCCATCGACAATGCCGGCACCACCT

ACTACGCCAGCTGGGCCAAGTCTCGTTTCACCATCTCTCGTAACACCGATTTACACA

CCGTCTATTTACAGATGAACTCTTTAAGGGCCGAGGACACAGCCGTGTACTTTTGCG

CTCGTGTGTTCTACGACATCAACAGCGGCTACTATTTAGACGGCATGGATCTGTGGG

GCCCCGGAACACTGGTGACCGTGAGCAGC

11.H2m1.L1

(SEQ ID NO: 84)

QLVLTQSPSASASLGASVKLTCTLSSAHKTYTIAWHQQQPEKGPRYLMKVKSDGSYSK

GDGIPDRFSGSSSGAERYLTISSLQSEDEADYYCGADDNGGYVFGGGTKLTVLGGGSSR

SSSSGGGGSGGGGEQSVKESGGGLVQPGGSLRLSCAASGFTLSRHALTWVRQAPGKGL

EWIGAIDNAGTTYYASWAKSRFTISRNTDLHTVYLQMNSLRAEDTAVYFCARVFYDINS

GYYLDGMDLWGPGTLVTVSS

12.H2m1.L1m1

(SEQ ID NO: 55)

CAGTTTGTGCTGACCCAGTCCCCTAGCGCCTCTGCCTCTTTAGGAGCCTCTGTGAAA

CTGACTTGTACTTTAAGCAGCGCCCACAAGACATACACCATCGACTGGTACCAGCAG

CAGCCCGAAAAGGGCCCTAGGTATTTAATGCAAGTTAAGAGCGACGGCAGCTACAC

AAAGGGCACTGGTGTGCCCGACAGATTCAGCGGCAGCAGCAGCGGCGCCGACAGAT

ACCTCACCATCAGCTCTTTACAGTCCGAGGACGAGGCCGACTACTATTGCGGCGCCG

-continued

ACGACAACGGCGGCTACGTGTTCGGCGGAGGAACCCAGCTGACCGTGACTGGTGGC

GGAAGCAGCAGAAGCAGCTCCTCCGGAGGCGGAGGTTCTGGCGGAGGTGGAGAAC

AGAGCGTGAAGGAGAGCGGAGGTGGACTGGTGCAGCCCGGTGGTTCTTTAAGACTG

AGCTGCGCTGCCTCCGGCTTCACCTTATCTCGTCACGCTTTAACATGGGTGAGACAA

GCTCCCGGTAAGGGTTTAGAGTGGATCGGCGCCATCGACAATGCTGGCACCACCTA

CTACGCCAGCTGGGCCAAGTCTCGTTTCACAATCTCTCGTAACACCGATCTGCACAC

CGTGTATTTACAGATGAACTCTTTAAGAGCCGAGGACACCGCCGTGTATTTCTGCGC

TCGTGTGTTCTACGACATCAACAGCGGCTACTATTTAGACGGCATGGATTTATGGGG

CCCCGGTACTTTAGTGACCGTGAGCTCC

12.H2m1.L1m1

(SEQ ID NO: 85)

QFVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVTGGGSSR

SSSSGGGGSGGGGEQSVKESGGGLVQPGGSLRLSCAASGFTLSRHALTWVRQAPGKGL

EWIGAIDNAGTTYYASWAKSRFTISRNTDLHTVYLQMNSLRAEDTAVYFCARVFYDINS

GYYLDGMDLWGPGTLVTVSS

13.H1.L1

(SEQ ID NO: 56)

CAGCTCGTGCTGACCCAGTCCCCCAGCGCCTCTGCCTCTTTAGGCGCCAGCGTGAAG

CTGACTTGTACTTTATCCAGCGCCCACAAGACATACACCATCGCTTGGCACCAGCAG

CAGCCCGAAAAGGGCCCTCGTTATTTAATGAAGGTCAAGTCCGACGGCTCCTACTCC

AAGGGCGACGGCATCCCCGATAGATTCAGCGGTAGCAGCAGCGGCGCCGAGAGATA

TTTAACAATCAGCTCTTTACAGAGCGAGGACGAGGCCGACTACTACTGCGGCGCCG

ACGACAATGGCGGCTACGTCTTCGGCGGCGGAACCAAGCTCACAGTGCTGGGTGGA

GGCTCCAGCAGAAGCAGCTCTAGCGGAGGCGGAGGTTCCGGCGGCGGAGGCCAAGT

TCAGCTGCAAGAATCCGGCCCCGGACTGGTGAAGCCCTCCGAAACACTGTCTTTAAC

ATGCGCCGTGAGCGGCTACAGCATTTCTCGTCACGCTTTAACTTGGATCAGACAGCC

CCCCGGCAAGGGTTTAGAATGGATCGGAGCCATCGATAACGCCGGCACCACATACT

ACGCCAGCTGGGCCAAGAGCAGAGTGACCATCTCCGTGGACACCAGCAAGAACCAG

TTTTCTTTAAAGCTCAGCTCCGTGACCGCCGCCGATACAGCCGTGTACTACTGCGCC

AGAGTGTTCTACGACATCAACAGCGGCTACTATTTAGACGGAATGGATTTATGGGGC

CCCGGTACTTTAGTGACCGTGAGCAGC

13.H1.L1

(SEQ ID NO: 86)

QLVLTQSPSASASLGASVKLTCTLSSAHKTYTIAWHQQQPEKGPRYLMKVKSDGSYSK

GDGIPDRFSGSSSGAERYLTISSLQSEDEADYYCGADDNGGYVFGGGTKLTVLGGGSSR

SSSSGGGGSGGGGQVQLQESGPGLVKPSETLSLTCAVSGYSISRHALTWIRQPPGKGLE

WIGAIDNAGTTYYASWAKSRVTISVDTSKNQFSLKLSSVTAADTAVYYCARVFYDINSG

YYLDGMDLWGPGTLVTVSS

14.H1.L1m1

(SEQ ID NO: 57)

CAGTTTGTGCTCACCCAAAGCCCTAGCGCCTCTGCCTCTTTAGGCGCTTCCGTGAAG

CTGACTTGTACTTTAAGCTCCGCCCATAAGACCTACACCATCGACTGGTACCAGCAG

CAGCCCGAGAAGGGCCCTCGTTATTTAATGCAAGTTAAGTCCGATGGCAGCTATACC

-continued

AAGGGCACCGGCGTGCCCGACAGATTCAGCGGCAGCTCCAGCGGAGCCGATCGTTA

TTTAACCATCAGCTCTTTACAGAGCGAGGACGAGGCTGACTACTACTGCGGCGCCGA

CGATAACGGCGGCTACGTGTTCGGCGGCGGCACCCAACTGACAGTGACCGGAGGCG

GTTCTTCTCGTAGCAGCAGCAGCGGAGGCGGCGGCTCCGGCGGCGGAGGCCAAGTT

CAGCTGCAAGAATCCGGCCCCGGTCTGGTGAAACCCAGCGAGACTTTATCTTTAACA

TGCGCCGTGAGCGGCTACTCCATCTCCAGACACGCTTTAACTTGGATCAGACAGCCT

CCCGGCAAGGGACTGGAGTGGATCGGCGCTATCGACAACGCCGGCACCACCTACTA

CGCCTCTTGGGCCAAGTCTCGTGTCACCATCAGCGTGGACACATCCAAGAACCAGTT

CTCTTTAAAGCTGTCCAGCGTGACCGCCGCCGATACAGCCGTGTACTACTGCGCTCG

TGTGTTCTACGACATCAACTCCGGCTACTATTTAGACGGCATGGATTTATGGGGACC

CGGTACTTTAGTGACCGTGTCCAGC

14.H1.L1m1

(SEQ ID NO: 87)

QFVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVTGGGSSR

SSSSGGGGSGGGGQVQLQESGPGLVKPSETLSLTCAVSGYSISRHALTWIRQPPGKGLE

WIGAIDNAGTTYYASWAKSRVTISVDTSKNQFSLKLSSVTAADTAVYYCARVFYDINSG

YYLDGMDLWGPGTLVTVSS

15.H1m1.L1

(SEQ ID NO: 58)

CAGCTGGTGCTGACACAAAGCCCCAGCGCCAGCGCCTCTTTAGGCGCCAGCGTCAA

ACTGACATGCACTTTAAGCAGCGCCCACAAGACCTACACCATCGCTTGGCACCAGC

AGCAGCCCGAGAAGGGCCCCAGATATTTAATGAAGGTGAAGTCCGATGGCAGCTAC

AGCAAGGGAGATGGCATTCCCGATCGTTTTAGCGGCTCCTCCAGCGGCGCCGAGAG

ATACTTAACCATCTCCTCTTTACAGAGCGAGGACGAGGCCGACTACTACTGCGGCGC

CGATGACAACGGCGGCTACGTGTTCGGCGGCGGAACCAAGCTGACCGTGCTGGGCG

GAGGCAGCTCCAGATCCAGCAGCAGCGGCGGAGGAGGAAGCGGAGGAGGAGGACA

GCAGTCCGTGAAAGAGAGCGGCCCCGGTTTAGTGAAACCCAGCGAGACTTTATCTTT

AACTTGTGCCGTGAGCGGCTTCAGCCTCTCTCGTCACGCTTTAACTTGGGTGAGACA

GCCTCCCGGCAAAGGTTTAGAGTGGATTGGCGCCATCGACAACGCCGGCACCACCT

ACTACGCCAGCTGGGCCAAATCTCGTGTGACCATTTCCAGAAACACCGATTTACACA

CCGTGTCTTTAAAGCTGTCCAGCGTGACCGCCGCTGACACCGCTGTCTACTTCTGCG

CTCGTGTGTTCTACGACATCAACTCCGGCTACTATTTAGACGGCATGGATTTATGGG

GCCCCGGTACTTTAGTGACCGTGAGCTCC

15.H1m1.L1

(SEQ ID NO: 88)

QLVLTQSPSASASLGASVKLTCTLSSAHKTYTIAWHQQQPEKGPRYLMKVKSDGSYSK

GDGIPDRFSGSSSGAERYLTISSLQSEDEADYYCGADDNGGYVFGGGTKLTVLGGGSSR

SSSSGGGGSGGGGQQSVKESGPGLVKPSETLSLTCAVSGFSLSRHALTWVRQPPGKGLE

WIGAIDNAGTTYYASWAKSRVTISRNTDLHTVSLKLSSVTAADTAVYFCARVFYDINSG

YYLDGMDLWGPGTLVTVSS

16.H1m1.L1m1

(SEQ ID NO: 59)

CAGTTCGTGCTCACACAGAGCCCTAGCGCTTCCGCCTCTTTAGGAGCCAGCGTGAAA

CTGACATGTACTTTAAGCAGCGCCCACAAAACCTACACCATCGACTGGTACCAGCA

-continued

GCAACCCGAGAAGGGCCCTAGATATTTAATGCAAGTTAAGAGCGACGGCTCCTACA

CCAAAGGCACCGGCGTGCCCGATAGGTTCAGCGGCTCCTCCTCCGGAGCCGATCGTT

ATTTAACAATCAGCTCTTTACAGAGCGAAGACGAGGCCGATTACTACTGCGGAGCC

GATGACAACGGCGGCTACGTCTTCGGAGGCGGAACCCAGCTGACAGTGACCGGAGG

CGGCAGCAGCAGATCCAGCAGCTCCGGAGGCGGAGGAAGCGGAGGAGGCGGCCAG

CAAAGCGTGAAGGAGAGCGGCCCCGGACTCGTGAAACCCTCCGAGACTTTATCTTT

AACTTGTGCCGTGAGCGGCTTCTCTTTATCTCGTCACGCTTTAACATGGGTGAGGCA

GCCTCCCGGTAAGGGTTTAGAGTGGATCGGCGCCATCGACAACGCCGGCACAACCT

ACTACGCCAGCTGGGCCAAGAGCAGAGTGACCATCTCTCGTAACACCGATTTACAC

ACCGTGTCTTTAAAGCTGAGCTCCGTGACCGCCGCCGATACCGCTGTGTACTTCTGC

GCTCGTGTCTTCTACGACATCAACTCCGGCTATTACCTCGACGGCATGGATCTGTGG

GGCCCCGGAACACTGGTGACCGTGAGCAGCG

16.H1m1.L1m1

(SEQ ID NO: 89)

QFVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVTGGGSSR

SSSSGGGGSGGGGQQSVKESGPGLVKPSETLSLTCAVSGFSLSRHALTWVRQPPGKGLE

WIGAIDNAGTTYYASWAKSRVTISRNTDLHTVSLKLSSVTAADTAVYFCARVFYDINSG

YYLDGMDLWGPGTLVTVSS

17.H1.L3m2

(SEQ ID NO: 60)

CAGTTCGTGCTGACCCAGCCCGCTTCTGTGAGCGGTTCTCCCGGTCAGAGCATCACC

ATCAGCTGCACTTTAAGCAGCGCCCACAAGACCTACACCATCGACTGGTACCAGCA

GCACCCCGGCAAGGCCCCCAAGCTGATGATCCAAGTTAAGTCCGACGGCAGCTACA

CCAAGGGCACCGGCGTGAGCAACAGATTCTCCGGCAGCAGCTCCGGCGCCGACAGA

TACTTAACCATCAGCGGTTTACAAGCTGAGGATGAGGCCGACTATTACTGCGGCGCC

GACGACAATGGCGGCTACGTGTTCGGCGGCGGCACACAGCTGACCGTGCTGGGTGG

AGGCTCCAGCAGATCCAGCTCCAGCGGCGGAGGAGGCAGCGGAGGCGGAGGACAA

GTGCAGCTCCAAGAATCCGGCCCCGGTCTCGTGAAGCCCAGCGAGACTTTATCTTTA

ACTTGTGCCGTGAGCGGCTACAGCATCTCTCGTCACGCTCTGACTTGGATTCGTCAA

CCTCCCGGAAAGGGTTTAGAGTGGATCGGCGCCATCGACAACGCCGGCACCACCTA

CTACGCCAGCTGGGCCAAATCTCGTGTGACCATTAGCGTGGACACCAGCAAGAACC

AGTTCTCTTTAAAACTGAGCAGCGTGACAGCTGCCGACACCGCCGTGTACTACTGCG

CTCGTGTGTTCTACGACATCAACAGCGGCTACTATTTAGACGGCATGGATTTATGGG

GCCCCGGTACTTTAGTGACCGTCAGCTCC

17.H1.L3m2

(SEQ ID NO: 90)

QFVLTQPASVSGSPGQSITISCTLSSAHKTYTIDWYQQHPGKAPKLMIQVKSDGSYTKGT

GVSNRFSGSSSGADRYLTISGLQAEDEADYYCGADDNGGYVFGGGTQLTVLGGGSSRS

SSSGGGGSGGGGQVQLQESGPGLVKPSETLSLTCAVSGYSISRHALTWIRQPPGKGLEWI

GAIDNAGTTYYASWAKSRVTISVDTSKNQFSLKLSSVTAADTAVYYCARVFYDINSGYY

LDGMDLWGPGTLVTVSS

-continued

18.H1.L3m3

(SEQ ID NO: 61)

CAGAGCGCCCTGACCCAGCCCGCTTCTGTGAGCGGTTCTCCCGGTCAGAGCATCACC

ATCAGCTGCACTGGCACCAGCGCCCACAAGACCTACACCATCGACTGGTACCAGCA

GCACCCCGGCAAGGCCCCCAAGCTGATGATCTATGTTAAGTCCGACGGCAGCTACA

CCAAGGGCACCGGCGTGAGCAACAGATTCTCCGGCAGCAAGTCCGGCAACACCGCC

AGCTTAACCATCAGCGGTTTACAAGCTGAGGATGAGGCCGACTATTACTGCGGCGCC

GACGACAATGGCGGCTACGTGTTCGGCGGCGGCACACAGCTGACCGTGCTGGGTGG

AGGCTCCAGCAGATCCAGCTCCAGCGGCGGAGGAGGCAGCGGAGGCGGAGGACAA

GTGCAGCTCCAAGAATCCGGCCCCGGTCTCGTGAAGCCCAGCGAGACTTTATCTTTA

ACTTGTGCCGTGAGCGGCTACAGCATCTCTCGTCACGCTCTGACTTGGATTCGTCAA

CCTCCCGGAAAGGGTTTAGAGTGGATCGGCGCCATCGACAACGCCGGCACCACCTA

CTACGCCAGCTGGGCCAAATCTCGTGTGACCATTAGCGTGGACACCAGCAAGAACC

AGTTCTCTTTAAAACTGAGCAGCGTGACAGCTGCCGACACCGCCGTGTACTACTGCG

CTCGTGTGTTCTACGACATCAACAGCGGCTACTATTTAGACGGCATGGATTTATGGG

GCCCCGGTACTTTAGTGACCGTCAGCTCC

18.H1.L3m3

(SEQ ID NO: 91)

QSALTQPASVSGSPGQSITISCTGTSAHKTYTIDWYQQHPGKAPKLMIYVKSDGSYTKGT

GVSNRFSGSKSGNTASLTISGLQAEDEADYYCGADDNGGYVFGGGTQLTVLGGGSSRSS

SSGGGGSGGGGQVQLQESGPGLVKPSETLSLTCAVSGYSISRHALTWIRQPPGKGLEWIG

AIDNAGTTYYASWAKSRVTISVDTSKNQFSLKLSSVTAADTAVYYCARVFYDINSGYYL

DGMDLWGPGTLVTVSS

19.H2.L2m2

(SEQ ID NO: 62)

CAGTTCGTGCTGACACAGCCTCCCAGCGCCTCTGGCACACCCGGTCAGAGGGTGACC

ATCTCTTGTACTTTATCCTCCGCCCACAAGACCTACACCATTGACTGGTACCAGCAG

CTGCCCGGTACCGCCCCTAAGCTGCTGATTTACGTGAAATCCGACGGCAGCTACACC

AAGGGAACCGGCGTGCCCGATCGTTTTTCCGGCAGCTCCAGCGGCGCCGATGCCAG

CTTAGCCATCAGCGGTTTACAGTCCGAGGATGAGGCCGACTACTACTGCGGCGCCG

ATGACAACGGCGGCTACGTGTTCGGCGGAGGAACCCAGCTCACCGTGCTGGGAGGA

GGCTCCTCTCGTAGCTCCAGCTCCGGAGGAGGAGGAAGCGGAGGCGGCGGAGAAGT

GCAACTGGTGGAGTCCGGCGGCGGACTGGTGCAGCCCGGTGGCTCTTTAAGACTGA

GCTGTGCCGCCTCCGGCTTCACCTTTAGCAGACACGCCCTCACTTGGGTCAGACAAG

CTCCCGGTAAGGGTTTAGAGTGGGTGAGCGCCATCGACAACGCCGGCACAACCTAC

TACGCCTCTTGGGCCAAGTCTCGTTTCACCATCAGCAGAGACAACGCCAAGAACTCT

TTATATTTACAGATGAACTCTTTAAGGGCCGAGGACACCGCCGTGTACTACTGCGCT

CGTGTGTTCTACGACATCAACAGCGGCTATTATTTAGATGGCATGGATTTATGGGGC

CCCGGTACTTTAGTGACAGTGTCCTCC

19.H2.L2m2

(SEQ ID NO: 92)

QFVLTQPPSASGTPGQRVTISCTLSSAHKTYTIDWYQQLPGTAPKLLIYVKSDGSYTKGT

GVPDRFSGSSSGADASLAISGLQSEDEADYYCGADDNGGYVFGGGTQLTVLGGGSSRSS

SSGGGGSGGGGEVQLVESGGGLVQPGGSLRLSCAASGFTFSRHALTWVRQAPGKGLEW

-continued

VSAIDNAGTTYYASWAKSRFTISRDNAKNSLYLQMNSLRAEDTAVYYCARVFYDINSG

YYLDGMDLWGPGTLVTVSS

20.H2.L2m3

(SEQ ID NO: 63)

CAGAGCGTGCTGACACAGCCTCCCAGCGCCTCTGGCACACCCGGTCAGAGGGTGAC

CATCTCTTGTACTTTATCCTCCGCCCACAAGACCTACACCATTGACTGGTACCAGCA

GCTGCCCGGTACCGCCCCTAAGCTGCTGATTTACGTGAAATCCGACGGCAGCTACAC

CAAGGGAACCGGCGTGCCCGATCGTTTTTCCGGCAGCAAGAGCGGCACCAGCGCCA

GCTTAGCCATCAGCGGTTTACAGTCCGAGGATGAGGCCGACTACTACTGCGGCGCC

GATGACAACGGCGGCTACGTGTTCGGCGGAGGAACCCAGCTCACCGTGCTGGGAGG

AGGCTCCTCTCGTAGCTCCAGCTCCGGAGGAGGAGGAAGCGGAGGCGGCGGAGAA

GTGCAACTGGTGGAGTCCGGCGGCGGACTGGTGCAGCCCGGTGGCTCTTTAAGACT

GAGCTGTGCCGCCTCCGGCTTCACCTTTAGCAGACACGCCCTCACTTGGGTCAGACA

AGCTCCCGGTAAGGGTTTAGAGTGGGTGAGCGCCATCGACAACGCCGGCACAACCT

ACTACGCCTCTTGGGCCAAGTCTCGTTTCACCATCAGCAGAGACAACGCCAAGAACT

CTTTATATTTACAGATGAACTCTTTAAGGGCCGAGGACACCGCCGTGTACTACTGCG

CTCGTGTGTTCTACGACATCAACAGCGGCTATTATTTAGATGGCATGGATTTATGGG

GCCCCGGTACTTTAGTGACAGTGTCCTCC

20.H2.L2m3

(SEQ ID NO: 93)

QSVLTQPPSASGTPGQRVTISCTLSSAHKTYTIDWYQQLPGTAPKLLIYVKSDGSYTKGT

GVPDRFSGSKSGTSASLAISGLQSEDEADYYCGADDNGGYVFGGGTQLTVLGGGSSRSS

SSGGGGSGGGGEVQLVESGGGLVQPGGSLRLSCAASGFTFSRHALTWVRQAPGKGLEW

VSAIDNAGTTYYASWAKSRFTISRDNAKNSLYLQMNSLRAEDTAVYYCARVFYDINSG

YYLDGMDLWGPGTLVTVSS

21.H2.L1m2

(SEQ ID NO: 64)

CAGTTTGTGCTGACCCAGAGCCCTAGCGCTTCCGCCTCTTTAGGAGCCAGCGTGAAG

CTGACTTGTACTTTATCCTCCGCCCACAAGACCTACACCATCGACTGGCACCAGCAG

CAGCCCGAAAAGGGCCCTCGTTATCTGATGCAAGTTAAGTCCGACGGCAGCTACAC

CAAGGGAACCGGCATCCCCGACAGATTCTCCGGTAGCAGCAGCGGCGCCGAGAGAT

ATTTAACCATCAGCTCTTTACAGTCCGAGGACGAGGCCGACTACTACTGCGGCGCCG

ACGACAATGGCGGCTACGTCTTCGGAGGCGGCACACAGCTGACCGTGCTGGGTGGA

GGCTCCTCCAGAAGCAGCTCTAGCGGAGGAGGAGGAAGCGGCGGAGGAGGCGAAG

TGCAGCTGGTGGAGTCCGGAGGAGGACTGGTGCAGCCCGGAGGTTCTTTAAGACTG

AGCTGCGCCGCCTCCGGCTTCACCTTTTCTCGTCACGCTTTAACATGGGTGAGACAA

GCTCCCGGCAAGGGACTGGAATGGGTCAGCGCCATCGATAACGCCGGCACCACCTA

TTACGCCAGCTGGGCTAAGTCTCGTTTCACCATCAGCAGAGACAACGCCAAGAACTC

TTTATATTTACAGATGAATTCTTTAAGAGCCGAGGACACCGCCGTGTATTACTGCGC

TCGTGTCTTCTACGACATCAACTCCGGCTACTATTTAGACGGCATGGATTTATGGGG

CCCCGGTACTTTAGTCACCGTGAGCTCC

21.H2.L1m2

(SEQ ID NO: 94)

QFVLTQSPSASASLGASVKLTCTLSSAHKTYTIDWHQQQPEKGPRYLMQVKSDGSYTK

GTGIPDRFSGSSSGAERYLTISSLQSEDEADYYCGADDNGGYVFGGGTQLTVLGGGSSRS

-continued

SSSGGGGSGGGGEVQLVESGGGLVQPGGSLRLSCAASGFTFSRHALTWVRQAPGKGLE

WVSAIDNAGTTYYASWAKSRFTISRDNAKNSLYLQMNSLRAEDTAVYYCARVFYDINS

GYYLDGMDLWGPGTLVTVSS

22.H1.L1m2

(SEQ ID NO: 65)

CAGTTTGTGCTCACCCAAAGCCCTAGCGCCTCTGCCTCTTTAGGCGCTTCCGTGAAG

CTGACTTGTACTTTAAGCTCCGCCCATAAGACCTACACCATCGACTGGCACCAGCAG

CAGCCCGAGAAGGGCCCTCGTTATTTAATGCAAGTTAAGTCCGATGGCAGCTATACC

AAGGGCACCGGCATCCCCGACAGATTCAGCGGCAGCTCCAGCGGAGCCGAGCGTTA

TTTAACCATCAGCTCTTTACAGAGCGAGGACGAGGCTGACTACTACTGCGGCGCCGA

CGATAACGGCGGCTACGTGTTCGGCGGCGGCACCCAACTGACAGTGCTGGGAGGCG

GTTCTTCTCGTAGCAGCAGCAGCGGAGGCGGCGGCTCCGGCGGCGGAGGCCAAGTT

CAGCTGCAAGAATCCGGCCCCGGTCTGGTGAAACCCAGCGAGACTTTATCTTTAACA

TGCGCCGTGAGCGGCTACTCCATCTCCAGACACGCTTTAACTTGGATCAGACAGCCT

CCCGGCAAGGGACTGGAGTGGATCGGCGCTATCGACAACGCCGGCACCACCTACTA

CGCCTCTTGGGCCAAGTCTCGTGTCACCATCAGCGTGGACACATCCAAGAACCAGTT

CTCTTTAAAGCTGTCCAGCGTGACCGCCGCCGATACAGCCGTGTACTACTGCGCTCG

TGTGTTCTACGACATCAACTCCGGCTACTATTTAGACGGCATGGATTTATGGGGACC

CGGTACTTTAGTGACCGTGTCCAGC

22.H1.L1m2

(SEQ ID NO: 95)

QFVLTQSPSASASLGASVKLTCTLSSAHKTYTIDWHQQQPEKGPRYLMQVKSDGSYTK

GTGIPDRFSGSSSGAERYLTISSLQSEDEADYYCGADDNGGYVFGGGTQLTVLGGGSSRS

SSSGGGGSGGGGQVQLQESGPGLVKPSETLSLTCAVSGYSISRHALTWIRQPPGKGLEWI

GAIDNAGTTYYASWAKSRVTISVDTSKNQFSLKLSSVTAADTAVYYCARVFYDINSGYY

LDGMDLWGPGTLVTVSS

23.H1.L2m1

(SEQ ID NO: 66)

CAGTTCGTGCTGACCCAGCCTCCTAGCGCTAGCGGAACACCCGGCCAGAGGGTGAC

CATCAGCTGCACTTTAAGCAGCGCCCACAAGACCTACACCATCGACTGGTACCAGC

AGCTGCCCGGTACCGCTCCCAAGCTGCTGATCTACGTGAAGAGCGACGGCAGCTAC

ACCAAGGGCACCGGCGTGCCCGATAGATTCAGCGGCAGCAGCAGCGGCGCCGACAG

ATATTTAGCCATCAGCGGTTTACAGAGCGAGGACGAGGCCGACTACTACTGCGGCG

CCGACGACAACGGAGGCTACGTGTTCGGCGGCGGCACACAGCTGACCGTGACCGGT

GGAGGCTCCAGCAGATCCAGCTCCAGCGGCGGAGGAGGCAGCGGAGGCGGAGGAC

AAGTGCAGCTCCAAGAATCCGGCCCCGGTCTCGTGAAGCCCAGCGAGACTTTATCTT

TAACTTGTGCCGTGAGCGGCTACAGCATCTCTCGTCACGCTCTGACTTGGATTCGTC

AACCTCCCGGAAAGGGTTTAGAGTGGATCGGCGCCATCGACAACGCCGGCACCACC

TACTACGCCAGCTGGGCCAAATCTCGTGTGACCATTAGCGTGGACACCAGCAAGAA

CCAGTTCTCTTTAAAACTGAGCAGCGTGACAGCTGCCGACACCGCCGTGTACTACTG

CGCTCGTGTGTTCTACGACATCAACAGCGGCTACTATTTAGACGGCATGGATTTATG

GGGCCCCGGTACTTTAGTGACCGTCAGCTCC

-continued

23.H1.L2m1

(SEQ ID NO: 96)

QFVLTQPPSASGTPGQRVTISCTLSSAHKTYTIDWYQQLPGTAPKLLIYVKSDGSYTKGT

GVPDRFSGSSSGADRYLAISGLQSEDEADYYCGADDNGGYVFGGGTQLTVTGGGSSRSS

SSGGGGSGGGGQVQLQESGPGLVKPSETLSLTCAVSGYSISRHALTWIRQPPGKGLEWIG

AIDNAGTTYYASWAKSRVTISVDTSKNQFSLKLSSVTAADTAVYYCARVFYDINSGYYL

DGMDLWGPGTLVTVSS

24.H2.L3m1

(SEQ ID NO: 67)

CAGTTCGTGCTGACCCAGCCCGCTTCTGTGAGCGGTTCTCCCGGTCAGAGCATCACC

ATCAGCTGCACTTTAAGCAGCGCCCACAAGACCTACACCATCGACTGGTACCAGCA

GCACCCCGGCAAGGCCCCCAAGTATTTAATGCAAGTTAAGTCCGACGGCAGCTACA

CCAAGGGCACCGGCGTGCCCAACAGATTCTCCGGCAGCAGCTCCGGCGCCGACAGA

TACTTAACCATCAGCGGTTTACAAGCTGAGGATGAGGCCGACTATGTGTGCGGCGCC

GACGACAATGGCGGCTACGTGTTCGGCGGCGGCACACAGCTGACCGTGACTGGCGG

TGGTTCCTCTAGATCTTCCTCCTCTGGTGGCGGTGGCTCGGGCGGTGGTGGGGAGGT

GCAGCTGGTGGAGAGCGGAGGAGGTTTAGTGCAGCCCGGTGGATCTTTAAGACTGA

GCTGCGCCGCCAGCGGCTTCACCTTCTCTCGTCACGCTTTAACATGGGTGAGACAAG

CTCCCGGTAAAGGTTTAGAGTGGGTGAGCGCCATCGACAACGCCGGCACCACCTAC

TACGCCAGCTGGGCCAAGTCTCGTTTCACCATCTCTCGTGACAACGCCAAGAACTCT

TTATATTTACAGATGAACTCTTTAAGGGCTGAGGACACCGCCGTGTACTACTGCGCT

CGTGTGTTCTACGACATCAACAGCGGCTACTATTTAGACGGAATGGATTTATGGGGC

CCCGGTACCCTCGTGACAGTGAGCAGC

24.H2.L3m1

(SEQ ID NO: 97)

QFVLTQPASVSGSPGQSITISCTLSSAHKTYTIDWYQQHPGKAPKYLMQVKSDGSYTKG

TGVPNRFSGSSSGADRYLTISGLQAEDEADYVCGADDNGGYVFGGGTQLTVTGGGSSR

SSSSGGGGSGGGGEVQLVESGGGLVQPGGSLRLSCAASGFTFSRHALTWVRQAPGKGL

EWVSAIDNAGTTYYASWAKSRFTISRDNAKNSLYLQMNSLRAEDTAVYYCARVFYDIN

SGYYLDGMDLWGPGTLVTVSS

25.H1.L1m3

(SEQ ID NO: 68)

CAGCTGGTGCTCACCCAAAGCCCTAGCGCCTCTGCCTCTTTAGGCGCTTCCGTGAAG

CTGACTTGTACTTTAAGCTCCGCCCATAAGACCTACACCATCGACTGGTACCAGCAG

CAGCCCGAGAAGGGCCCTCGTTATTTAATGCAAGTTAAGTCCGATGGCAGCTATACC

AAGGGCACCGGCGTGCCCGACAGATTCAGCGGCAGCTCCAGCGGAGCCGATCGTTA

TTTAACCATCAGCTCTTTACAGAGCGAGGACGAGGCTGACTACTACTGCGGCGCCGA

CGATAACGGCGGCTACGTGTTCGGCGGCGGCACCCAACTGACAGTGCTGGGAGGCG

GTTCTTCTCGTAGCAGCAGCAGCGGAGGCGGCGGCTCCGGCGGCGGAGGCCAAGTG

CAGCTCCAAGAATCCGGCCCCGGTCTCGTGAAGCCCAGCGAGACTTTATCTTTAACT

TGTGCCGTGAGCGGCTACAGCATCTCTCGTCACGCTCTGACTTGGATTCGTCAACCT

CCCGGAAAGGGTTTAGAGTGGATCGGCGCCATCGACAACGCCGGCACCACCTACTA

CGCCAGCTGGGCCAAATCTCGTGTGACCATTAGCGTGGACACCAGCAAGAACCAGT

TCTCTTTAAAACTGAGCAGCGTGACAGCTGCCGACACCGCCGTGTACTACTGCGCTC

-continued

GTGTGTTCTACGACATCAACAGCGGCTACTATTTAGACGGCATGGATTTATGGGGCC

CCGGTACTTTAGTGACCGTCAGCTCC

25.H1.L1m3

(SEQ ID NO: 98)

QLVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVLGGGSSR

SSSSGGGGSGGGGQVQLQESGPGLVKPSETLSLTCAVSGYSISRHALTWIRQPPGKGLE

WIGAIDNAGTTYYASWAKSRVTISVDTSKNQFSLKLSSVTAADTAVYYCARVFYDINSG

YYLDGMDLWGPGTLVTVSS

26.H1.L1m4

(SEQ ID NO: 69)

CAGTTGGTGCTCACCCAAAGCCCTAGCGCCTCTGCCTCTTTAGGCGCTTCCGTGAAG

CTGACTTGTACTTTAAGCTCCGCCCATAAGACCTACACCATCGCCTGGCATCAGCAG

CAGCCCGAGAAGGGCCCTCGTTATTTAATGCAAGTTAAGTCCGATGGCAGCTATACC

AAGGGCACCGGCGTGCCCGACAGATTCAGCGGCAGCTCCAGCGGAGCCGATCGTTA

TTTAACCATCAGCTCTTTACAGAGCGAGGACGAGGCTGACTACTACTGCGGCGCCGA

CGATAACGGCGGCTACGTGTTCGGCGGCGGCACCCAACTGACAGTGCTCGGAGGCG

GTTCTTCTCGTAGCAGCAGCAGCGGAGGCGGCGGCTCCGGCGGCGGAGGCCAAGTG

CAGCTCCAAGAATCCGGCCCCGGTCTCGTGAAGCCCAGCGAGACTTTATCTTTAACT

TGTGCCGTGAGCGGCTACAGCATCTCTCGTCACGCTCTGACTTGGATTCGTCAACCT

CCCGGAAAGGGTTTAGAGTGGATCGGCGCCATCGACAACGCCGGCACCACCTACTA

CGCCAGCTGGGCCAAATCTCGTGTGACCATTAGCGTGGACACCAGCAAGAACCAGT

TCTCTTTAAAACTGAGCAGCGTGACAGCTGCCGACACCGCCGTGTACTACTGCGCTC

GTGTGTTCTACGACATCAACAGCGGCTACTATTTAGACGGCATGGATTTATGGGGCC

CCGGTACTTTAGTGACCGTCAGCTCC

26.H1.L1m4

(SEQ ID NO: 99)

QLVLTQSPSASASLGASVKLTCTLSSAHKTYTIAWHQQQPEKGPRYLMQVKSDGSYTK

GTGVPDRFSGSSSGADRYLTISSLQSEDEADYYCGADDNGGYVFGGGTQLTVLGGGSSR

SSSSGGGGSGGGGQVQLQESGPGLVKPSETLSLTCAVSGYSISRHALTWIRQPPGKGLE

WIGAIDNAGTTYYASWAKSRVTISVDTSKNQFSLKLSSVTAADTAVYYCARVFYDINSG

YYLDGMDLWGPGTLVTVSS

27.H1.L3m4

(SEQ ID NO: 70)

CAGAGCGCTCTGACCCAGCCCGCTTCTGTGAGCGGTTCTCCCGGTCAGAGCATCACC

ATCAGCTGCACTGGCACAAGCGCCCACAAGACCTACACCGTGAGCTGGTACCAGCA

GCACCCCGGCAAGGCCCCCAAGTATTTAATGCAAGTTAAGTCCGACGGCAGCTACA

CCAAGGGCACCGGCGTGCCCAACAGATTCTCCGGCAGCAGCTCCGGCGCCGACAGA

TACTTAACCATCAGCGGTTTACAAGCTGAGGATGAGGCCGACTATTACTGCGGCGCC

GACGACAATGGCGGCTACGTGTTCGGCGGCGGCACCCAACTGACAGTGCTGGGTGG

AGGCTCCAGCAGATCCAGCTCCAGCGGCGGAGGAGGCAGCGGAGGCGGAGGACAA

GTGCAGCTCCAAGAATCCGGCCCCGGTCTCGTGAAGCCCAGCGAGACTTTATCTTTA

ACTTGTGCCGTGAGCGGCTACAGCATCTCTCGTCACGCTCTGACTTGGATTCGTCAA

CCTCCCGGAAAGGGTTTAGAGTGGATCGGCGCCATCGACAACGCCGGCACCACCTA

CTACGCCAGCTGGGCCAAATCTCGTGTGACCATTAGCGTGGACACCAGCAAGAACC

-continued

AGTTCTCTTTAAAACTGAGCAGCGTGACAGCTGCCGACACCGCCGTGTACTACTGCG

CTCGTGTGTTCTACGACATCAACAGCGGCTACTATTTAGACGGCATGGATTTATGGG

GCCCCGGTACTTTAGTGACCGTCAGCTCC

27.H1.L3m4

(SEQ ID NO: 100)

QSALTQPASVSGSPGQSITISCTGTSAHKTYTVSWYQQHPGKAPKYLMQVKSDGSYTKG

TGVPNRFSGSSSGADRYLTISGLQAEDEADYYCGADDNGGYVFGGGTQLTVLGGGSSR

SSSSGGGGSGGGGQVQLQESGPGLVKPSETLSLTCAVSGYSISRHALTWIRQPPGKGLE

WIGAIDNAGTTYYASWAKSRVTISVDTSKNQFSLKLSSVTAADTAVYYCARVFYDINSG

YYLDGMDLWGPGTLVTVSS

28.H1.L3m5

(SEQ ID NO: 71)

CAGTCTGCTCTGACCCAGCCCGCTTCTGTGAGCGGTTCTCCCGGTCAGAGCATCACC

ATCAGCTGCACTGGCACAAGCGCCCACAAGACCTACACCGTGAGTTGGTACCAGCA

GCACCCCGGCAAGGCCCCCAAGTTGATGATCTACGTTAAGTCCGACGGCAGCTACA

CCAAGGGCACCGGCGTGCCCAACAGATTCTCCGGCAGCAGCTCCGGCGCCGACAGA

TACTTAACCATCAGCGGTTTACAAGCTGAGGATGAGGCCGACTATTATTGCGGCG

CCGACGACAATGGCGGCTACGTGTTCGGCGGCGGCACCCAACTGACAGTGCTCGGT

GGAGGCTCCAGCAGATCCAGCTCCAGCGGCGGAGGAGGCAGCGGAGGCGGAGGAC

AAGTGCAGCTCCAAGAATCCGGCCCCGGTCTCGTGAAGCCCAGCGAGACTTTATCTT

TAACTTGTGCCGTGAGCGGCTACAGCATCTCTCGTCACGCTCTGACTTGGATTCGTC

AACCTCCCGGAAAGGGTTTAGAGTGGATCGGCGCCATCGACAACGCCGGCACCACC

TACTACGCCAGCTGGGCCAAATCTCGTGTGACCATTAGCGTGGACACCAGCAAGAA

CCAGTTCTCTTTAAAACTGAGCAGCGTGACAGCTGCCGACACCGCCGTGTACTACTG

CGCTCGTGTGTTCTACGACATCAACAGCGGCTACTATTTAGACGGCATGGATTTATG

GGGCCCCGGTACTTTAGTGACCGTCAGCTCC

28.H1.L3m5

(SEQ ID NO: 101)

QSALTQPASVSGSPGQSITISCTGTSAHKTYTVSWYQQHPGKAPKLMIYVKSDGSYTKG

TGVPNRFSGSSSGADRYLTISGLQAEDEADYYCGADDNGGYVFGGGTQLTVLGGGSSR

SSSSGGGGGGGGQVQLQESGPGLVKPSETLSLTCAVSGYSISRHALTWIRQPPGKGLE

WIGAIDNAGTTYYASWAKSRVTISVDTSKNQFSLKLSSVTAADTAVYYCARVFYDINSG

YYLDGMDLWGPGTLVTVSS

29.H2.L1m3

(SEQ ID NO: 72)

CAGCTGGTGCTGACCCAGAGCCCTAGCGCTTCCGCCTCTTTAGGAGCCAGCGTGAAG

CTGACTTGTACTTTATCCTCCGCCCACAAGACCTACACCATCGACTGGTACCAGCAG

CAGCCCGAAAAGGGCCCTCGTTATCTGATGCAAGTTAAGTCCGACGGCAGCTACAC

CAAGGGAACCGGCGTGCCCGACAGATTCTCCGGTAGCAGCAGCGGCGCCGACAGAT

ATTTAACCATCAGCTCTTTACAGTCCGAGGACGAGGCCGACTACTACTGCGGCGCCG

ACGACAATGGCGGCTACGTCTTCGGAGGCGGCACACAGCTGACCGTGACTGGTGGA

GGCTCCTCCAGAAGCAGCTCTAGCGGAGGAGGAGGAAGCGGCGGAGGAGGCGAAG

TGCAGCTGGTGGAGTCCGGAGGAGGACTGGTGCAGCCCGGAGGTTCTTTAAGACTG

AGCTGCGCCGCCTCCGGCTTCACCTTTTCTCGTCACGCTTTAACATGGGTGAGACAA

-continued

GCTCCCGGCAAGGGACTGGAATGGGTCAGCGCCATCGATAACGCCGGCACCACCTA

TTACGCCAGCTGGGCTAAGTCTCGTTTCACCATCAGCAGAGACAACGCCAAGAACTC

TTTATATTTACAGATGAATTCTTTAAGAGCCGAGGACACCGCCGTGTATTACTGCGC

TCGTGTCTTCTACGACATCAACTCCGGCTACTATTTAGACGGCATGGATTTATGGGG

CCCCGGTACTTTAGTCACCGTGAGCTCC

29.H2.L1m3

(SEQ ID NO: 102)

QLVLTQSPSASASLGASVKLTCTLSSAHKTYTIDWYQQQPEKGPRYLMQVKSDGSYTK

GTGVPDRFSGSSSGADRYLTISSLQSEDEADYYCGADDNGGYVFGGGTQLTVTGGGSSR

SSSSGGGGSGGGGEVQLVESGGGLVQPGGSLRLSCAASGFTFSRHALTWVRQAPGKGL

EWVSAIDNAGTTYYASWAKSRFTISRDNAKNSLYLQMNSLRAEDTAVYYCARVFYDIN

SGYYLDGMDLWGPGTLVTVSS scFv constructs of humanized rabbit P4-10 variants for CARs 10, 14, 25, and 29

CAR10

(SEQ ID NO: 103)

GAGGTGCAGCTGGTGGAGTCTGGAGGAGGACTGGTGCAACCCGGTGGCTCTTTAAG

ACTGAGCTGCGCCGCCTCTGGCTTCACCTTTTCTCGTCACGCTTTAACATGGGTGAGA

CAAGCTCCCGGAAAGGGACTGGAGTGGGTGTCCGCCATCGACAACGCCGGCACCAC

CTACTACGCCAGCTGGGCCAAGAGCAGATTCACCATCTCTCGTGACAACGCCAAGA

ACTCTTTATATTTACAGATGAACTCTTTAAGGGCCGAGGACACCGCCGTGTACTACT

GCGCTCGTGTGTTCTACGACATCAACTCCGGCTACTATTTAGACGGCATGGATTTAT

GGGGACCCGGTACACTGGTCACAGTGAGCTCTGGAGGCGGAGGTAGCGGAGGCGGA

GGAAGCAGCGGTGGAGGCAGCCAGTTTGTGCTGACACAGTCCCCTTCCGCTTCCGCC

TCTTTAGGAGCCTCCGTGAAGCTGACTTGTACTTTAAGCAGCGCCCACAAAACCTAC

ACCATCGACTGGTACCAGCAGCAGCCCGAGAAGGGCCCACGTTATTTAATGCAAGT

TAAGTCCGACGGCTCCTACACCAAGGGCACCGGCGTGCCCGATAGATTCAGCGGCT

CCAGCAGCGGCGCCGATAGGTATTTAACCATCTCCTCTTTACAGAGCGAGGACGAG

GCCGACTACTACTGTGGCGCCGACGACAACGGCGGCTACGTGTTTGGAGGCGGCAC

CCAGCTGACCGTGCTG

CAR10

(SEQ ID NO: 107)

EVQLVESGGGLVQPGGSLRLSCAASGFTFSRHALTWVRQAPGKGLEWVSAIDNAGTTY

YASWAKSRFTISRDNAKNSLYLQMNSLRAEDTAVYYCARVFYDINSGYYLDGMDLWG

PGTLVTVSSGGGGSGGGGSSGGGSQFVLTQSPSASASLGASVKLTCTLSSAHKTYTIDW

YQQQPEKGPRYLMQVKSDGSYTKGTGVPDRFSGSSSGADRYLTISSLQSEDEADYYCG

ADDNGGYVFGGGTQLTVL

Figure 17:
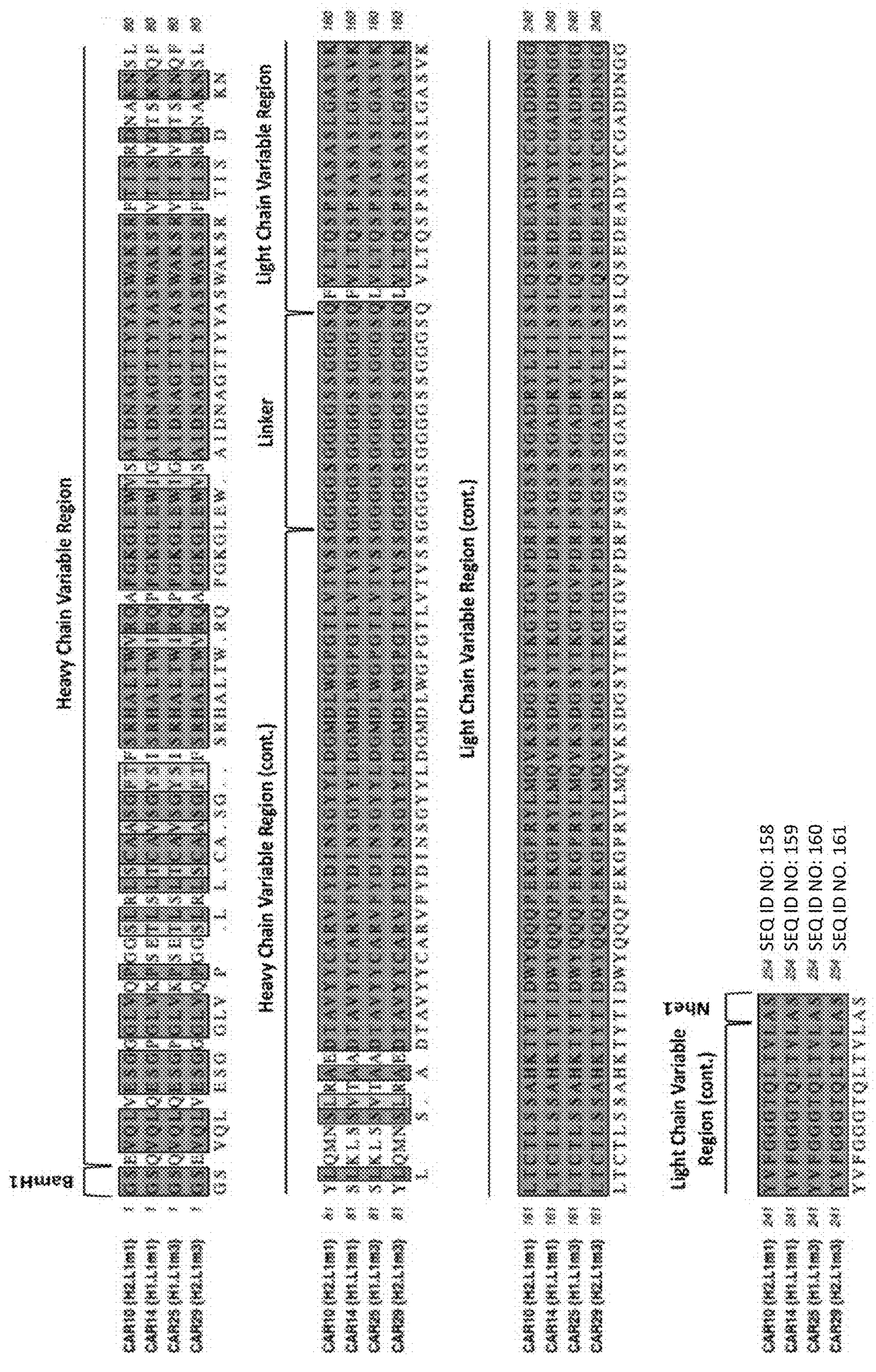
FIG. 17 is a sequence alignment illustrating amino acid alignments of scFv gene segments for CARs 10, 14, 25, and 29.

CAR10-From FIG. 17

(SEQ ID NO: 158)

GSEVQLVESGGGLVQPGGSLRLSCAASGFTFSRHALTWVRQAPGKGLEWVSAIDNAGT

TYYASWAKSRFTISRDNAKNSLYLQMNSLRAEDTAVYYCARVFYDINSGYYLDGMDL

WGPGTLVTVSSGGGGSGGGGSSGGGSQFVLTQSPSASASLGASVKLTCTLSSAHKTYTI

DWYQQQPEKGPRYLMQVKSDGSYTKGTGVPDRFSGSSSGADRYLTISSLQSEDEADYY

CGADDNGGYVFGGGTQLTVLAS

-continued

CAR14

(SEQ ID NO: 104)

CAAGTTCAGCTGCAAGAAAGCGGACCCGGTTTAGTGAAACCCTCCGAGACTTTATCT
TTAACATGCGCCGTGAGCGGCTACAGCATCTCTCGTCATGCTTTAACTTGGATTCGTC
AGCCTCCCGGAAAGGGTTTAGAGTGGATCGGCGCCATCGACAACGCCGGCACCACC
TATTACGCCAGCTGGGCCAAGTCTCGTGTGACCATCAGCGTGGACACCAGCAAGAA
CCAGTTCTCTTTAAAGCTGTCCAGCGTGACCGCTGCCGACACAGCCGTGTACTACTG
CGCTCGTGTGTTCTACGACATCAACAGCGGCTACTATTTAGACGGAATGGATCTGTG
GGGCCCCGGAACTTTAGTGACAGTCAGCAGCGGAGGCGGAGGAAGCGGAGGAGGA
GGAAGCTCCGGAGGCGGTTCTCAATTCGTGCTGACACAGAGCCCTAGCGCCTCTGCC
TCTTTAGGAGCCTCCGTGAAGCTGACTTGTACTTTAAGCAGCGCCCACAAGACCTAC
ACCATCGACTGGTACCAGCAGCAGCCCGAGAAGGGCCCTAGATATTTAATGCAAGT
TAAGAGCGACGGCAGCTACACCAAAGGCACTGGTGTGCCCGATCGTTTTAGCGGCA
GCAGCAGCGGCGCCGATAGGTATTTAACCATCAGCTCTTTACAGAGCGAGGACGAG
GCCGACTACTACTGTGGCGCCGACGACAACGGCGGCTACGTGTTTGGCGGCGGCAC
ACAGCTGACCGTTTTA

CAR14

(SEQ ID NO: 108)

QVQLQESGPGLVKPSETLSLTCAVSGYSISRHALTWIRQPPGKGLEWIGAIDNAGTTYYA
SWAKSRVTISVDTSKNQFSLKLSSVTAADTAVYYCARVFYDINSGYYLDGMDLWGPGT
LVTVSSGGGGSGGGGSSGGGSQFVLTQSPSASASLGASVKLTCTLSSAHKTYTIDWYQQ
QPEKGPRYLMQVKSDGSYTKGTGVPDRFSGSSSGADRYLTISSLQSEDEADYYCGADD
NGGYVFGGGTQLTVL

CAR15-From FIG. 17

(SEQ ID NO: 159)

GSQVQLQESGPGLVKPSETLSLTCAVSGYSISRHALTWIRQPPGKGLEWIGAIDNAGTTY
YASWAKSRVTISVDTSKNQFSLKLSSVTAADTAVYYCARVFYDINSGYYLDGMDLWGP
GTLVTVSSGGGGSGGGGSSGGGSQFVLTQSPSASASLGASVKLTCTLSSAHKTYTIDWY
QQQPEKGPRYLMQVKSDGSYTKGTGVPDRFSGSSSGADRYLTISSLQSEDEADYYCGA
DDNGGYVFGGGTQLTVLAS

CAR25

(SEQ ID NO: 105)

CAAGTTCAGCTGCAAGAAAGCGGACCCGGTTTAGTGAAACCCTCCGAGACTTTATCT
TTAACATGCGCCGTGAGCGGCTACAGCATCTCTCGTCATGCTTTAACTTGGATTCGTC
AGCCTCCCGGAAAGGGTTTAGAGTGGATCGGCGCCATCGACAACGCCGGCACCACC
TATTACGCCAGCTGGGCCAAGTCTCGTGTGACCATCAGCGTGGACACCAGCAAGAA
CCAGTTCTCTTTAAAGCTGTCCAGCGTGACCGCTGCCGACACAGCCGTGTACTACTG
CGCTCGTGTGTTCTACGACATCAACAGCGGCTACTATTTAGACGGAATGGATCTGTG
GGGCCCCGGAACTTTAGTGACAGTCAGCAGCGGAGGCGGAGGAAGCGGAGGAGGA
GGAAGCTCCGGAGGCGGTTCTCAACTGGTGCTGACACAGAGCCCTAGCGCCTCTGC
CTCTTTAGGAGCCTCCGTGAAGCTGACTTGTACTTTAAGCAGCGCCCACAAGACCTA
CACCATCGACTGGTACCAGCAGCAGCCCGAGAAGGGCCCTAGATATTTAATGCAAG
TTAAGAGCGACGGCAGCTACACCAAAGGCACTGGTGTGCCCGATCGTTTTAGCGGC
AGCAGCAGCGGCGCCGATAGGTATTTAACCATCAGCTCTTTACAGAGCGAGGACGA

-continued

GGCCGACTACTACTGTGGCGCCGACGACAACGGCGGCTACGTGTTTGGCGGCGGCA

CACAGCTGACCGTTTTA

CAR25

(SEQ ID NO: 109)
QVQLQESGPGLVKPSETLSLTCAVSGYSISRHALTWIRQPPGKGLEWIGAIDNAGTTYYA

SWAKSRVTISVDTSKNQFSLKLSSVTAADTAVYYCARVFYDINSGYYLDGMDLWGPGT

LVTVSSGGGGSGGGGSSGGGSQLVLTQSPSASASLGASVKLTCTLSSAHKTYTIDWYQQ

QPEKGPRYLMQVKSDGSYTKGTGVPDRFSGSSSGADRYLTISSLQSEDEADYYCGADD

NGGYVFGGGTQLTVL

CAR25-From FIG. 17

(SEQ ID NO: 160)
GSQVQLQESGPGLVKPSETLSLTCAVSGYSISRHALTWIRQPPGKGLEWIGAIDNAGTTY

YASWAKSRVTISVDTSKNQFSLKLSSVTAADTAVYYCARVFYDINSGYYLDGMDLWGP

GTLVTVSSGGGGSGGGGSSGGGSQLVLTQSPSASASLGASVKLTCTLSSAHKTYTIDWY

QQQPEKGPRYLMQVKSDGSYTKGTGVPDRFSGSSSGADRYLTISSLQSEDEADYYCGA

DDNGGYVFGGGTQLTVLAS

CAR29

(SEQ ID NO: 106)
GAGGTGCAGCTGGTGGAGTCTGGAGGAGGACTGGTGCAACCCGGTGGCTCTTTAAG

ACTGAGCTGCGCCGCCTCTGGCTTCACCTTTTCTCGTCACGCTTTAACATGGGTGAGA

CAAGCTCCCGGAAAGGGACTGGAGTGGGTGTCCGCCATCGACAACGCCGGCACCAC

CTACTACGCCAGCTGGGCCAAGAGCAGATTCACCATCTCTCGTGACAACGCCAAGA

ACTCTTTATATTTACAGATGAACTCTTTAAGGGCCGAGGACACCGCCGTGTACTACT

GCGCTCGTGTGTTCTACGACATCAACTCCGGCTACTATTTAGACGGCATGGATTTAT

GGGGACCCGGTACACTGGTCACAGTGAGCTCTGGAGGCGGAGGTAGCGGAGGCGGA

GGAAGCAGCGGTGGAGGCAGCCAGCTGGTGCTGACACAGTCCCCTTCCGCTTCCGC

CTCTTTAGGAGCCTCCGTGAAGCTGACTTGTACTTTAAGCAGCGCCCACAAAACCTA

CACCATCGACTGGTACCAGCAGCAGCCCGAGAAGGGCCCACGTTATTTAATGCAAG

TTAAGTCCGACGGCTCCTACACCAAGGGCACCGGCGTGCCCGATAGATTCAGCGGC

TCCAGCAGCGGCGCCGATAGGTATTTAACCATCTCCTCTTTACAGAGCGAGGACGAG

GCCGACTACTACTGTGGCGCCGACGACAACGGCGGCTACGTGTTTGGAGGCGGCAC

CCAGCTGACCGTGCTG

CAR29

(SEQ ID NO: 110)
EVQLVESGGGLVQPGGSLRLSCAASGFTFSRHALTWVRQAPGKGLEWVSAIDNAGTTY

YASWAKSRFTISRDNAKNSLYLQMNSLRAEDTAVYYCARVFYDINSGYYLDGMDLWG

PGTLVTVSSGGGGSGGGGSSGGGSQLVLTQSPSASASLGASVKLTCTLSSAHKTYTIDW

YQQQPEKGPRYLMQVKSDGSYTKGTGVPDRFSGSSSGADRYLTISSLQSEDEADYYCG

ADDNGGYVFGGGTQLTVL

CAR29-From FIG. 17

(SEQ ID NO: 161)
GSEVQLVESGGGLVQPGGSLRLSCAASGFTFSRHALTWVRQAPGKGLEWVSAIDNAGT

TYYASWAKSRFTISRDNAKNSLYLQMNSLRAEDTAVYYCARVFYDINSGYYLDGMDL

WGPGTLVTVSSGGGGSGGGGSSGGGSQLVLTQSPSASASLGASVKLTCTLSSAHKTYTI

DWYQQQPEKGPRYLMQVKSDGSYTKGTGVPDRFSGSSSGADRYLTISSLQSEDEADYY

CGADDNGGYVFGGGTQLTVLAS

-continued

CAR plasmids for lentivirus
pTRPE-C10-gs-BBz (plasmid for CAR10)

(SEQ ID NO: 111)

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

GAGAGAAAAAGCACCGTGCATGCCGATTGGTGGAAGTAAGGTGGTACGATCGTGCC

TTATTAGGAAGGCAACAGACGGGTCTGACATGGATTGGACGAACCACTGAATTGCC

GCATTGCAGAGATATTGTATTTAAGTGCCTAGCTCGATACATAAACGGGTCTCTCTG

-continued

GTTAGACCAGATCTGAGCCTGGGAGCTCTCTGGCTAACTAGGGAACCCACTGCTTAA

GCCTCAATAAAGCTTGCCTTGAGTGCTTCAAGTAGTGTGTGCCCGTCTGTTGTGTGA

CTCTGGTAACTAGAGATCCCTCAGACCCTTTTAGTCAGTGTGGAAAATCTCTAGCAG

TGGCGCCCGAACAGGGACTTGAAAGCGAAAGGGAAACCAGAGGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCGCTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGATTAGACTGTAGCCC

AGGAATATGGCAGCTAGATTGTACACATTTAGAAGGAAAAGTTATCTTGGTAGCAG

TTCATGTAGCCAGTGGATATATAGAAGCAGAAGTAATTCCAGCAGAGACAGGGCAA

GAAACAGCATACTTCCTCTTAAAATTAGCAGGAAGATGGCCAGTAAAAACAGTACA

TACAGACAATGGCAGCAATTTCACCAGTACTACAGTTAAGGCCGCCTGTTGGTGGGC

GGGGATCAAGCAGGAATTTGGCATTCCCTACAATCCCCAAAGTCAAGGAGTAATAG

AATCTATGAATAAAGAATTAAAGAAAATTATAGGACAGGTAAGAGATCAGGCTGAA

CATCTTAAGACAGCAGTACAAATGGCAGTATTCATCCACAATTTTAAAAGAAAAGG

GGGGATTGGGGGGTACAGTGCAGGGGAAAGAATAGTAGACATAATAGCAACAGAC

ATACAAACTAAAGAATTACAAAAACAAATTACAAAAATTCAAAATTTTCGGGTTTAT

TACAGGGACAGCAGAGATCCAGTTTGGCTGCATACGCGTCGTGAGGCTCCGGTGCC

CGTCAGTGGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAAAGTGATG

-continued

TCGTGTACTGGCTCCGCCTTTTTCCCGAGGGTGGGGGAGAACCGTATATAAGTGCAG

TAGTCGCCGTGAACGTTCTTTTTCGCAACGGGTTTGCCGCCAGAACACAGGTAAGTG

CCGTGTGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTGGAAG

TGGGTGGGAGAGTTCGAGGCCTTGCGCTTAAGGAGCCCCTTCGCCTCGTGCTTGAGT

TGAGGCCTGGCCTGGGCGCTGGGGCCGCCGCGTGCGAATCTGGTGGCACCTTCGCG

CCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGC

GGGTGAGTCACCCACACAAAGGAAAAGGGCCTTTCCGTCCTCAGCCGTCGCTTCATG

TGACTCCACTGAGTACCGGGCGCCGTCCAGGCACCTCGATTAGTTCTCGTGCTTTTG

GAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGA

ATTTGCCCTTTTTGAGTTTGGATCTTGGTTCATTCTCAAGCCTCAGACAGTGGTTCAA

AGTTTTTTTCTTCCATTTCAGGTGTCGTGAGCTAGAGCCACCATGGAGTTTGGGCTGA

GCTGGCTTTTTCTTGTGGCTATTTTAAAAGGTGTCCAGTGCGGATCCGAGGTGCAGC

TGGTGGAGTCTGGAGGAGGACTGGTGCAACCCGGTGGCTCTTTAAGACTGAGCTGC

GCCGCCTCTGGCTTCACCTTTTCTCGTCACGCTTTAACATGGGTGAGACAAGCTCCC

GGAAAGGGACTGGAGTGGGTGTCCGCCATCGACAACGCCGGCACCACCTACTACGC

CAGCTGGGCCAAGAGCAGATTCACCATCTCTCGTGACAACGCCAAGAACTCTTTATA

TTTACAGATGAACTCTTTAAGGGCCGAGGACACCGCCGTGTACTACTGCGCTCGTGT

GTTCTACGACATCAACTCCGGCTACTATTTAGACGGCATGGATTTATGGGGACCCGG

TACACTGGTCACAGTGAGCTCTGGAGGCGGAGGTAGCGGAGGCGGAGGAAGCAGC

GGTGGAGGCAGCCAGTTTGTGCTGACACAGTCCCCTTCCGCTTCCGCCTCTTTAGGA

GCCTCCGTGAAGCTGACTTGTACTTTAAGCAGCGCCCACAAAACCTACACCATCGAC

TGGTACCAGCAGCAGCCCGAGAAGGGCCCACGTTATTTAATGCAAGTTAAGTCCGA

CGGCTCCTACACCAAGGGCACCGGCGTGCCCGATAGATTCAGCGGCTCCAGCAGCG

GCGCCGATAGGTATTTAACCATCTCCTCTTTACAGAGCGAGGACGAGGCCGACTACT

ACTGTGGCGCCGACGACAACGGCGGCTACGTGTTTGGAGGCGGCACCCAGCTGACC

GTGCTGGCTAGCGGTGGCGGAGGTTCTGGAGGTGGAGGTTCCTCCGGAATCTACATC

TGGGCGCCCTTGGCCGGGACTTGTGGGGTCCTTCTCCTGTCACTGGTTATCACCCTTT

ACTGCAAACGGGGCAGAAAGAAACTCCTGTATATATTCAAACAACCATTTATGAGA

CCAGTACAAACTACTCAAGAGGAAGATGGCTGTAGCTGCCGATTTCCAGAAGAAGA

AGAAGGAGGATGTGAACTGAGAGTGAAGTTCAGCAGGAGCGCAGACGCCCCCGCGT

ACCAGCAGGGCCAGAACCAGCTCTATAACGAGCTCAATCTAGGACGAAGAGAGGA

GTACGATGTTTTGGACAAGAGACGTGGCCGGGACCCTGAGATGGGGGGAAAGCCGA

GAAGGAAGAACCCTCAGGAAGGCCTGTACAATGAACTGCAGAAAGATAAGATGGC

-continued

GGAGGCCTACAGTGAGATTGGGATGAAAGGCGAGCGCCGGAGGGGCAAGGGGCAC

GATGGCCTTTACCAGGGTCTCAGTACAGCCACCAAGGACACCTACGACGCCCTTCAC

ATGCAGGCCCTGCCCCCTCGCTAAGTCGACAATCAACCTCTGGATTACAAAATTTGT

GAAAGATTGACTGGTATTCTTAACTATGTTGCTCCTTTTACGCTATGTGGATACGCTG

CTTTAATGCCTTTGTATCATGCTATTGCTTCCCGTATGGCTTTCATTTTCTCCTCCTTG

TATAAATCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATTGCCACC

ACCTGTCAGCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGCACTGACA

ATTCCGTGGTGTTGTCGGGGAAGCTGACGTCCTTTCCTTGGCTGCTCGCCTGTGTTGC

CACCTGGATTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGTCTTCGCCTT

CGCCCTCAGACGAGTCGGATCTCCCTTTGGGCCGCCTCCCCGCCTGGAATTCGAGCT

CGGTACCTTTAAGACCAATGACTTACAAGGCAGCTGTAGATCTTAGCCACTTTTTAA

AAGAAAAGGGGGGACTGGAAGGGCTAATTCACTCCCAACGAAGACAAGATCTGCTT

TTTGCTTGTACTGGGTCTCTCTGGTTAGACCAGATCTGAGCCTGGGAGCTCTCTGGCT

AACTAGGGAACCCACTGCTTAAGCCTCAATAAAGCTTGCCTTGAGTGCTTCAAGTAG

TGTGTGCCCGTCTGTTGTGTGACTCTGGTAACTAGAGATCCCTCAGACCCTTTTAGTC

AGTGTGGAAAATCTCTAGCAGTAGTAGTTCATGTCATCTTATTATTCAGTATTTATAA

CTTGCAAAGAAATGAATATCAGAGAGTGAGAGGAACTTGTTTATTGCAGCTTATAAT

GGTTACAAATAAAGCAATAGCATCACAAATTTCACAAATAAAGCATTTTTTTCACTG

CATTCTAGTTGTGGTTTGTCCAAACTCATCAATGTATCTTATCATGTCTGGCTCTAGC

TATCCCGCCCCTAACTCCGCCCAGTTCCGCCCATTCTCCGCCCCATGGCTGACTAATT

TTTTTTATTTATGCAGAGGCCGAGGCCGCCTCGGCCTCTGAGCTATTCCAGAAGTAG

TGAGGAGGCTTTTTTGGAGGCCTAGCTAGGGACGTACCCAATTCGCCCTATAGTGAG

TCGTATTACGCGCGCTCACTGGCCGTCGTTTTACAACGTCGTGACTGGGAAAACCCT

GGCGTTACCCAACTTAATCGCCTTGCAGCACATCCCCCTTTCGCCAGCTGGCGTAAT

AGCGAAGAGGCCCGCACCGATCGCCCTTCCCAACAGTTGCGCAGCCTGAATGGCGA

ATGGGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTTTA

GGGTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGGAG

TCCACGTTCTTTAATAGTGGACTCTTGTTCCAAACTGGAACAACACTCAACCCTATCT

CGGTCTATTCTTTTGATTTATAAGGGATTTTGCCGATTTCGGCCTATTGGTTAAAAAA

TGAGCTGATTTAACAAAAATTTAACGCGAATTTTAACAAAATATTAACGCTTACAAT

TTAGGTGGCACTTTTCGGGGAAATGTGCGCGGAACCCCTATTTGTTTATTTTTCTAAA

TACATTCAAATATGTATCCGCTCATGAGACAATAACCCTGATAAATGCTTCAATAAT

-continued

ATTGAAAAAGGAAGAGTATGAGTATTCAACATTTCCGTGTCGCCCTTATTCCCTTTTT

TGCGGCATTTTGCCTTCCTGTTTTTGCTCACCCAGAAACGCTGGTGAAAGTAAAAGA

TGCTGAAGATCAGTTGG pTRPE-C14-gs-BBz (plasmid for CAR14)

(SEQ ID NO: 112)

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

-continued

GAGAGAAAAAGCACCGTGCATGCCGATTGGTGGAAGTAAGGTGGTACGATCGTGCC

TTATTAGGAAGGCAACAGACGGGTCTGACATGGATTGGACGAACCACTGAATTGCC

GCATTGCAGAGATATTGTATTTAAGTGCCTAGCTCGATACATAAACGGGTCTCTCTG

GTTAGACCAGATCTGAGCCTGGGAGCTCTCTGGCTAACTAGGGAACCCACTGCTTAA

GCCTCAATAAAGCTTGCCTTGAGTGCTTCAAGTAGTGTGTGCCCGTCTGTTGTGTGA

CTCTGGTAACTAGAGATCCCTCAGACCCTTTTAGTCAGTGTGGAAAATCTCTAGCAG

TGGCGCCCGAACAGGGACTTGAAAGCGAAAGGGAAACCAGAGGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCGCTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGATTAGACTGTAGCCC

AGGAATATGGCAGCTAGATTGTACACATTTAGAAGGAAAAGTTATCTTGGTAGCAG

TTCATGTAGCCAGTGGATATATAGAAGCAGAAGTAATTCCAGCAGAGACAGGGCAA

GAAACAGCATACTTCCTCTTAAAATTAGCAGGAAGATGGCCAGTAAAAACAGTACA

TACAGACAATGGCAGCAATTTCACCAGTACTACAGTTAAGGCCGCCTGTTGGTGGGC

GGGGATCAAGCAGGAATTTGGCATTCCCTACAATCCCCAAAGTCAAGGAGTAATAG

AATCTATGAATAAAGAATTAAAGAAAATTATAGGACAGGTAAGAGATCAGGCTGAA

CATCTTAAGACAGCAGTACAAATGGCAGTATTCATCCACAATTTTAAAAGAAAAGG

GGGGATTGGGGGGTACAGTGCAGGGGAAAGAATAGTAGACATAATAGCAACAGAC

ATACAAACTAAAGAATTACAAAAACAAATTACAAAAATTCAAAATTTTCGGGTTTAT

TACAGGGACAGCAGAGATCCAGTTTGGCTGCATACGCGTCGTGAGGCTCCGGTGCC

-continued

CGTCAGTGGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAG

TAGTCGCCGTGAACGTTCTTTTTCGCAACGGGTTTGCCGCCAGAACACAGGTAAGTG

CCGTGTGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTGGAAG

TGGGTGGGAGAGTTCGAGGCCTTGCGCTTAAGGAGCCCCTTCGCCTCGTGCTTGAGT

TGAGGCCTGGCCTGGGCGCTGGGGCCGCCGCGTGCGAATCTGGTGGCACCTTCGCG

CCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGC

GGGTGAGTCACCCACACAAAGGAAAAGGGCCTTTCCGTCCTCAGCCGTCGCTTCATG

TGACTCCACTGAGTACCGGGCGCCGTCCAGGCACCTCGATTAGTTCTCGTGCTTTTG

GAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGA

ATTTGCCCTTTTTGAGTTTGGATCTTGGTTCATTCTCAAGCCTCAGACAGTGGTTCAA

AGTTTTTTTCTTCCATTTCAGGTGTCGTGAGCTAGAGCCACCATGGAGTTTGGGCTGA

GCTGGCTTTTTCTTGTGGCTATTTTAAAAGGTGTCCAGTGCGGATCCCAAGTTCAGCT

GCAAGAAAGCGGACCCGGTTTAGTGAAACCCTCCGAGACTTTATCTTTAACATGCGC

CGTGAGCGGCTACAGCATCTCTCGTCATGCTTTAACTTGGATTCGTCAGCCTCCCGG

AAAGGGTTTAGAGTGGATCGGCGCCATCGACAACGCCGGCACCACCTATTACGCCA

GCTGGGCCAAGTCTCGTGTGACCATCAGCGTGGACACCAGCAAGAACCAGTTCTCTT

TAAAGCTGTCCAGCGTGACCGCTGCCGACACAGCCGTGTACTACTGCGCTCGTGTGT

TCTACGACATCAACAGCGGCTACTATTTAGACGGAATGGATCTGTGGGGCCCCGGA

ACTTTAGTGACAGTCAGCAGCGGAGGCGGAGGAAGCGGAGGAGGAGGAAGCTCCG

GAGGCGGTTCTCAATTCGTGCTGACACAGAGCCCTAGCGCCTCTGCCTCTTTAGGAG

CCTCCGTGAAGCTGACTTGTACTTTAAGCAGCGCCCACAAGACCTACACCATCGACT

GGTACCAGCAGCAGCCCGAGAAGGGCCCTAGATATTTAATGCAAGTTAAGAGCGAC

GGCAGCTACACCAAAGGCACTGGTGTGCCCGATCGTTTTAGCGGCAGCAGCAGCGG

CGCCGATAGGTATTTAACCATCAGCTCTTTACAGAGCGAGGACGAGGCCGACTACTA

CTGTGGCGCCGACGACAACGGCGGCTACGTGTTTGGCGGCGGCACACAGCTGACCG

TTTTAGCTAGCGGTGGCGGAGGTTCTGGAGGTGGAGGTTCCTCCGGAATCTACATCT

GGGCGCCCTTGGCCGGGACTTGTGGGGTCCTTCTCCTGTCACTGGTTATCACCCTTTA

CTGCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA

-continued

CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGAGA

AGGAAGAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGGCACGA

TGGCCTTTACCAGGGTCTCAGTACAGCCACCAAGGACACCTACGACGCCCTTCACAT

GCAGGCCCTGCCCCCTCGCTAAGTCGACAATCAACCTCTGGATTACAAAATTTGTGA

AAGATTGACTGGTATTCTTAACTATGTTGCTCCTTTTACGCTATGTGGATACGCTGCT

TTAATGCCTTTGTATCATGCTATTGCTTCCCGTATGGCTTTCATTTTCTCCTCCTTGTA

TAAATCCTGGTTGCTGTCTCTTTATGAGGAGTTGTGGCCCGTTGTCAGGCAACGTGG

CGTGGTGTGCACTGTGTTTGCTGACGCAACCCCCACTGGTTGGGGCATTGCCACCAC

CTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAAT

TCCGTGGTGTTGTCGGGGAAGCTGACGTCCTTTCCTTGGCTGCTCGCCTGTGTTGCCA

CCTGGATTCTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTGGAATTCGAGCTCG

GTACCTTTAAGACCAATGACTTACAAGGCAGCTGTAGATCTTAGCCACTTTTTAAAA

GAAAAGGGGGGACTGGAAGGGCTAATTCACTCCCAACGAAGACAAGATCTGCTTTT

TGCTTGTACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTCAAGTAGT

GTGTGCCCGTCTGTTGTGTGACTCTGGTAACTAGAGATCCCTCAGACCCTTTTAGTCA

GTGTGGAAAATCTCTAGCAGTAGTAGTTCATGTCATCTTATTATTCAGTATTTATAAC

TTGCAAAGAAATGAATATCAGAGAGTGAGAGGAACTTGTTTATTGCAGCTTATAATG

GTTACAAATAAAGCAATAGCATCACAAATTTCACAAATAAAGCATTTTTTTCACTGC

ATTCTAGTTGTGGTTTGTCCAAACTCATCAATGTATCTTATCATGTCTGGCTCTAGCT

ATCCCGCCCCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAGAAGTAGT

GAGGAGGCTTTTTTGGAGGCCTAGCTAGGGACGTACCCAATTCGCCCTATAGTGAGT

CGTATTACGCGCGCTCACTGGCCGTCGTTTTACAACGTCGTGACTGGGAAAACCCTG

GCGTTACCCAACTTAATCGCCTTGCAGCACATCCCCCTTTCGCCAGCTGGCGTAATA

GCGAAGAGGCCCGCACCGATCGCCCTTCCCAACAGTTGCGCAGCCTGAATGGCGAA

TGGGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTTCC

TTTCTCGCCACGTTCGCCGGCTTTCCCCGTCAAGCTCTAAATCGGGGGCTCCCTTTAG

GGTTCCGATTTAGTGCTTTACGGCACCTCGACCCCAAAAAACTTGATTAGGGTGATG

GTTCACGTAGTGGGCCATCGCCCTGATAGACGGTTTTTCGCCCTTTGACGTTGGAGT

CCACGTTCTTTAATAGTGGACTCTTGTTCCAAACTGGAACAACACTCAACCCTATCTC

GGTCTATTCTTTTGATTTATAAGGGATTTTGCCGATTTCGGCCTATTGGTTAAAAAAT

GAGCTGATTTAACAAAAATTTAACGCGAATTTTAACAAAATATTAACGCTTACAATT

TAGGTGGCACTTTTCGGGGAAATGTGCGCGGAACCCCTATTTGTTTATTTTTCTAAAT

ACATTCAAATATGTATCCGCTCATGAGACAATAACCCTGATAAATGCTTCAATAATA

-continued

TTGAAAAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAAAGAT

GCTGAAGATCAGTTGG pTRPE-C25-gs-BBz (plasmid for CAR25)

(SEQ ID NO: 113)

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

-continued

GAGAGAAAAAGCACCGTGCATGCCGATTGGTGGAAGTAAGGTGGTACGATCGTGCC

TTATTAGGAAGGCAACAGACGGGTCTGACATGGATTGGACGAACCACTGAATTGCC

GCATTGCAGAGATATTGTATTTAAGTGCCTAGCTCGATACATAAACGGGTCTCTCTG

GTTAGACCAGATCTGAGCCTGGGAGCTCTCTGGCTAACTAGGGAACCCACTGCTTAA

GCCTCAATAAAGCTTGCCTTGAGTGCTTCAAGTAGTGTGTGCCCGTCTGTTGTGTGA

CTCTGGTAACTAGAGATCCCTCAGACCCTTTTAGTCAGTGTGGAAAATCTCTAGCAG

TGGCGCCCGAACAGGGACTTGAAAGCGAAAGGGAAACCAGAGGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCGCTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGATTAGACTGTAGCCC

AGGAATATGGCAGCTAGATTGTACACATTTAGAAGGAAAAGTTATCTTGGTAGCAG

TTCATGTAGCCAGTGGATATATAGAAGCAGAAGTAATTCCAGCAGAGACAGGGCAA

GAAACAGCATACTTCCTCTTAAAATTAGCAGGAAGATGGCCAGTAAAAACAGTACA

TACAGACAATGGCAGCAATTTCACCAGTACTACAGTTAAGGCCGCCTGTTGGTGGGC

GGGGATCAAGCAGGAATTTGGCATTCCCTACAATCCCCAAAGTCAAGGAGTAATAG

AATCTATGAATAAAGAATTAAAGAAAATTATAGGACAGGTAAGAGATCAGGCTGAA

CATCTTAAGACAGCAGTACAAATGGCAGTATTCATCCACAATTTTAAAAGAAAAGG

GGGGATTGGGGGGTACAGTGCAGGGGAAAGAATAGTAGACATAATAGCAACAGAC

ATACAAACTAAAGAATTACAAAAACAAATTACAAAAATTCAAAATTTTCGGGTTTAT

TACAGGGACAGCAGAGATCCAGTTTGGCTGCATACGCGTCGTGAGGCTCCGGTGCC

-continued

CGTCAGTGGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAG

TAGTCGCCGTGAACGTTCTTTTTCGCAACGGGTTTGCCGCCAGAACACAGGTAAGTG

CCGTGTGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTGGAAG

TGGGTGGGAGAGTTCGAGGCCTTGCGCTTAAGGAGCCCCTTCGCCTCGTGCTTGAGT

TGAGGCCTGGCCTGGGCGCTGGGGCCGCCGCGTGCGAATCTGGTGGCACCTTCGCG

CCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGC

GGGTGAGTCACCCACACAAAGGAAAAGGGCCTTTCCGTCCTCAGCCGTCGCTTCATG

TGACTCCACTGAGTACCGGGCGCCGTCCAGGCACCTCGATTAGTTCTCGTGCTTTTG

GAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGA

ATTTGCCCTTTTTGAGTTTGGATCTTGGTTCATTCTCAAGCCTCAGACAGTGGTTCAA

AGTTTTTTTCTTCCATTTCAGGTGTCGTGAGCTAGAGCCACCATGGAGTTTGGGCTGA

GCTGGCTTTTTCTTGTGGCTATTTTAAAAGGTGTCCAGTGCGGATCCCAAGTTCAGCT

GCAAGAAAGCGGACCCGGTTTAGTGAAACCCTCCGAGACTTTATCTTTAACATGCGC

CGTGAGCGGCTACAGCATCTCTCGTCATGCTTTAACTTGGATTCGTCAGCCTCCCGG

AAAGGGTTTAGAGTGGATCGGCGCCATCGACAACGCCGGCACCACCTATTACGCCA

GCTGGGCCAAGTCTCGTGTGACCATCAGCGTGGACACCAGCAAGAACCAGTTCTCTT

TAAAGCTGTCCAGCGTGACCGCTGCCGACACAGCCGTGTACTACTGCGCTCGTGTGT

TCTACGACATCAACAGCGGCTACTATTTAGACGGAATGGATCTGTGGGGCCCCGGA

ACTTTAGTGACAGTCAGCAGCGGAGGCGGAGGAAGCGGAGGAGGAGGAAGCTCCG

GAGGCGGTTCTCAACTGGTGCTGACACAGAGCCCTAGCGCCTCTGCCTCTTTAGGAG

CCTCCGTGAAGCTGACTTGTACTTTAAGCAGCGCCCACAAGACCTACACCATCGACT

GGTACCAGCAGCAGCCCGAGAAGGGCCCTAGATATTTAATGCAAGTTAAGAGCGAC

GGCAGCTACACCAAAGGCACTGGTGTGCCCGATCGTTTTAGCGGCAGCAGCAGCGG

CGCCGATAGGTATTTAACCATCAGCTCTTTACAGAGCGAGGACGAGGCCGACTACTA

CTGTGGCGCCGACGACAACGGCGGCTACGTGTTTGGCGGCGGCACACAGCTGACCG

TTTTAGCTAGCGGTGGCGGAGGTTCTGGAGGTGGAGGTTCCTCCGGAATCTACATCT

GGGCGCCCTTGGCCGGGACTTGTGGGGTCCTTCTCCTGTCACTGGTTATCACCCTTTA

CTGCAAACGGGGCAGAAAGAAACTCCTGTATATATTCAAACAACCATTTATGAGAC

CAGTACAAACTACTCAAGAGGAAGATGGCTGTAGCTGCCGATTTCCAGAAGAAGAA

GAAGGAGGATGTGAACTGAGAGTGAAGTTCAGCAGGAGCGCAGACGCCCCCGCGTA

-continued

CCAGCAGGGCCAGAACCAGCTCTATAACGAGCTCAATCTAGGACGAAGAGAGGAGT

ACGATGTTTTGGACAAGAGACGTGGCCGGGACCCTGAGATGGGGGGAAAGCCGAGA

AGGAAGAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGGCACGA

TGGCCTTTACCAGGGTCTCAGTACAGCCACCAAGGACACCTACGACGCCCTTCACAT

GCAGGCCCTGCCCCCTCGCTAAGTCGACAATCAACCTCTGGATTACAAAATTTGTGA

AAGATTGACTGGTATTCTTAACTATGTTGCTCCTTTTACGCTATGTGGATACGCTGCT

TTAATGCCTTTGTATCATGCTATTGCTTCCCGTATGGCTTTCATTTTCTCCTCCTTGTA

TAAATCCTGGTTGCTGTCTCTTTATGAGGAGTTGTGGCCCGTTGTCAGGCAACGTGG

CGTGGTGTGCACTGTGTTTGCTGACGCAACCCCCACTGGTTGGGGCATTGCCACCAC

CTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAAT

TCCGTGGTGTTGTCGGGGAAGCTGACGTCCTTTCCTTGGCTGCTCGCCTGTGTTGCCA

CCTGGATTCTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTGGAATTCGAGCTCG

GTACCTTTAAGACCAATGACTTACAAGGCAGCTGTAGATCTTAGCCACTTTTTAAAA

GAAAAGGGGGGACTGGAAGGGCTAATTCACTCCCAACGAAGACAAGATCTGCTTTT

TGCTTGTACTGGGTCTCTCTGGTTAGACCAGATCTGAGCCTGGGAGCTCTCTGGCTA

ACTAGGGAACCCACTGCTTAAGCCTCAATAAAGCTTGCCTTGAGTGCTTCAAGTAGT

GTGTGCCCGTCTGTTGTGTGACTCTGGTAACTAGAGATCCCTCAGACCCTTTTAGTCA

GTGTGGAAAATCTCTAGCAGTAGTAGTTCATGTCATCTTATTATTCAGTATTTATAAC

TTGCAAAGAAATGAATATCAGAGAGTGAGAGGAACTTGTTTATTGCAGCTTATAATG

GTTACAAATAAAGCAATAGCATCACAAATTTCACAAATAAAGCATTTTTTTCACTGC

ATTCTAGTTGTGGTTTGTCCAAACTCATCAATGTATCTTATCATGTCTGGCTCTAGCT

ATCCCGCCCCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAGAAGTAGT

GAGGAGGCTTTTTTGGAGGCCTAGCTAGGGACGTACCCAATTCGCCCTATAGTGAGT

CGTATTACGCGCGCTCACTGGCCGTCGTTTTACAACGTCGTGACTGGGAAAACCCTG

GCGTTACCCAACTTAATCGCCTTGCAGCACATCCCCCTTTCGCCAGCTGGCGTAATA

GCGAAGAGGCCCGCACCGATCGCCCTTCCCAACAGTTGCGCAGCCTGAATGGCGAA

TGGGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTTCC

TTTCTCGCCACGTTCGCCGGCTTTCCCCGTCAAGCTCTAAATCGGGGGCTCCCTTTAG

GGTTCCGATTTAGTGCTTTACGGCACCTCGACCCCAAAAAACTTGATTAGGGTGATG

GTTCACGTAGTGGGCCATCGCCCTGATAGACGGTTTTTCGCCCTTTGACGTTGGAGT

CCACGTTCTTTAATAGTGGACTCTTGTTCCAAACTGGAACAACACTCAACCCTATCTC

GGTCTATTCTTTTGATTTATAAGGGATTTTGCCGATTTCGGCCTATTGGTTAAAAAAT

GAGCTGATTTAACAAAAATTTAACGCGAATTTTAACAAAATATTAACGCTTACAATT

TAGGTGGCACTTTTCGGGGAAATGTGCGCGGAACCCCTATTTGTTTATTTTTCTAAAT

ACATTCAAATATGTATCCGCTCATGAGACAATAACCCTGATAAATGCTTCAATAATA

-continued

TTGAAAAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAAAGAT

GCTGAAGATCAGTTGG pTRPE-C29-gs-BBz (plasmid for CAR29)

(SEQ ID NO: 114)

GTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCG

CGGTATTATCCCGTATTGACGCCGGGCAAGAGCAACTCGGTCGCCGCATACACTATT

CTCAGAATGACTTGGTTGAGTACTCACCAGTCACAGAAAAGCATCTTACGGATGGCA

TGACAGTAAGAGAATTATGCAGTGCTGCCATAACCATGAGTGATAACACTGCGGCC

AACTTACTTCTGACAACGATCGGAGGACCGAAGGAGCTAACCGCTTTTTTGCACAAC

ATGGGGGATCATGTAACTCGCCTTGATCGTTGGGAACCGGAGCTGAATGAAGCCAT

ACCAAACGACGAGCGTGACACCACGATGCCTGTAGCAATGGCAACAACGTTGCGCA

AACTATTAACTGGCGAACTACTTACTCTAGCTTCCCGGCAACAATTAATAGACTGGA

TGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCAC

TGGGGCCAGATGGTAAGCCCTCCCGTATCGTAGTTATCTACACGACGGGGAGTCAG

GCAACTATGGATGAACGAAATAGACAGATCGCTGAGATAGGTGCCTCACTGATTAA

GCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAA

GGATCTTCTTGAGATCCTTTTTTTCTGCGCGTAATCTGCTGCTTGCAAACAAAAAAAC

CACCGCTACCAGCGGTGGTTTGTTTGCCGGATCAAGAGCTACCAACTCTTTTTCCGA

AGGTAACTGGCTTCAGCAGAGCGCAGATACCAAATACTGTTCTTCTAGTGTAGCCGT

AGTTAGGCCACCACTTCAAGAACTCTGTAGCACCGCCTACATACCTCGCTCTGCTAA

TCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGC

ACACAGCCCAGCTTGGAGCGAACGACCTACACCGAACTGAGATACCTACAGCGTGA

GCTATGAGAAAGCGCCACGCTTCCCGAAGGGAGAAAGGCGGACAGGTATCCGGTAA

GCGGCAGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGATTTTTGTGA

TGCTCGTCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTATCCCCTGATT

CTGTGGATAACCGTATTACCGCCTTTGAGTGAGCTGATACCGCTCGCCGCAGCCGAA

CGACCGAGCGCAGCGAGTCAGTGAGCGAGGAAGCGGAAGAGCGCCCAATACGCAA

ACCGCCTCTCCCCGCGCGTTGGCCGATTCATTAATGCAGCTGGCACGACAGGTTTCC

CGACTGGAAAGCGGGCAGTGAGCGCAACGCAATTAATGTGAGTTAGCTCACTCATT

AGGCACCCCAGGCTTTACACTTTATGCTTCCGGCTCGTATGTTGTGTGGAATTGTGA

GCGGATAACAATTTCACACAGGAAACAGCTATGACCATGATTACGCCAAGCGCGCA

ATTAACCCTCACTAAAGGGAACAAAAGCTGGAGCTGCAAGCTTAATGTAGTCTTATG

CAATACTCTTGTAGTCTTGCAACATGGTAACGATGAGTTAGCAACATGCCTTACAAG

-continued

GAGAGAAAAAGCACCGTGCATGCCGATTGGTGGAAGTAAGGTGGTACGATCGTGCC

TTATTAGGAAGGCAACAGACGGGTCTGACATGGATTGGACGAACCACTGAATTGCC

GCATTGCAGAGATATTGTATTTAAGTGCCTAGCTCGATACATAAACGGGTCTCTCTG

GTTAGACCAGATCTGAGCCTGGGAGCTCTCTGGCTAACTAGGGAACCCACTGCTTAA

GCCTCAATAAAGCTTGCCTTGAGTGCTTCAAGTAGTGTGTGCCCGTCTGTTGTGTGA

CTCTGGTAACTAGAGATCCCTCAGACCCTTTTAGTCAGTGTGGAAAATCTCTAGCAG

TGGCGCCCGAACAGGGACTTGAAAGCGAAAGGGAAACCAGAGGAGCTCTCTCGAC

GCAGGACTCGGCTTGCTGAAGCGCGCACGGCAAGAGGCGAGGGGCGGCGACTGGT

GAGTACGCCAAAAATTTTGACTAGCGGAGGCTAGAAGGAGAGAGATGGGTGCGAG

AGCGTCAGTATTAAGCGGGGGAGAATTAGATCGCGATGGGAAAAAATTCGGTTAAG

GCCAGGGGGAAAGAAAAAATATAAATTAAAACATATAGTATGGGCAAGCAGGGAG

CTAGAACGATTCGCAGTTAATCCTGGCCTGTTAGAAACATCAGAAGGCTGTAGACA

AATACTGGGACAGCTACAACCATCCCTTCAGACAGGATCAGAAGAACTTAGATCAT

TATATAATACAGTAGCAACCCTCTATTGTGTGCATCAAAGGATAGAGATAAAAGAC

ACCAAGGAAGCTTTAGACAAGATAGAGGAAGAGCAAAACAAAAGTAAGACCACCG

CACAGCAAGCGGCCGCTGATCTTCAGACCTGGAGGAGGAGATATGAGGGACAATTG

GAGAAGTGAATTATATAAATATAAAGTAGTAAAAATTGAACCATTAGGAGTAGCAC

CCACCAAGGCAAAGAGAAGAGTGGTGCAGAGAGAAAAAAGAGCAGTGGGAATAGG

AGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACA

ATTTGCTGAGGGCTATTGAGGCGCAACAGCATCTGTTGCAACTCACAGTCTGGGGCA

TCAAGCAGCTCCAGGCAAGAATCCTGGCTGTGGAAAGATACCTAAAGGATCAACAG

CTCCTGGGGATTTGGGGTTGCTCTGGAAAACTCATTTGCACCACTGCTGTGCCTTGG

AATGCTAGTTGGAGTAATAAATCTCTGGAACAGATTTGGAATCACACGACCTGGATG

GAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGG

CAAGTTTGTGGAATTGGTTTAACATAACAAATTGGCTGTGGTATATAAAATTATTCA

TAATGATAGTAGGAGGCTTGGTAGGTTTAAGAATAGTTTTTGCTGTACTTTCTATAGT

GAATAGAGTTAGGCAGGGATATTCACCATTATCGTTTCAGACCCACCTCCCAACCCC

GAGGGGACCCGACAGGCCCGAAGGAATAGAAGAAGAAGGTGGAGAGAGAGACAG

AGACAGATCCATTCGATTAGTGAACGGATCTCGACGGTATCGATTAGACTGTAGCCC

AGGAATATGGCAGCTAGATTGTACACATTTAGAAGGAAAAGTTATCTTGGTAGCAG

TTCATGTAGCCAGTGGATATATAGAAGCAGAAGTAATTCCAGCAGAGACAGGGCAA

GAAACAGCATACTTCCTCTTAAAATTAGCAGGAAGATGGCCAGTAAAAACAGTACA

TACAGACAATGGCAGCAATTTCACCAGTACTACAGTTAAGGCCGCCTGTTGGTGGGC

GGGGATCAAGCAGGAATTTGGCATTCCCTACAATCCCCAAAGTCAAGGAGTAATAG

AATCTATGAATAAAGAATTAAAGAAAATTATAGGACAGGTAAGAGATCAGGCTGAA

CATCTTAAGACAGCAGTACAAATGGCAGTATTCATCCACAATTTTAAAAGAAAAGG

GGGGATTGGGGGGTACAGTGCAGGGGAAAGAATAGTAGACATAATAGCAACAGAC

ATACAAACTAAAGAATTACAAAAACAAATTACAAAAATTCAAAATTTTCGGGTTTAT

TACAGGGACAGCAGAGATCCAGTTTGGCTGCATACGCGTCGTGAGGCTCCGGTGCC

-continued

CGTCAGTGGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAG

TAGTCGCCGTGAACGTTCTTTTTCGCAACGGGTTTGCCGCCAGAACACAGGTAAGTG

CCGTGTGTGGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGGTTGGAAG

TGGGTGGGAGAGTTCGAGGCCTTGCGCTTAAGGAGCCCCTTCGCCTCGTGCTTGAGT

TGAGGCCTGGCCTGGGCGCTGGGGCCGCCGCGTGCGAATCTGGTGGCACCTTCGCG

CCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGG

TATTTCGGTTTTTGGGGCCGCGGGCGGCGACGGGGCCCGTGCGTCCCAGCGCACATG

TTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCT

GGGCGGCAAGGCTGGCCCGGTCGGCACCAGTTGCGTGAGCGGAAAGATGGCCGCTT

CCCGGCCCTGCTGCAGGGAGCTCAAAATGGAGGACGCGGCGCTCGGGAGAGCGGGC

GGGTGAGTCACCCACACAAAGGAAAAGGGCCTTTCCGTCCTCAGCCGTCGCTTCATG

TGACTCCACTGAGTACCGGGCGCCGTCCAGGCACCTCGATTAGTTCTCGTGCTTTTG

GAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGA

ATTTGCCCTTTTTGAGTTTGGATCTTGGTTCATTCTCAAGCCTCAGACAGTGGTTCAA

AGTTTTTTTCTTCCATTTCAGGTGTCGTGAGCTAGAGCCACCATGGAGTTTGGGCTGA

GCTGGCTTTTTCTTGTGGCTATTTTAAAAGGTGTCCAGTGCGGATCCGAGGTGCAGC

TGGTGGAGTCTGGAGGAGGACTGGTGCAACCCGGTGGCTCTTTAAGACTGAGCTGC

GCCGCCTCTGGCTTCACCTTTTCTCGTCACGCTTTAACATGGGTGAGACAAGCTCCC

GGAAAGGGACTGGAGTGGGTGTCCGCCATCGACAACGCCGGCACCACCTACTACGC

CAGCTGGGCCAAGAGCAGATTCACCATCTCTCGTGACAACGCCAAGAACTCTTTATA

TTTACAGATGAACTCTTTAAGGGCCGAGGACACCGCCGTGTACTACTGCGCTCGTGT

GTTCTACGACATCAACTCCGGCTACTATTTAGACGGCATGGATTTATGGGGACCCGG

TACACTGGTCACAGTGAGCTCTGGAGGCGGAGGTAGCGGAGGCGGAGGAAGCAGC

GGTGGAGGCAGCCAGCTGGTGCTGACACAGTCCCCTTCCGCTTCCGCCTCTTTAGGA

GCCTCCGTGAAGCTGACTTGTACTTTAAGCAGCGCCCACAAAACCTACACCATCGAC

TGGTACCAGCAGCAGCCCGAGAAGGGCCCACGTTATTTAATGCAAGTTAAGTCCGA

CGGCTCCTACACCAAGGGCACCGGCGTGCCCGATAGATTCAGCGGCTCCAGCAGCG

GCGCCGATAGGTATTTAACCATCTCCTCTTTACAGAGCGAGGACGAGGCCGACTACT

ACTGTGGCGCCGACGACAACGGCGGCTACGTGTTTGGAGGCGGCACCCAGCTGACC

GTGCTGGCTAGCGGTGGCGGAGGTTCTGGAGGTGGAGGTTCCTCCGGAATCTACATC

TGGGCGCCCTTGGCCGGGACTTGTGGGGTCCTTCTCCTGTCACTGGTTATCACCCTTT

ACTGCAAACGGGGCAGAAAGAAACTCCTGTATATATTCAAACAACCATTTATGAGA

CCAGTACAAACTACTCAAGAGGAAGATGGCTGTAGCTGCCGATTTCCAGAAGAAGA

AGAAGGAGGATGTGAACTGAGAGTGAAGTTCAGCAGGAGCGCAGACGCCCCCGCGT

-continued

ACCAGCAGGGCCAGAACCAGCTCTATAACGAGCTCAATCTAGGACGAAGAGAGGA

GTACGATGTTTTGGACAAGAGACGTGGCCGGGACCCTGAGATGGGGGGAAAGCCGA

GAAGGAAGAACCCTCAGGAAGGCCTGTACAATGAACTGCAGAAAGATAAGATGGC

GGAGGCCTACAGTGAGATTGGGATGAAAGGCGAGCGCCGGAGGGGCAAGGGGCAC

GATGGCCTTTACCAGGGTCTCAGTACAGCCACCAAGGACACCTACGACGCCCTTCAC

ATGCAGGCCCTGCCCCCTCGCTAAGTCGACAATCAACCTCTGGATTACAAAATTTGT

GAAAGATTGACTGGTATTCTTAACTATGTTGCTCCTTTTACGCTATGTGGATACGCTG

CTTTAATGCCTTTGTATCATGCTATTGCTTCCCGTATGGCTTTCATTTTCTCCTCCTTG

TATAAATCCTGGTTGCTGTCTCTTTATGAGGAGTTGTGGCCCGTTGTCAGGCAACGT

GGCGTGGTGTGCACTGTGTTTGCTGACGCAACCCCCACTGGTTGGGGCATTGCCACC

ACCTGTCAGCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGCACTGACA

ATTCCGTGGTGTTGTCGGGGAAGCTGACGTCCTTTCCTTGGCTGCTCGCCTGTGTTGC

CACCTGGATTCTGCGCGGGACGTCCTTCTGCTACGTCCCTTCGGCCCTCAATCCAGC

GGACCTTCCTTCCCGCGGCCTGCTGCCGGCTCTGCGGCCTCTTCCGCGTCTTCGCCTT

CGCCCTCAGACGAGTCGGATCTCCCTTTGGGCCGCCTCCCCGCCTGGAATTCGAGCT

CGGTACCTTTAAGACCAATGACTTACAAGGCAGCTGTAGATCTTAGCCACTTTTTAA

AAGAAAAGGGGGGACTGGAAGGGCTAATTCACTCCCAACGAAGACAAGATCTGCTT

TTTGCTTGTACTGGGTCTCTCTGGTTAGACCAGATCTGAGCCTGGGAGCTCTCTGGCT

AACTAGGGAACCCACTGCTTAAGCCTCAATAAAGCTTGCCTTGAGTGCTTCAAGTAG

TGTGTGCCCGTCTGTTGTGTGACTCTGGTAACTAGAGATCCCTCAGACCCTTTTAGTC

AGTGTGGAAAATCTCTAGCAGTAGTAGTTCATGTCATCTTATTATTCAGTATTTATAA

CTTGCAAAGAAATGAATATCAGAGAGTGAGAGGAACTTGTTTATTGCAGCTTATAAT

GGTTACAAATAAAGCAATAGCATCACAAATTTCACAAATAAAGCATTTTTTTCACTG

CATTCTAGTTGTGGTTTGTCCAAACTCATCAATGTATCTTATCATGTCTGGCTCTAGC

TATCCCGCCCCTAACTCCGCCCAGTTCCGCCCATTCTCCGCCCCATGGCTGACTAATT

TTTTTTATTTATGCAGAGGCCGAGGCCGCCTCGGCCTCTGAGCTATTCCAGAAGTAG

TGAGGAGGCTTTTTTGGAGGCCTAGCTAGGGACGTACCCAATTCGCCCTATAGTGAG

TCGTATTACGCGCGCTCACTGGCCGTCGTTTTACAACGTCGTGACTGGGAAAACCCT

GGCGTTACCCAACTTAATCGCCTTGCAGCACATCCCCCTTTCGCCAGCTGGCGTAAT

AGCGAAGAGGCCCGCACCGATCGCCCTTCCCAACAGTTGCGCAGCCTGAATGGCGA

ATGGGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTTTA

GGGTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGGAG

TCCACGTTCTTTAATAGTGGACTCTTGTTCCAAACTGGAACAACACTCAACCCTATCT

CGGTCTATTCTTTTGATTTATAAGGGATTTTGCCGATTTCGGCCTATTGGTTAAAAAA

TGAGCTGATTTAACAAAAATTTAACGCGAATTTTAACAAAATATTAACGCTTACAAT

TTAGGTGGCACTTTTCGGGGAAATGTGCGCGGAACCCCTATTTGTTTATTTTTCTAAA

TACATTCAAATATGTATCCGCTCATGAGACAATAACCCTGATAAATGCTTCAATAAT

-continued

ATTGAAAAAGGAAGAGTATGAGTATTCAACATTTCCGTGTCGCCCTTATTCCCTTTTT

TGCGGCATTTTGCCTTCCTGTTTTTGCTCACCCAGAAACGCTGGTGAAAGTAAAAGA

TGCTGAAGATCAGTTGG

Antigen sequences
GFRα1

(SEQ ID NO: 115)

ATGTTCCTGGCCACCCTGTACTTCGCCCTGCCTCTGCTGGACCTGCTGCTGAGCGCCG

AAGTGAGCGGAGGAGACAGACTGGACTGCGTGAAGGCCAGCGACCAATGTCTGAA

GGAGCAATCCTGCTCCACCAAGTACAGGACACTCAGGCAGTGCGTGGCCGGAAAGG

AAACCAACTTCAGCCTGGCCAGCGGCCTCGAAGCTAAGGACGAATGCAGGAGCGCC

ATGGAGGCCCTGAAACAGAAGAGCCTGTACAACTGCAGGTGCAAGAGGGGCATGA

AGAAGGAGAAAAACTGCCTGAGGATCTACTGGAGCATGTATCAGAGCCTCCAGGGC

AACGATCTGCTGGAGGACAGCCCCTACGAGCCTGTCAACAGCAGGCTGTCCGATAT

CTTCAGGGTGGTGCCTTTCATTAGCGACGTGTTCCAGCAGGTGGAGCACATCCCCAA

AGGCAACAATTGTCTGGACGCTGCCAAAGCTTGCAACCTCGATGACATCTGTAAGA

AATACAGGAGCGCCTACATCACCCCCTGCACCACATCCGTGAGCAATGACGTGTGT

AACAGGAGGAAGTGCCACAAAGCTCTGAGGCAGTTCTTCGACAAGGTGCCTGCCAA

GCACAGCTACGGAATGCTCTTTTGCAGCTGCAGAGACATCGCCTGTACCGAGAGGA

GGAGACAAACCATCGTGCCCGTGTGCTCCTATGAAGAGAGGGAGAAACCCAACTGC

CTGAATCTGCAGGACAGCTGCAAGACCAACTACATCTGCAGGAGCAGGCTGGCCGA

CTTCTTCACCAATTGTCAGCCCGAATCCAGATCCGTGAGCTCCTGCCTGAAAGAGAA

TTATGCCGACTGCCTGCTGGCTTACAGCGGACTGATCGGCACAGTCATGACACCCAA

CTACATCGACAGCTCCTCCCTGTCCGTGGCCCCTTGGTGCGATTGCTCCAACTCCGG

CAACGACCTGGAGGAGTGTCTGAAGTTCCTGAACTTCTTCAAGGACAATACCTGCCT

CAAGAACGCCATCCAGGCTTTCGGAAACGGCAGCGACGTGACCGTGTGGCAGCCCG

CCTTTCCCGTGCAGACCACCACAGCTACCACAACCACCGCCCTGAGGGTGAAGAAT

AAGCCTCTGGGCCCCGCCGGCAGCGAGAATGAGATCCCCACACACGTGCTGCCTCC

TTGTGCCAATCTCCAGGCCCAGAAGCTGAAGTCCAACGTGAGCGGCAATACCCACC

TCTGCATCTCCAATGGCAACTACGAGAAGGAGGGACTGGGAGCCAGCAGCCACATT

ACCACCAAATCCATGGCTGCCCCTCCCAGCTGTGGACTGAGCCCTCTCCTCGTGCTG

GTGGTCACCGCCCTGTCCACACTGCTGTCCCTCACCGAGACCAGCTGA

GFRα2

(SEQ ID NO: 116)

ATGATCCTCGCCAACGTGTTCTGCCTGTTCTTTTTCCTGGACGAGACCCTGAGAAGCC

TGGCTAGCCCCTCCAGCCTCCAGGGACCTGAACTGCACGGCTGGAGGCCCCCTGTGG

ATTGCGTGAGAGCCAACGAGCTGTGCGCCGCCGAGAGCAACTGTTCCAGCAGATAC

AGGACCCTCAGACAGTGCCTGGCCGGCAGAGACAGAAACACCATGCTGGCCAACAA

GGAGTGTCAGGCCGCCCTGGAAGTGCTGCAAGAGTCCCCTCTGTACGATTGTAGGTG

CAAGAGGGGCATGAAGAAGGAACTGCAGTGCCTGCAGATCTATTGGAGCATCCATC

TGGGCCTCACCGAGGGCGAAGAATTTTATGAGGCCAGCCCCTACGAGCCCGTGACC

TCCAGACTCAGCGACATCTTCAGGCTCGCTTCCATCTTCAGCGGCACAGGCGCCGAT

CCTGTGGTGAGCGCCAAGAGCAACCATTGCCTGGACGCTGCCAAGGCCTGCAACCT

CAACGACAACTGCAAGAAGCTCAGGAGCTCCTATATCAGCATTTGCAACAGGGAGA

-continued

TTTCCCCCACCGAGAGGTGTAACAGGAGAAAGTGCCACAAGGCCCTGAGACAGTTC

TTCGACAGAGTGCCTTCCGAGTACACCTACAGGATGCTCTTCTGCAGCTGCCAGGAC

CAAGCCTGCGCTGAGAGAAGGAGGCAGACCATCCTGCCCTCCTGCAGCTACGAAGA

CAAGGAGAAGCCTAACTGCCTGGATCTCAGGGGCGTCTGCAGAACCGACCACCTCT

GTAGGTCCAGACTGGCCGACTTCCACGCCAATTGCAGGGCCAGCTACCAAACCGTG

ACCAGCTGCCCCGCCGACAACTATCAGGCCTGCCTGGGCAGCTACGCCGGCATGATT

GGCTTCGACATGACCCCCAATTACGTTGATAGCTCCCCCACAGGCATCGTGGTGAGC

CCTTGGTGCAGCTGCAGGGGCAGCGGCAACATGGAGGAAGAGTGCGAGAAGTTCCT

GAGGGACTTCACCGAGAATCCCTGCCTGAGAAACGCCATCCAGGCCTTCGGCAACG

GCACAGACGTGAACGTGTCCCCCAAAGGCCCCAGCTTTCAGGCCACCCAAGCTCCC

AGGGTCGAGAAAACCCCTTCCCTGCCCGACGACCTGAGCGATTCCACATCCCTCGGC

ACCTCCGTGATCACCACCTGCACATCCGTGCAGGAACAGGGCCTGAAGGCCAATAA

CTCCAAGGAGCTGAGCATGTGCTTCACAGAGCTGACCACCAACATTATCCCCGGCA

GCAACAAGGTGATCAAGCCCAATTCCGGACCTAGCAGAGCCAGACCCAGCGCCGCT

CTGACAGTGCTGTCCGTGCTGATGCTGAAACTGGCCCTGTGA

GFRα3

(SEQ ID NO: 117)

ATGGTGAGGCCTCTGAATCCCAGACCCCTGCCTCCCGTGGTGCTGATGCTGCTGCTG

CTGCTCCCTCCCTCCCCTCTGCCCCTGGCCGCTGGAGATCCTCTGCCCACAGAGAGC

AGACTCATGAACAGCTGCCTCCAGGCCAGGAGAAAGTGCCAGGCCGACCCTACCTG

TTCCGCCGCCTACCACCACCTGGACTCCTGCACCAGCAGCATCAGCACCCCTCTGCC

CAGCGAAGAACCCTCCGTCCCCGCTGATTGCCTGGAAGCCGCCCAGCAGCTGAGAA

ATAGCAGCCTGATCGGCTGCATGTGCCACAGAAGGATGAAGAACCAGGTGGCCTGC

CTGGATATTTACTGGACCGTCCACAGGGCCAGAAGCCTGGGAAATTACGAACTGGA

CGTGTCCCCCTACGAGGACACAGTGACAAGCAAGCCCTGGAAGATGAACCTCAGCA

AGCTGAACATGCTCAAGCCCGACAGCGACCTGTGCCTCAAATTCGCCATGCTGTGCA

CCCTGAACGACAAGTGCGACAGGCTGAGGAAAGCCTACGGAGAAGCCTGTAGCGGC

CCCCATTGCCAGAGGCACGTGTGCCTGAGACAGCTGCTGACCTTCTTCGAGAAGGCC

GCTGAGCCTCACGCCCAAGGACTGCTCCTGTGCCCTTGCGCCCCCAATGATAGGGGC

TGCGGCGAGAGGAGAAGAAACACCATCGCTCCCAACTGCGCCCTGCCCCCTGTGGC

CCCTAATTGCCTCGAGCTGAGAAGACTGTGCTTCTCCGACCCTCTGTGCAGGAGCAG

ACTGGTGGATTTCCAGACCCACTGTCACCCCATGGACATCCTCGGAACCTGCGCCAC

CGAGCAGAGCAGGTGTCTCAGAGCCTACCTGGGCCTGATCGGCACCGCCATGACCC

CCAATTTTGTGAGCAACGTGAACACCTCCGTGGCCCTGTCCTGTACCTGCAGGGGAA

GCGGCAACCTCCAGGAGGAGTGCGAGATGCTCGAGGGCTTCTTCTCCCACAATCCCT

GCCTGACCGAGGCCATCGCCGCCAAGATGAGGTTCCACAGCCAGCTGTTCTCCCAG

GATTGGCCCCACCCCACCTTCGCTGTGATGGCCCACCAGAACGAAAACCCCGCTGTG

AGACCCCAGCCTTGGGTGCCCTCCCTGTTCAGCTGCACCCTGCCTCTCATCCTGCTGC

TGAGCCTGTGGTGA

-continued

GFRα4 isoform a (SEQ ID NO: 118)

NRCVDAAEACTADARCQRLRSEYVAQCLGRAAQGGCPRARCRRALRRFFARGPPALT

HALLFCPCAGPACAERRRQTFVPSCAFSGPGPAPPSCLEPLNFCERSRVCRPRLLAFQVSC

TPAPSAPDGCLLDQGARCLRAYAGLVGTAVTPNYVDNVSARVAPWCDCGASGNRRED

CEAFRGLFTRNRCLDGAIQAFASGWPPVLLDQLNPQGDPEHSLLQVSIEGRMDPKSCDK

THTCPPCPAPEAEGAPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPENNYKATPPVL

DSDGSFFLYSKLTVDKSRWQQGNVFSCSVMHEALHNHYTQKSLSLSPGKHHHHHH

GFRα4 isoform b (SEQ ID NO: 119)

NRCVDAAEACTADARCQRLRSEYVAQCLGRAAQGGCPRARCRRALRRFFARGPPALT

HALLFCPCAGPACAERRRQTFVPSCAFSGPGPAPPSCLEPLNFCERSRVCRCARAAAGP

WRGWGRGLSPAHRPPAAQASPPGLSGLVHPSAQRPRRLPAGPGRPLPARLRGPRGVPA

GTAVTPNYVDNVSARVAPWCDCGASGNRREDCEAFRGLFTRNRCLDGAIQAFASGWPP

VLLDQLNPQGDPEHSLLQVGGGENLYFQGGGGGAGGGGDKTHTCPPCPAPELLGGPSV

FLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSR

WQQGNVFSCSVMHEALHNHYTQKSLSLSPGK

TABLE 1

| Nomenclature for heavy chain/light chain composition of humanized rabbit P4-10 antibodies |
|---|
| 0. 410HC.410LC |
| 1. H1.L3 |
| 2. H1.L3m1 |
| 3. H1m1.L3 |
| 4. H1m1.L3m1 |
| 5. H2.L2 |
| 6. H2.L2m1 |
| 7. H2m1.L2 |
| 8. H2m1.L2m1 |
| 9. H2.L1 |
| 10. H2.L1m1 |
| 11. H2m1.L1 |
| 12. H2m1.L1m1 |
| 13. H1.L1 |
| 14. H1.L1m1 |
| 15. H1m1.L1 |
| 16. H1m1.L1m1 |
| 17. H1.L3m2 |
| 18. H1.L3m3 |
| 19. H2.L2m2 |
| 20. H2.L2m3 |
| 21. H2.L1m2 |
| 22. H1.L1m2 |
| 23. H1.L2m1 |
| 24. H2.L3m1 |
| 25. H1.L1m3 |
| 26. H1.L1m4 |
| 27. H1.L3m4 |
| 28. H1.L3m5 |
| 29. H2.L1m3 |

TABLE 2

Summary of binding results to GFRα4a/GFRα4b for humanized P4-10 antibodies

| | H1 GFRα4a/ GFRα4b | H1m1 GFRα4a/ GFRα4b | H2 GFRα4a/ GFRα4b | H2m1 GFRα4a/ GFRα4b |
|---|---|---|---|---|
| L1 | –/NT | –/NT | –/NT | –/NT |
| L1m2 | –/– | | –/– | |
| L1m4 | –/– | | | |
| L1m3 | +/+ | | +/+ | |
| L1m1 | +/+ | +/+ | +/+ | +/+ |
| L2 | | | –/NT | –/NT |
| L2m3 | | | –/– | |
| L2m2 | | | –/– | |
| L2m1 | w/+ | | +/+ | +/+ |
| L3 | –/NT | –/NT | | |
| L3m3 | –/– | | | |
| L3m5 | –/– | | | |
| L3m4 | –/– | | | |
| L3m2 | w/+ | | | |
| L3m1 | +/+ | +/+ | +/+ | |

Key:
"–" no binding
"+" binding
W weak binding
NT not tested

TABLE 3

Heavy chain/light chain % amino acid identity to human VH and VL germline genes for humanized scFv 10, 14, 25 and 29.

| | % Human | |
|---|---|---|
| | Heavy chain | Light chain |
| 14. H1.L1m1 | 85 | 84 |
| 25. H1.L1m3 | 85 | 85 |
| 10. H2.L1m1 | 85 | 84 |
| 29. H2.L1m3 | 85 | 85 |

Embodiments of the Disclosure

In some aspects, the invention provides an isolated binding polypeptide comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds a glial cell derived neurotrophic factor (GDNF) family receptor alpha-4 (GFRα4). In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region comprising an amino acid sequence having at least 95-99% identity to the amino acid sequence of any of the heavy chain variable regions set forth in SEQ ID NOs: 7-10. In some embodiments, the binding polypeptide comprises a heavy chain variable region comprising at least 1, 2, or 3 modifications but not more than 20 modifications of the amino acid sequence of any of the heavy chain variable regions set forth in SEQ ID NOs: 7-10. In further embodiments, the binding polypeptide comprises a heavy chain variable region comprising an amino acid sequence of any of the heavy chain variable regions set forth in SEQ ID NOs: 7-10. In yet further embodiments, the binding polypeptide comprises a heavy chain variable region consisting of an amino acid sequence of any of the heavy chain variable regions set forth in SEQ ID NOs: 7-10.

In some embodiments, the binding polypeptide comprises a light chain variable region comprising an amino acid sequence having at least 95-99% identity to the amino acid sequence of any of the light chain variable regions set forth in SEQ ID NOs: 28-42. In some embodiments, the binding polypeptide comprises a light chain variable region comprising at least 1, 2, or 3 modifications but not more than 20 modifications of the amino acid sequence of any of the light chain variable regions set forth in SEQ ID NOs: 28-42. In further embodiments, the binding polypeptide comprises a light chain variable region comprising an amino acid sequence of any of the light chain variable regions set forth in SEQ ID NOs: 28-42. In yet further embodiments, the binding polypeptide comprises a light chain variable region consisting of an amino acid sequence of any of the light chain variable regions set forth in SEQ ID NOs: 28-42.

Provided is an isolated binding polypeptide comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

In some aspects, the invention provides a single-chain variable fragment (scFv) comprising: a heavy chain variable region that comprises three heavy chain complementarity determining regions (HCDRs), wherein HCDR1 comprises the amino acid sequence RHALT (SEQ ID NO:162), HCDR2 comprises the amino acid sequence AIDNAGTTYYASWAKS (SEQ ID NO:163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides a single-chain variable fragment (scFv) comprising: a heavy chain variable region comprising the amino acid sequence of any of the heavy chain variable regions set forth in SEQ ID NOs: 7-10; and a light chain variable region comprising the amino acid sequence of any of the light chain variable regions set forth in SEQ ID NOs: 28-42.

In some aspects, the invention provides a single chain variable fragment comprising any one of the amino acid sequences set forth in SEQ ID NOs: 74-102. Also provided is a is a single chain variable fragment consisting of any one of the amino acid sequences set forth in SEQ ID NOs: 74-102.

In some aspects, the invention provides an isolated nucleic acid encoding the binding polypeptide or scFv of any preceding embodiment.

In some aspects, the invention provides an isolated nucleic acid encoding a binding polypeptide comprising:

a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the binding polypeptide binds GFRα4a and GFRα4b. In further embodiments, the binding polypeptide comprises an antibody or an antigen-binding fragment thereof. In yet further embodiments, the antigen-binding fragment is selected from the group consisting of a Fab, a single-chain variable fragment (scFv), or a single-domain antibody.

In some embodiments, the antibody is a full-length antibody. In some embodiments, the antibody or antigen-binding fragment is a humanized antibody or an antigen-binding fragment thereof.

In some embodiments, the binding polypeptide comprises a heavy chain variable region encoded by a nucleotide sequence having at least 95-99% identity to the nucleotide sequence of any of the heavy chain variable regions set forth in SEQ ID NOs: 2-5. In further embodiments, the binding polypeptide comprises a heavy chain variable region encoded by a nucleotide sequence comprising any of the heavy chain variable region sequences provided in SEQ ID NOs: 2-5. In yet further embodiments, the binding polypeptide comprises a heavy chain variable region encoded by a nucleotide sequence consisting of any of the heavy chain variable region sequences provided in SEQ ID NOs: 2-5.

In some embodiments, the binding polypeptide comprises a light chain variable region encoded by a nucleotide sequence having at least 95-99% identity to the nucleotide sequence of any of the light chain variable regions provided in SEQ ID NOs: 12-26. In further embodiments, the binding polypeptide comprises a light chain variable region encoded by a nucleotide sequence comprising any of the light chain variable region sequences provided in SEQ ID NOs: 12-26. In yet further embodiments, the binding polypeptide comprises a light chain variable region encoded by a nucleotide sequence consisting of any of the light chain variable region sequences provided in SEQ ID NOs: 12-26.

In some aspects, the invention provides an isolated nucleic acid encoding a binding polypeptide comprising:

a heavy chain variable region encoded by any of the nucleotide sequences set forth in SEQ ID NO: 2-5; and a light chain variable region encoded by any of the nucleotide sequences set forth in SEQ ID NO: 12-26.

In some aspects, the invention provides an isolated nucleic acid encoding a single-chain variable fragment (scFv) comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides an isolated nucleic acid encoding a single-chain variable fragment (scFv) comprising: a heavy chain variable region comprising any of the nucleotide sequences set forth in SEQ ID NO: 2-5; and a light chain variable region comprising any of the nucleotide sequences set forth in SEQ ID NO: 12-26. Also provided is an isolated nucleic acid encoding a single-chain variable fragment (scFv) comprising any one of the nucleotide sequences set forth in SEQ ID NOs: 43-72. Also provided is an isolated nucleic acid encoding a single-chain variable fragment (scFv) consisting of any one of the nucleotide sequences set forth in SEQ ID NOs: 43-72.

In some aspects, the invention provides a vector comprising the isolated nucleic acid of any one of the preceding embodiments. In further embodiments, the vector is an expression vector. In yet further embodiments, the vector is selected from the group consisting of a DNA vector, an RNA vector, a plasmid, a lentiviral vector, an adenoviral vector, an adeno-associated viral vector, and a retroviral vector.

In some aspects, the invention provides a host cell comprising the vector of any one of the preceding embodiments. In further embodiments, the host cell is of eukaryotic or prokaryotic origin. In some embodiments, the host cell is of mammalian origin. In some embodiments, the host cell is of bacterial origin.

In some aspects, the invention provides a pharmaceutical composition comprising the binding polypeptide or scFv of any one of the preceding embodiments. Also provided is a pharmaceutical composition comprising the antibody or an antigen-binding fragment of any one of the preceding embodiments.

In some aspects, the invention provides a chimeric chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody.

In some embodiments, the antibody or antigen-binding fragment is a humanized antibody or a fragment thereof. In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42. In some embodiments, the antigen binding domain comprises a light chain variable region comprising at least 1, 2, or 3 modifications but not more than 20 modifications of the amino acid sequence of any of the light chain variable regions set forth in SEQ ID NOs: 28-42. In further embodiments, the antigen binding domain comprises a light chain variable region comprising an amino acid sequence of any of the light chain variable regions set forth in SEQ ID NOs: 28-42. In yet further embodiments, the antigen binding domain comprises a light chain variable region consisting of an amino acid sequence of any of the light chain variable regions set forth in SEQ ID NOs: 28-42.

In some aspects, the invention provides a chimeric antigen receptor (CAR) comprising an antigen binding domain, a transmembrane domain, and an intracellular domain, wherein the antigen binding domain comprises: a heavy chain variable region comprising any of the amino acid sequences set forth in SEQ ID NO: 7-10; and a light chain variable region comprising any of the amino acid sequences set forth in SEQ ID NO: 28-42.

In some aspects, the invention provides a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

In some aspects, the invention provides a chimeric antigen receptor (CAR) comprising: an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

In some aspects, the invention provides a chimeric antigen receptor (CAR) comprising: an antigen binding domain comprising: a heavy chain variable region comprising any of the amino acid sequences set forth in SEQ ID NO: 7-10; and a light chain variable region comprising any of the amino acid sequences set forth in SEQ ID NO: 28-42; a CD8 transmembrane domain; a 4-1BB costimulatory domain; and a CD3ζ intracellular signaling domain.

In some aspects, the invention provides a chimeric antigen receptor (CAR) comprising any one of the amino acid sequences set forth in SEQ ID NOs: 107-110. Also provided is a chimeric antigen receptor (CAR) consisting of any one of the amino acid sequences set forth in SEQ ID NOs: 107-110.

In some aspects, the invention provides a nucleic acid encoding for the CAR of any one of the preceding embodiments.

In some aspects, the invention provides a nucleic acid encoding a chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region encoded by a nucleotide sequence having at least 95-99% identity to the nucleotide sequence of any of the heavy chain variable regions set forth in SEQ ID NOs: 2-5. In some embodiments, the antigen binding domain comprises a heavy chain variable region encoded by a nucleotide sequence comprising any of the heavy chain variable region sequences set forth in SEQ ID NOs: 2-5. In further embodiments, the antigen binding domain comprises a heavy chain variable region encoded by a nucleotide sequence consisting of any of the heavy chain variable region sequences set forth in SEQ ID NOs: 2-5.

In some embodiments, the antigen binding domain comprises a light chain variable region encoded by a nucleotide sequence having at least 95-99% identity to the nucleotide sequence of any of the light chain variable regions set forth in SEQ ID NOs: 12-26. In some embodiments, the antigen binding domain comprises a light chain variable region encoded by a nucleotide sequence comprising any of the light chain variable region sequences set forth in SEQ ID NOs: 12-26. In further embodiments, the antigen binding domain comprises a light chain variable region encoded by a nucleotide sequence consisting of any of the light chain variable region sequences set forth in SEQ ID NOs: 12-26.

In some aspects, the invention provides a nucleic acid encoding a chimeric antigen receptor (CAR) comprising an antigen binding domain, a transmembrane domain, and an intracellular domain, wherein the antigen binding domain comprises: a heavy chain variable region encoded by any of the nucleotide sequences set forth in SEQ ID NO: 2-5; and a light chain variable region encoded by any of the nucleotide sequences set forth in SEQ ID NO: 12-26.

In some aspects, the invention provides a nucleic acid encoding a chimeric antigen receptor (CAR) comprising an antigen binding domain, a transmembrane domain, and an intracellular signaling domain, wherein the antigen binding domain is encoded by any one of the nucleotide sequences set forth in SEQ ID NOs: 103-106.

In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In some embodiments, the costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcγRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

In some aspects, the invention provides a nucleic acid encoding a chimeric antigen receptor (CAR) comprising: an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

Provided is a nucleic acid encoding a chimeric antigen receptor (CAR) comprising: an antigen binding domain comprising: a heavy chain variable region encoded by any of the nucleotide sequences set forth in SEQ ID NO: 2-5; and a light chain variable region encoded by any of the nucleotide sequences set forth in SEQ ID NO: 12-26; a CD8 transmembrane domain; a 4-1BB costimulatory domain; and a CD3ζ intracellular signaling domain.

In some aspects, the invention provides a nucleic acid encoding a chimeric antigen receptor (CAR) comprising any one of the nucleotide sequences set forth in SEQ ID NOs: 111-114.

In some aspects, the invention provides a nucleic acid encoding a chimeric antigen receptor (CAR) consisting of any one of the nucleotide sequences set forth in SEQ ID NOs: 111-114.

In some aspects, the invention provides a vector comprising the nucleic acid of any one of the preceding embodiments. In some embodiments, the vector is an expression vector. In some embodiments, the vector is selected from the group consisting of a DNA vector, an RNA vector, a plasmid, a lentiviral vector, an adenoviral vector, an adeno-associated viral vector, and a retroviral vector. In some embodiments, the vector further comprises an EF-1 a promoter. In some embodiments, the vector further comprises a woodchuck hepatitis virus posttranscriptional regulatory element (WPRE). In further embodiments, the vector further comprises a rev response element (RRE). In further embodiments, the vector further comprises a cPPT sequence. In yet further embodiments, the vector is a self-inactivating vector.

In some aspects, the invention provides a cell comprising the CAR of any one of the preceding embodiments, the nucleic acid of any one of the preceding embodiments, or the vector of any one of the preceding embodiments. In some embodiments, the cell is selected from the group consisting of a T cell, a natural killer (NK) cell, a cytotoxic T lymphocyte (CTL), and a regulatory T cell.

In some aspects, the invention provides the CAR of any one of the preceding embodiments, the nucleic acid of any one of the preceding embodiments, the vector of any one of the preceding embodiments, or the cell of any one of the preceding embodiments, for use in the treatment of a disease associated with expression of a thyroid cell antigen.

In some aspects, the invention provides a modified immune cell or precursor cell thereof, comprising a chimeric antigen receptor (CAR) comprising an antigen binding domain, a transmembrane domain, and an intracellular domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some embodiments, the CAR binds GFRα4a and GFRα4b. In some embodiments, the antigen binding domain comprises an antibody or an antigen-binding fragment thereof. In some embodiments, the antigen-binding fragment is selected from the group consisting of a Fab, a single-chain variable fragment (scFv), or a single-domain antibody. In further embodiments, the antibody is a full-length antibody. In yet further embodiments, the antibody or antigen-binding fragment is a humanized antibody or a fragment thereof.

In some embodiments, the antigen binding domain comprises a heavy chain variable region comprising an amino acid sequence having at least 95-99% identity to the amino acid sequence of any of the heavy chain variable regions set forth in SEQ ID NOs: 7-10. In some embodiments, the antigen binding domain comprises a heavy chain variable region comprising at least 1, 2, or 3 modifications but not more than 20 modifications of the amino acid sequence of any of the heavy chain variable regions set forth in SEQ ID NOs: 7-10. In further embodiments, the antigen binding domain comprises a heavy chain variable region comprising an amino acid sequence of any of the heavy chain variable regions set forth in SEQ ID NOs: 7-10. In yet further embodiments, the antigen binding domain comprises a heavy chain variable region consisting of an amino acid sequence of any of the heavy chain variable regions set forth in SEQ ID NOs: 7-10.

In some embodiments, the antigen binding domain comprises a light chain variable region comprising an amino acid sequence having at least 95-99% identity to the amino acid sequence of any of the light chain variable regions set forth in SEQ ID NOs: 28-42.

In some aspects, the invention provides the cell of any one of the preceding embodiments, wherein the antigen binding domain comprises a light chain variable region comprising at least 1, 2, or 3 modifications but not more than 20 modifications of the amino acid sequence of any of the light chain variable regions set forth in SEQ ID NOs: 28-42. Provided is the cell of any one of the preceding embodiments, wherein the antigen binding domain comprises a light chain variable region comprising an amino acid sequence of any of the light chain variable regions set forth in SEQ ID NOs: 28-42. In some embodiments, the antigen binding domain comprises a light chain variable region consisting of an amino acid sequence of any of the light chain variable regions set forth in SEQ ID NOs: 28-42.

In some aspects, the invention provides a modified immune cell or precursor cell thereof, comprising a chimeric antigen receptor (CAR) comprising an antigen binding domain, a transmembrane domain, and an intracellular domain, wherein the antigen binding domain comprises: a heavy chain variable region comprising any of the amino acid sequences set forth in SEQ ID NO: 7-10; and a light chain variable region comprising any of the amino acid sequences set forth in SEQ ID NO: 28-42.

Also provided is a modified immune cell or precursor cell thereof, comprising a chimeric antigen receptor (CAR) comprising an antigen binding domain, a transmembrane domain, and an intracellular signaling domain, wherein the antigen binding domain comprises any one of the amino acid sequences set forth in SEQ ID NOs: 74-102. In some embodiments, the transmembrane domain is selected from the group consisting of an artificial hydrophobic sequence, and a transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, OX40 (CD134), 4-1BB (CD137), and CD154. In some embodiments, the transmembrane domain comprises a transmembrane domain of CD8. In some embodiments, the CAR further comprises a hinge domain. In further embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of a CD8 hinge, or any combination thereof. In yet further embodiments, the artificial hinge domain is a glycine/serine (GS)-rich linker comprising GGGGSGGGGS (SEQ ID NO: 168).

In some embodiments, the intracellular domain comprises a costimulatory signaling domain and an intracellular signaling domain. In some embodiments, the costimulatory signaling domain comprises a costimulatory domain of a protein selected from the group consisting of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof. In some embodiments, costimulatory signaling domain comprises a costimulatory domain of 4-1BB. In further embodiments, the intracellular signaling domain comprises an intracellular domain selected from the group consisting of cytoplasmic signaling domains of a human CD3 zeta chain (CD3ζ), FcyRIII, FcsRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof. In yet further embodiments, the intracellular signaling domain comprises an intracellular domain of CD3ζ.

In some aspects, the invention provides a modified immune cell or precursor cell thereof, comprising a chimeric antigen receptor (CAR) comprising: an antigen binding domain comprising: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO:164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167); a CD8 transmembrane domain; a 4-1BB costimulatory domain; and a CD3ζ intracellular signaling domain.

In some aspects, the invention provides a modified immune cell or precursor cell thereof, comprising chimeric antigen receptor (CAR) comprising an antigen binding domain comprising: a heavy chain variable region comprising any of the amino acid sequences set forth in SEQ ID NO: 7-10; a light chain variable region comprising any of the amino acid sequences set forth in SEQ ID NO: 28-42; a CD8 transmembrane domain; a 4-1BB costimulatory domain; and a CD3ζ intracellular signaling domain.

In some aspects, the invention provides a modified immune cell or precursor cell thereof, comprising a chimeric antigen receptor (CAR) comprising any one of the amino acid sequences set forth in SEQ ID NOs: 107-110.

In some aspects, the invention provides a modified immune cell or precursor cell thereof, comprising a chimeric antigen receptor (CAR) consisting of any one of the amino acid sequences set forth in SEQ ID NOs: 107-110.

In some embodiments, the modified cell is a modified immune cell. In some embodiments, the modified cell is a modified T cell. In some embodiments, the modified cell is an autologous cell. In further embodiments, the modified cell is an autologous cell obtained from a human subject.

In some aspects, the invention provides a pharmaceutical composition comprising a therapeutically effective amount of the modified cell of any one of the preceding embodiments.

In some aspects, the invention provides a method of treating a disease in a subject in need thereof, comprising administering to the subject an effective amount of the cell of any one of the preceding embodiments, or the pharmaceutical composition of any one of the preceding embodiments. In some embodiments, the disease is associated with expression of a thyroid cell antigen. In further embodiments, the disease is associated with expression of GFRα4. In yet further embodiments, the disease is a cancer. In yet further embodiments, the cancer is medullary thyroid carcinoma (MTC) or a metastasis resulting from MTC.

In some aspects, the invention provides a method of treating a disease associated with expression of a thyroid cell antigen in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides a method of treating a GFRα4-associated disease in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

In some aspects, the invention provides a method of treating medullary thyroid cancer (MTC) in a subject in need thereof, comprising administering to the subject an effective amount of a T cell comprising a chimeric antigen receptor (CAR) comprising an antigen binding domain, a transmembrane domain, and an intracellular signaling domain, wherein the antigen binding domain comprises: a heavy chain variable region that comprises three heavy chain complementarity determining regions (HCDRs), wherein HCDR1 comprises the amino acid sequence RHALT (SEQ ID NO: 162), HCDR2 comprises the amino acid sequence AIDNAGTTYYASWAKS (SEQ ID NO: 163), and HCDR3 comprises the amino acid sequence VFYDINSGYYLDGMDL (SEQ ID NO: 164); and a light chain variable region that comprises three light chain complementarity determining regions (LCDRs), wherein LCDR1 comprises the amino acid sequence SAHKTYT (SEQ ID NO: 165), LCDR2 comprises the amino acid sequence VKSDGSY (SEQ ID NO: 166), and LCDR3 comprises the amino acid sequence GADDNGGYV (SEQ ID NO: 167).

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore specifically point out the preferred embodiments of the present invention and are not to be construed as limiting in any way the remainder of the disclosure.

Example 1: In Silico Design of Humanized Versions of Rabbit P4-10 Antibody

Rabbit and human antibodies comprise heterodimers of heavy chains and light chains. In both humans and rabbits, the heavy chain variable region is encoded by the rearrangement of 3 germline genes designated $V_H$, D and $J_H$. In the human repertoire, there are approximately 70 $V_H$ gene segments, approximately 25 D gene segments, and 7 $J_H$ segments. During B cell development in the bone marrow, a given B cell selects one $V_H$ gene segment, one D segment, and one $J_H$ segment and splices them together to form a single gene that encodes the entire heavy chain variable region. With respect to FRs and CDRs, the $V_H$ gene segment contributes FR1-CDR1-FR2-CDR2-FR3, the D gene contributes the bulk of CDR3, and the $J_H$ gene contributes the bulk of FR4. During the splicing process, nucleotides can be added or removed at the junctions between the $V_H$ and D gene segments and between the D and $J_H$ gene segments that can result in increases or decreases in the number of amino acid residues in the CDR3, or shift the reading frame of the CDR3 entirely, creating yet additional diversity.

Light chain variable regions are also encoded by rearranged genes, though there are no light chain D gene segments, just $V_L$'s and $J_L$'s. In humans and rabbits, there are 2 classes of light chains—kappa and lambda—and thus their genomes comprise 2 distinct sets of light chain germline genes. A given B cell expresses either a kappa or lambda light chain paired with the heavy chain whose gene was rearranged as described above. During B cell development in humans, a kappa light gene is created through the selection and splicing together of 1 of approximately 30 Vkappa gene segments and 1 of 5 Jkappa gene segments. A lambda light chain gene is created through the selection and splicing together of 1 of approximately 30 Vlambda gene segments and 1 of 7 Jlambda gene segments. The rabbit anti-GFRα4 antibody P4-10 which humanization is described herein comprises a lambda light chain.

Figure 1B:
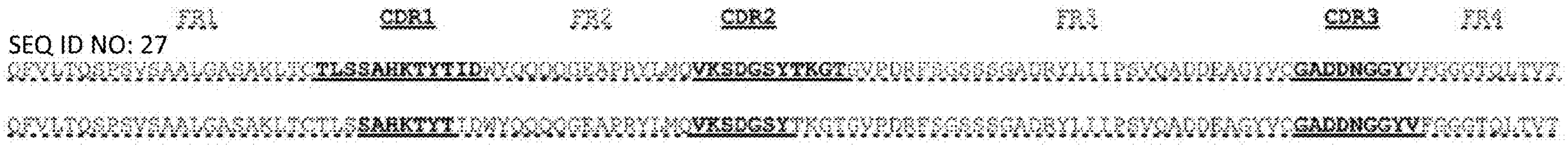

The amino acid sequences for the heavy and light chain variable regions of the rabbit antibody P4-10 are shown in FIG. 1. One approach for humanizing rabbit P4-10 would be to retain the 6 rabbit antigen-contacting CDR sequences but replace the bulk of the heavy and light chain variable regions with framework sequences chosen from human germline genes that are closest in identity to the original rabbit framework residues. In order to accomplish this, it is first necessary to identify framework and CDR regions in rabbit antibody P4-10. Using two different conventions used in the art for identifying CDR regions—Kabat and IMGT nomenclatures—the 4 FRs (plain text, dashed underlines) and 3 CDRs (bold text and solid underlines) are shown for the P4-10 heavy chain (FIG. 1A) and P4-10 light chain (FIG. 1B). The internet tool IgBlast (ncbi.nlm.nih.gov) was used to identify CDR regions using either Kabat or IMGT nomenclatures.

The process of humanizing rabbit P4-10 utilized several approaches for identifying prospective human heavy and light chain germline sequences to combine with rabbit CDRs. Each construct would be designed in silico, synthesized as a single-chain Fv (scFv) antibody gene fragment, expressed in *E coli*, and tested for binding to the GFRα4 antigen.

In order to select human VH and VL germline genes based on amino acid identity to rabbit P4-10 VH and VL, a search was performed using an internet tool that analyzed the P4-10 heavy and light chain amino acid sequences and identified the closest human heavy and light chain germline VH or Vλ based on amino acid sequence identity to the rabbit antibody. Once identified, potential humanized versions of P4-10 could be designed in silico by replacing the 2 human heavy chain CDRs and 2 human light chain CDRs with their P4-10 rabbit counterparts. Human heavy and light chain CDR3 and FR4 regions would then be appended after the VH or Vλ to complete the variable region sequences.

Figure 2A:
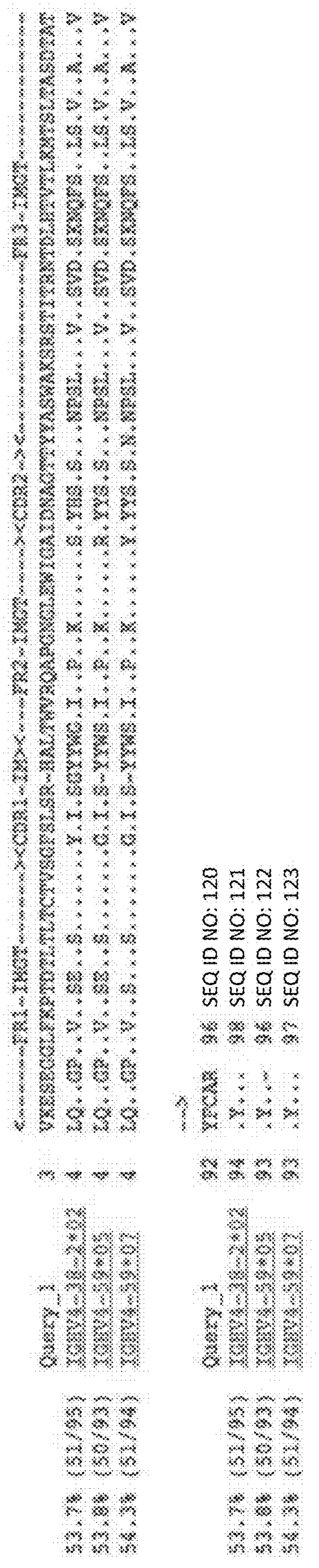
FIGS. 2A-2B illustrate the alignments of rabbit P4-10 anti-GFRα4 antibody variable regions with human variable region genes with closest homology. P4-10 heavy chain (FIG. 2A) (SEQ ID NO: 120) or light chain (FIG. 2B) (SEQ ID NO: 124) amino acid sequences ("Query 1") were submitted to IgBlast to identify human VH or VL genes with greatest amino acid identity. The search returned human VH and VL genes that encode proteins with the greatest amino acid identity to the VH (SEQ ID NOs: 121-123) or VL (SEQ ID NOs: 125-126) queries. Percent identity and number of identical amino acids/total amino acids indicated to the left of the name of each human heavy or light chain gene.

Using IgBlast (ncbi.nlm.nih.gov), a search of rabbit P4-10 VH identified the closest human VH germline genes based on amino acid sequence identity. FIG. 2A shows the 3 top candidates all with amino acid identities of ~54%. IGHV4-38-2*02 was chosen over IGHV4-59*05 and *07 because the former has only 2 human polymorphisms and the latter has 10 (see the Locus and Genes listing for the IMGTrepertoire, imgt.org). It was reasoned that increased polymorphisms could lead to increased immunogenicity since the version of IGHV4-59 we might choose could be different than the polymorphic variant(s) present in a given patient.

Figure 2B:
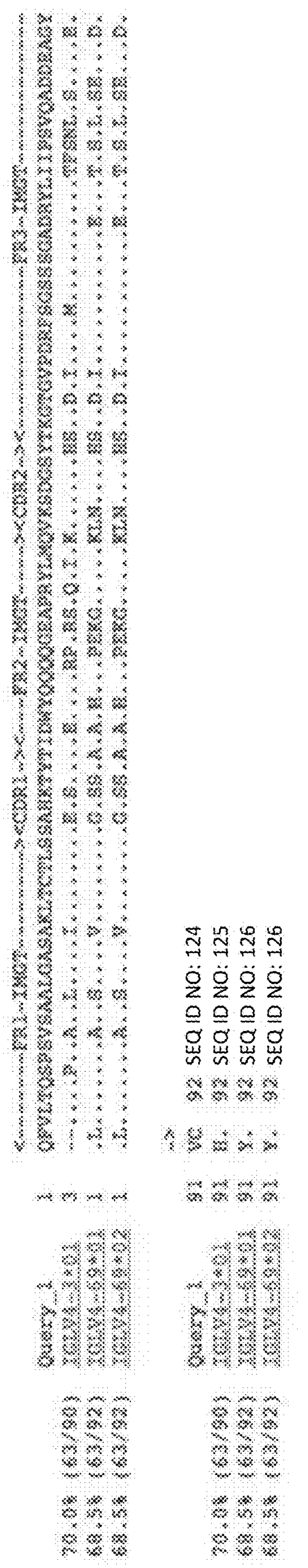

A search of rabbit P4-10 VL identified human Vλ IGLV4-3*01 as a closest match (FIG. 2B). Further analysis of this germline gene revealed that it has a stop codon in its CDR3 (see the entry for human IGLV4-3, imgt.org) as shown in FIG. 3B (bottom line, stop codon indicated by an asterisk) suggesting that antibodies attempting to use this germline gene would not be present in vivo. Because of this, without wishing to be bound by theory, it was hypothesized that a humanized antibody based on the human light chain Vλ gene IGLV4-3*01 might be immunogenic. Therefore, the second closest human Vλ germline gene, IGLV4-69*01 was selected.

In order to select human VH and VL germline genes based on pairing frequency, additional human variable region germline genes were selected as possible structural frameworks on which to build humanized versions of rabbit P4-10 by considering pairing frequencies observed in vivo of human heavy and light chains based on germline gene of origin. Use of such pairs might produce antibody variable regions that were more stable. For example, the human light chain Vλ IGLV4-69*01 identified above is most commonly found paired with a heavy chain encoded by VH germline gene IGHV3-48*03 (DeKosky et al. (2016) *Proc Natl Acad Sci* 113:E2636-E2645). Therefore, germline gene IGHV3-48*03 was added to germline gene IGHV4-38-2*02 as a potential candidate on which to graft the rabbit heavy chain CDRs. An alignment of rabbit P4-10 VH with each of these human germline genes is shown in FIG. 3A with their % homologies to the original rabbit sequence indicated. Since these are VH germline gene segments, CDR3 and FR4 regions are not part of this analysis and not shown in the figure. Similarly, for selection of additional human Vλ genes, a review of the literature revealed that human VH germline gene IGHV4-38-2 is seen commonly paired with light chain Vλ germline gene IGLV2-14*01, and human heavy chain VH germline gene IGHV3-48*03 is commonly paired with human light chain Vλ germline gene IGLV1-44*01 (DeKosky et al. (2016) *Proc Natl Acad Sci.* 113: E2636-E2645). An alignment of rabbit P4-10 light chain VL region is shown with each of these human germline genes in FIG. 3B. Unlike VH germline genes, VL germline genes include most of the light chain CDR3 (light chains do not use D gene segments as do heavy chains). Like heavy chains, FR4 is not part of this analysis and not shown in the figure.

Repertoires of humanized rabbit P4-10 VH and VL were then created using human germline genes, CDR substitution, and back mutation to rabbit amino acid residues. To create humanized versions of rabbit P4-10 heavy and light chain variable regions, the rabbit CDRs could be substituted into the human germline genes, however, it was unpredictable as to whether the resultant collection of heavy and light chains when paired together in different combinations would retain binding to antigen. As can be seen in FIG. 3, the rabbit and human CDRs do not precisely line up within the sequences of VH or VL, the corresponding rabbit/human CDRs are of different lengths, and even the precise identification of rabbit CDRs varies depending on whether one uses Kabat or IMGT definitions for CDR. Furthermore, the importance of retaining additional rabbit amino acids that flank the P4-10 rabbit CDRs is not obvious nor is the potential importance of retaining certain rabbit framework region amino acids that may contribute to antigen binding as described in the literature. Even without these considerations, it can be seen that the overall lengths of the P4-10 heavy and light chains are not the same as their closest matching human counterparts (gaps indicated with dashes in FIG. 3) so that it is not clear that the human frameworks even in the most ideal alignments would position the rabbit CDRs appropriately in space to retain affinity for the GFRα4 antigen. To address these potentially confounding issues, collections of humanized versions of rabbit P4-10 were designed that started with straightforward CDR substitutions into a human germline gene and then continued by "back mutating" to rabbit amino acid residues to decrease the degree of "humanness" and potential disruption to the ability to bind to antigen. Overall, this comprised an iterative process by which variable region sequences were designed in silico, expressed as scFv, and tested for binding to antigen as described in the examples below. For example, FIG. 4 shows the creation of heavy chains H1 and H2 derived from substitution of rabbit CDR1 and CDR2 into human germline VH genes IGHV-38-2*02 and IGHV3-48*03, respectively. These idealized humanized versions of rabbit P4-10 VH brought the degree of identity match between rabbit and human from 54% to 85% for IGHV4-38-2*02 and 51% to 85% for IGHV3-48*03 (see the DomainGapAligntool at imgt.org). Less human versions of H1 and H2 were then designed by substituting certain amino acid residues back to their rabbit counterparts from the original P4-10 antibody. This resulted in the design of H1m3, H1m2, and H1m1 that show sequence identities to P4-10 heavy chain of decreasing percentage as shown (back-mutated amino acids shown in white lettering with dark background). The positions and priority of which amino acid residues to "back mutate" were based in part on the significance of certain rabbit heavy chain amino acid residue positions described in the literature, notably the identification of non-CDR antigen-contacting loops in FR3 of both rabbit heavy and light chains (Zhang and Ho (2017) *MABS,* 9:419-429).

Similarly, for the light chain, FIG. 5 illustrates the design of light chains L1, L2, and L3 from direct substitution of CDR1, CDR2, and CDR3 from rabbit P4-10 into human Vλ germline genes along with sets of rabbit back-mutated versions.

Example 2: Expression of Humanized Rabbit P4-10 Variants as scFv and Testing for Binding to Antigen In order to test whether in silico-designed humanized VH and Vλ retained binding to GFRα4, an initial cohort of VH/Vλ pairs were created that (1) took into account the germline derivation of those heavy and light chains that pair most frequently in vivo and (2) paired the most human and least human heavy and light chains as a starting point. This resulted in the creation of 16 scFvs numbered 1 through 16 as listed in Table 1. To express these 16 scFvs along with the original rabbit P4-10 as a positive control (numbered "0" in Table 1), the nucleotide sequence for each scFv was synthesized in the order Vλ-VH where the gene block was flanked by SfiI restriction enzyme sites for cloning into the pComb3X phagemid vector, and the light and heavy chain variable regions were separated by a nucleic acid sequence encoding the linker "GGSSRSSSSGGGGSGGGG" (SEQ ID NO: 169) (Andris-Widhoff, et al. (2001) Phage Display: A Laboratory Manual, Chapter 9, Cold Spring Harbor Press). For gene block synthesis of each scFv (Genewiz, South Plainfield, NJ), rabbit P4-10 heavy chain CDR3 and FR4 (FIG. 1A) were appended to the amino acid sequences for each VH in FIG. 4. For gene block synthesis of the light chains, rabbit P4-10 light chain FR4 was appended to the amino acid sequences for each Vλ in FIG. 5. The only change to light chain FR4 was substitution of the terminal threonine (T, FIG. 1B) by leucine (L), an amino acid residue that can be found in that position in both rabbit and human lambda light chain FR4 regions (IMGT Repertoire, www.imgt.org). For gene block synthesis of all scFv, human codon usage was used.

After restriction digestion and agarose gel purification of scFv gene blocks, Vλ-VH constructs were ligated into SfiI-digested pComb3X as described (Andris-Widhoff, Steinberger, Fuller, Rader, and Barbas in Phage Display: A Laboratory Manual, Chapter 9, Cold Spring Harbor Press, 2001). Ligated DNA was electroporated into the ER2738 strain of *E. coli*, and transformed bacterial colonies were grown in culture and rescued with VCSM13 helper phage to create phage particles expressing recombinant scFv linked to the pIII M13 coat protein (Rader, Steinberger, and Barbas in Phage Display: A Laboratory Manual, Chapter 10, Cold Spring Harbor Press, 2001).

To screen phage-displayed scFvs for binding to the two isoforms of GFRα4, isoform "a" (GFRα4a) and isoform "b" (GFRα4b), phage ELISAs were performed where the binding of scFv to antigen-coated plates was detected with a horseradish peroxidase-conjugated anti-M13 monoclonal antibody (Steinberger, Rader, and Barbas in Phage Display: A Laboratory Manual, Chapter 11, Cold Spring Harbor Press, 2001). To perform these ELISAs, the GFRα4a isoform comprising a portion of GFRα4a (Asn24-Ser245, UniProt accession #Q9GZZ7-2) was used, followed by a Factor Xa cleavage site/linker, a portion of optimized IgG1 Fc domain (Pro100-Lys330), and 6 His residues for purification. The GFRα4b isoform comprised a portion of GFRα4b (Asn24-Val274, UniProt #Q9GZZ7-1), followed by a TEV cleavage site linker, and a portion of human IgG1 Fc domain (Asp104-Lys330).

Figure 6:
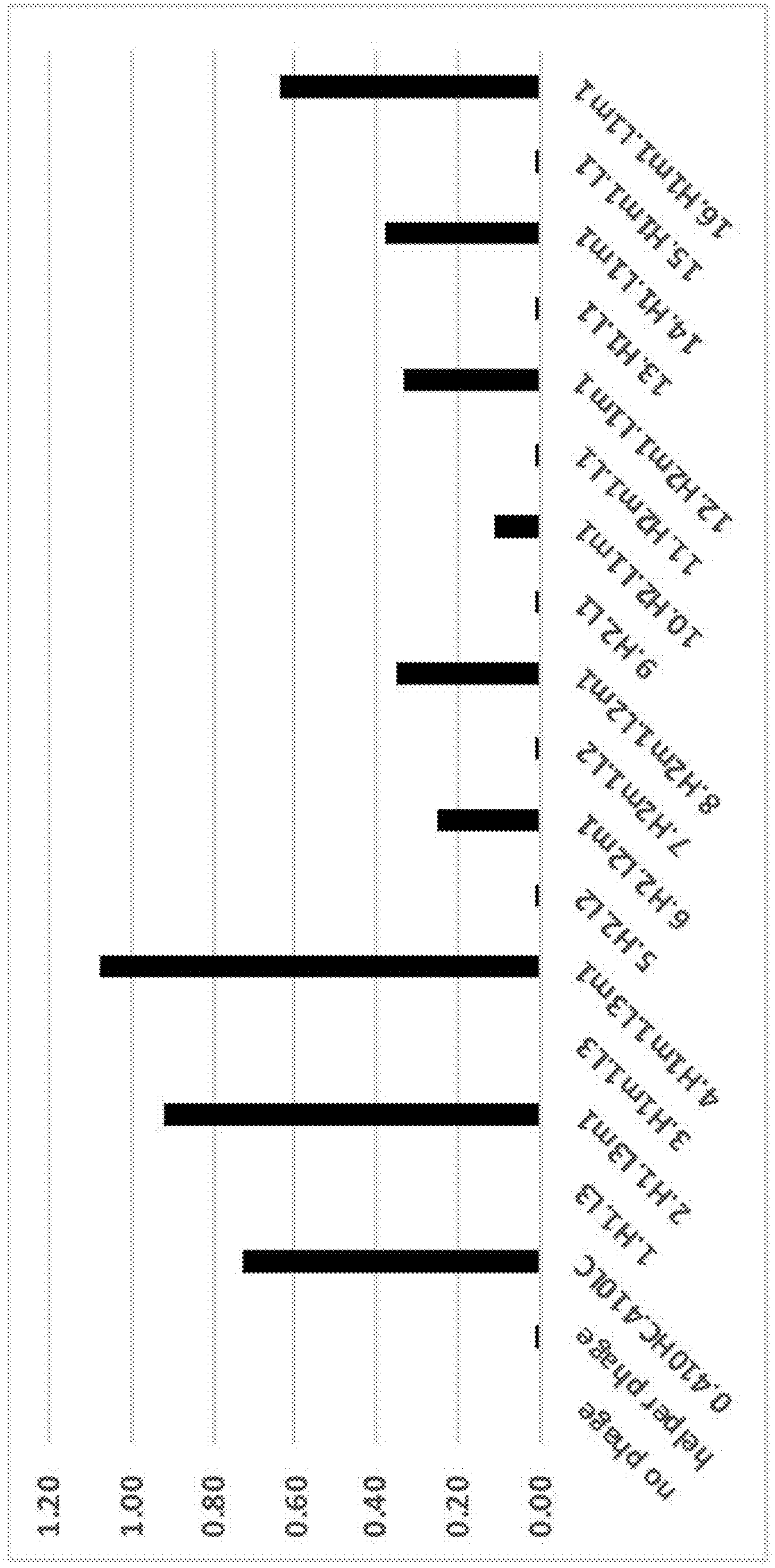
FIG. 6 is a graph illustrating the binding of humanized scFv 1 through 16 to immobilized GFRα4 isoform a (GFR4α4a) as measured by ELISA. "410HC.410LC" is an scFv of the original rabbit antibody for comparison. scFV names include the heavy and light chains of which they are comprised (e.g. "H1.L3" is heavy chain "H1" and light chain "L3").
Figure 7:
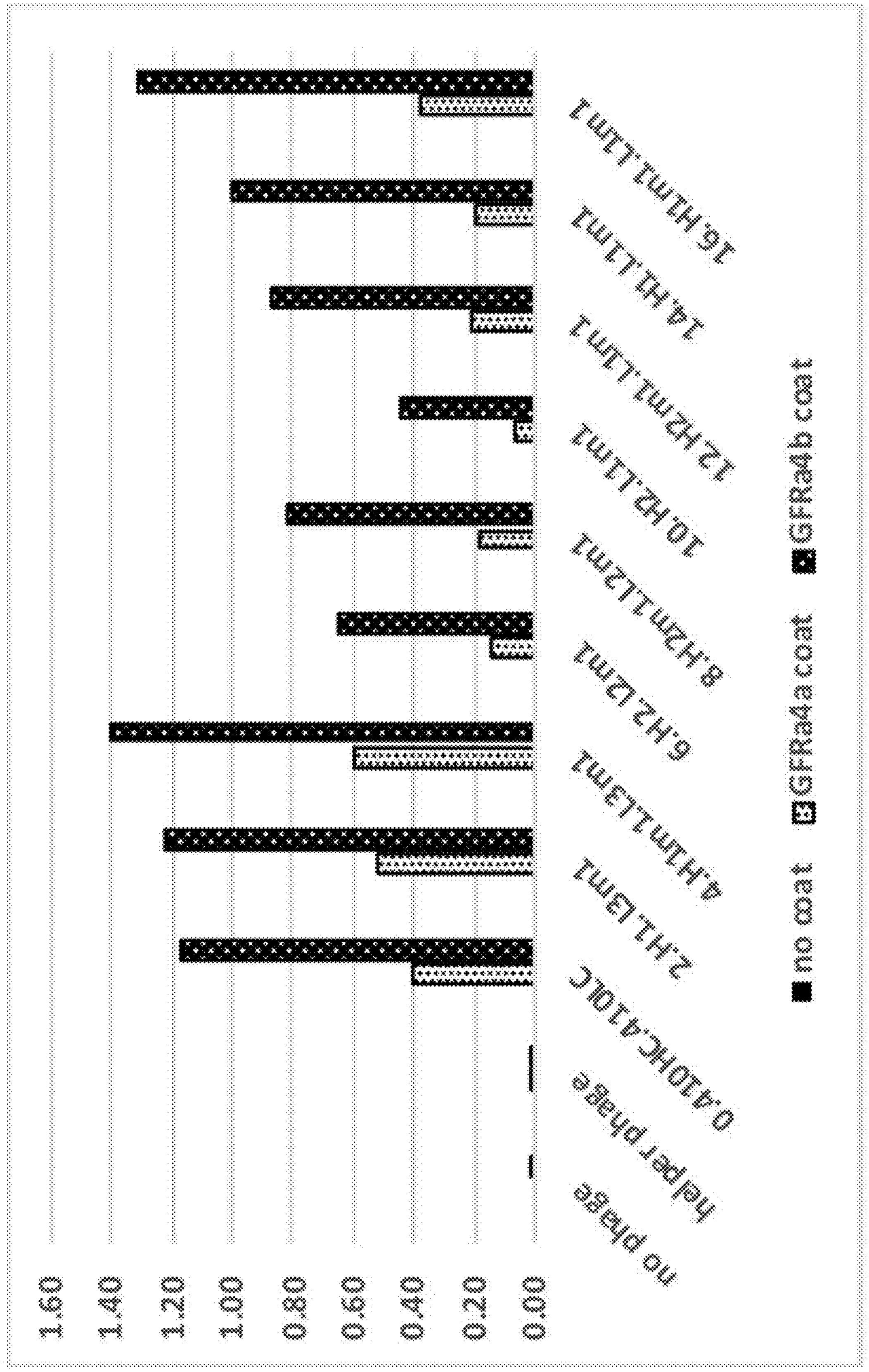
FIG. 7 is a bar graph showing the binding of humanized scFv 1 through 16 to immobilized GFRα4 isoform a (GFR4α4a) and isoform b (GFR4α4b) as measured by ELISA.

FIG. 6 shows the results of a phage ELISA performed with immobilized GFRα4a and humanized scFvs 1 through 16 using VCSM13 helper phage and the original rabbit P4-10 scFv as negative and positive controls, respectively. The results demonstrate that both the most and least humanized heavy chains (H1, H1m1, H2, H2m1) confer binding to antigen but only when paired with the least humanized version of light chain (L1m1, L2m1, L3m1). Binding of the positive scFvs from this experiment were also screened for binding to GFRα4b (FIG. 7). The results demonstrated that those scFvs that were positive against GFRα4a were also positive against GFRα4b. As observed in previous ELISAs of this type with the original rabbit P4-10 expressed as an antibody fragment on phage, reactivity always appears greater against the GFRα4b isoform.

From this point on, additional scFvs were constructed using the most human of the in silico designed heavy chains, H1 and H2, but with various light chain sequences illustrated in FIG. 5 in an iterative fashion. Since only the least human of the initial set of tested light chains conferred binding when compared with most human, a second set of scFvs was constructed that paired H1 and H2 with light chains that were intermediate in amino acid sequence between those two extremes (scFvs 17-22, Table 1; FIG. 5). In addition, 2 heavy/light chain combinations were constructed that had not been tested in the first experiment by pairing H1 and H2 with L2m1 and L3m1, respectively (scFvs 23-24, Table 1; FIG. 5). As above, gene blocks were synthesized, ligated into the pComb3X vector, and scFvs were expressed on phage and screened by ELISA.

Figure 8:
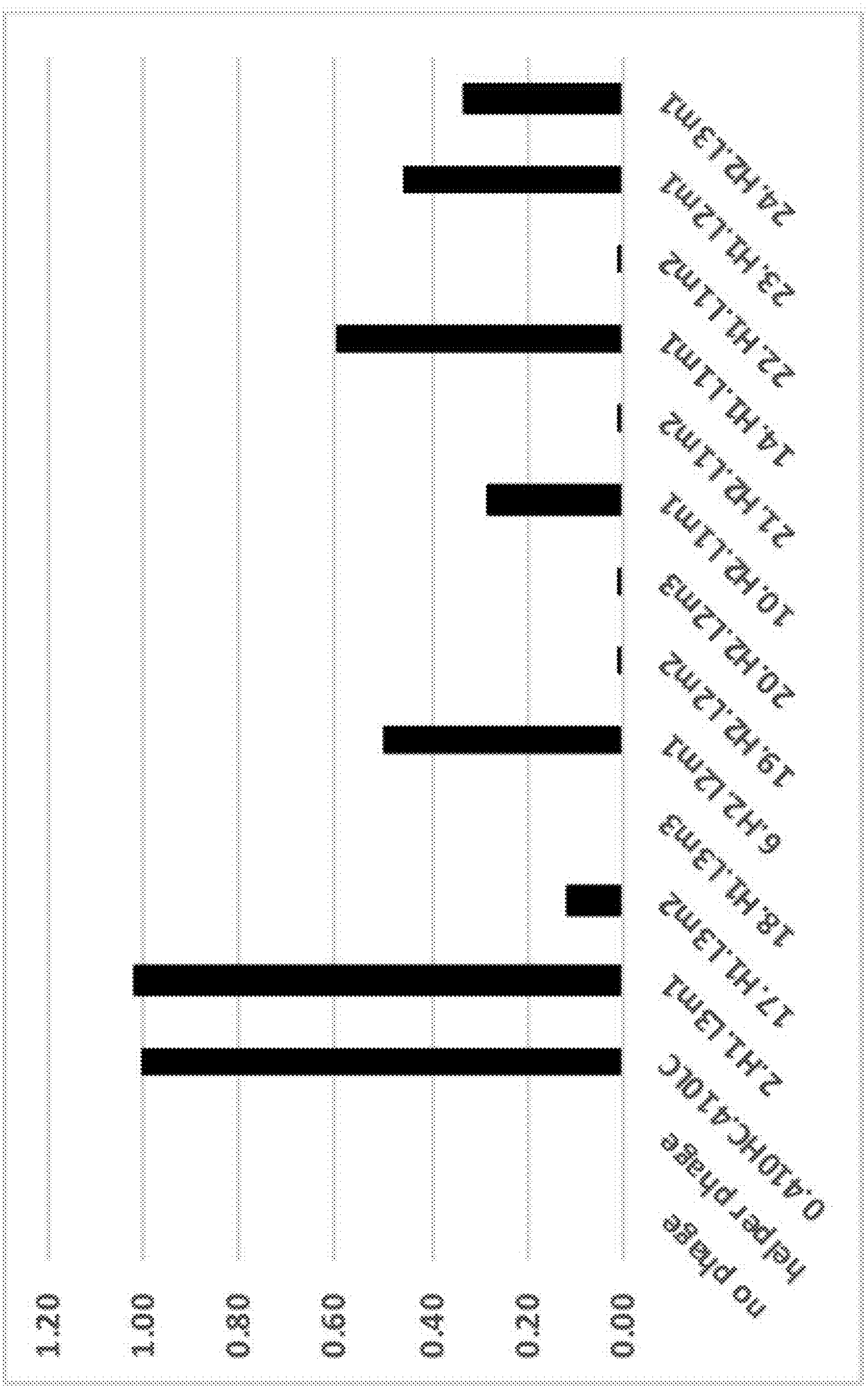
FIG. 8 is a bar graph illustrating the binding of humanized scFv 17 through 24 and select previously tested positive clones to immobilized GFRα4 isoform b (GFR4α4b) as measured by ELISA.
Figure 9:
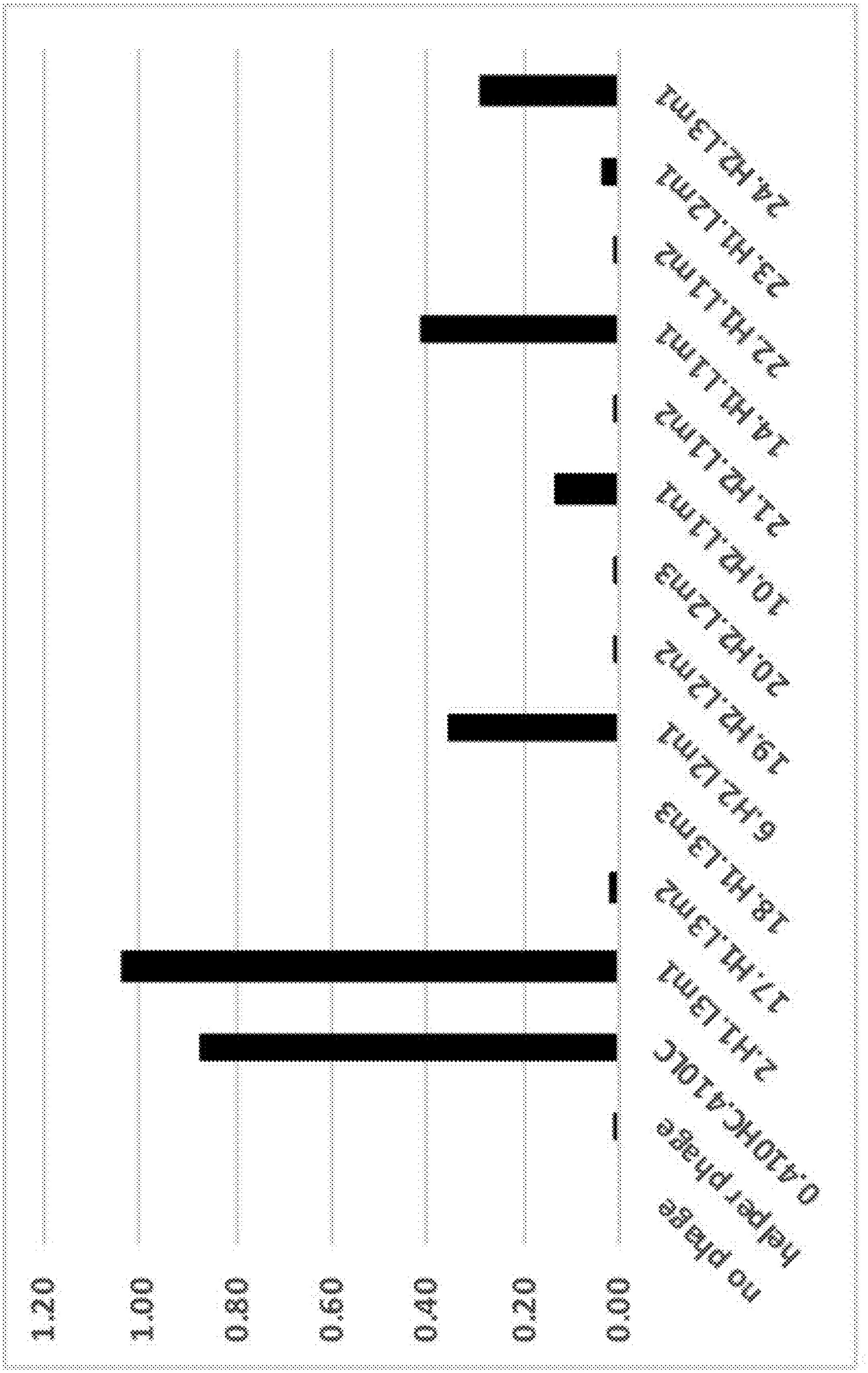
FIG. 9 is a bar graph showing the binding of humanized scFv 17 through 24 and select previously tested positive clones to immobilized GFRα4 isoform a (GFR4α4a) as measured by ELISA.
Figure 10:
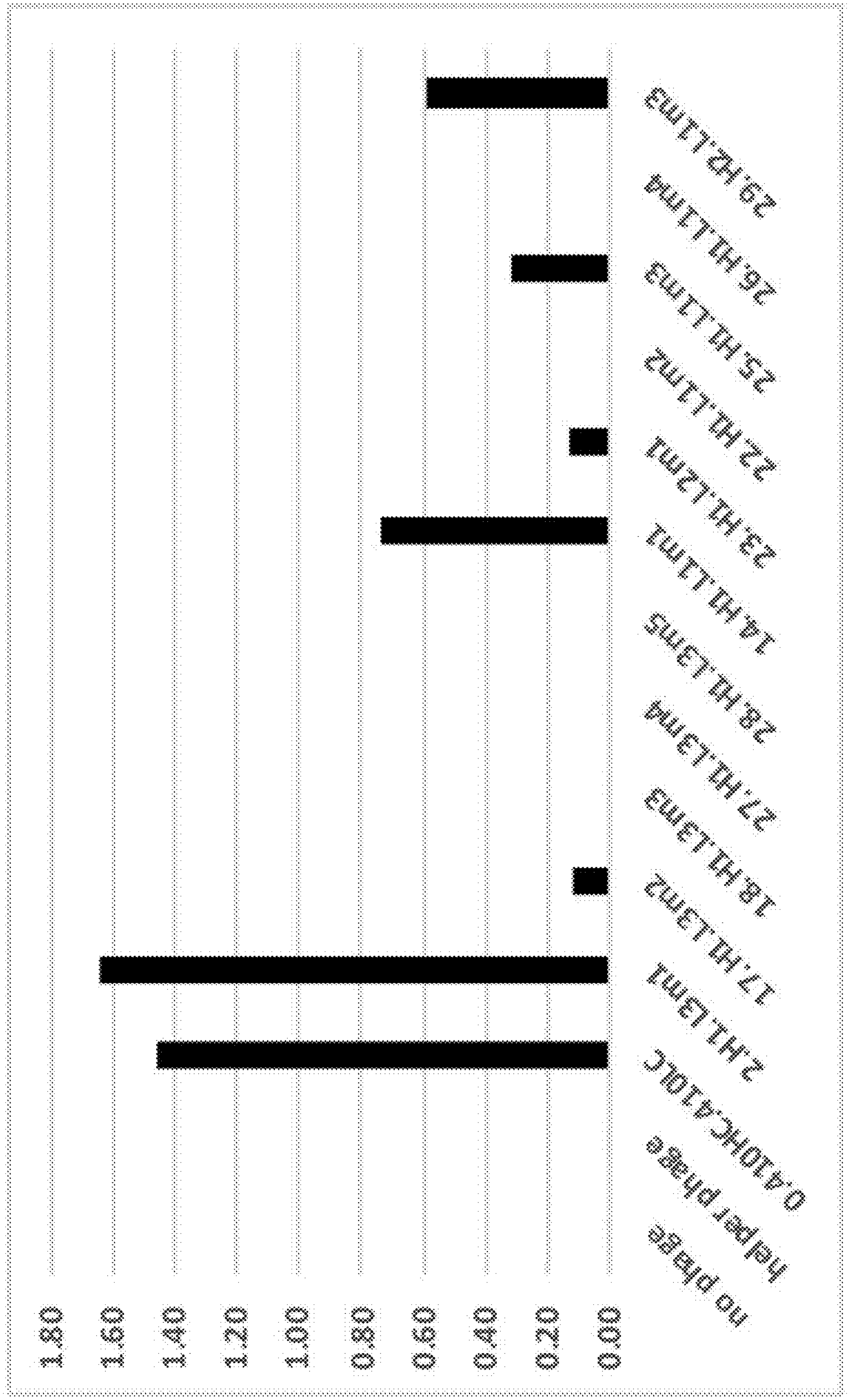
FIG. 10 is a bar graph showing binding of humanized scFvs 25 through 29 and select previously tested positive clones to immobilized GFRα4 isoform b (GFR4α4b) as measured by ELISA.
Figure 11:
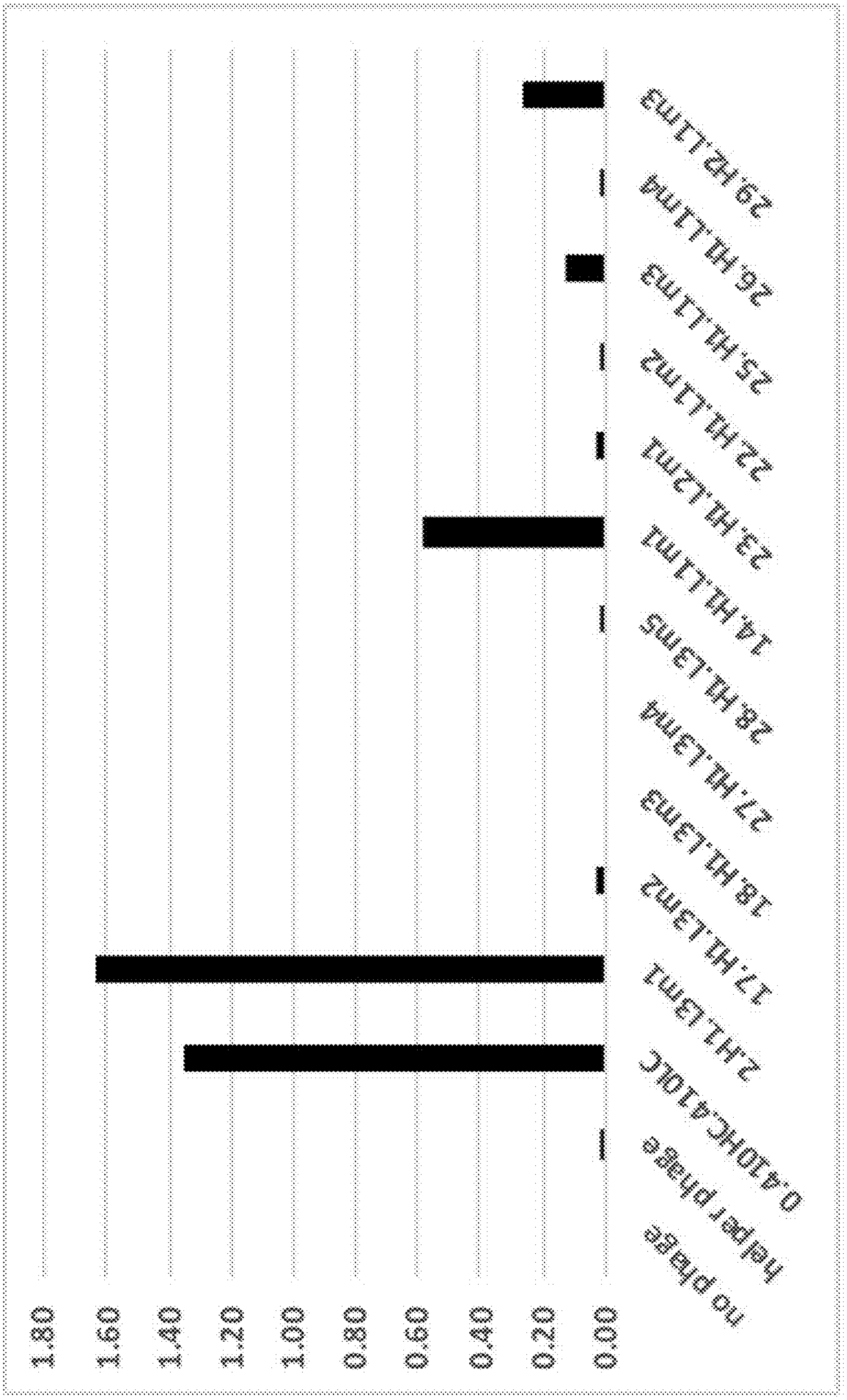
FIG. 11 is a bar graph showing the binding of humanized scFvs 25 though 29 and select previously tested positive clones to immobilized GFRα4 isoform a (GFR4α4a) by ELISA.

FIGS. 8 and 9 show the ELISA results for this second cohort of scFvs run in parallel with previous positives tested against GFRα4b and GFRα4a, respectively. Of the new scFvs, only the combination of the previously-positive light chain L3 m1 now in combination with H2 (scFv 24) was clearly positive against both isoforms of GFRα4. ScFvs 17 and 23 were positive against GFRα4b but marginally positive against GFRα4a. Attempts to improve the percent human amino acid identity of scFv 17's light chain L3m2 by testing scFv 27 (H1/L1m4), and scFv 28 (H1/L1m5) were unsuccessful (FIGS. 10 and 11). Similarly, pairing H1 with L1m4 (scFv 26), a more humanized L1m1 (scFv 14) was unsuccessful. However, pairing H1 and H2 with L1m3, a light chain more human than L1m1 but less than L1m4, created scFvs 25 and 29 that screened positive against GFRα4a and GFRα4b. The binding results for all 29 humanized scFv variants of rabbit P4-10 are summarized in Table 2.

In order to determine which variants to pursue for further development into chimeric antigen receptor T-cells, reference was made to reports of the World Health Organization (WHO) International Nonproprietary Name (INN) Expert Group that helped define requirements for non-human derived antibodies to be considered "humanized". According to guidelines, comparison of a candidate antibody to human sequences should be done through the International Immunogenetics Information System® (IMGT®) Domain-GapAlign tool (www.imgt.org). This tool interrogates the IMGT® database of antibody germline variable region genes where the alignment score is made only against germline sequence variable region exons, thus omitting part of CDR3 and the J region from the analysis. As well as being "closer to human than to other species", the top "hit" should be human and the identity to human sequences must be ≥85%, otherwise the antibody would be designated as "chimeric" not "humanized".

Based on the antigen binding results summarized in Table 2, scFvs 10, 14, 25 and 29 were analyzed using the above approach. As illustrated in FIG. 12, heavy chain H1 (forming the heavy chain in scFvs 14 and 25) was found to be "closer to human than to other species" with identity to human sequences ≥85%. Similar results were found for heavy chain H2 (FIG. 13), the heavy chain used in scFvs 10 and 29. For light chain L1m3 (used in scFvs 25 and 29), the top hit was human with amino acid identity ≥85% (FIG. 14). For light chain L1m1 (used in scFvs 10 and 14), the first hit was rabbit; the second hit was human with an amino acid identity to human sequences of 84%, just below the 85% convention.

Figure 16A:
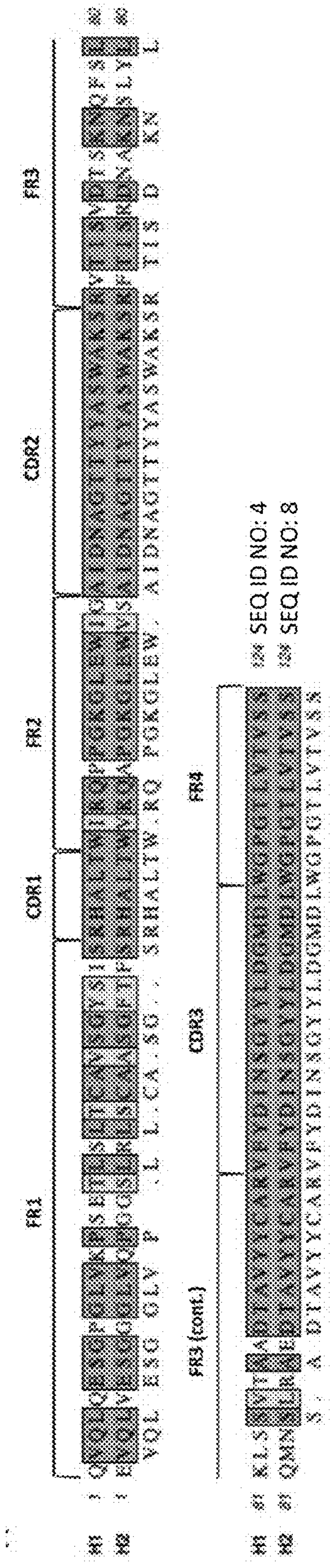
FIGS. 16A-16B illustrate amino acid alignments of top P4-10 humanized heavy chain (FIG. 16A) and light chain (FIG. 16B) variable regions.
Figure 16B:
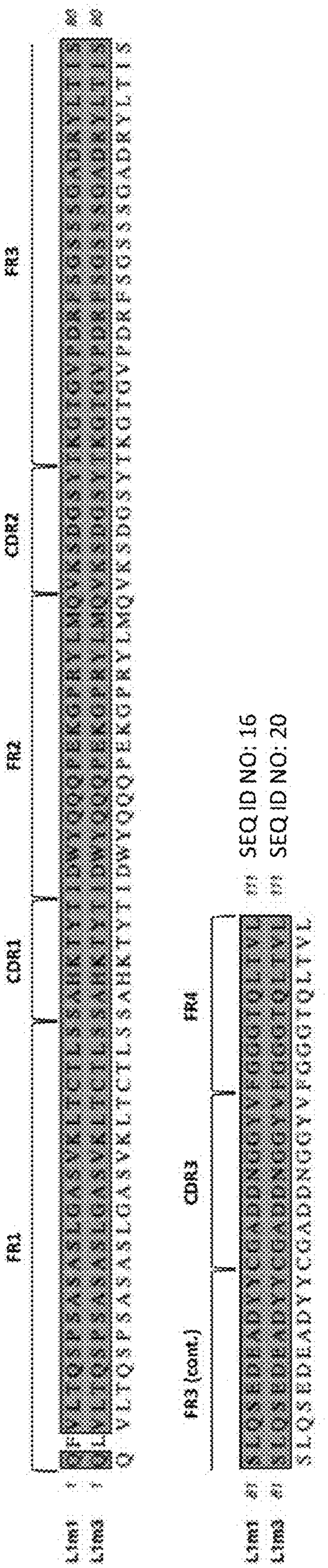

Table 3 summarizes the heavy chain/light chain compositions of scFvs 10, 14, 25 and 29 with their respective homologies to human sequences. Amino acid alignments (with CDR3 and FR4 regions appended) of heavy chains H1 with H2 and light chains L1m1 with L1m3 are shown in FIGS. 16A and 16B, respectively. Heavy chains H1 and H2 are significantly different from each other by virtue of homology to very distinct human germline genes derived from different human VH germline gene families (VH3 and VH4, FIG. 3) and sharing only ~75% sequence homology with each other. Light chains L1m1 and L1m3 are identical to each other except for a single amino acid change at position 2 in FR1 (99% sequence homology, FIG. 5). The additional "human" amino acid at position 2 (a leucine for a phenylalanine) increases the homology to human sequences from 84% to 85%.

Example 3: Design of CAR-T scFv Constructs

Figure 18:
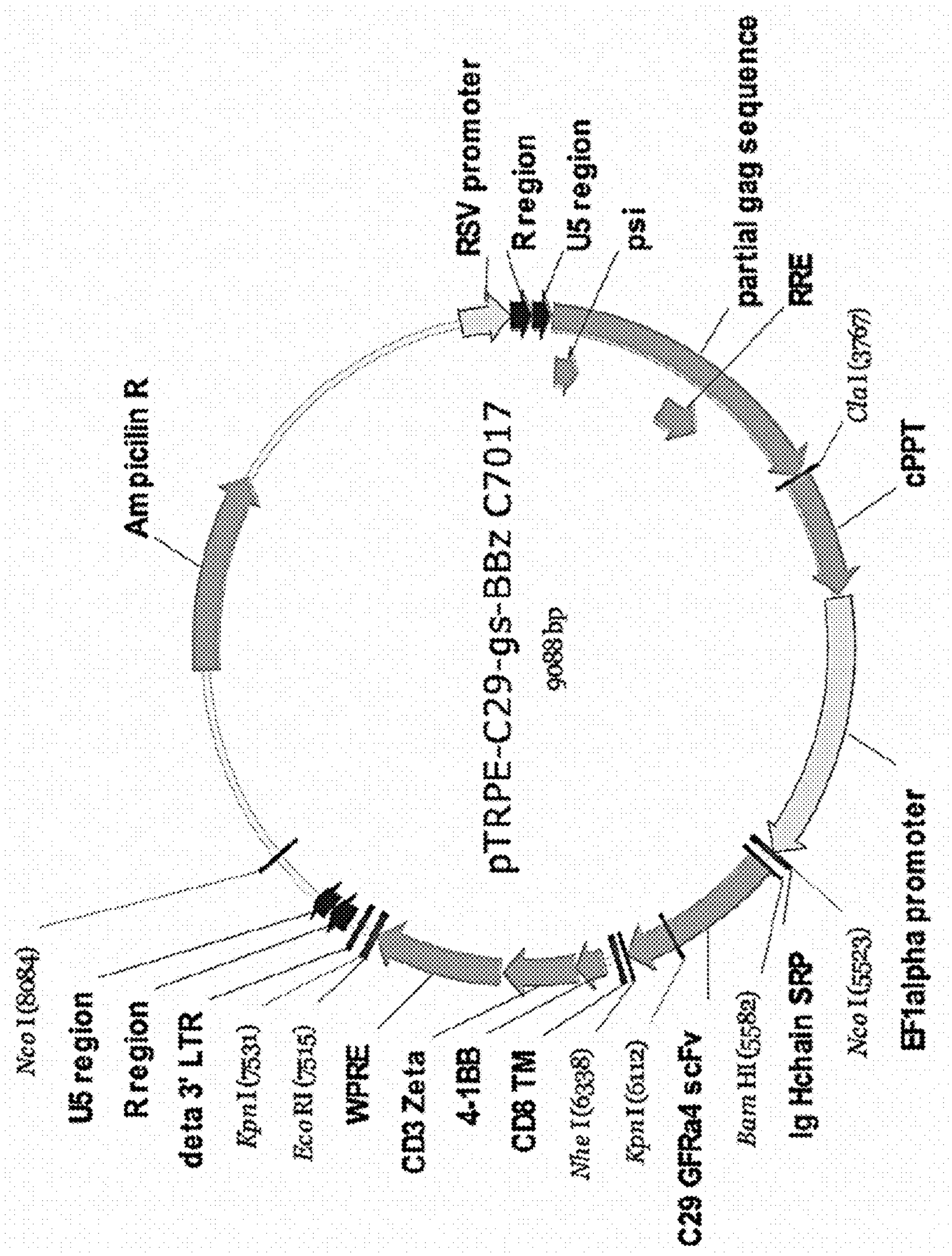
FIG. 18 is an illustration showing the map of the plasmid vector containing CAR29.

Constructs for scFv humanized antibodies 10, 14, 25, and 29 for CAR-T were designed in the orientation VH-linker-VL with the linker comprising nucleotides to encode a 15-amino acid glycine/serine rich peptide and with 5' and 3' BamHl and Nhel restriction sites, respectively (FIG. 17). Constructs were synthesized, restriction digested with BamHl and Nhel, agarose gel purified, and ligated into the corresponding restriction sites of plasmid vectors that provide a 10-amino acid glycine/serine (GS)-rich linker (GGGGSGGGGS) (SEQ ID NO: 168) at the carboxy terminus of the scFv, followed by the transmembrane domain of human CD8, a 4-1BB domain, and CD3zeta domain sequentially (FIG. 18 shown for the plasmid containing scFv 29). The resulting vectors for scFvs 10, 14, 25, and 29 encode CARs termed CAR-10, CAR-14, CAR-25, and CAR-29, respectively.

Example 4: Production of Lentivirus and Transduction of Human T Cells

To generate lentiviral supernatants, LentiX-293T cells were seeded on Day 0 and transfected using Lipofectamine 2000 on Day 1 as described (Milone et al. (2009) *Molecular Therapy*., 17: 1453-1464). For each construct, the plasmids used were pVSV-G (VSV glycoprotein expression plasmid), pRSV.REV (Rev expression plasmid), pMDLg/p-l.RRE (Gag/Pol expression plasmid), and the CAR transfer vectors (pTRPE) described above. Lentiviral supernatants were filtered through 0.45 um pore size filters and concentrated by centrifugation at 12,000×g at 4° C. for 12-18 hours.

Figure 19A:
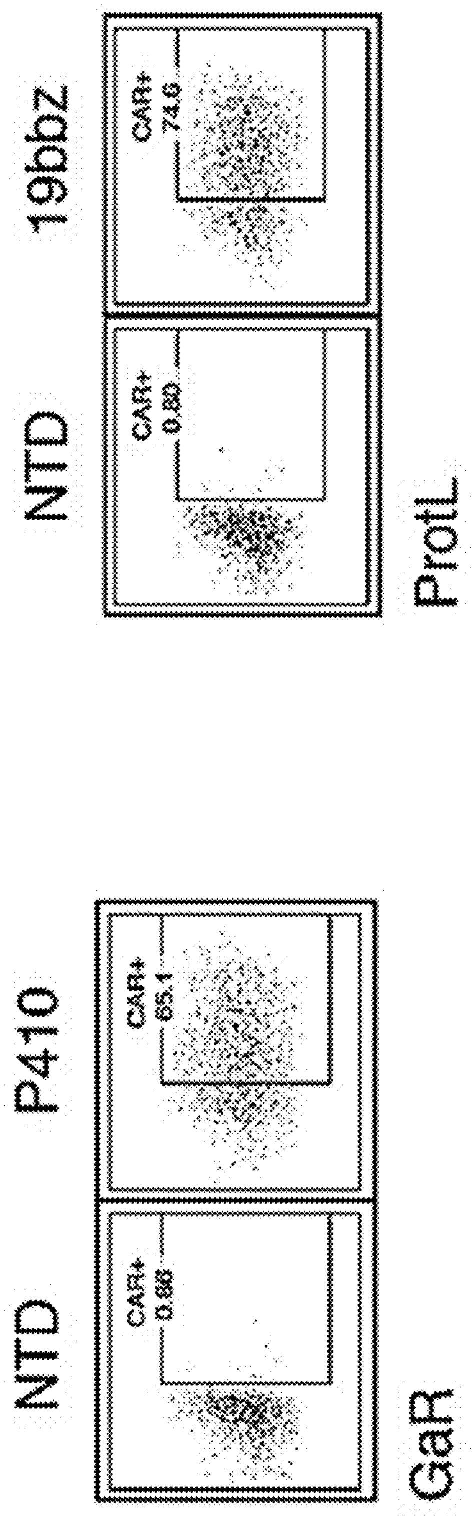
FIGS. 19A-19C are a series of plots showing expression of cell-surface CARs. Original rabbit P4-10 GFRα4-directed and murine 19bbz CD19-directed CARs were detected with goat anti-rabbit antibody (FIG. 19A, left panel) or Protein L (FIG. 19A, right panel). Humanized GFRα4-directed CARs 10, 14, 25, 29 were detected with rabbit anti-human antibody (FIG. 19B), and GFRα4-directed P4-10, 10, 14, 25, 29 CARs and CD19-directed CAR detected with Fc-conjugated soluble GFRα4b or CD19 antigen (FIG. 19C, upper and lower rows, respectively).
Figure 19B:
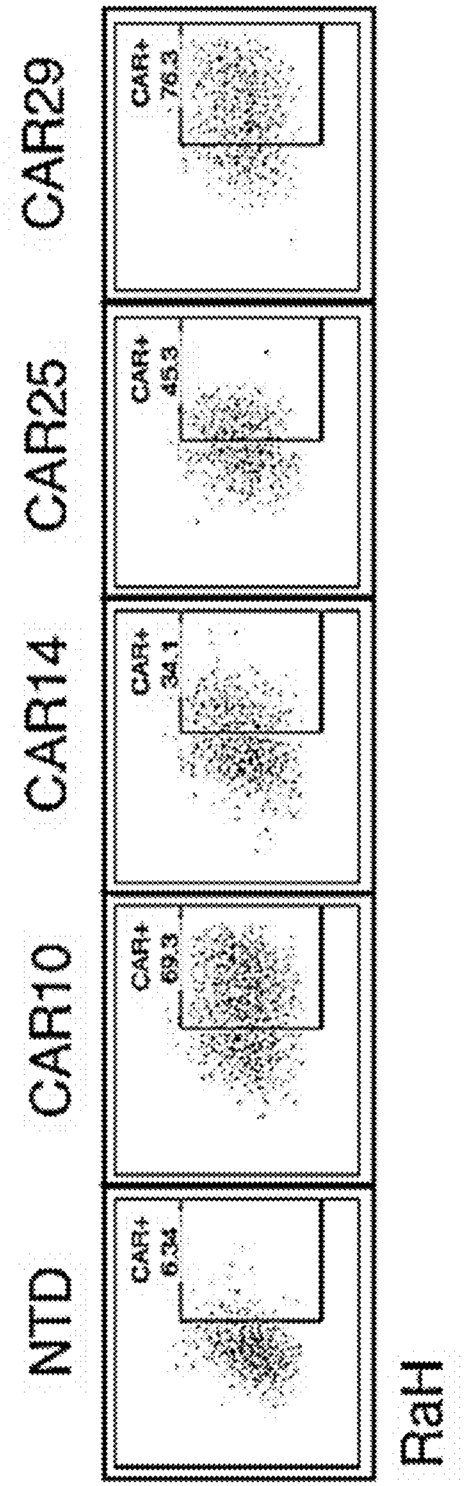
Figure 19C:
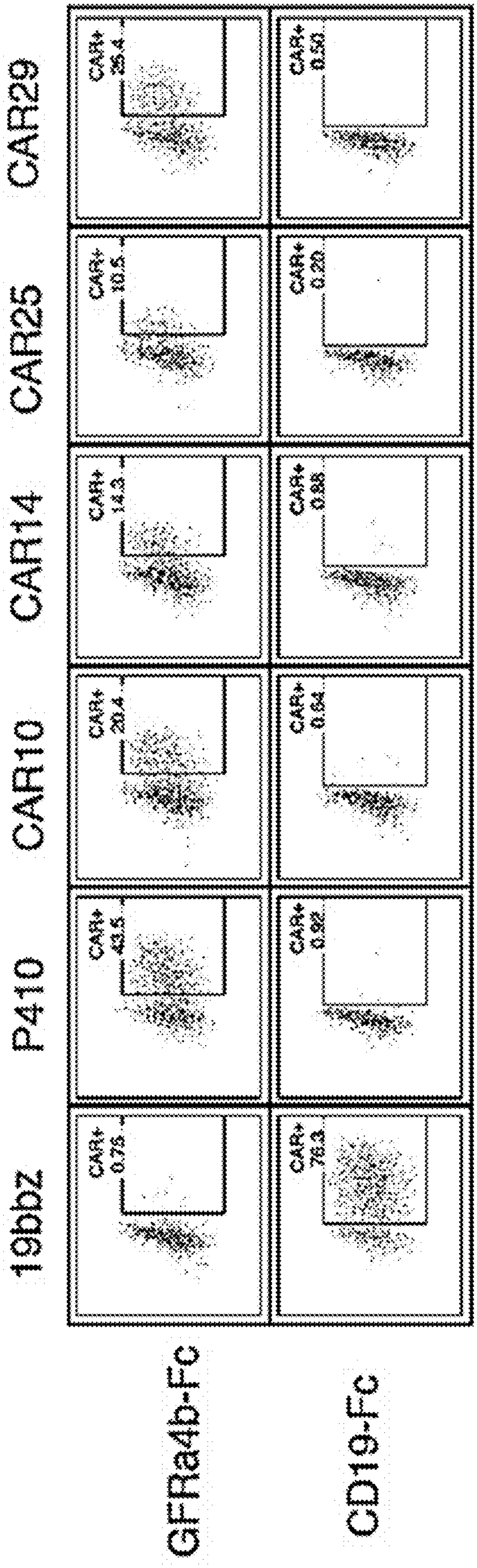

To create CAR-T expressing cells, human T cells from healthy donors were activated with anti-CD3 and anti-CD28 coated paramagnetic beads (DYNABEADS® Human T-Activator CD3/CD28, Life Technologies). One day following activation, cells were transduced with lentiviral vectors encoding GFRα4-directed CARs (original rabbit P4-10 and humanized versions), a CD19-directed control CAR (FMC63(cd8)bbz), or were left non-transduced (NTD). Cells were expanded and on day 7, cells were evaluated for cell-surface expression of the CARs by flow cytometry (FACSCalibur, BD Biosciences, Franklin Lakes, NJ). Fluorescently-labeled goat anti-rabbit antibodies detected CAR P4-10, the original rabbit GFRα4-directed CAR, and fluorescently-labeled Protein L detected the murine CD19-directed CAR (FIG. 19A, "P410" and "19bbz", respectively). Fluorescently-labeled rabbit anti-human antibodies ("RaH") detected CARs 10, 14, 25, and 29 (FIG. 19B). Expression of cell-surface CARs were also detected by staining with antigen using recombinant human Fc-fusions of GFRα4 or CD19 antigen followed by detection of bound antigen with fluorescently-labeled anti-human Fc-specific antibodies (FIG. 19C). Appropriately, CD19-Fc only bound to CD19-directed CARs while GFRα4-Fc bound to both rabbit P4-10 and humanized P4-10 CARs but not the CD19-directed CAR.

Example 5: In Vitro Killing of GFRα4-Expressing Cells by Humanized P4-10 CAR-T Cells Cytotoxicity of target cells by GFRα4-directed CAR-T cells was evaluated using a 51Cr release-assay. Target cells comprised either Nalm6 cells (a CD19-expressing B-cell precursor leukemia cell line (ATCC® CRL-3273TM)), Nalm6 cells expressing the GFRα4 isoform a (GFRα4a) or isoform b (GFRα4b), or TT cells (a human medullary thyroid cancer cell line (ATCC® CRL-1803TM)). Nalm6 cells expressing GFRα4 proteins were produced by transduction with lentiviral vectors encoding human GFRα4a-T2A-GFP or human GFRα4b-T2A-GFP (Milone et al. (2009) *Molecular Therapy.,* 17: 1453-1464). Cells were stained with P4-10 antibody followed by AlexaFluor 647-conjugated donkey anti-rabbit antibody and FACS sorted to >98% purity. P4-10 antibody comprised a full-length rabbit IgG containing the P4-10 rabbit variable regions and was a gift of Novartis Pharmaceuticals.

Figure 20:
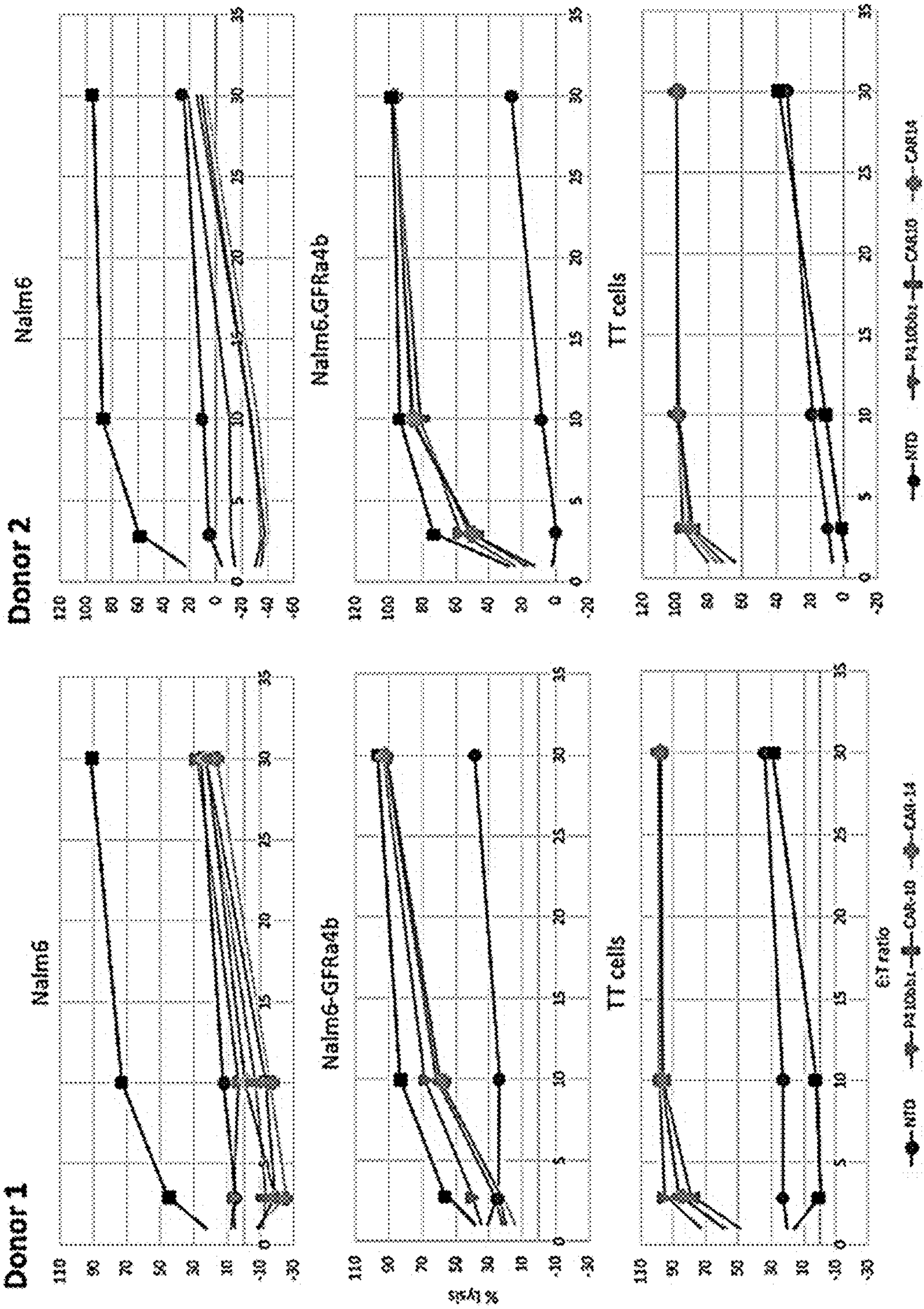
FIG. 20 is a series of graphs showing in vitro killing of GFRα4-expressing cells by GFRα4-directed CAR-T cells. T cells from 2 human donors (left and right panels) were transduced with lentiviral vectors that encoded CARs directed to CD19 (19bbz) or GFRα4 (P410bbz, CAR-10, CAR-14, CAR-25, CAR-29) and incubated with CD19-expressing Nalm6 cells (top row), CD19- and GFRα4 isoform b-expressing Nalm6 cells (middle row), or GFRα4-expressing TT medullary thyroid cancer cells (bottom row). (NTD, non-transduced T cells). T cells from 2 donors (left and right panels) were transduced with lentiviral vectors that encoded CARs directed to CD19 (19bbz) or GFRα4 (P410bbz, CAR-10, CAR-14, CAR-25, CAR-29) and incubated with CD19-expressing Nalm6 cells (top row), CD19- and GFRα4 isoform b-expressing Nalm6 cells (middle row), or GFRα4-expressing TT medullary thyroid cancer cells (bottom row). (NTD, non-transduced T cells).
Figure 21:
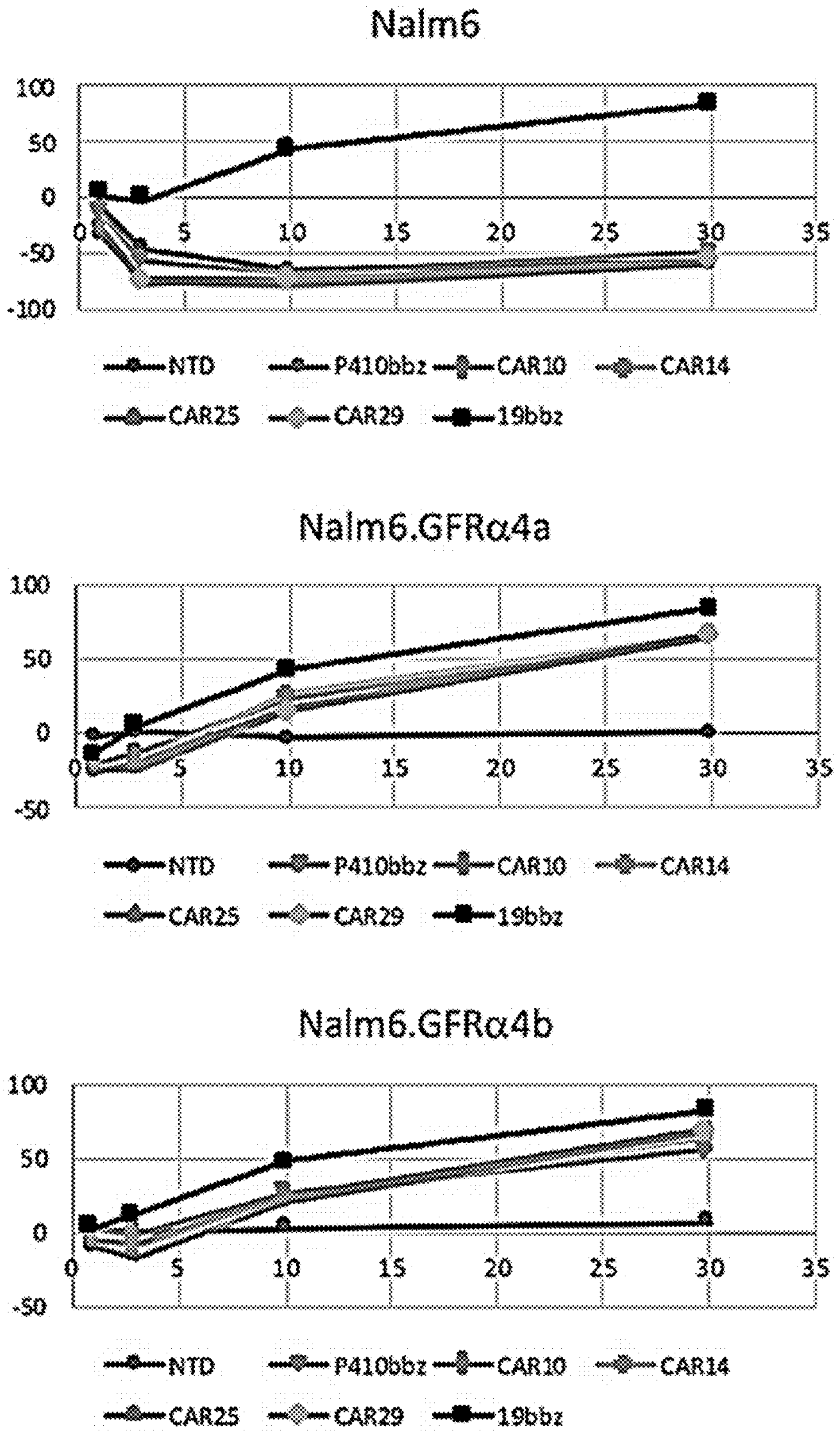
FIG. 21 is a series of graphs showing in vitro killing of GFRα4a and GFRα4b isoform-expressing Nalm 6 cells. Human T cells transduced with lentiviral vectors that encoded CARs directed to CD19 (19bbz) or GFRα4 (P410bbz, CAR-10, CAR-14, CAR-25, CAR-29) were incubated with CD19-expressing Nalm6 cells (top row), CD19- and GFRα4 isoform a-expressing Nalm6 cells (middle row), and CD19- and GFRα4 isoform b-expressing Nalm6 cells (bottom row). (NTD, non-transduced T cells).

To perform the in vitro killing assay, target cells were labeled with 51Cr (sodium dichromate salt), washed, and co-cultured with effector CAR T cells at effector:target ratios of 30:1, 10:1, and 3:1. Ten thousand target cells were co-cultured with the appropriate number of effector T cells in each well. Supernatants were collected after overnight co-culture and placed into 96-well Lumaplates (Perkin Elmer, Inc., Walthan MA). The amount of 51Cr released from the labeled target cells was measured on a liquid scintillation counter (MicroBeta Trilux, Perkin Elmer). Target cells incubated in medium alone or with 1% SDS were used to determine spontaneous (S) or maximum (M) 51Cr release. Percentage of specific lysis was calculated as follow: [(cpm experimental release−cpm S release)/(cpm M release−cpm S release)]×100. As shown in FIG. 20 for CAR-T cells made from 2 different healthy human donors (left and right panels), Nalm6 cells expressing only endogenous CD19 are only killed by a CD19-directed CAR-T ("19bbz", row A) whereas Nalm6 cells expressing both CD19 and GFRα4b were killed by both CD19-directed and GFRα4-directed CAR-T cells (row B). Conversely, TT cells were only killed by GFRα4-directed CAR-T cells (row C). FIG. 21 shows that the humanized GFRα4-directed CAR-Ts also recognize and kill Nalm6 cells expressing GFRα4 isoform a. GFRα4 is a member of a related group of 4 glial cell-derived neurotrophic factor (GDNF) receptors including those designated GFRα1, GFRα2, and GFRα3. Because non-GFRα4 GDNF receptor proteins are found in non-thyroid tissues including the central nervous system, lack of reactivity of humanized GFRα4-directed CAR-Ts to GFRα1-, GFRα2-, and GFRα3-expressing cells was confirmed. Target cells expressing human GFRα1, GFRα2, GFRα3 and GFRα4 were created by transducing K562 cells (ATCC® CCL-243™) with lentiviral vectors encoding a respective GFRα sequence followed by a T2A sequence derived from Thosea asigna virus followed by GFP. Expression of GFRα4 on the surface of K562 cells was confirmed as described above for GFRα4-expressing Nalm6 cells. Expression of GFRα1, GFRα2, and GFRα3 on the surface of K562 cells was confirmed using commercially-available murine monoclonal antibodies specific to the respective GFRα isoform (R&D Systems, Minneapolis, MN).

Figure 22:
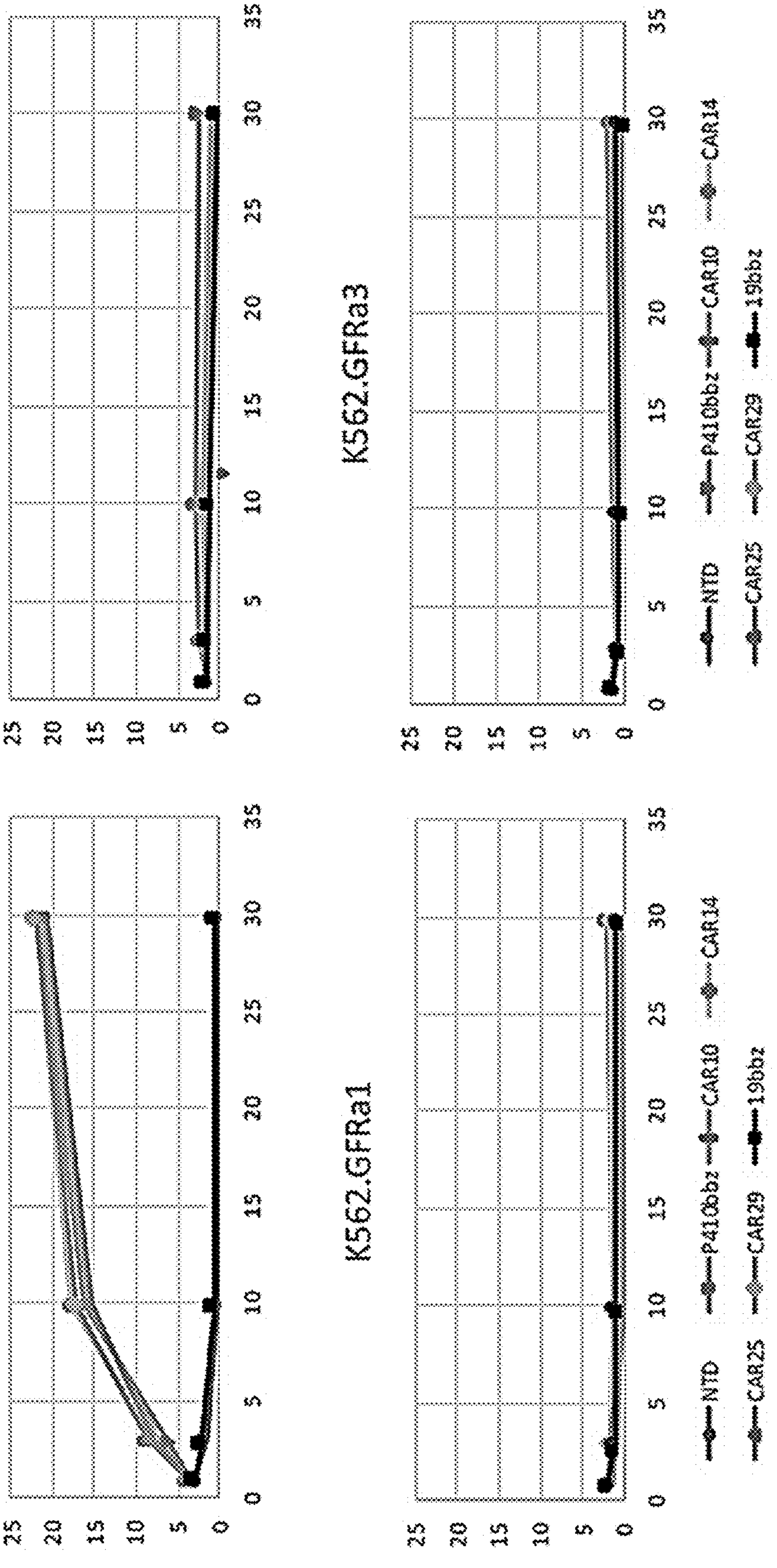
FIG. 22 is a series of graphs illustrating the lack of in vitro killing of Nalm 6 cells expressing non-GFRα4 members of the glial cell-derived neurotrophic factor (GDNF) receptor family. Human T cells transduced with lentiviral vectors that encoded CARs directed to CD19 (19bbz) or GFRα4 (P410bbz, CAR-10, CAR-14, CAR-25, CAR-29) were incubated with CD19-expressing Nalm6 cells co-expressing GFRα1, GFRα2, GFRα3, or GFRα4b as indicated. (NTD, non-transduced T cells).
Figure 23:
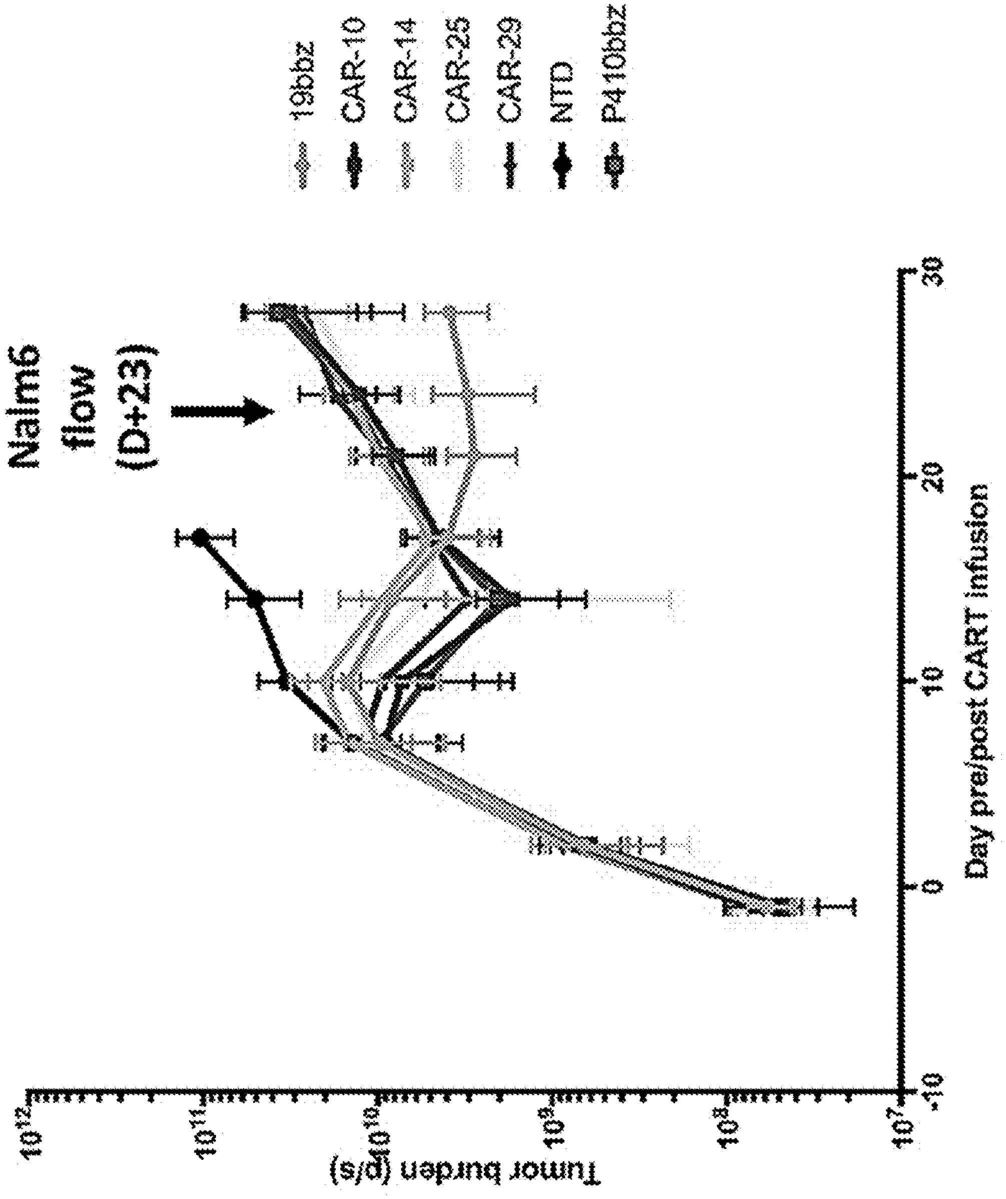
FIG. 23 is a graph demonstrating the in vivo killing of GFRα4-expressing cells by GFRα4-directed CAR-T cells in a mouse model. On Day −4, $5\times10^6$ Nalm6 cells engineered to express click-beetle green luciferase and human GFRα4b were injected intravenously into NOD-SCID-Y−/− (NSG) mice. On Day 0, $5\times10^6$ non-transduced human T cells (NTD, n=6 mice), or human T cells transduced with CARs 19bbz (n=9 mice), P410 (n=9 mice), CAR-10 (n=9 mice), CAR-14 (n=9 mice), CAR-25 (n=9 mice), or CAR-29 (n=9) were injected intravenously. Bioluminescence photons/second (p/s) was measured twice weekly over a 28-day period. Values for each group at each time point represent means+/− one standard deviation. Mice were bled on Day 23 and Nalm6 cells in the blood were analyzed for antigen expression by flow cytometry.

As shown in FIG. 22, cells expressing non-GFRα4 GDNF receptors are not killed by any of the GFRα4-directed CAR-T cells.

Figure 24B:
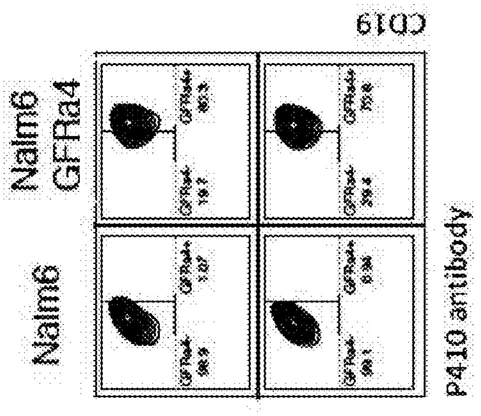
FIGS. 24A-24B are a series of graphs showing Nalm6 cell phenotype after in vivo killing of GFRα4-expressing targets.
Figure 24A:
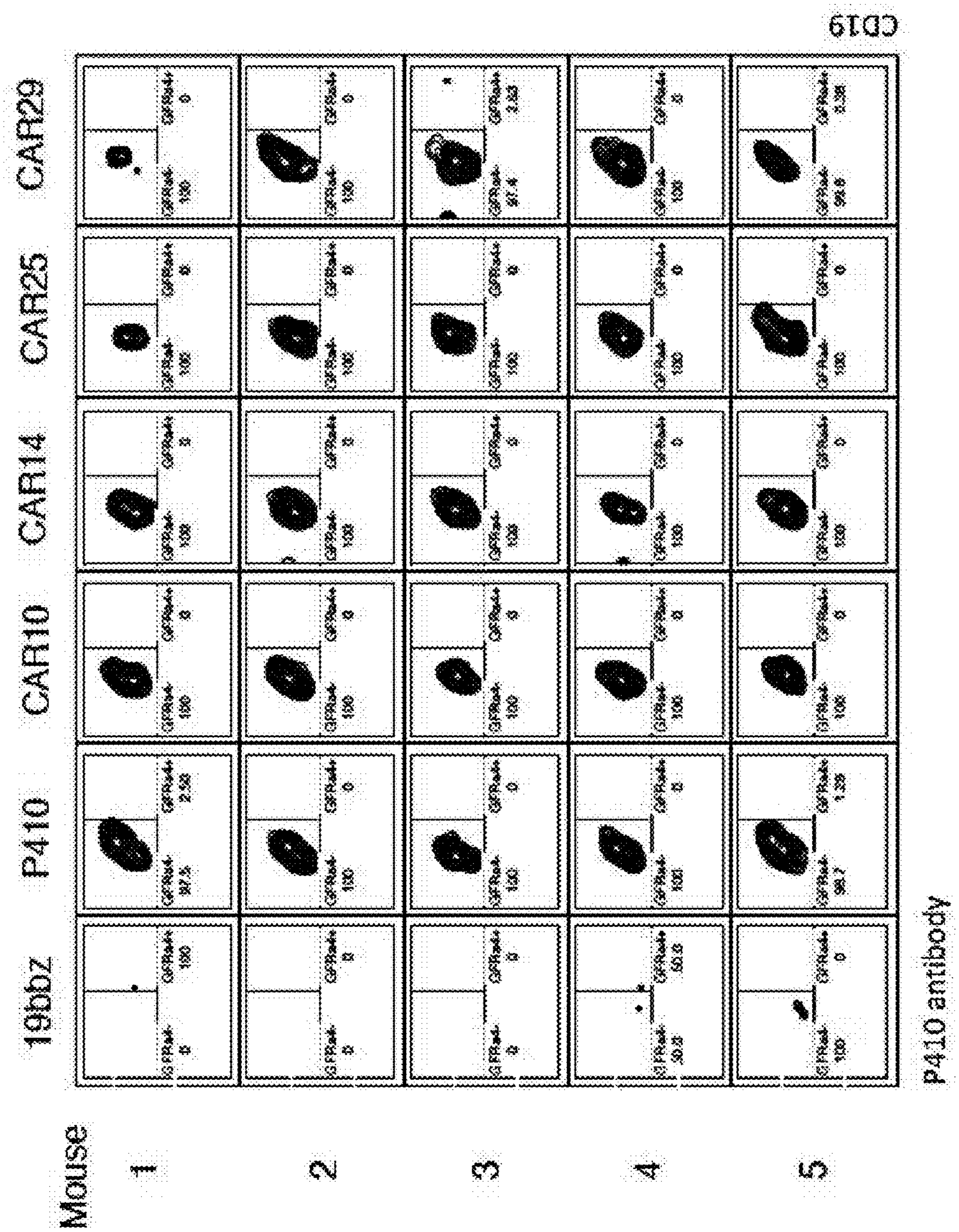

Example 6: In Vivo Killing of GFRα4-Expressing Cells by Humanized P4-10 CAR-T Cells On Day −4, $5\times10^6$ Nalm6 cells engineered to express click-beetle green luciferase (Ghassemi et al. Cancer Immunol Res 6:1100-1109, 2018) and human GFRα4b were injected intravenously into NOD-SCID-Y−/− (NSG) mice. On Day 0, $5\times10^6$ non-transduced human T cells (NTD, n=6 mice), or human T cells transduced with CARs 19bbz (n=9 mice), P4-10 (n=9 mice), CAR10 (n=9 mice), CAR14 (n=9 mice), CAR25 (n=9 mice), or CAR29 (n=9) were injected intravenously. Bioluminescence was measured twice weekly over a 28-day period. As shown in FIG. 22, Nalm6 cells began to shrink in size beginning around Day 9 in mice infused with CD19-directed and all GFRα4-directed CAR-T cells until about Day 18 when tumors in mice treated with GFRα4-directed CAR-T cells began to re-expand. On Day 23, mice were bled and Nalm6 cells in blood were stained with anti-CD19 and P4-10 antibodies to assess expression of CD19 and GFRα4b in residual Nalm6 cells post treatment with CAR-Ts (FIG. 24, panel A, 5 representative mice from each group). Also stained with anti-CD19 and P4-10 antibodies are control samples of wild-type Nalm6 cells and Nalm6-GFRα4 target cells spiked into mouse blood (FIG. 24B in duplicate). These data show that the majority of Nalm6 cells initially injected into the mice were positive for both CD19 and GFRα4 and, following their killing by GFRα4-directed CAR-T cells, Nalm6 cells that subsequently grew out around Day 18 were GFRα4-negative.

Figure 25:
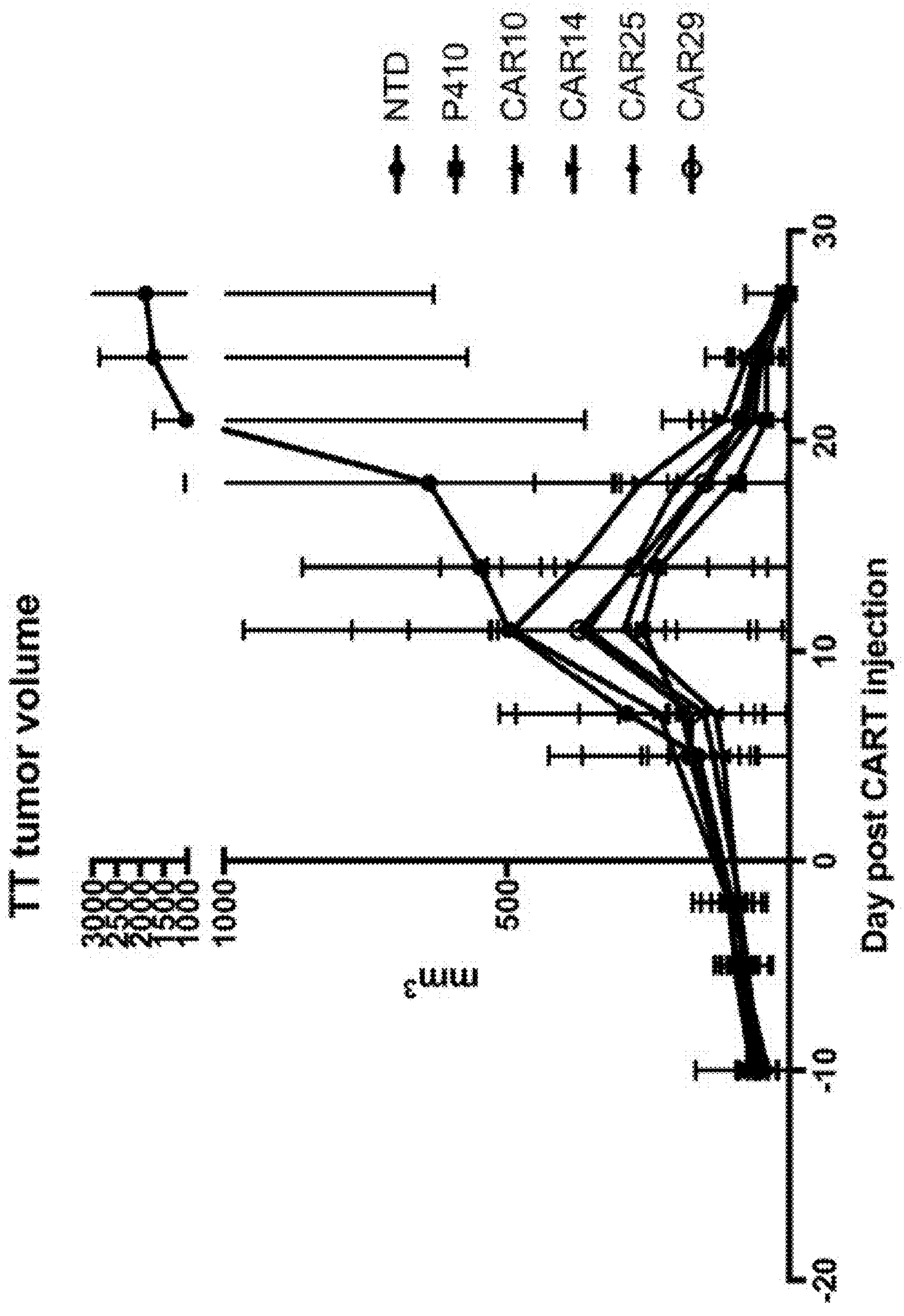
FIG. 25 is a graph illustrating the in vivo killing of TT medullary thyroid cancer cells in a mouse model. TT tumor volumes measured over time in NSG mice treated with $5\times10^6$ P4-10 (n=8 mice), CAR10 (n=8 mice), CAR14 (n=7 mice), CAR25 (n=7 mice), and CAR29 (n=8 mice) CAR+T cells or an equivalent number of non-transduced cells (NTD, n=7 mice) 10 days after subcutaneous implantation of $5\times10^6$ wild-type TT cells. Curves plots means of tumor volumes in mm3+/−one standard deviation for each experimental group.
Figure 26:
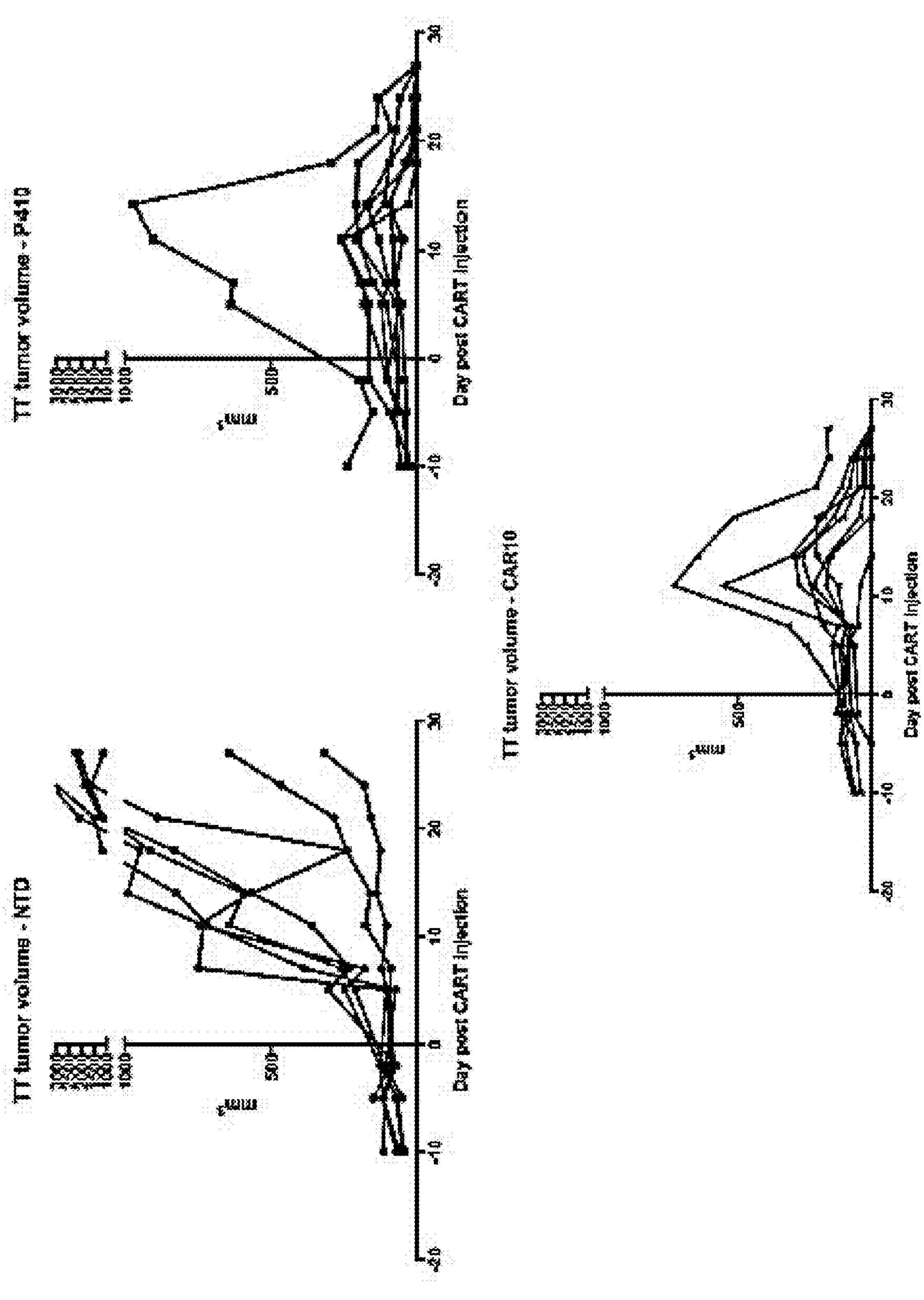
FIG. 26 is a series of graphs demonstrating in vivo killing of TT medullary thyroid cancer cells in individual mice from each experimental group. Data is from the experiment shown in FIG. 25 where curves show tumor volumes over time for individual mice in each CAR-T treatment group.
Figure 27:
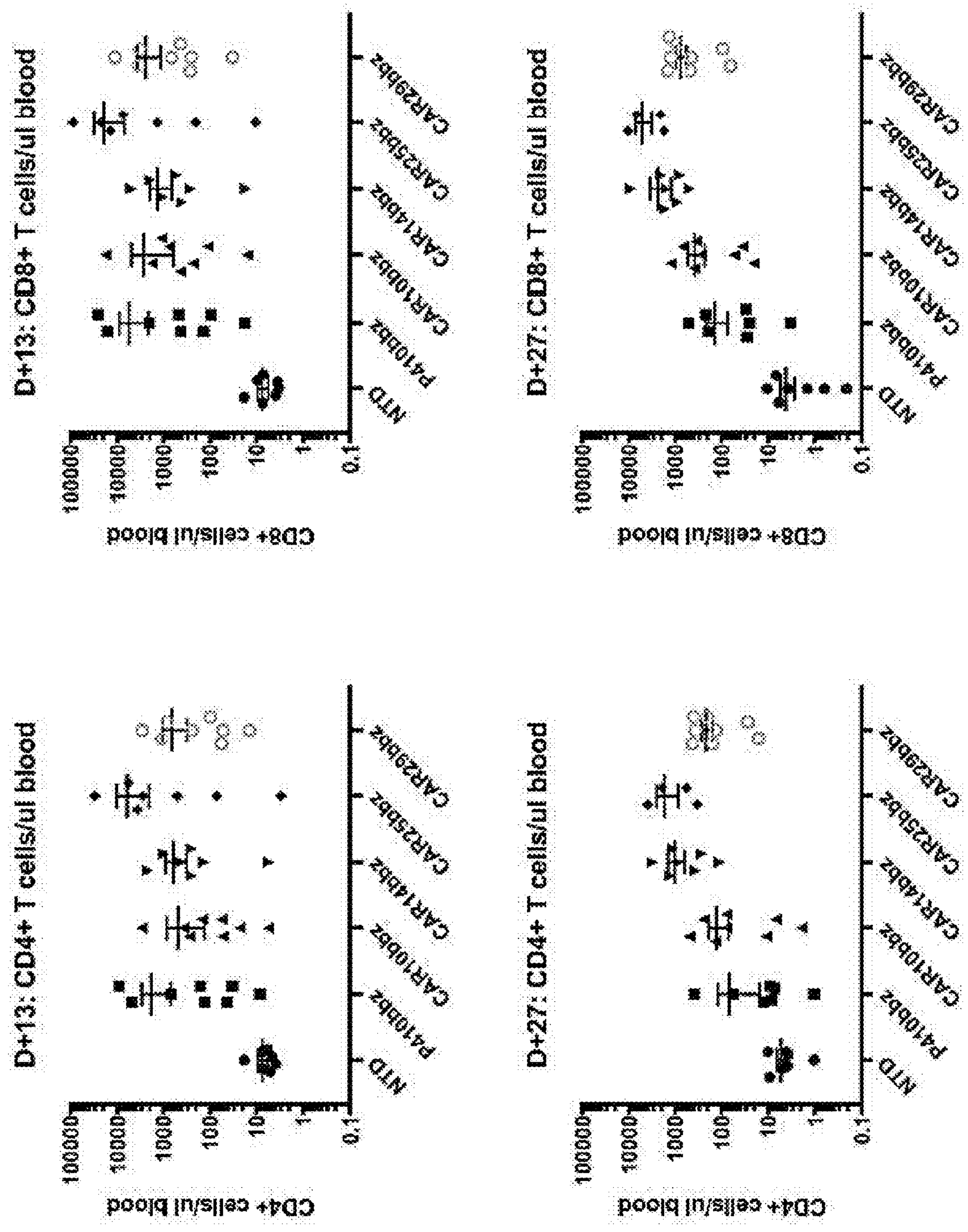
FIG. 27 is a series of graphs showing the measurement of GFRα4-directed CAR-T cell levels in mice challenged with TT medullary thyroid cancer cells. In the experiment shown in FIGS. 25 and 26, blood samples were collected from mice on Day 13 (top row) and Day 27 (bottom row), and human CD3+CD4+ T cells (left column) and CD3+CD8+ T cells (right column) were enumerated by flow cytometry. Values for individual mice are shown and error bars represent SEM. Using a Kriskal-Wallis ANOVA test with Dunn's multiple comparisons test and an alpha value of 0.05, all CAR groups were significantly different from the non-transduced (NTD) control group except for NTD vs. CAR10bbz on Day 13 CD3+CD4+ T cells, NTD vs. P410bbz and NTD vs. CAR10bbz on Day 27 CD3+CD4+ T cells, and NTD vs. P410bbz and NTD vs. CAR10bbz on Day27 CD3+CD8+ T cells.

Example 7: In Vivo Killing of TT Medullary Cancer Cell Line by Humanized P4-10 CAR-T Cells NSG mice were implanted subcutaneously with $5\times10^6$ TT cells. When tumors reached approximately 100 $mm^3$ 10 days later ("Day 0"), $5\times10^6$ P4-10 (n=8 mice), CAR10 (n=8 mice), CAR14 (n=7 mice), CAR25 (n=7 mice), and CAR29 (n=8 mice) CAR+ T cells or an equivalent number of non-transduced cells (NTD, n=7 mice) were injected via the tail vein. Tumors size was measured over time in two dimensions by caliper measurement, and tumor volume was estimated using the formula: (D1×D1×D2)/2, where D1 is the smaller dimension. As shown in FIG. 25 where the mean tumor volumes are charted for all mice in each treatment group, all GFRα4-expressing CAR-T cells resulted in tumor eradication. Data for individual mice in each group are shown in FIG. 26. To assess levels of circulating CAR-T cells in mice, blood samples were collected on Day 13 and Day 27, and CD3+CD4+ T cells and CD3+CD8+ T cells were enumerated by flow cytometry (FIG. 27). These data show the presence of adoptively transferred T cells in all groups with higher levels seen in CAR groups compared to the NTD group, likely due to antigen stimulated proliferation.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments 5 and variations of this invention may be devised by others skilled in the art without departing from the true spirit and scope of the invention. The appended claims are intended to be construed to include all such embodiments and equivalent variations.

What is claimed is:

1. A modified immune cell or precursor cell thereof comprising a vector that comprises an isolated nucleic acid encoding a binding polypeptide that binds a glial cell derived neurotrophic factor (GDNF) family receptor alpha-4a (GFRα4a) or GFRα4b, wherein the isolated nucleic acid comprises a nucleotide sequence encoding:

(a) a heavy chain variable region comprising the nucleic acid sequence of SEQ ID NO: 2 and a light chain variable region comprising the nucleic acid sequence of SEQ ID NO: 13, 15, 18, 22, or 23;

(b) a heavy chain variable region comprising the nucleic acid sequence of SEQ ID NO: 3 and a light chain variable region comprising the nucleic acid sequence of SEQ ID NO: 13 or 22;

(c) a heavy chain variable region comprising the nucleic acid sequence of SEQ ID NO: 4 and a light chain variable region comprising the nucleic acid sequence of SEQ ID NO: 13, 15, 18, or 22; or (d) a heavy chain variable region comprising the nucleic acid sequence of SEQ ID NO: 5 and a light chain variable region comprising the nucleic acid sequence of SEQ ID NO: 13 or 18.

2. The modified immune cell or precursor cell thereof of claim 1, wherein the vector is:

(a) an expression vector; or (b) selected from the group consisting of a DNA vector, an RNA vector, a plasmid, a lentiviral vector, an adenoviral vector, an adeno-associated viral vector, and a retroviral vector; and/or (c) a self-inactivating vector.

3. The modified immune cell or precursor cell thereof of claim 1, wherein the vector further comprises one or more of:

(a) an EF-1α promoter;

(b) a woodchuck hepatitis virus posttranscriptional regulatory element (WPRE);

(c) a rev response element (RRE); and/or (d) a cPPT sequence.

4. The modified immune cell or precursor cell thereof of claim 1, wherein the binding polypeptide comprises an antibody or antigen binding fragment thereof.

5. The modified immune cell or precursor cell thereof of claim 4, wherein the antigen-binding fragment is selected from the group consisting of a Fab, a single-chain variable fragment (scFv), or a single-domain antibody.

6. The modified immune cell or precursor cell thereof of claim 1, wherein the isolated nucleic acid encodes an scFv comprising the amino acid sequence selected from the group consisting of SEQ ID NOs: 75, 77, 79, 81, 83, 85, 87, 89, 90, 96-98, and 102.

7. The modified immune cell or precursor cell thereof of claim 1, wherein the isolated nucleic acid comprises the nucleic acid sequence selected from the group consisting of SEQ ID NOs: 45, 47, 49, 51, 53, 55, 57, 59,60, 66-68, and 72.

8. The modified immune cell or precursor cell thereof of claim 1, wherein the vector comprises the nucleotide sequence set forth in SEQ ID NO: 111-114.

9. A modified immune cell or precursor cell thereof comprising a nucleic acid encoding a chimeric antigen receptor (CAR) that binds a glial cell derived neurotrophic factor (GDNF) family receptor alpha-4a (GFRα4a) or GFRα4b, wherein the CAR comprises:

(a) an antigen binding domain comprising:

(i) a heavy chain variable region encoded by the nucleic acid sequence of SEQ ID NO: 2 and a light chain variable region encoded by the nucleic acid sequence of SEQ ID NO: 13, 15, 18, 22, or 23;

(ii) a heavy chain variable region encoded by the nucleic acid sequence of SEQ ID NO: 3 and a light chain variable region encoded by the nucleic acid sequence of SEQ ID NO: 13 or 22;

(iii) a heavy chain variable region encoded by the nucleic acid sequence of SEQ ID NO: 4 and a light chain variable region encoded by the nucleic acid sequence of SEQ ID NO: 13, 15, 18, or 22; or (iv) a heavy chain variable region encoded by the nucleic acid sequence of SEQ ID NO: 5 and a light chain variable region encoded by the nucleic acid sequence of SEQ ID NO: 13 or 18;

(b) a transmembrane domain;

(c) a costimulatory domain; and (d) an intracellular signaling domain.

10. The modified immune cell or precursor cell thereof of claim 9, wherein:

(a) the antigen binding domain comprises the polypeptide encoded by the nucleic acid sequence selected from the group consisting of SEQ ID NOs: 45, 47, 49, 51, 53, 55, 57, 59, 60, 66-68, and 72; or (b) the antigen binding domain is encoded by the nucleotide sequence set forth in SEQ ID NO: 103-106.

11. The modified immune cell or precursor cell thereof of claim 9, wherein:

(a) the transmembrane domain is selected from the group consisting of an artificial hydrophobic sequence, and a transmembrane domain of a type I transmembrane protein, an alpha, beta, or zeta chain of a T cell receptor, CD28, CD3epsilon, CD45, CD4, CD5, CD9, CD16, CD22, CD33, CD37, CD64, CD80, CD86, OX40 (CD134), 4-1BB (CD137), and CD154;

(b) the costimulatory signaling domain comprises a costimulatory domain of a protein selected from the group consisting of proteins in the TNFR superfamily, CD28, OX40 (CD134), PD-1, CD7, LIGHT, CD83L, DAP10, DAP12, CD27, CD2, CD5, ICAM-1, LFA-1, Lck, TNFR-I, TNFI-II, Fas, CD30, CD40, ICOS, NKG2C, and B7-H3 (CD276), or a variant thereof; and/or (c) the intracellular signaling domain comprises an intracellular domain selected from the group consisting of cytoplasmic signaling domains of FcγRIII, FcεRI, a cytoplasmic tail of an Fc receptor, an immunoreceptor tyrosine-based activation motif (ITAM) bearing cytoplasmic receptor, TCR zeta, FcR gamma, CD3 gamma, CD3 delta, CD3 epsilon, CD5, CD22, CD79a, CD79b, and CD66d, or a variant thereof.

12. The modified immune cell or precursor cell thereof of claim 9, wherein the CAR further comprises a hinge domain, and wherein the hinge domain is:

(a) selected from the group consisting of an Fc fragment of an antibody, a hinge region of an antibody, a CH2 region of an antibody, a CH3 region of an antibody, an artificial hinge domain, and a CD8 hinge domain, or any combination thereof; or (b) a glycine/serine (GS)-rich linker comprising the amino acid sequence of SEQ ID NO: 168.

13. The modified immune cell or precursor cell thereof of claim 9, wherein the nucleic acid encoding the CAR comprises:

(a) an antigen binding domain polynucleotide that encodes the amino acid sequence of SEQ ID NO: 107-110 or 158-161;

(b) a polynucleotide encoding a CD8 transmembrane domain;

(c) a polynucleotide encoding a 4-1BB costimulatory domain; and (d) a polynucleotide encoding a CD3ζ intracellular signaling domain.

14. The modified immune cell or precursor cell thereof of claim 9, wherein:

(a) the antigen binding domain comprises the amino acid sequence set forth in SEQ ID NO: 107-110 or 158-161; or (b) the nucleic acid encoding the CAR comprises the nucleotide sequence set forth in SEQ ID NO: 111-114; or (c) the modified immune cell is selected from the group consisting of a T cell, a natural killer (NK) cell, a cytotoxic T lymphocyte (CTL), and a regulatory T cell; or (d) any combination of (a), (b), and (c).

15. A pharmaceutical composition comprising a therapeutically effective amount of the modified cell of claim 9.

16. A method of treating a disease associated with expression of GFRα4 in a subject in need thereof, comprising administering to the subject an effective amount of the modified immune cell or precursor cell thereof of claim 9.

17. The method of claim 16, wherein the disease associated with expression of GFRα4 is:

(a) a cancer;

(b) a medullary thyroid carcinoma (MTC); or (c) a metastasis resulting from a MTC.

* * * * *

SEQUENCE LISTING

```
Sequence total quantity: 169
SEQ ID NO: 1            moltype = DNA  length = 369
FEATURE                 Location/Qualifiers
misc_feature            1..369
                        note = Heavy Chain
misc_feature            1..369
                        note = Rabbit P4-10 heavy chain variable region
source                  1..369
                        mol_type = other DNA
                        organism = synthetic construct
SEQUENCE: 1
cagtccgtga aggagagcga gggcggcctg ttcaagccca ccgacaccct gaccctgacc  60
tgcacagtga gcggcttcag cctgtccaga cacgccctga catgggtgag acaggcccct  120
ggcaacggcc tggaatggat cggcgccatc gacaacgccg gcaccaccta ctacgccagc  180
tgggccaagt ccaggtccac catcaccagg aacaccgacc tccacaccgt gaccctgaag  240
atgacaagcc tgaccgcctc cgacaccgcc acctacttct gcgccagggt gttctacgac  300
atcaacagcg gctactacct ggatggcatg gacctgtggg gacctggcac actggtgacc  360
gtgagcagc                                                          369

SEQ ID NO: 2            moltype = DNA  length = 372
FEATURE                 Location/Qualifiers
misc_feature            1..372
                        note = Heavy Chain
misc_feature            1..372
                        note = H1
source                  1..372
                        mol_type = other DNA
                        organism = synthetic construct
SEQUENCE: 2
caagttcagc tgcaagaaag cggacccggt ttagtcaagc ccagcgagac tttatcttta  60
acatgcgccg tgagcggcta ctccatctct cgtcacgctt taacatggat taggcagccc  120
cccggtaagg gtttagaatg gatcggcgcc atcgacaacg ctggcaccac ctactacgcc  180
tcttgggcta agtctcgtgt gacaatcagc gtggacacct ccaagaacca gttttcttta  240
aagctgagca gcgtgaccgc tgccgacacc gctgtgtact attgcgctcg tgtcttctac  300
gacatcaaca gcggctacta tttagatggc atggatttat ggggacccgg tactttagtg  360
accgtgagct cc                                                      372

SEQ ID NO: 3            moltype = DNA  length = 372
FEATURE                 Location/Qualifiers
misc_feature            1..372
                        note = Heavy Chain
misc_feature            1..372
                        note = H1m1
source                  1..372
                        mol_type = other DNA
                        organism = synthetic construct
SEQUENCE: 3
cagcagagcg tgaaggagag cggccccggt ctggtgaagc ccagcgagac tttatcttta  60
acatgcgccg tgagcggctt ctctttatct cgtcacgctt taacttgggt gagacagcct  120
cccggtaaag gtttagagtg gatcggcgcc atcgacaacg ccggcacaac ctactacgcc  180
agctgggcca agtctcgtgt gaccatctct cgtaacaccg atttacacac cgtgtcttta  240
aagctgagct ccgtgaccgc tgccgatacc gccgtgtact tctgcgctag ggtgttctac  300
gacatcaaca gcggctacta tttagatggc atggatctgt ggggccccgg cacactggtc  360
acagtgtcca gc                                                      372

SEQ ID NO: 4            moltype = DNA  length = 372
FEATURE                 Location/Qualifiers
misc_feature            1..372
                        note = Heavy Chain
misc_feature            1..372
                        note = H2
source                  1..372
                        mol_type = other DNA
                        organism = synthetic construct
SEQUENCE: 4
gaggtgcagc tggtggaaag cggcggagga ctggtgcagc ccggtggctc tttaagactg  60
agctgtgctg ccagcggctt cacattctct cgtcacgctt taacttgggt gagacaagct  120
cccggaaagg gtttagaatg ggtgagcgcc atcgacaacg ccggaaccac ctactacgcc  180
agctgggcca agtctcgttt caccatctct cgtgataacg ccaagaacag cctctattta  240
cagatgaact ctttaagggc cgaggacacc gccgtgtact actgcgctag ggtgttctac  300
gacatcaaca gcggctacta tctggacggc atggatttat ggggccccgg tacactggtc  360
accgtgagca gc                                                      372

SEQ ID NO: 5            moltype = DNA  length = 369
FEATURE                 Location/Qualifiers
misc_feature            1..369
                        note = Heavy Chain
misc_feature            1..369
```

-continued

```
                       note = H2m1
source                 1..369
                       mol_type = other DNA
                       organism = synthetic construct
SEQUENCE: 5
cagagcgtca aggagtccgg aggaggactg gtgcagcccg gtggctcttt aaggctgagc  60
tgtgccgcct ctggctttac tttatctcgt cacgctttaa catgggtgag acaagctccc  120
ggtaagggac tggagtggat cggcgccatc gacaacgccg gcaccaccta ctacgcctct  180
tgggccaagt ctcgtttcac catctctcgt aacaccgatt tacacaccgt gtatttacag  240
atgaactctt taagggccga ggacacagcc gtctatttct gcgctcgtgt gttctacgac  300
atcaatagcg gctactacct cgacggaatg gatctgtggg gccccggtac tttagtgaca  360
gtcagcagc                                                          369

SEQ ID NO: 6           moltype = AA  length = 123
FEATURE                Location/Qualifiers
REGION                 1..123
                       note = Heavy Chain
REGION                 1..123
                       note = Rabbit P4-10 heavy chain variable region
source                 1..123
                       mol_type = protein
                       organism = synthetic construct
SEQUENCE: 6
QSVKESEGGL FKPTDTLTLT CTVSGFSLSR HALTWVRQAP GNGLEWIGAI DNAGTTYYAS  60
WAKSRSTITR NTDLHTVTLK MTSLTASDTA TYFCARVFYD INSGYYLDGM DLWGPGTLVT  120
VSS                                                                123

SEQ ID NO: 7           moltype = AA  length = 124
FEATURE                Location/Qualifiers
REGION                 1..124
                       note = Heavy Chain
REGION                 1..124
                       note = H1
source                 1..124
                       mol_type = protein
                       organism = synthetic construct
SEQUENCE: 7
QVQLQESGPG LVKPSETLSL TCAVSGYSIS RHALTWIRQP PGKGLEWIGA IDNAGTTYYA  60
SWAKSRVTIS VDTSKNQFSL KLSSVTAADT AVYYCARVFY DINSGYYLDG MDLWGPGTLV  120
TVSS                                                               124

SEQ ID NO: 8           moltype = AA  length = 124
FEATURE                Location/Qualifiers
REGION                 1..124
                       note = Heavy Chain
REGION                 1..124
                       note = H1m1
source                 1..124
                       mol_type = protein
                       organism = synthetic construct
SEQUENCE: 8
QQSVKESGPG LVKPSETLSL TCAVSGFSLS RHALTWVRQP PGKGLEWIGA IDNAGTTYYA  60
SWAKSRVTIS RNTDLHTVSL KLSSVTAADT AVYFCARVFY DINSGYYLDG MDLWGPGTLV  120
TVSS                                                               124

SEQ ID NO: 9           moltype = AA  length = 124
FEATURE                Location/Qualifiers
REGION                 1..124
                       note = Heavy Chain
REGION                 1..124
                       note = H2
source                 1..124
                       mol_type = protein
                       organism = synthetic construct
SEQUENCE: 9
EVQLVESGGG LVQPGGSLRL SCAASGFTFS RHALTWVRQA PGKGLEWVSA IDNAGTTYYA  60
SWAKSRFTIS RDNAKNSLYL QMNSLRAEDT AVYYCARVFY DINSGYYLDG MDLWGPGTLV  120
TVSS                                                               124

SEQ ID NO: 10          moltype = AA  length = 123
FEATURE                Location/Qualifiers
REGION                 1..123
                       note = Heavy Chain
REGION                 1..123
                       note = H2m1
source                 1..123
                       mol_type = protein
                       organism = synthetic construct
SEQUENCE: 10
```

```
QSVKESGGGL VQPGGSLRLS CAASGFTLSR HALTWVRQAP GKGLEWIGAI DNAGTTYYAS  60
WAKSRFTISR NTDLHTVYLQ MNSLRAEDTA VYFCARVFYD INSGYYLDGM DLWGPGTLVT  120
VSS                                                                123

SEQ ID NO: 11           moltype = DNA  length = 333
FEATURE                 Location/Qualifiers
misc_feature            1..333
                        note = Light Chain
misc_feature            1..333
                        note = Rabbit P4-10 light chain variable region
source                  1..333
                        mol_type = other DNA
                        organism = synthetic construct
SEQUENCE: 11
cagttcgtgc tgacacagag ccctagcgtg agcgccgccc tgggagcctc cgctaaactg  60
acctgcaccc tgagcagcgc ccacaagacc tacaccatcg actggtacca acagcagcag  120
ggcgaggccc ccaggtatct gatgcaggtg aagtccgacg gcagctacac caaaggcacc  180
ggcgtgcctg acaggttcag cggcagctcc agcggagccg acaggtacct gatcatcccc  240
tccgtgcagg ccgacgacga ggctggctac gtgtgtggcg ccgacgacaa tggcggctac  300
gtgttcggag gcggcaccca gctgaccgtg aca                               333

SEQ ID NO: 12           moltype = DNA  length = 333
FEATURE                 Location/Qualifiers
misc_feature            1..333
                        note = Light Chain
misc_feature            1..333
                        note = L1
source                  1..333
                        mol_type = other DNA
                        organism = synthetic construct
SEQUENCE: 12
cagctggtgc tgacccagag ccccagcgct tccgcctctt taggagccag cgtgaagctg  60
acttgtactt taagcagcgc ccacaagacc tacacaatcg cttggcacca gcagcagccc  120
gaaaagggcc ccagatatct gatgaaggtc aagtccgacg gcagctactc caagggcgac  180
ggcatccccg atcgtttcag cggttcttcc agcggcgccg agaggtattt aaccatcagc  240
tctttacaga gcgaggacga ggccgactac tactgcggcg ctgacgacaa cggcggctac  300
gtctttggcg gcggcacaaa actgaccgtg ctg                               333

SEQ ID NO: 13           moltype = DNA  length = 333
FEATURE                 Location/Qualifiers
misc_feature            1..333
                        note = Light Chain
misc_feature            1..333
                        note = L1m1
source                  1..333
                        mol_type = other DNA
                        organism = synthetic construct
SEQUENCE: 13
cagtttgtgc tgacccagag ccctagcgct tccgcctctt taggagccag cgtgaagctg  60
acttgtactt tatcctccgc ccacaagacc tacaccatcg actggtacca gcagcagccc  120
gaaaagggcc ctcgttatct gatgcaagtt aagtccgacg gcagctacac caagggaacc  180
ggcgtgcccg acagattctc cggtagcagc agcggcgccg acagatattt aaccatcagc  240
tctttacagt ccgaggacga ggccgactac tactgcggcg ccgacgacaa tggcggctac  300
gtcttcggag gcggcacaca gctgaccgtg act                               333

SEQ ID NO: 14           moltype = DNA  length = 333
FEATURE                 Location/Qualifiers
misc_feature            1..333
                        note = Light Chain
misc_feature            1..333
                        note = L1m2
source                  1..333
                        mol_type = other DNA
                        organism = synthetic construct
SEQUENCE: 14
cagtttgtgc tgacccagag ccctagcgct tccgcctctt taggagccag cgtgaagctg  60
acttgtactt tatcctccgc ccacaagacc tacaccatcg actggcacca gcagcagccc  120
gaaaagggcc ctcgttatct gatgcaagtt aagtccgacg gcagctacac caagggaacc  180
ggcatccccg acagattctc cggtagcagc agcggcgccg agagatattt aaccatcagc  240
tctttacagt ccgaggacga ggccgactac tactgcggcg ccgacgacaa tggcggctac  300
gtcttcggag gcggcacaca gctgaccgtg ctg                               333

SEQ ID NO: 15           moltype = DNA  length = 333
FEATURE                 Location/Qualifiers
misc_feature            1..333
                        note = Light Chain
misc_feature            1..333
                        note = L1m3
source                  1..333
```

```
                       mol_type = other DNA
                       organism = synthetic construct
SEQUENCE: 15
cagctggtgc tcacccaaag ccctagcgcc tctgcctctt taggcgcttc cgtgaagctg  60
acttgtactt taagctccgc ccataagacc tacaccatcg actggtacca gcagcagccc  120
gagaagggcc ctcgttattt aatgcaagtt aagtccgatg gcagctatac caagggcacc  180
ggcgtgcccg acagattcag cggcagctcc agcggagccg atcgttattt aaccatcagc  240
tctttacaga gcgaggacga ggctgactac tactgcggcg ccgacgataa cggcggctac  300
gtgttcggcg gcggcaccca actgacagtg ctg                                333

SEQ ID NO: 16          moltype = DNA  length = 333
FEATURE                Location/Qualifiers
misc_feature           1..333
                       note = Light Chain
misc_feature           1..333
                       note = L1m4
source                 1..333
                       mol_type = other DNA
                       organism = synthetic construct
SEQUENCE: 16
cagttggtgc tcacccaaag ccctagcgcc tctgcctctt taggcgcttc cgtgaagctg  60
acttgtactt taagctccgc ccataagacc tacaccatcg cctggcatca gcagcagccc  120
gagaagggcc ctcgttattt aatgcaagtt aagtccgatg gcagctatac caagggcacc  180
ggcgtgcccg acagattcag cggcagctcc agcggagccg atcgttattt aaccatcagc  240
tctttacaga gcgaggacga ggctgactac tactgcggcg ccgacgataa cggcggctac  300
gtgttcggcg gcggcaccca actgacagtg ctc                                333

SEQ ID NO: 17          moltype = DNA  length = 333
FEATURE                Location/Qualifiers
misc_feature           1..333
                       note = Light Chain
misc_feature           1..333
                       note = L2
source                 1..333
                       mol_type = other DNA
                       organism = synthetic construct
SEQUENCE: 17
cagagcgtgc tgacacagcc tcctagcgcc agcggcacac ccggtcagag agtgaccatc  60
agctgctccg gcagcagcgc ccacaagacc tacaccgtga actggtacca gcagctgccc  120
ggcacagccc ctaagctgct gatctacgtg aaatccgacg gcagctacca gaggcctagc  180
ggagtgcccg atcgtttcag cggcagcaaa agcggcacaa gcgcctcttt agctatcagc  240
ggtttacaga gcgaggacga ggccgactat tactgcggcg ccgacgataa cggcggctac  300
gtgttcggcg gcggaaccaa gctgacagtg ctg                                333

SEQ ID NO: 18          moltype = DNA  length = 333
FEATURE                Location/Qualifiers
misc_feature           1..333
                       note = Light Chain
misc_feature           1..333
                       note = L2m1
source                 1..333
                       mol_type = other DNA
                       organism = synthetic construct
SEQUENCE: 18
cagttcgtgc tgacacagcc tcccagcgcc tctggcacac ccggtcagag ggtgaccatc  60
tcttgtactt tatcctccgc ccacaagacc tacaccattg actggtacca gcagctgccc  120
ggtaccgccc ctaagctgct gatttacgtg aaatccgacg gcagctacac caagggaacc  180
ggcgtgcccg atcgtttttc cggcagctcc agcggcgccg ataggtattt agccatcagc  240
ggtttacagt ccgaggatga ggccgactac tactgcggcg ccgatgacaa cggcggctac  300
gtgttcggcg gaggaaccca gctcaccgtg acc                                333

SEQ ID NO: 19          moltype = DNA  length = 333
FEATURE                Location/Qualifiers
misc_feature           1..333
                       note = Light Chain
misc_feature           1..333
                       note = L2m2
source                 1..333
                       mol_type = other DNA
                       organism = synthetic construct
SEQUENCE: 19
cagttcgtgc tgacacagcc tcccagcgcc tctggcacac ccggtcagag ggtgaccatc  60
tcttgtactt tatcctccgc ccacaagacc tacaccattg actggtacca gcagctgccc  120
ggtaccgccc ctaagctgct gatttacgtg aaatccgacg gcagctacac caagggaacc  180
ggcgtgcccg atcgtttttc cggcagctcc agcggcgccg atgccagctt agccatcagc  240
ggtttacagt ccgaggatga ggccgactac tactgcggcg ccgatgacaa cggcggctac  300
gtgttcggcg gaggaaccca gctcaccgtg ctg                                333

SEQ ID NO: 20          moltype = DNA  length = 333
```

```
FEATURE                Location/Qualifiers
misc_feature           1..333
                       note = Light Chain
misc_feature           1..333
                       note = L2m3
source                 1..333
                       mol_type = other DNA
                       organism = synthetic construct
SEQUENCE: 20
cagagcgtgc tgacacagcc tcccagcgcc tctggcacac ccggtcagag ggtgaccatc  60
tcttgtactt tatcctccgc ccacaagacc tacaccattg actggtacca gcagctgccc  120
ggtaccgccc ctaagctgct gatttacgtg aaatccgacg gcagctacac caagggaacc  180
ggcgtgcccg atcgtttttc cggcagcaag agcggcacca gcgccagctt agccatcagc  240
ggtttacagt ccgaggatga ggccgactac tactgcggcg ccgatgacaa cggcggctac  300
gtgttcggcg gaggaaccca gctcaccgtg ctg                               333

SEQ ID NO: 21          moltype = DNA  length = 333
FEATURE                Location/Qualifiers
misc_feature           1..333
                       note = Light Chain
misc_feature           1..333
                       note = L3
source                 1..333
                       mol_type = other DNA
                       organism = synthetic construct
SEQUENCE: 21
cagtccgctt taacacagcc cgcttctgtg tccggaagcc ccggtcagag catcaccatc  60
agctgcaccg gcaccagcgc tcacaagacc tacaccgtga gctggtacca gcagcacccc  120
ggtaaggccc ccaaactgat gatctacgtg aagagcgacg gcagctacaa cagacccagc  180
ggcgtgagca atcgtttcag cggcagcaag agcggcaaca ccgcttcttt aaccatcagc  240
ggtttacaag ctgaagacga ggctgactac tactgcggcg ccgacgataa cggcggctac  300
gtgtttggcg gcggcaccaa actgaccgtg ctg                               333

SEQ ID NO: 22          moltype = DNA  length = 333
FEATURE                Location/Qualifiers
misc_feature           1..333
                       note = Light Chain
misc_feature           1..333
                       note = L3m1
source                 1..333
                       mol_type = other DNA
                       organism = synthetic construct
SEQUENCE: 22
cagttcgtgc tgacccagcc cgcttctgtg agcggttctc ccggtcagag catcaccatc  60
agctgcactt taagcagcgc ccacaagacc tacaccatcg actggtacca gcagcacccc  120
ggcaaggccc ccaagtattt aatgcaagtt aagtccgacg gcagctacac caagggcacc  180
ggcgtgccca acagattctc cggcagcagc tccggcgccg acagatactt aaccatcagc  240
ggtttacaag ctgaggatga ggccgactat gtgtgcggcg ccgacgacaa tggcggctac  300
gtgttcggcg gcggcacaca gctgaccgtg act                               333

SEQ ID NO: 23          moltype = DNA  length = 333
FEATURE                Location/Qualifiers
misc_feature           1..333
                       note = Light Chain
misc_feature           1..333
                       note = L3m2
source                 1..333
                       mol_type = other DNA
                       organism = synthetic construct
SEQUENCE: 23
cagttcgtgc tgacccagcc cgcttctgtg agcggttctc ccggtcagag catcaccatc  60
agctgcactt taagcagcgc ccacaagacc tacaccatcg actggtacca gcagcacccc  120
ggcaaggccc ccaagctgat gatccaagtt aagtccgacg gcagctacac caagggcacc  180
ggcgtgagca acagattctc cggcagcagc tccggcgccg acagatactt aaccatcagc  240
ggtttacaag ctgaggatga ggccgactat tactgcggcg ccgacgacaa tggcggctac  300
gtgttcggcg gcggcacaca gctgaccgtg ctg                               333

SEQ ID NO: 24          moltype = DNA  length = 333
FEATURE                Location/Qualifiers
misc_feature           1..333
                       note = Light Chain
misc_feature           1..333
                       note = L3m3
source                 1..333
                       mol_type = other DNA
                       organism = synthetic construct
SEQUENCE: 24
cagagcgccc tgacccagcc cgcttctgtg agcggttctc ccggtcagag catcaccatc  60
agctgcactg gcaccagcgc ccacaagacc tacaccatcg actggtacca gcagcacccc  120
```

```
ggcaaggccc ccaagctgat gatctatgtt aagtccgacg gcagctacac caagggcacc  180
ggcgtgagca acagattctc cggcagcaag tccggcaaca ccgccagctt aaccatcagc  240
ggtttacaag ctgaggatga ggccgactat tactgcggcg ccgacgacaa tggcggctac  300
gtgttcggcg gcggcacaca gctgaccgtg ctg                               333

SEQ ID NO: 25          moltype = DNA  length = 333
FEATURE                Location/Qualifiers
misc_feature           1..333
                       note = Light Chain
misc_feature           1..333
                       note = L3m4
source                 1..333
                       mol_type = other DNA
                       organism = synthetic construct
SEQUENCE: 25
cagagcgctc tgacccagcc cgcttctgtg agcggttctc ccggtcagag catcaccatc  60
agctgcactg gcacaagcgc ccacaagacc tacaccgtga gctggtacca gcagcacccc  120
ggcaaggccc ccaagtattt aatgcaagtt aagtccgacg gcagctacac caagggcacc  180
ggcgtgccca acagattctc cggcagcagc tccggcgccg acagatactt aaccatcagc  240
ggtttacaag ctgaggatga ggccgactat tactgcggcg ccgacgacaa tggcggctac  300
gtgttcggcg gcggcaccca actgacagtg ctg                               333

SEQ ID NO: 26          moltype = DNA  length = 333
FEATURE                Location/Qualifiers
misc_feature           1..333
                       note = Light Chain
misc_feature           1..333
                       note = L3m5
source                 1..333
                       mol_type = other DNA
                       organism = synthetic construct
SEQUENCE: 26
cagtctgctc tgacccagcc cgcttctgtg agcggttctc ccggtcagag catcaccatc  60
agctgcactg gcacaagcgc ccacaagacc tacaccgtga gttggtacca gcagcacccc  120
ggcaaggccc ccaagttgat gatctacgtt aagtccgacg gcagctacac caagggcacc  180
ggcgtgccca acagattctc cggcagcagc tccggcgccg acagatactt aaccatcagc  240
ggtttacaag ctgaggatga ggccgactat tattgcggcg ccgacgacaa tggcggctac  300
gtgttcggcg gcggcaccca actgacagtg ctc                               333

SEQ ID NO: 27          moltype = AA  length = 111
FEATURE                Location/Qualifiers
REGION                 1..111
                       note = Light Chain
REGION                 1..111
                       note = Rabbit P4-10 light chain variable region
source                 1..111
                       mol_type = protein
                       organism = synthetic construct
SEQUENCE: 27
QFVLTQSPSV SAALGASAKL TCTLSSAHKT YTIDWYQQQQ GEAPRYLMQV KSDGSYTKGT  60
GVPDRFSGSS SGADRYLIIP SVQADDEAGY VCGADDNGGY VFGGGTQLTV T           111

SEQ ID NO: 28          moltype = AA  length = 111
FEATURE                Location/Qualifiers
REGION                 1..111
                       note = Light Chain
REGION                 1..111
                       note = L1
source                 1..111
                       mol_type = protein
                       organism = synthetic construct
SEQUENCE: 28
QLVLTQSPSA SASLGASVKL TCTLSSAHKT YTIAWHQQQP EKGPRYLMKV KSDGSYSKGD  60
GIPDRFSGSS SGAERYLTIS SLQSEDEADY YCGADDNGGY VFGGGTKLTV L           111

SEQ ID NO: 29          moltype = AA  length = 111
FEATURE                Location/Qualifiers
REGION                 1..111
                       note = Light Chain
REGION                 1..111
                       note = L1m1
source                 1..111
                       mol_type = protein
                       organism = synthetic construct
SEQUENCE: 29
QFVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV T           111

SEQ ID NO: 30          moltype = AA  length = 111
```

-continued

```
FEATURE                Location/Qualifiers
REGION                 1..111
                       note = Light Chain
REGION                 1..111
                       note = L1m2
source                 1..111
                       mol_type = protein
                       organism = synthetic construct
SEQUENCE: 30
QFVLTQSPSA SASLGASVKL TCTLSSAHKT YTIDWHQQQP EKGPRYLMQV KSDGSYTKGT  60
GIPDRFSGSS SGAERYLTIS SLQSEDEADY YCGADDNGGY VFGGGTQLTV L           111

SEQ ID NO: 31          moltype = AA  length = 111
FEATURE                Location/Qualifiers
REGION                 1..111
                       note = Light Chain
REGION                 1..111
                       note = L1m3
source                 1..111
                       mol_type = protein
                       organism = synthetic construct
SEQUENCE: 31
QLVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV L           111

SEQ ID NO: 32          moltype = AA  length = 111
FEATURE                Location/Qualifiers
REGION                 1..111
                       note = Light Chain
REGION                 1..111
                       note = L1m4
source                 1..111
                       mol_type = protein
                       organism = synthetic construct
SEQUENCE: 32
QLVLTQSPSA SASLGASVKL TCTLSSAHKT YTIAWHQQQP EKGPRYLMQV KSDGSYTKGT  60
GVPDRFSGSS SGADRYLTIS SLQSEDEADY YCGADDNGGY VFGGGTQLTV L           111

SEQ ID NO: 33          moltype = AA  length = 111
FEATURE                Location/Qualifiers
REGION                 1..111
                       note = Light Chain
REGION                 1..111
                       note = L2
source                 1..111
                       mol_type = protein
                       organism = synthetic construct
SEQUENCE: 33
QSVLTQPPSA SGTPGQRVTI SCSGSSAHKT YTVNWYQQLP GTAPKLLIYV KSDGSYQRPS  60
GVPDRFSGSK SGTSASLAIS GLQSEDEADY YCGADDNGGY VFGGGTKLTV L           111

SEQ ID NO: 34          moltype = AA  length = 111
FEATURE                Location/Qualifiers
REGION                 1..111
                       note = Light Chain
REGION                 1..111
                       note = L2m1
source                 1..111
                       mol_type = protein
                       organism = synthetic construct
SEQUENCE: 34
QFVLTQPPSA SGTPGQRVTI SCTLSSAHKT YTIDWYQQLP GTAPKLLIYV KSDGSYTKGT  60
GVPDRFSGSS SGADRYLAIS GLQSEDEADY YCGADDNGGY VFGGGTQLTV T           111

SEQ ID NO: 35          moltype = AA  length = 111
FEATURE                Location/Qualifiers
REGION                 1..111
                       note = Light Chain
REGION                 1..111
                       note = L2m2
source                 1..111
                       mol_type = protein
                       organism = synthetic construct
SEQUENCE: 35
QFVLTQPPSA SGTPGQRVTI SCTLSSAHKT YTIDWYQQLP GTAPKLLIYV KSDGSYTKGT  60
GVPDRFSGSS SGADASLAIS GLQSEDEADY YCGADDNGGY VFGGGTQLTV L           111

SEQ ID NO: 36          moltype = AA  length = 111
FEATURE                Location/Qualifiers
```

-continued

```
REGION                  1..111
                        note = Light Chain
REGION                  1..111
                        note = L2m3
source                  1..111
                        mol_type = protein
                        organism = synthetic construct
SEQUENCE: 36
QSVLTQPPSA SGTPGQRVTI SCTLSSAHKT YTIDWYQQLP GTAPKLLIYV KSDGSYTKGT  60
GVPDRFSGSK SGTSASLAIS GLQSEDEADY YCGADDNGGY VFGGGTQLTV L           111

SEQ ID NO: 37           moltype = AA  length = 111
FEATURE                 Location/Qualifiers
REGION                  1..111
                        note = Light Chain
REGION                  1..111
                        note = L3
source                  1..111
                        mol_type = protein
                        organism = synthetic construct
SEQUENCE: 37
QSALTQPASV SGSPGQSITI SCTGTSAHKT YTVSWYQQHP GKAPKLMIYV KSDGSYNRPS  60
GVSNRFSGSK SGNTASLTIS GLQAEDEADY YCGADDNGGY VFGGGTKLTV L           111

SEQ ID NO: 38           moltype = AA  length = 111
FEATURE                 Location/Qualifiers
REGION                  1..111
                        note = Light Chain
REGION                  1..111
                        note = L3m1
source                  1..111
                        mol_type = protein
                        organism = synthetic construct
SEQUENCE: 38
QFVLTQPASV SGSPGQSITI SCTLSSAHKT YTIDWYQQHP GKAPKYLMQV KSDGSYTKGT  60
GVPNRFSGSS SGADRYLTIS GLQAEDEADY VCGADDNGGY VFGGGTQLTV T           111

SEQ ID NO: 39           moltype = AA  length = 111
FEATURE                 Location/Qualifiers
REGION                  1..111
                        note = Light Chain
REGION                  1..111
                        note = L3m2
source                  1..111
                        mol_type = protein
                        organism = synthetic construct
SEQUENCE: 39
QFVLTQPASV SGSPGQSITI SCTLSSAHKT YTIDWYQQHP GKAPKLMIQV KSDGSYTKGT  60
GVSNRFSGSS SGADRYLTIS GLQAEDEADY YCGADDNGGY VFGGGTQLTV L           111

SEQ ID NO: 40           moltype = AA  length = 111
FEATURE                 Location/Qualifiers
REGION                  1..111
                        note = Light Chain
REGION                  1..111
                        note = L3m3
source                  1..111
                        mol_type = protein
                        organism = synthetic construct
SEQUENCE: 40
QSALTQPASV SGSPGQSITI SCTGTSAHKT YTIDWYQQHP GKAPKLMIYV KSDGSYTKGT  60
GVSNRFSGSK SGNTASLTIS GLQAEDEADY YCGADDNGGY VFGGGTQLTV L           111

SEQ ID NO: 41           moltype = AA  length = 111
FEATURE                 Location/Qualifiers
REGION                  1..111
                        note = Light Chain
REGION                  1..111
                        note = L3m4
source                  1..111
                        mol_type = protein
                        organism = synthetic construct
SEQUENCE: 41
QSALTQPASV SGSPGQSITI SCTGTSAHKT YTVSWYQQHP GKAPKYLMQV KSDGSYTKGT  60
GVPNRFSGSS SGADRYLTIS GLQAEDEADY YCGADDNGGY VFGGGTQLTV L           111

SEQ ID NO: 42           moltype = AA  length = 111
FEATURE                 Location/Qualifiers
REGION                  1..111
```

```
                         note = Light Chain
REGION                   1..111
                         note = L3m5
source                   1..111
                         mol_type = protein
                         organism = synthetic construct
SEQUENCE: 42
QSALTQPASV SGSPGQSITI SCTGTSAHKT YTVSWYQQHP GKAPKLMIYV KSDGSYTKGT  60
GVPNRFSGSS SGADRYLTIS GLQAEDEADY YCGADDNGGY VFGGGTQLTV L           111

SEQ ID NO: 43            moltype = DNA  length = 759
FEATURE                  Location/Qualifiers
misc_feature             1..759
                         note = scFv
misc_feature             1..759
                         note = 0.410HC.410LC
source                   1..759
                         mol_type = other DNA
                         organism = synthetic construct
SEQUENCE: 43
cagttcgtgc tgacccagag ccctagcgtg agcgctgctc tgggagccag cgccaagctc  60
acttgtactt taagctccgc ccacaaaacc tacaccatcg actggtacca gcagcagcaa  120
ggtgaggccc ccagatattt aatgcaagtt aagtccgatg gcagctacac caagggcacc  180
ggagtgcccg ataggttcag cggcagctcc agcggcgccg ataggtattt aatcatcccc  240
agcgtgcaag ctgatgatga ggccggctac gtgtgtggcg ccgacgacaa cggcggctac  300
gtgttcggag gcggaaccca gctgacagtg accggaggcg gaagctccag aagctccagc  360
agcggaggag gaggaagcgg aggaggcgga cagtccgtca aggagagcga gggcggttta  420
tttaagccca ccgacacttt aactttaact tgtacagtga gcggcttctc tttatccaga  480
cacgctttaa catgggtgag gcaagctccc ggtaatggtt tagagtggat cggcgccatc  540
gacaacgccg gcaccaccta ctacgccagc tgggccaagt ctcgttccac catcacaaga  600
aacaccgatt tacacaccgt gactttaaag atgacctctt taaccgcctc cgacaccgcc  660
acatacttct gcgctcgtgt gttctacgac atcaattccg gctactattt agacggcatg  720
gatttatggg gccccggtac tttagtgacc gtctccagc                         759

SEQ ID NO: 44            moltype = DNA  length = 762
FEATURE                  Location/Qualifiers
misc_feature             1..762
                         note = scFv
misc_feature             1..762
                         note = 1.H1.L3
source                   1..762
                         mol_type = other DNA
                         organism = synthetic construct
SEQUENCE: 44
cagtccgctt taacacagcc cgcttctgtg tccggaagcc ccggtcagag catcaccatc  60
agctgcaccg gcaccagcgc tcacaagacc tacaccgtga gctggtacca gcagcacccc  120
ggtaaggccc ccaaactgat gatctacgtg aagagcgacg gcagctacaa cagacccagc  180
ggcgtgagca atcgtttcag cggcagcaag agcggcaaca ccgcttcttt aaccatcagc  240
ggtttacaag ctgaagacga ggctgactac tactgcggcg ccgacgataa cggcggctac  300
gtgtttggcg gcggcaccaa actgaccgtg ctgggaggcg gctccagcag aagctcctcc  360
agcggaggag gaggaagcgg aggcggagga caagttcagc tgcaagaaag cggacccggt  420
ttagtcaagc ccagcgagac tttatcttta acatgcgccg tgagcggcta ctccatctct  480
cgtcacgctt taacatggat taggcagccc cccggtaagg gtttagaatg gatcggcgcc  540
atcgacaacg ctggcaccac ctactacgcc tcttgggcta agtctcgtgt gacaatcagc  600
gtggacacct ccaagaacca gttttcttta aagctgagca gcgtgaccgc tgccgacacc  660
gctgtgtact attgcgctcg tgtcttctac gacatcaaca gcggctacta tttagatggc  720
atggatttat ggggacccgg tactttagtg accgtgagct cc                      762

SEQ ID NO: 45            moltype = DNA  length = 762
FEATURE                  Location/Qualifiers
misc_feature             1..762
                         note = scFv
misc_feature             1..762
                         note = 2.H1.L3m1
source                   1..762
                         mol_type = other DNA
                         organism = synthetic construct
SEQUENCE: 45
cagttcgtgc tgacccagcc cgcttctgtg agcggttctc ccggtcagag catcaccatc  60
agctgcactt taagcagcgc ccacaagacc tacaccatcg actggtacca gcagcacccc  120
ggcaaggccc ccaagtattt aatgcaagtt aagtccgacg gcagctacac caagggcacc  180
ggcgtgccca acagattctc cggcagcagc tccggcgccg acagatactt aaccatcagc  240
ggtttacaag ctgaggatga ggccgactat gtgtgcggcg ccgacgacaa tggcggctac  300
gtgttcggcg gcggcacaca gctgaccgtg actggtggag gctccagcag atccagctcc  360
agcggcggag gaggcagcgg aggcggagga caagtgcagc tccaagaatc cggcccccggt  420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
```

```
gccgtgtact actgcgctcg tgtgttctac gacatcaaca gcggctacta tttagacggc  720
atggatttat ggggccccgg tactttagtg accgtcagct cc                     762

SEQ ID NO: 46          moltype = DNA  length = 762
FEATURE                Location/Qualifiers
misc_feature           1..762
                       note = scFv
misc_feature           1..762
                       note = 3.H1m1.L3
source                 1..762
                       mol_type = other DNA
                       organism = synthetic construct
SEQUENCE: 46
cagtccgctt taacccagcc cgcctctgtg tccggaagcc ccggccagag catcaccatc  60
agctgcaccg gcacctccgc ccacaagacc tacaccgtga gctggtatca gcagcacccc  120
ggcaaggccc ccaagctcat gatctacgtg aagagcgacg gctcctacaa tcgtcccagc  180
ggagtgagca atcgtttcag cggctccaag tccggcaaca ccgcctcttt aaccattagc  240
ggtttacaag ctgaggacga ggctgattac tactgcggcg ccgacgataa cggaggctac  300
gtgttcggcg gcggaacaaa gctgaccgtg ctgggcggag gctccagcag aagcagctcc  360
agcggaggcg gaggaagcgg aggaggagga cagcagagcg tgaaggagag cggcccccggt  420
ctggtgaagc ccagcgagac tttatcttta acatgcgccg tgagcggctt ctctttatct  480
cgtcacgctt taacttgggt gagacagcct cccggtaaag gtttagagtg gatcggcgcc  540
atcgacaacg ccggcacaac ctactacgcc agctgggcca agtctcgtgt gaccatctct  600
cgtaacaccg atttacacac cgtgtcttta aagctgagct ccgtgaccgc tgccgatacc  660
gccgtgtact tctgcgctag ggtgttctac gacatcaaca gcggctacta tttagatggc  720
atggatctgt ggggccccgg cacactggtc acagtgtcca gc                     762

SEQ ID NO: 47          moltype = DNA  length = 762
FEATURE                Location/Qualifiers
misc_feature           1..762
                       note = scFv
misc_feature           1..762
                       note = 4.H1m1.L3m1
source                 1..762
                       mol_type = other DNA
                       organism = synthetic construct
SEQUENCE: 47
cagttcgtgc tgacccagcc cgcttccgtg agcggttctc ccggacagag catcaccatt  60
agctgcactt taagcagcgc ccacaagacc tacaccatcg actggtacca gcagcatccc  120
ggcaaggccc ccaagtacct catgcaagtt aagagcgacg gaagctatac caagggcacc  180
ggagtgccca acagattcag cggcagcagc tccggagccg atcgttattt aacaatcagc  240
ggactgcaag ctgaggacga ggccgactac gtgtgtggcg ccgacgacaa tggcggctac  300
gtgtttggag gcggaaccca gctgaccgtg actggaggcg gcagcagcag aagcagcagc  360
agcggaggag gtggcagcgg cggaggcgga cagcagagcg tgaaggagag cggacccggt  420
ttagtgaagc ctagcgagac tttatcttta acatgcgccg tgtccggctt ctctttaagc  480
agacacgctc tgacttgggt gaggcagcct cccggtaagg gtttagagtg gatcggcgcc  540
atcgacaacg ccggcaccac ctactacgcc agctgggcca agtccagagt gaccatctcc  600
agaaacaccg acctccacac agtgtcttta aagctgtcct ccgtcacagc tgccgacacc  660
gccgtgtact tctgcgctcg tgtgttctac gacatcaaca gcggctatta tttagacggc  720
atggatttat ggggccccgg tactttagtg accgtgagca gc                     762

SEQ ID NO: 48          moltype = DNA  length = 762
FEATURE                Location/Qualifiers
misc_feature           1..762
                       note = scFv
misc_feature           1..762
                       note = 5.H2.L2
source                 1..762
                       mol_type = other DNA
                       organism = synthetic construct
SEQUENCE: 48
cagagcgtgc tgacacagcc tcctagcgcc agcggcacac ccggtcagag agtgaccatc  60
agctgctccg gcagcagcgc ccacaagacc tacaccgtga actggtacca gcagctgccc  120
ggcacagccc ctaagctgct gatctacgtg aaatccgacg gcagctacca gaggcctagc  180
ggagtgcccg atcgtttcag cggcagcaaa agcggcacaa gcgcctcttt agctatcagc  240
ggtttacaga gcgaggacga ggccgactat tactgcggcg ccgacgataa cggcggctac  300
gtgttcggcg gcggaaccaa gctgacagtg ctgggcggcg gaagcagcag aagcagcagc  360
tctggaggag gaggaagcgg aggtggaggc gaggtgcagc tggtggaaag cggcggagga  420
ctggtgcagc ccggtggctc tttaagactg agctgtgctg ccagcggctt cacattctct  480
cgtcacgctt taacttgggt gagacaagct cccggaaagg gtttagaatg ggtgagcgcc  540
atcgacaacg ccggaaccac ctactacgcc agctgggcca agtctcgttt caccatctct  600
cgtgataacg ccaagaacag cctctattta cagatgaact ctttaagggc cgaggacacc  660
gccgtgtact actgcgctag ggtgttctac gacatcaaca gcggctacta tctggacggc  720
atggatttat ggggccccgg tacactggtc accgtgagca gc                     762

SEQ ID NO: 49          moltype = DNA  length = 762
FEATURE                Location/Qualifiers
misc_feature           1..762
                       note = scFv
```

```
misc_feature           1..762
                       note = 6.H2.L2m1
source                 1..762
                       mol_type = other DNA
                       organism = synthetic construct
SEQUENCE: 49
cagttcgtgc tgacacagcc tcccagcgcc tctggcacac ccggtcagag ggtgaccatc  60
tcttgtactt tatcctccgc ccacaagacc tacaccattg actggtacca gcagctgccc  120
ggtaccgccc ctaagctgct gatttacgtg aaatccgacg gcagctacac caagggaacc  180
ggcgtgcccg atcgttttc cggcagctcc agcggcgccg ataggtattt agccatcagc  240
ggtttacagt ccgaggatga ggccgactac tactgcggcg ccgatgacaa cggcggctac  300
gtgttcggcg gaggaaccca gctcaccgtg accggaggag gctcctctcg tagctccagc  360
tccggaggag gaggaagcgg aggcggcgga gaagtgcaac tggtggagtc cggcggcgga  420
ctggtgcagc ccggtggctc tttaagactg agctgtgccg cctccggctt cacctttagc  480
agacacgccc tcacttgggt cagacaagct cccggtaagg gtttagagtg ggtgagcgcc  540
atcgacaacg ccggcacaac ctactacgcc tcttgggcca agtctcgttt caccatcagc  600
agagacaacg ccaagaactc tttatattta cagatgaact ctttaagggc cgaggacacc  660
gccgtgtact actgcgctcg tgtgttctac gacatcaaca gcggctatta tttagatggc  720
atggatttat ggggccccgg tactttagtg acagtgtcct cc                    762

SEQ ID NO: 50          moltype = DNA  length = 762
FEATURE                Location/Qualifiers
misc_feature           1..762
                       note = scFv
misc_feature           1..762
                       note = 7.H2m1.L2
source                 1..762
                       mol_type = other DNA
                       organism = synthetic construct
SEQUENCE: 50
cagagcgtgc tgacccagcc tcctagcgcc tctggcacac ccggtcagag ggtgaccatc  60
agctgctccg gctcctccgc ccacaagacc tacaccgtga actggtacca gcagctgccc  120
ggtaccgctc ccaagctgct gatttacgtg aaaagcgacg gcagctacca gagacctagc  180
ggcgtgcccg atcgtttctc cggttctaag agcggcacca gcgcctcttt agccattagc  240
ggcctccaga gcgaggacga ggccgattac tactgcggag ccgacgacaa tggcggctac  300
gtgttcggcg gcggaacaaa gctgaccgtt ttaggtggcg gaagcagcag aagcagcagc  360
tctggcggcg gcggtagcgg cggtggcgga gagcagagcg tcaaggagtc cggaggagga  420
ctggtgcagc ccggtggctc tttaaggctg agctgtgccg cctctggctt tactttatct  480
cgtcacgctt taacatgggt gagacaagct cccggtaagg gactggagtg gatcggcgcc  540
atcgacaacg ccggcaccac ctactacgcc tcttgggcca agtctcgttt caccatctct  600
cgtaacaccg atttacacac cgtgtattta cagatgaact ctttaagggc cgaggacaca  660
gccgtctatt tctgcgctcg tgtgttctac gacatcaata gcggctacta cctcgacgga  720
atggatctgt ggggccccgg tactttagtg acagtcagca gc                    762

SEQ ID NO: 51          moltype = DNA  length = 762
FEATURE                Location/Qualifiers
misc_feature           1..762
                       note = scFv
misc_feature           1..762
                       note = 8.H2m1.L2m1
source                 1..762
                       mol_type = other DNA
                       organism = synthetic construct
SEQUENCE: 51
cagtttgttt taacccagcc tcctagcgcc tctggaacac ccggccaaag ggtcaccatc  60
agctgcactt tatcctccgc ccacaagacc tacaccatcg actggtacca gcagctgccc  120
ggaaccgccc ctaagctgct gatctacgtg aagagcgacg gcagctacac caagggcacc  180
ggcgtgcccg ataggttcag cggcagcagc agcggcgccg atagatattt agccatttcc  240
ggtttacaga gcgaggacga ggccgattac tactgtggcg ctgacgacaa cggaggctac  300
gtgttcggag gcggcaccca gctgaccgtg actggtggcg gttctagcag aagcagcagc  360
tccggaggcg gaggctctgg cggcggtggc gagcagtccg tgaaggaaag cggcggcgga  420
ctggtgcagc ccggtggatc tttaagactg agctgcgccg cctctggctt cactttatcc  480
agacatgctt taacatgggt gagacaagct cccggcaagg gactggagtg gatcggcgcc  540
atcgacaacg ccggcaccac ctactacgcc agctgggcca aatctcgttt caccatctct  600
cgtaacaccg atttacacac cgtgtattta cagatgaatt ctttaagggc cgaggacacc  660
gccgtgtact tctgcgctcg tgtgttctac gacatcaaca gcggctacta tttagacggc  720
atggatttat ggggacccgg tacactcgtg accgtgtcca gc                    762

SEQ ID NO: 52          moltype = DNA  length = 762
FEATURE                Location/Qualifiers
misc_feature           1..762
                       note = scFv
misc_feature           1..762
                       note = 9.H2.L1
source                 1..762
                       mol_type = other DNA
                       organism = synthetic construct
SEQUENCE: 52
cagctggtgc tgacccagag ccccagcgct tccgcctctt taggagccag cgtgaagctg  60
```

```
acttgtactt taagcagcgc ccacaagacc tacacaatcg cttggcacca gcagcagccc  120
gaaaagggcc ccagatatct gatgaaggtc aagtccgacg gcagctactc caagggcgac  180
ggcatccccg atcgtttcag cggttcttcc agcggcgccg agaggtattt aaccatcagc  240
tctttacaga gcgaggacga ggccgactac tactgcggcg ctgacgacaa cggcggctac  300
gtctttggcg gcggcacaaa actgaccgtg ctgggcggcg gaagcagcag aagctccagc  360
tctggaggag gaggttctgg aggtggagga gaggtgcagc tggtggagag cggcggagga  420
ctggtgcagc ccggtggatc tttaagactg agctgtgccg ccagcggctt caccttctct  480
cgtcacgctc tgacatgggt gaggcaagcc cccggtaagg gtttagaatg ggtgagcgcc  540
atcgacaatg ccggaaccac ctattacgcc tcttgggcca agtctcgttt caccatctct  600
cgtgacaatg ccaagaactc tttatattta cagatgaact ctttaagagc tgaggacacc  660
gccgtctact actgcgccag agtgttctac gacatcaaca gcggctacta cctcgacggc  720
atggatttat ggggccccgg tactttagtg accgtgagca gc                    762

SEQ ID NO: 53          moltype = DNA  length = 762
FEATURE                Location/Qualifiers
misc_feature           1..762
                       note = scFv
misc_feature           1..762
                       note = 10.H2.L1m1
source                 1..762
                       mol_type = other DNA
                       organism = synthetic construct
SEQUENCE: 53
cagtttgtgc tgacccagag ccctagcgct tccgcctctt taggagccag cgtgaagctg  60
acttgtactt tatcctccgc ccacaagacc tacaccatcg actggtacca gcagcagccc  120
gaaaagggcc ctcgttatct gatgcaagtt aagtccgacg gcagctacac caagggaacc  180
ggcgtgcccg acagattctc cggtagcagc agcggcgccg acagatattt aaccatcagc  240
tctttacagt ccgaggacga ggccgactac tactgcggcg ccgacgacaa tggcggctac  300
gtcttcggag gcggcacaca gctgaccgtg actggtggag gctcctccag aagcagctct  360
agcggaggag gaggaagcgg cggaggaggc gaagtgcagc tggtggagtc cggaggagga  420
ctggtgcagc ccggaggttc tttaagactg agctgcgccg cctccggctt caccttttct  480
cgtcacgctt taacatgggt gagacaagct cccggcaagg gactggaatg ggtcagcgcc  540
atcgataacg ccggcaccac ctattacgcc agctgggcta agtctcgttt caccatcagc  600
agagacaacg ccaagaactc tttatattta cagatgaatt ctttaagagc cgaggacacc  660
gccgtgtatt actgcgctcg tgtcttctac gacatcaact ccggctacta tttagacggc  720
atggatttat ggggccccgg tactttagtc accgtgagct cc                    762

SEQ ID NO: 54          moltype = DNA  length = 762
FEATURE                Location/Qualifiers
misc_feature           1..762
                       note = scFv
misc_feature           1..762
                       note = 11.H2m1.L1
source                 1..762
                       mol_type = other DNA
                       organism = synthetic construct
SEQUENCE: 54
cagctggtgc tgacacagag cccctccgcc tccgcctctt taggcgcttc cgtgaagctg  60
acttgtactt tatccagcgc ccacaagacc tacaccatcg cttggcacca gcagcagccc  120
gagaaaggcc ctcgttacct catgaaagtg aagtccgacg gcagctactc caagggcgac  180
ggcatccccg atcgttttag cggcagcagc tccggcgccg agaggtattt aaccatcagc  240
tctttacaga gcgaagacga ggccgactat tactgcggcg ccgatgacaa cggaggctac  300
gtgttcggcg gaggcaccaa actgaccgtg ctgggcggcg gaagcagcag aagctccagc  360
agcggaggag gaggttctgg aggaggcgga gagcagagcg tgaaagagtc cggcggaggt  420
ttagtgcagc ccggtggttc tttaagactg agctgcgccg ccagcggctt cacactgtcc  480
agacacgctt taacatgggt gagacaagct cccggtaagg gactggagtg gatcggcgcc  540
atcgacaatg ccggcaccac ctactacgcc agctgggcca agtctcgttt caccatctct  600
cgtaacaccg atttacacac cgtctattta cagatgaact ctttaagggc cgaggacaca  660
gccgtgtact tttgcgctcg tgtgttctac gacatcaaca gcggctacta tttagacggc  720
atggatctgt ggggccccgg aacactggtg accgtgagca gc                    762

SEQ ID NO: 55          moltype = DNA  length = 762
FEATURE                Location/Qualifiers
misc_feature           1..762
                       note = scFv
misc_feature           1..762
                       note = 12.H2m1.L1m1
source                 1..762
                       mol_type = other DNA
                       organism = synthetic construct
SEQUENCE: 55
cagtttgtgc tgacccagtc ccctagcgcc tctgcctctt taggagcctc tgtgaaactg  60
acttgtactt taagcagcgc ccacaagaca tacaccatcg actggtacca gcagcagccc  120
gaaaagggcc ctaggtattt aatgcaagtt aagagcgacg gcagctacac aaagggcact  180
ggtgtgcccg acagattcag cggcagcagc agcggcgccg acagatacct caccatcagc  240
tctttacagt ccgaggacga ggccgactac tattgcggcg ccgacgacaa cggcggctac  300
gtgttcggcg gaggaaccca gctgaccgtg actggtggcg gaagcagcag aagcagctcc  360
tccggaggcg gaggttctgg cggaggtgga gaacagagcg tgaaggagag cggaggtgga  420
ctggtgcagc ccggtggttc tttaagactg agctgcgctg cctccggctt caccttatct  480
```

-continued

```
cgtcacgctt taacatgggt gagacaagct cccggtaagg gtttagagtg gatcggcgcc  540
atcgacaatg ctggcaccac ctactacgcc agctgggcca agtctcgttt cacaatctct  600
cgtaacaccg atctgcacac cgtgtattta cagatgaact ctttaagagc cgaggacacc  660
gccgtgtatt tctgcgctcg tgtgttctac gacatcaaca gcggctacta tttagacggc  720
atggatttat ggggccccgg tactttagtg accgtgagct cc                    762

SEQ ID NO: 56          moltype = DNA  length = 762
FEATURE                Location/Qualifiers
misc_feature           1..762
                       note = scFv
misc_feature           1..762
                       note = 13.H1.L1
source                 1..762
                       mol_type = other DNA
                       organism = synthetic construct
SEQUENCE: 56
cagctcgtgc tgacccagtc ccccagcgcc tctgcctctt taggcgccag cgtgaagctg  60
acttgtactt tatccagcgc ccacaagaca tacaccatcg cttggcacca gcagcagccc  120
gaaaagggcc ctcgttattt aatgaaggtc aagtccgacg gctcctactc caagggcgac  180
ggcatccccg atagattcag cggtagcagc agcggcgccg agagatattt aacaatcagc  240
tctttacaga gcgaggacga ggccgactac tactgcggcg ccgacgacaa tggcggctac  300
gtcttcggcg gcggaaccaa gctcacagtg ctgggtggag gctccagcag aagcagctct  360
agcggaggcg gaggttccgg cggcggaggc caagttcagc tgcaagaatc cggccccgga  420
ctggtgaagc cctccgaaac actgtcttta acatgcgccg tgagcggcta cagcatttct  480
cgtcacgctt taacttggat cagacagccc cccggcaagg gtttagaatg gatcggagcc  540
atcgataacg ccggcaccac atactacgcc agctgggcca agagcagagt gaccatctcc  600
gtggacacca gcaagaacca gttttcttta aagctcagct ccgtgaccgc cgccgataca  660
gccgtgtact actgcgccag agtgttctac gacatcaaca gcggctacta tttagacgga  720
atggatttat ggggccccgg tactttagtg accgtgagca gc                    762

SEQ ID NO: 57          moltype = DNA  length = 762
FEATURE                Location/Qualifiers
misc_feature           1..762
                       note = scFv
misc_feature           1..762
                       note = 14.H1.L1m1
source                 1..762
                       mol_type = other DNA
                       organism = synthetic construct
SEQUENCE: 57
cagtttgtgc tcacccaaag ccctagcgcc tctgcctctt taggcgcttc cgtgaagctg  60
acttgtactt taagctccgc ccataagacc tacaccatcg actggtacca gcagcagccc  120
gagaagggcc ctcgttattt aatgcaagtt aagtccgatg gcagctatac caagggcacc  180
ggcgtgcccg acagattcag cggcagctcc agcggagccg atcgttattt aaccatcagc  240
tctttacaga gcgaggacga ggctgactac tactgcggcg ccgacgataa cggcggctac  300
gtgttcggcg gcggcaccca actgacagtg accggaggcg gttcttctcg tagcagcagc  360
agcggaggcg gcggctccgg cggcggaggc caagttcagc tgcaagaatc cggccccggt  420
ctggtgaaac ccagcgagac tttatcttta acatgcgccg tgagcggcta ctccatctcc  480
agacacgctt taacttggat cagacagcct cccggcaagg gactggagtg gatcggcgct  540
atcgacaacg ccggcaccac ctactacgcc tcttgggcca agtctcgtgt caccatcagc  600
gtggacacat ccaagaacca gttctcttta aagctgtcca gcgtgaccgc cgccgataca  660
gccgtgtact actgcgctcg tgtgttctac gacatcaact ccggctacta tttagacggc  720
atggatttat ggggacccgg tactttagtg accgtgtcca gc                    762

SEQ ID NO: 58          moltype = DNA  length = 762
FEATURE                Location/Qualifiers
misc_feature           1..762
                       note = scFv
misc_feature           1..762
                       note = 15.H1m1.L1
source                 1..762
                       mol_type = other DNA
                       organism = synthetic construct
SEQUENCE: 58
cagctggtgc tgacacaaag ccccagcgcc agcgcctctt taggcgccag cgtcaaactg  60
acatgcactt taagcagcgc ccacaagacc tacaccatcg cttggcacca gcagcagccc  120
gagaagggcc ccagatattt aatgaaggtg aagtccgatg gcagctacag caagggagat  180
ggcattcccg atcgttttag cggctcctcc agcggcgccg agagatactt aaccatctcc  240
tctttacaga gcgaggacga ggccgactac tactgcggcg ccgatgacaa cggcggctac  300
gtgttcggcg gcggaaccaa gctgaccgtg ctgggcggag gcagctccag atccagcagc  360
agcggcggag gaggaagcgg aggaggagga cagcagtccg tgaaagagag cggccccggt  420
ttagtgaaac ccagcgagac tttatcttta acttgtgccg tgagcggctt cagcctctct  480
cgtcacgctt taacttgggt gagacagcct cccggcaaag gtttagagtg gattggcgcc  540
atcgacaacg ccggcaccac ctactacgcc agctgggcca aatctcgtgt gaccatttcc  600
agaaacaccg atttacacac cgtgtcttta aagctgtcca gcgtgaccgc cgctgacacc  660
gctgtctact tctgcgctcg tgtgttctac gacatcaact ccggctacta tttagacggc  720
atggatttat ggggccccgg tactttagtg accgtgagct cc                    762

SEQ ID NO: 59          moltype = DNA  length = 763
```

-continued

```
FEATURE                Location/Qualifiers
misc_feature           1..763
                       note = scFv
misc_feature           1..763
                       note = 16.H1m1.L1m1
source                 1..763
                       mol_type = other DNA
                       organism = synthetic construct
SEQUENCE: 59
cagttcgtgc tcacacagag ccctagcgct tccgcctctt taggagccag cgtgaaactg  60
acatgtactt taagcagcgc ccacaaaacc tacaccatcg actggtacca gcagcaaccc  120
gagaagggcc ctagatattt aatgcaagtt aagagcgacg gctcctacac caaaggcacc  180
ggcgtgcccg ataggttcag cggctcctcc tccggagccg atcgttattt aacaatcagc  240
tctttacaga gcgaagacga ggccgattac tactgcggag ccgatgacaa cggcggctac  300
gtcttcggag gcggaaccca gctgacagtg accggaggcg gcagcagcag atccagcagc  360
tccggaggcg gaggaagcgg aggaggcggc cagcaaagcg tgaaggagag cggccccgga  420
ctcgtgaaac cctccgagac tttatcttta acttgtgccg tgagcggctt ctctttatct  480
cgtcacgctt taacatgggt gaggcagcct cccggtaagg gtttagagtg gatcggcgcc  540
atcgacaacg ccggcacaac ctactacgcc agctgggcca agagcagagt gaccatctct  600
cgtaacaccg atttacacac cgtgtcttta aagctgagct ccgtgaccgc cgccgatacc  660
gctgtgtact tctgcgctcg tgtcttctac gacatcaact ccggctatta cctcgacggc  720
atggatctgt ggggccccgg aacactggtg accgtgagca gcg                    763

SEQ ID NO: 60          moltype = DNA  length = 762
FEATURE                Location/Qualifiers
misc_feature           1..762
                       note = scFv
misc_feature           1..762
                       note = 17.H1.L3m2
source                 1..762
                       mol_type = other DNA
                       organism = synthetic construct
SEQUENCE: 60
cagttcgtgc tgacccagcc cgcttctgtg agcggttctc ccggtcagag catcaccatc  60
agctgcactt taagcagcgc ccacaagacc tacaccatcg actggtacca gcagcacccc  120
ggcaaggccc ccaagctgat gatccaagtt aagtccgacg gcagctacac caagggcacc  180
ggcgtgagca acagattctc cggcagcagc tccggcgccg acagatactt aaccatcagc  240
ggtttacaag ctgaggatga ggccgactat tactgcggcg ccgacgacaa tggcggctac  300
gtgttcggcg gcggcacaca gctgaccgtg ctgggtggag gctccagcag atccagctcc  360
agcggcggag gaggcagcgg aggcggagga caagtgcagc tccaagaatc cggccccggt  420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
gccgtgtact actgcgctcg tgtgttctac gacatcaaca gcggctacta tttagacggc  720
atggatttat ggggccccgg tactttagtg accgtcagct cc                     762

SEQ ID NO: 61          moltype = DNA  length = 762
FEATURE                Location/Qualifiers
misc_feature           1..762
                       note = scFv
misc_feature           1..762
                       note = 18.H1.L3m3
source                 1..762
                       mol_type = other DNA
                       organism = synthetic construct
SEQUENCE: 61
cagagcgccc tgacccagcc cgcttctgtg agcggttctc ccggtcagag catcaccatc  60
agctgcactg gcaccagcgc ccacaagacc tacaccatcg actggtacca gcagcacccc  120
ggcaaggccc ccaagctgat gatctatgtt aagtccgacg gcagctacac caagggcacc  180
ggcgtgagca acagattctc cggcagcaag tccggcaaca ccgccagctt aaccatcagc  240
ggtttacaag ctgaggatga ggccgactat tactgcggcg ccgacgacaa tggcggctac  300
gtgttcggcg gcggcacaca gctgaccgtg ctgggtggag gctccagcag atccagctcc  360
agcggcggag gaggcagcgg aggcggagga caagtgcagc tccaagaatc cggccccggt  420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
gccgtgtact actgcgctcg tgtgttctac gacatcaaca gcggctacta tttagacggc  720
atggatttat ggggccccgg tactttagtg accgtcagct cc                     762

SEQ ID NO: 62          moltype = DNA  length = 762
FEATURE                Location/Qualifiers
misc_feature           1..762
                       note = scFv
misc_feature           1..762
                       note = 19.H2.L2m2
source                 1..762
                       mol_type = other DNA
```

```
                        organism = synthetic construct
SEQUENCE: 62
cagttcgtgc tgacacagcc tcccagcgcc tctggcacac ccggtcagag ggtgaccatc  60
tcttgtactt tatcctccgc ccacaagacc tacaccattg actggtacca gcagctgccc  120
ggtaccgccc ctaagctgct gatttacgtg aaatccgacg gcagctacac caagggaacc  180
ggcgtgcccg atcgtttttc cggcagctcc agcggcgccg atgccagctt agccatcagc  240
ggtttacagt ccgaggatga ggccgactac tactgcggcg ccgatgacaa cggcggctac  300
gtgttcggcg gaggaaccca gctcaccgtg ctgggaggag gctcctctcg tagctccagc  360
tccggaggag gaggaagcgg aggcggcgga gaagtgcaac tggtggagtc cggcggcgga  420
ctggtgcagc ccggtggctc tttaagactg agctgtgccg cctccggctt cacctttagc  480
agacacgccc tcacttgggt cagacaagct cccggtaagg gtttagagtg ggtgagcgcc  540
atcgacaacg ccggcacaac ctactacgcc tcttgggcca agtctcgttt caccatcagc  600
agagacaacg ccaagaactc tttatattta cagatgaact ctttaagggc cgaggacacc  660
gccgtgtact actgcgctcg tgtgttctac gacatcaaca gcggctatta tttagatggc  720
atggatttat ggggccccgg tactttagtg acagtgtcct cc                    762

SEQ ID NO: 63           moltype = DNA  length = 762
FEATURE                 Location/Qualifiers
misc_feature            1..762
                        note = scFv
misc_feature            1..762
                        note = 20.H2.L2m3
source                  1..762
                        mol_type = other DNA
                        organism = synthetic construct
SEQUENCE: 63
cagagcgtgc tgacacagcc tcccagcgcc tctggcacac ccggtcagag ggtgaccatc  60
tcttgtactt tatcctccgc ccacaagacc tacaccattg actggtacca gcagctgccc  120
ggtaccgccc ctaagctgct gatttacgtg aaatccgacg gcagctacac caagggaacc  180
ggcgtgcccg atcgtttttc cggcagcaag agcggcacca gcgccagctt agccatcagc  240
ggtttacagt ccgaggatga ggccgactac tactgcggcg ccgatgacaa cggcggctac  300
gtgttcggcg gaggaaccca gctcaccgtg ctgggaggag gctcctctcg tagctccagc  360
tccggaggag gaggaagcgg aggcggcgga gaagtgcaac tggtggagtc cggcggcgga  420
ctggtgcagc ccggtggctc tttaagactg agctgtgccg cctccggctt cacctttagc  480
agacacgccc tcacttgggt cagacaagct cccggtaagg gtttagagtg ggtgagcgcc  540
atcgacaacg ccggcacaac ctactacgcc tcttgggcca agtctcgttt caccatcagc  600
agagacaacg ccaagaactc tttatattta cagatgaact ctttaagggc cgaggacacc  660
gccgtgtact actgcgctcg tgtgttctac gacatcaaca gcggctatta tttagatggc  720
atggatttat ggggccccgg tactttagtg acagtgtcct cc                    762

SEQ ID NO: 64           moltype = DNA  length = 762
FEATURE                 Location/Qualifiers
misc_feature            1..762
                        note = scFv
misc_feature            1..762
                        note = 21.H2.L1m2
source                  1..762
                        mol_type = other DNA
                        organism = synthetic construct
SEQUENCE: 64
cagtttgtgc tgacccagag ccctagcgct tccgcctctt taggagccag cgtgaagctg  60
acttgtactt tatcctccgc ccacaagacc tacaccatcg actggcacca gcagcagccc  120
gaaaagggcc ctcgttatct gatgcaagtt aagtccgacg gcagctacac caagggaacc  180
ggcatccccg acagattctc cggtagcagc agcggcgccg agagatattt aaccatcagc  240
tctttacagt ccgaggacga ggccgactac tactgcggcg ccgacgacaa tggcggctac  300
gtcttcggag gcggcacaca gctgaccgtg ctgggtggag gctcctccag aagcagctct  360
agcggaggag gaggaagcgg cggaggaggc gaagtgcagc tggtggagtc cggaggagga  420
ctggtgcagc ccggaggttc tttaagactg agctgcgccg cctccggctt cacctttttct  480
cgtcacgctt taacatgggt gagacaagct cccggcaagg gactggaatg ggtcagcgcc  540
atcgataacg ccggcaccac ctattacgcc agctgggcta agtctcgttt caccatcagc  600
agagacaacg ccaagaactc tttatattta cagatgaatt ctttaagagc cgaggacacc  660
gccgtgtatt actgcgctcg tgtcttctac gacatcaact ccggctacta tttagacggc  720
atggatttat ggggccccgg tactttagtc accgtgagct cc                    762

SEQ ID NO: 65           moltype = DNA  length = 762
FEATURE                 Location/Qualifiers
misc_feature            1..762
                        note = scFv
misc_feature            1..762
                        note = 22.H1.L1m2
source                  1..762
                        mol_type = other DNA
                        organism = synthetic construct
SEQUENCE: 65
cagtttgtgc tcacccaaag ccctagcgcc tctgcctctt taggcgcttc cgtgaagctg  60
acttgtactt taagctccgc ccataagacc tacaccatcg actggcacca gcagcagccc  120
gagaagggcc ctcgttattt aatgcaagtt aagtccgatg gcagctatac caagggcacc  180
ggcatccccg acagattcag cggcagctcc agcggagccg agcgttattt aaccatcagc  240
tctttacaga gcgaggacga ggctgactac tactgcggcg ccgacgataa cggcggctac  300
```

```
gtgttcggcg gcggcaccca actgacagtg ctgggaggcg gttcttctcg tagcagcagc  360
agcggaggcg gcggctccgg cggcggaggc caagttcagc tgcaagaatc cggccccggt  420
ctggtgaaac ccagcgagac tttatcttta acatgcgccg tgagcggcta ctccatctcc  480
agacacgctt taacttggat cagacagcct cccggcaagg gactggagtg gatcggcgct  540
atcgacaacg ccggcaccac ctactacgcc tcttgggcca agtctcgtgt caccatcagc  600
gtggacacat ccaagaacca gttctcttta aagctgtcca gcgtgaccgc cgccgataca  660
gccgtgtact actgcgctcg tgtgttctac gacatcaact ccggctacta tttagacggc  720
atggatttat ggggacccgg tactttagtg accgtgtcca gc                    762

SEQ ID NO: 66          moltype = DNA  length = 762
FEATURE                Location/Qualifiers
misc_feature           1..762
                       note = scFv
misc_feature           1..762
                       note = 23.H1.L2m1
source                 1..762
                       mol_type = other DNA
                       organism = synthetic construct
SEQUENCE: 66
cagttcgtgc tgacccagcc tcctagcgct agcggaacac ccggccagag ggtgaccatc  60
agctgcactt taagcagcgc ccacaagacc tacaccatcg actggtacca gcagctgccc  120
ggtaccgctc ccaagctgct gatctacgtg aagagcgacg gcagctacac caagggcacc  180
ggcgtgcccg atagattcag cggcagcagc agcggcgccg acagatattt agccatcagc  240
ggtttacaga gcgaggacga ggccgactac tactgcggcg ccgacgacaa cggaggctac  300
gtgttcggcg gcggcacaca gctgaccgtg accggtggag gctccagcag atccagctcc  360
agcggcggag gaggcagcgg aggcggagga caagtgcagc tccaagaatc cggccccggt  420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
gccgtgtact actgcgctcg tgtgttctac gacatcaaca gcggctacta tttagacggc  720
atggatttat ggggccccgg tactttagtg accgtcagct cc                    762

SEQ ID NO: 67          moltype = DNA  length = 762
FEATURE                Location/Qualifiers
misc_feature           1..762
                       note = scFv
misc_feature           1..762
                       note = 24.H2.L3m1
source                 1..762
                       mol_type = other DNA
                       organism = synthetic construct
SEQUENCE: 67
cagttcgtgc tgacccagcc cgcttctgtg agcggttctc ccggtcagag catcaccatc  60
agctgcactt taagcagcgc ccacaagacc tacaccatcg actggtacca gcagcacccc  120
ggcaaggccc ccaagtattt aatgcaagtt aagtccgacg gcagctacac caagggcacc  180
ggcgtgccca acagattctc cggcagcagc tccggcgccg acagatactt aaccatcagc  240
ggtttacaag ctgaggatga ggccgactat gtgtgcggcg ccgacgacaa tggcggctac  300
gtgttcggcg gcggcacaca gctgaccgtg actggcggtg gttcctctag atcttcctcc  360
tctggtggcg gtggctcggg cggtggtggg gaggtgcagc tggtggagag cggaggaggt  420
ttagtgcagc ccggtggatc tttaagactg agctgcgccg ccagcggctt caccttctct  480
cgtcacgctt taacatgggt gagacaagct cccggtaaag gtttagagtg ggtgagcgcc  540
atcgacaacg ccggcaccac ctactacgcc agctgggcca agtctcgttt caccatctct  600
cgtgacaacg ccaagaactc tttatattta cagatgaact ctttaagggc tgaggacacc  660
gccgtgtact actgcgctcg tgtgttctac gacatcaaca gcggctacta tttagacgga  720
atggatttat ggggccccgg taccctcgtg acagtgagca gc                    762

SEQ ID NO: 68          moltype = DNA  length = 762
FEATURE                Location/Qualifiers
misc_feature           1..762
                       note = scFv
misc_feature           1..762
                       note = 25.H1.L1m3
source                 1..762
                       mol_type = other DNA
                       organism = synthetic construct
SEQUENCE: 68
cagctggtgc tcacccaaag ccctagcgcc tctgcctctt taggcgcttc cgtgaagctg  60
acttgtactt taagctccgc ccataagacc tacaccatcg actggtacca gcagcagccc  120
gagaagggcc ctcgttattt aatgcaagtt aagtccgatg gcagctatac caagggcacc  180
ggcgtgcccg acagattcag cggcagctcc agcggagccg atcgttattt aaccatcagc  240
tctttacaga gcgaggacga ggctgactac tactgcggcg ccgacgataa cggcggctac  300
gtgttcggcg gcggcaccca actgacagtg ctgggaggcg gttcttctcg tagcagcagc  360
agcggaggcg gcggctccgg cggcggaggc caagtgcagc tccaagaatc cggccccggt  420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
gccgtgtact actgcgctcg tgtgttctac gacatcaaca gcggctacta tttagacggc  720
```

```
atggatttat ggggccccgg tactttagtg accgtcagct cc                      762

SEQ ID NO: 69           moltype = DNA  length = 762
FEATURE                 Location/Qualifiers
misc_feature            1..762
                        note = scFv
misc_feature            1..762
                        note = 26.H1.L1m4
source                  1..762
                        mol_type = other DNA
                        organism = synthetic construct
SEQUENCE: 69
cagttggtgc tcacccaaag ccctagcgcc tctgcctctt taggcgcttc cgtgaagctg  60
acttgtactt taagctccgc ccataagacc tacaccatcg cctggcatca gcagcagccc  120
gagaagggcc ctcgttattt aatgcaagtt aagtccgatg gcagctatac caagggcacc  180
ggcgtgcccg acagattcag cggcagctcc agcggagccg atcgttattt aaccatcagc  240
tctttacaga gcgaggacga ggctgactac tactgcggcg ccgacgataa cggcggctac  300
gtgttcggcg gcggcaccca actgacagtg ctcggaggcg gttcttctcg tagcagcagc  360
agcggaggcg gcggctccgg cggcggaggc caagtgcagc tccaagaatc cggcccggt   420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
gccgtgtact actgcgctcg tgtgttctac gacatcaaca gcggctacta tttagacggc  720
atggatttat ggggccccgg tactttagtg accgtcagct cc                      762

SEQ ID NO: 70           moltype = DNA  length = 762
FEATURE                 Location/Qualifiers
misc_feature            1..762
                        note = scFv
misc_feature            1..762
                        note = 27.H1.L3m4
source                  1..762
                        mol_type = other DNA
                        organism = synthetic construct
SEQUENCE: 70
cagagcgctc tgacccagcc cgcttctgtg agcggttctc ccggtcagag catcaccatc  60
agctgcactg gcacaagcgc ccacaagacc tacaccgtga gctggtacca gcagcacccc  120
ggcaaggccc ccaagtattt aatgcaagtt aagtccgacg gcagctacac caagggcacc  180
ggcgtgccca acagattctc cggcagcagc tccggcgccg acagatactt aaccatcagc  240
ggtttacaag ctgaggatga ggccgactat tactgcggcg ccgacgacaa tggcggctac  300
gtgttcggcg gcggcaccca actgacagtg ctgggtggag gctccagcag atccagctcc  360
agcggcggag gaggcagcgg aggcggagga caagtgcagc tccaagaatc cggcccggt   420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
gccgtgtact actgcgctcg tgtgttctac gacatcaaca gcggctacta tttagacggc  720
atggatttat ggggccccgg tactttagtg accgtcagct cc                      762

SEQ ID NO: 71           moltype = DNA  length = 762
FEATURE                 Location/Qualifiers
misc_feature            1..762
                        note = scFv
misc_feature            1..762
                        note = 28.H1.L3m5
source                  1..762
                        mol_type = other DNA
                        organism = synthetic construct
SEQUENCE: 71
cagtctgctc tgacccagcc cgcttctgtg agcggttctc ccggtcagag catcaccatc  60
agctgcactg gcacaagcgc ccacaagacc tacaccgtga gttggtacca gcagcacccc  120
ggcaaggccc ccaagttgat gatctacgtt aagtccgacg gcagctacac caagggcacc  180
ggcgtgccca acagattctc cggcagcagc tccggcgccg acagatactt aaccatcagc  240
ggtttacaag ctgaggatga ggccgactat tattgcggcg ccgacgacaa tggcggctac  300
gtgttcggcg gcggcaccca actgacagtg ctcggtggag gctccagcag atccagctcc  360
agcggcggag gaggcagcgg aggcggagga caagtgcagc tccaagaatc cggcccggt   420
ctcgtgaagc ccagcgagac tttatcttta acttgtgccg tgagcggcta cagcatctct  480
cgtcacgctc tgacttggat tcgtcaacct cccggaaagg gtttagagtg gatcggcgcc  540
atcgacaacg ccggcaccac ctactacgcc agctgggcca aatctcgtgt gaccattagc  600
gtggacacca gcaagaacca gttctcttta aaactgagca gcgtgacagc tgccgacacc  660
gccgtgtact actgcgctcg tgtgttctac gacatcaaca gcggctacta tttagacggc  720
atggatttat ggggccccgg tactttagtg accgtcagct cc                      762

SEQ ID NO: 72           moltype = DNA  length = 762
FEATURE                 Location/Qualifiers
misc_feature            1..762
                        note = scFv
misc_feature            1..762
```

```
                         note = 29.H2.L1m3
source                   1..762
                         mol_type = other DNA
                         organism = synthetic construct
SEQUENCE: 72
cagctggtgc tgacccagag ccctagcgct tccgcctctt taggagccag cgtgaagctg  60
acttgtactt tatcctccgc ccacaagacc tacaccatcg actggtacca gcagcagccc  120
gaaaagggcc ctcgttatct gatgcaagtt aagtccgacg gcagctacac caagggaacc  180
ggcgtgcccg acagattctc cggtagcagc agcggcgccg acagatattt aaccatcagc  240
tctttacagt ccgaggacga ggccgactac tactgcggcg ccgacgacaa tggcggctac  300
gtcttcggag gcggcacaca gctgaccgtg actggtggag gctcctccag aagcagctct  360
agcggaggag gaggaagcgg cggaggaggc gaagtgcagc tggtggagtc cggaggagga  420
ctggtgcagc ccggaggttc tttaagactg agctgcgccg cctccggctt caccttttct  480
cgtcacgctt taacatgggt gagacaagct cccggcaagg gactggaatg ggtcagcgcc  540
atcgataacg ccggcaccac ctattacgcc agctgggcta agtctcgttt caccatcagc  600
agagacaacg ccaagaactc tttatattta cagatgaatt ctttaagagc cgaggacacc  660
gccgtgtatt actgcgctcg tgtcttctac gacatcaact ccggctacta tttagacggc  720
atggatttat ggggccccgg tactttagtc accgtgagct cc                    762

SEQ ID NO: 73            moltype = AA  length = 253
FEATURE                  Location/Qualifiers
REGION                   1..253
                         note = scFv
REGION                   1..253
                         note = 0.410HC.410LC
source                   1..253
                         mol_type = protein
                         organism = synthetic construct
SEQUENCE: 73
QFVLTQSPSV SAALGASAKL TCTLSSAHKT YTIDWYQQQQ GEAPRYLMQV KSDGSYTKGT  60
GVPDRFSGSS SGADRYLIIP SVQADDEAGY VCGADDNGGY VFGGGTQLTV TGGGSSRSSS  120
SGGGGSGGGG QSVKESEGGL FKPTDTLTLT CTVSGFSLSR HALTWVRQAP GNGLEWIGAI  180
DNAGTTYYAS WAKSRSTITR NTDLHTVTLK MTSLTASDTA TYFCARVFYD INSGYYLDGM  240
DLWGPGTLVT VSS                                                    253

SEQ ID NO: 74            moltype = AA  length = 254
FEATURE                  Location/Qualifiers
REGION                   1..254
                         note = scFv
REGION                   1..254
                         note = 1.H1.L3
source                   1..254
                         mol_type = protein
                         organism = synthetic construct
SEQUENCE: 74
QSALTQPASV SGSPGQSITI SCTGTSAHKT YTVSWYQQHP GKAPKLMIYV KSDGSYNRPS  60
GVSNRFSGSK SGNTASLTIS GLQAEDEADY YCGADDNGGY VFGGGTKLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 75            moltype = AA  length = 264
FEATURE                  Location/Qualifiers
REGION                   1..264
                         note = scFv
REGION                   1..264
                         note = 2.H1.L3m1
source                   1..264
                         mol_type = protein
                         organism = synthetic construct
SEQUENCE: 75
QFVLTQPASV SGSPGQSITI SCTLSSAHKT YTIDWYQQHP GKAPKYLMQV KSDGSYTKGT  60
GVPNRFSGSS SGADRYLTIS GLQAEDEADY VCGADDNGGY VFGGGTQLTV TGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSSASTKGP SVTS                                        264

SEQ ID NO: 76            moltype = AA  length = 254
FEATURE                  Location/Qualifiers
REGION                   1..254
                         note = scFv
REGION                   1..254
                         note = 3.H1m1.L3
source                   1..254
                         mol_type = protein
                         organism = synthetic construct
SEQUENCE: 76
QSALTQPASV SGSPGQSITI SCTGTSAHKT YTVSWYQQHP GKAPKLMIYV KSDGSYNRPS  60
GVSNRFSGSK SGNTASLTIS GLQAEDEADY YCGADDNGGY VFGGGTKLTV LGGGSSRSSS  120
```

```
SGGGGSGGGG QQSVKESGPG LVKPSETLSL TCAVSGFSLS RHALTWVRQP PGKGLEWIGA  180
IDNAGTTYYA SWAKSRVTIS RNTDLHTVSL KLSSVTAADT AVYFCARVFY DINSGYYLDG  240
MDLWGPGTLV TVSS                                                    254

SEQ ID NO: 77           moltype = AA  length = 254
FEATURE                 Location/Qualifiers
REGION                  1..254
                        note = scFv
REGION                  1..254
                        note = 4.H1m1.L3m1
source                  1..254
                        mol_type = protein
                        organism = synthetic construct
SEQUENCE: 77
QFVLTQPASV SGSPGQSITI SCTLSSAHKT YTIDWYQQHP GKAPKYLMQV KSDGSYTKGT   60
GVPNRFSGSS SGADRYLTIS GLQAEDEADY VCGADDNGGY VFGGGTQLTV TGGGSSRSSS  120
SGGGGSGGGG QQSVKESGPG LVKPSETLSL TCAVSGFSLS RHALTWVRQP PGKGLEWIGA  180
IDNAGTTYYA SWAKSRVTIS RNTDLHTVSL KLSSVTAADT AVYFCARVFY DINSGYYLDG  240
MDLWGPGTLV TVSS                                                    254

SEQ ID NO: 78           moltype = AA  length = 254
FEATURE                 Location/Qualifiers
REGION                  1..254
                        note = scFv
REGION                  1..254
                        note = 5.H2.L2
source                  1..254
                        mol_type = protein
                        organism = synthetic construct
SEQUENCE: 78
QSVLTQPPSA SGTPGQRVTI SCSGSSAHKT YTVNWYQQLP GTAPKLLIYV KSDGSYQRPS   60
GVPDRFSGSK SGTSASLAIS GLQSEDEADY YCGADDNGGY VFGGGTKLTV LGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                    254

SEQ ID NO: 79           moltype = AA  length = 254
FEATURE                 Location/Qualifiers
REGION                  1..254
                        note = scFv
REGION                  1..254
                        note = 6.H2.L2m1
source                  1..254
                        mol_type = protein
                        organism = synthetic construct
SEQUENCE: 79
QFVLTQPPSA SGTPGQRVTI SCTLSSAHKT YTIDWYQQLP GTAPKLLIYV KSDGSYTKGT   60
GVPDRFSGSS SGADRYLAIS GLQSEDEADY YCGADDNGGY VFGGGTQLTV TGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                    254

SEQ ID NO: 80           moltype = AA  length = 254
FEATURE                 Location/Qualifiers
REGION                  1..254
                        note = scFv
REGION                  1..254
                        note = 7.H2m1.L2
source                  1..254
                        mol_type = protein
                        organism = synthetic construct
SEQUENCE: 80
QSVLTQPPSA SGTPGQRVTI SCSGSSAHKT YTVNWYQQLP GTAPKLLIYV KSDGSYQRPS   60
GVPDRFSGSK SGTSASLAIS GLQSEDEADY YCGADDNGGY VFGGGTKLTV LGGGSSRSSS  120
SGGGGSGGGG EQSVKESGGG LVQPGGSLRL SCAASGFTLS RHALTWVRQA PGKGLEWIGA  180
IDNAGTTYYA SWAKSRFTIS RNTDLHTVYL QMNSLRAEDT AVYFCARVFY DINSGYYLDG  240
MDLWGPGTLV TVSS                                                    254

SEQ ID NO: 81           moltype = AA  length = 254
FEATURE                 Location/Qualifiers
REGION                  1..254
                        note = scFv
REGION                  1..254
                        note = 8.H2m1.L2m1
source                  1..254
                        mol_type = protein
                        organism = synthetic construct
SEQUENCE: 81
QFVLTQPPSA SGTPGQRVTI SCTLSSAHKT YTIDWYQQLP GTAPKLLIYV KSDGSYTKGT   60
```

```
GVPDRFSGSS SGADRYLAIS GLQSEDEADY YCGADDNGGY VFGGGTQLTV TGGGSSRSSS  120
SGGGGSGGGG EQSVKESGGG LVQPGGSLRL SCAASGFTLS RHALTWVRQA PGKGLEWIGA  180
IDNAGTTYYA SWAKSRFTIS RNTDLHTVYL QMNSLRAEDT AVYFCARVFY DINSGYYLDG  240
MDLWGPGTLV TVSS                                                    254

SEQ ID NO: 82          moltype = AA  length = 254
FEATURE                Location/Qualifiers
REGION                 1..254
                       note = scFv
REGION                 1..254
                       note = 9.H2.L1
source                 1..254
                       mol_type = protein
                       organism = synthetic construct
SEQUENCE: 82
QLVLTQSPSA SASLGASVKL TCTLSSAHKT YTIAWHQQQP EKGPRYLMKV KSDGSYSKGD  60
GIPDRFSGSS SGAERYLTIS SLQSEDEADY YCGADDNGGY VFGGGTKLTV LGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                    254

SEQ ID NO: 83          moltype = AA  length = 254
FEATURE                Location/Qualifiers
REGION                 1..254
                       note = scFv
REGION                 1..254
                       note = 10.H2.L1m1
source                 1..254
                       mol_type = protein
                       organism = synthetic construct
SEQUENCE: 83
QFVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV TGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                    254

SEQ ID NO: 84          moltype = AA  length = 254
FEATURE                Location/Qualifiers
REGION                 1..254
                       note = scFv
REGION                 1..254
                       note = 11.H2m1.L1
source                 1..254
                       mol_type = protein
                       organism = synthetic construct
SEQUENCE: 84
QLVLTQSPSA SASLGASVKL TCTLSSAHKT YTIAWHQQQP EKGPRYLMKV KSDGSYSKGD  60
GIPDRFSGSS SGAERYLTIS SLQSEDEADY YCGADDNGGY VFGGGTKLTV LGGGSSRSSS  120
SGGGGSGGGG EQSVKESGGG LVQPGGSLRL SCAASGFTLS RHALTWVRQA PGKGLEWIGA  180
IDNAGTTYYA SWAKSRFTIS RNTDLHTVYL QMNSLRAEDT AVYFCARVFY DINSGYYLDG  240
MDLWGPGTLV TVSS                                                    254

SEQ ID NO: 85          moltype = AA  length = 254
FEATURE                Location/Qualifiers
REGION                 1..254
                       note = scFv
REGION                 1..254
                       note = 12.H2m1.L1m1
source                 1..254
                       mol_type = protein
                       organism = synthetic construct
SEQUENCE: 85
QFVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV TGGGSSRSSS  120
SGGGGSGGGG EQSVKESGGG LVQPGGSLRL SCAASGFTLS RHALTWVRQA PGKGLEWIGA  180
IDNAGTTYYA SWAKSRFTIS RNTDLHTVYL QMNSLRAEDT AVYFCARVFY DINSGYYLDG  240
MDLWGPGTLV TVSS                                                    254

SEQ ID NO: 86          moltype = AA  length = 254
FEATURE                Location/Qualifiers
REGION                 1..254
                       note = scFv
REGION                 1..254
                       note = 13.H1.L1
source                 1..254
                       mol_type = protein
                       organism = synthetic construct
SEQUENCE: 86
```

-continued

```
QLVLTQSPSA SASLGASVKL TCTLSSAHKT YTIAWHQQQP EKGPRYLMKV KSDGSYSKGD  60
GIPDRFSGSS SGAERYLTIS SLQSEDEADY YCGADDNGGY VFGGGTKLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                  254

SEQ ID NO: 87          moltype = AA  length = 254
FEATURE                Location/Qualifiers
REGION                 1..254
                       note = scFv
REGION                 1..254
                       note = 14.H1.L1m1
source                 1..254
                       mol_type = protein
                       organism = synthetic construct
SEQUENCE: 87
QFVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV TGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                  254

SEQ ID NO: 88          moltype = AA  length = 254
FEATURE                Location/Qualifiers
REGION                 1..254
                       note = scFv
REGION                 1..254
                       note = 15.H1m1.L1
source                 1..254
                       mol_type = protein
                       organism = synthetic construct
SEQUENCE: 88
QLVLTQSPSA SASLGASVKL TCTLSSAHKT YTIAWHQQQP EKGPRYLMKV KSDGSYSKGD  60
GIPDRFSGSS SGAERYLTIS SLQSEDEADY YCGADDNGGY VFGGGTKLTV LGGGSSRSSS  120
SGGGGSGGGG QQSVKESGPG LVKPSETLSL TCAVSGFSLS RHALTWVRQP PGKGLEWIGA  180
IDNAGTTYYA SWAKSRVTIS RNTDLHTVSL KLSSVTAADT AVYFCARVFY DINSGYYLDG  240
MDLWGPGTLV TVSS                                                  254

SEQ ID NO: 89          moltype = AA  length = 254
FEATURE                Location/Qualifiers
REGION                 1..254
                       note = scFv
REGION                 1..254
                       note = 16.H1m1.L1m1
source                 1..254
                       mol_type = protein
                       organism = synthetic construct
SEQUENCE: 89
QFVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV TGGGSSRSSS  120
SGGGGSGGGG QQSVKESGPG LVKPSETLSL TCAVSGFSLS RHALTWVRQP PGKGLEWIGA  180
IDNAGTTYYA SWAKSRVTIS RNTDLHTVSL KLSSVTAADT AVYFCARVFY DINSGYYLDG  240
MDLWGPGTLV TVSS                                                  254

SEQ ID NO: 90          moltype = AA  length = 254
FEATURE                Location/Qualifiers
REGION                 1..254
                       note = scFv
REGION                 1..254
                       note = 17.H1.L3m2
source                 1..254
                       mol_type = protein
                       organism = synthetic construct
SEQUENCE: 90
QFVLTQPASV SGSPGQSITI SCTLSSAHKT YTIDWYQQHP GKAPKLMIQV KSDGSYTKGT  60
GVSNRFSGSS SGADRYLTIS GLQAEDEADY YCGADDNGGY VFGGGTQLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                  254

SEQ ID NO: 91          moltype = AA  length = 254
FEATURE                Location/Qualifiers
REGION                 1..254
                       note = scFv
REGION                 1..254
                       note = 18.H1.L3m3
source                 1..254
                       mol_type = protein
                       organism = synthetic construct
```

```
SEQUENCE: 91
QSALTQPASV SGSPGQSITI SCTGTSAHKT YTIDWYQQHP GKAPKLMIYV KSDGSYTKGT  60
GVSNRFSGSK SGNTASLTIS GLQAEDEADY YCGADDNGGY VFGGGTQLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 92          moltype = AA  length = 254
FEATURE                Location/Qualifiers
REGION                 1..254
                       note = scFv
REGION                 1..254
                       note = 19.H2.L2m2
source                 1..254
                       mol_type = protein
                       organism = synthetic construct
SEQUENCE: 92
QFVLTQPPSA SGTPGQRVTI SCTLSSAHKT YTIDWYQQLP GTAPKLLIYV KSDGSYTKGT  60
GVPDRFSGSS SGADASLAIS GLQSEDEADY YCGADDNGGY VFGGGTQLTV LGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                   254

SEQ ID NO: 93          moltype = AA  length = 254
FEATURE                Location/Qualifiers
REGION                 1..254
                       note = scFv
REGION                 1..254
                       note = 20.H2.L2m3
source                 1..254
                       mol_type = protein
                       organism = synthetic construct
SEQUENCE: 93
QSVLTQPPSA SGTPGQRVTI SCTLSSAHKT YTIDWYQQLP GTAPKLLIYV KSDGSYTKGT  60
GVPDRFSGSK SGTSASLAIS GLQSEDEADY YCGADDNGGY VFGGGTQLTV LGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                   254

SEQ ID NO: 94          moltype = AA  length = 254
FEATURE                Location/Qualifiers
REGION                 1..254
                       note = scFv
REGION                 1..254
                       note = 21.H2.L1m2
source                 1..254
                       mol_type = protein
                       organism = synthetic construct
SEQUENCE: 94
QFVLTQSPSA SASLGASVKL TCTLSSAHKT YTIDWHQQQP EKGPRYLMQV KSDGSYTKGT  60
GIPDRFSGSS SGAERYLTIS SLQSEDEADY YCGADDNGGY VFGGGTQLTV LGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                   254

SEQ ID NO: 95          moltype = AA  length = 254
FEATURE                Location/Qualifiers
REGION                 1..254
                       note = scFv
REGION                 1..254
                       note = 22.H1.L1m2
source                 1..254
                       mol_type = protein
                       organism = synthetic construct
SEQUENCE: 95
QFVLTQSPSA SASLGASVKL TCTLSSAHKT YTIDWHQQQP EKGPRYLMQV KSDGSYTKGT  60
GIPDRFSGSS SGAERYLTIS SLQSEDEADY YCGADDNGGY VFGGGTQLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 96          moltype = AA  length = 254
FEATURE                Location/Qualifiers
REGION                 1..254
                       note = scFv
REGION                 1..254
                       note = 23.H1.L2m1
source                 1..254
                       mol_type = protein
```

```
                       organism = synthetic construct
SEQUENCE: 96
QFVLTQPPSA SGTPGQRVTI SCTLSSAHKT YTIDWYQQLP GTAPKLLIYV KSDGSYTKGT  60
GVPDRFSGSS SGADRYLAIS GLQSEDEADY YCGADDNGGY VFGGGTQLTV TGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 97          moltype = AA  length = 254
FEATURE                Location/Qualifiers
REGION                 1..254
                       note = scFv
REGION                 1..254
                       note = 24.H2.L3m1
source                 1..254
                       mol_type = protein
                       organism = synthetic construct
SEQUENCE: 97
QFVLTQPASV SGSPGQSITI SCTLSSAHKT YTIDWYQQHP GKAPKYLMQV KSDGSYTKGT  60
GVPNRFSGSS SGADRYLTIS GLQAEDEADY VCGADDNGGY VFGGGTQLTV TGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                   254

SEQ ID NO: 98          moltype = AA  length = 254
FEATURE                Location/Qualifiers
REGION                 1..254
                       note = scFv
REGION                 1..254
                       note = 25.H1.L1m3
source                 1..254
                       mol_type = protein
                       organism = synthetic construct
SEQUENCE: 98
QLVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 99          moltype = AA  length = 254
FEATURE                Location/Qualifiers
REGION                 1..254
                       note = scFv
REGION                 1..254
                       note = 26.H1.L1m4
source                 1..254
                       mol_type = protein
                       organism = synthetic construct
SEQUENCE: 99
QLVLTQSPSA SASLGASVKL TCTLSSAHKT YTIAWHQQQP EKGPRYLMQV KSDGSYTKGT  60
GVPDRFSGSS SGADRYLTIS SLQSEDEADY YCGADDNGGY VFGGGTQLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 100         moltype = AA  length = 254
FEATURE                Location/Qualifiers
REGION                 1..254
                       note = scFv
REGION                 1..254
                       note = 27.H1.L3m4
source                 1..254
                       mol_type = protein
                       organism = synthetic construct
SEQUENCE: 100
QSALTQPASV SGSPGQSITI SCTGTSAHKT YTVSWYQQHP GKAPKYLMQV KSDGSYTKGT  60
GVPNRFSGSS SGADRYLTIS GLQAEDEADY YCGADDNGGY VFGGGTQLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 101         moltype = AA  length = 254
FEATURE                Location/Qualifiers
REGION                 1..254
                       note = scFv
REGION                 1..254
                       note = 28.H1.L3m5
source                 1..254
```

```
                        mol_type = protein
                        organism = synthetic construct
SEQUENCE: 101
QSALTQPASV SGSPGQSITI SCTGTSAHKT YTVSWYQQHP GKAPKLMIYV KSDGSYTKGT  60
GVPNRFSGSS SGADRYLTIS GLQAEDEADY YCGADDNGGY VFGGGTQLTV LGGGSSRSSS  120
SGGGGSGGGG QVQLQESGPG LVKPSETLSL TCAVSGYSIS RHALTWIRQP PGKGLEWIGA  180
IDNAGTTYYA SWAKSRVTIS VDTSKNQFSL KLSSVTAADT AVYYCARVFY DINSGYYLDG  240
MDLWGPGTLV TVSS                                                   254

SEQ ID NO: 102          moltype = AA  length = 254
FEATURE                 Location/Qualifiers
REGION                  1..254
                        note = scFv
REGION                  1..254
                        note = 29.H2.L1m3
source                  1..254
                        mol_type = protein
                        organism = synthetic construct
SEQUENCE: 102
QLVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY VFGGGTQLTV TGGGSSRSSS  120
SGGGGSGGGG EVQLVESGGG LVQPGGSLRL SCAASGFTFS RHALTWVRQA PGKGLEWVSA  180
IDNAGTTYYA SWAKSRFTIS RDNAKNSLYL QMNSLRAEDT AVYYCARVFY DINSGYYLDG  240
MDLWGPGTLV TVSS                                                   254

SEQ ID NO: 103          moltype = DNA  length = 750
FEATURE                 Location/Qualifiers
misc_feature            1..750
                        note = scFv
misc_feature            1..750
                        note = CAR10
source                  1..750
                        mol_type = other DNA
                        organism = synthetic construct
SEQUENCE: 103
gaggtgcagc tggtggagtc tggaggagga ctggtgcaac ccggtggctc tttaagactg  60
agctgcgccg cctctggctt caccttttct cgtcacgctt taacatgggt gagacaagct  120
cccggaaagg gactggagtg ggtgtccgcc atcgacaacg ccggcaccac ctactacgcc  180
agctgggcca agagcagatt caccatctct cgtgacaacg ccaagaactc tttatattta  240
cagatgaact ctttaagggc cgaggacacc gccgtgtact actgcgctcg tgtgttctac  300
gacatcaact ccggctacta tttagacggc atggatttat ggggacccgg tacactggtc  360
acagtgagct ctggaggcgg aggtagcgga ggcggaggaa gcagcggtgg aggcagccag  420
tttgtgctga cacagtcccc ttccgcttcc gcctctttag gagcctccgt gaagctgact  480
tgtactttaa gcagcgccca caaaacctac accatcgact ggtaccagca gcagcccgag  540
aagggcccac gttatttaat gcaagttaag tccgacggct cctacaccaa gggcaccggc  600
gtgcccgata gattcagcgg ctccagcagc ggcgccgata ggtatttaac catctcctct  660
ttacagagcg aggacgaggc cgactactac tgtggcgccg acgacaacgg cggctacgtg  720
tttggaggcg gcacccagct gaccgtgctg                                  750

SEQ ID NO: 104          moltype = DNA  length = 750
FEATURE                 Location/Qualifiers
misc_feature            1..750
                        note = scFv
misc_feature            1..750
                        note = CAR14
source                  1..750
                        mol_type = other DNA
                        organism = synthetic construct
SEQUENCE: 104
caagttcagc tgcaagaaag cggacccggt ttagtgaaac cctccgagac tttatcttta  60
acatgcgccg tgagcggcta cagcatctct cgtcatgctt taacttggat tcgtcagcct  120
cccggaaagg gtttagagtg gatcggcgcc atcgacaacg ccggcaccac ctattacgcc  180
agctgggcca agtctcgtgt gaccatcagc gtggacacca gcaagaacca gttctcttta  240
aagctgtcca gcgtgaccgc tgccgacaca gccgtgtact actgcgctcg tgtgttctac  300
gacatcaaca gcggctacta tttagacgga atggatctgt ggggccccgg aactttagtg  360
acagtcagca gcggaggcgg aggaagcgga ggaggaggaa gctccggagg cggttctcaa  420
ttcgtgctga cacagagccc tagcgcctct gcctctttag gagcctccgt gaagctgact  480
tgtactttaa gcagcgccca caagacctac accatcgact ggtaccagca gcagcccgag  540
aagggcccta gatatttaat gcaagttaag agcgacggca gctacaccaa aggcactggt  600
gtgcccgatc gttttagcgg cagcagcagc ggcgccgata ggtatttaac catcagctct  660
ttacagagcg aggacgaggc cgactactac tgtggcgccg acgacaacgg cggctacgtg  720
tttggcggcg gcacacagct gaccgtttta                                  750

SEQ ID NO: 105          moltype = DNA  length = 750
FEATURE                 Location/Qualifiers
misc_feature            1..750
                        note = scFv
misc_feature            1..750
                        note = CAR25
```

```
source                  1..750
                        mol_type = other DNA
                        organism = synthetic construct
SEQUENCE: 105
caagttcagc tgcaagaaag cggacccggt ttagtgaaac cctccgagac tttatcttta  60
acatgcgccg tgagcggcta cagcatctct cgtcatgctt taacttggat tcgtcagcct  120
cccggaaagg gtttagagtg gatcggcgcc atcgacaacg ccggcaccac ctattacgcc  180
agctgggcca agtctcgtgt gaccatcagc gtggacacca gcaagaacca gttctcttta  240
aagctgtcca gcgtgaccgc tgccgacaca gccgtgtact actgcgctcg tgtgttctac  300
gacatcaaca gcggctacta tttagacgga atggatctgt ggggccccgg aactttagtg  360
acagtcagca gcggaggcgg aggaagcgga ggaggaggaa gctccggagg cggttctcaa  420
ctggtgctga cacagagccc tagcgcctct gcctctttag gagcctccgt gaagctgact  480
tgtactttaa gcagcgccca caagacctac accatcgact ggtaccagca gcagcccgag  540
aagggcccta gatatttaat gcaagttaag agcgacggca gctacaccaa aggcactggt  600
gtgcccgatc gttttagcgg cagcagcagc ggcgccgata ggtatttaac catcagctct  660
ttacagagcg aggacgaggc cgactactac tgtggcgccg acgacaacgg cggctacgtg  720
tttggcggcg gcacacagct gaccgtttta                                    750

SEQ ID NO: 106          moltype = DNA  length = 750
FEATURE                 Location/Qualifiers
misc_feature            1..750
                        note = scFv
misc_feature            1..750
                        note = CAR29
source                  1..750
                        mol_type = other DNA
                        organism = synthetic construct
SEQUENCE: 106
gaggtgcagc tggtggagtc tggaggagga ctggtgcaac ccggtggctc tttaagactg  60
agctgcgccg cctctggctt caccttttct cgtcacgctt taacatgggt gagacaagct  120
cccggaaagg gactggagtg ggtgtccgcc atcgacaacg ccggcaccac ctactacgcc  180
agctgggcca agagcagatt caccatctct cgtgacaacg ccaagaactc tttatattta  240
cagatgaact ctttaagggc cgaggacacc gccgtgtact actgcgctcg tgtgttctac  300
gacatcaact ccggctacta tttagacggc atggatttat ggggacccgg tacactggtc  360
acagtgagct ctggaggcgg aggtagcgga ggcggaggaa gcagcggtgg aggcagccag  420
ctggtgctga cacagtcccc ttccgcttcc gcctctttag gagcctccgt gaagctgact  480
tgtactttaa gcagcgccca caaaacctac accatcgact ggtaccagca gcagcccgag  540
aagggcccac gttatttaat gcaagttaag tccgacggct cctacaccaa gggcaccggc  600
gtgcccgata gattcagcgg ctccagcagc ggcgccgata ggtatttaac catctcctct  660
ttacagagcg aggacgaggc cgactactac tgtggcgccg acgacaacgg cggctacgtg  720
tttggaggcg gcacccagct gaccgtgctg                                    750

SEQ ID NO: 107          moltype = AA  length = 250
FEATURE                 Location/Qualifiers
REGION                  1..250
                        note = scFv
REGION                  1..250
                        note = CAR10
source                  1..250
                        mol_type = protein
                        organism = synthetic construct
SEQUENCE: 107
EVQLVESGGG LVQPGGSLRL SCAASGFTFS RHALTWVRQA PGKGLEWVSA IDNAGTTYYA  60
SWAKSRFTIS RDNAKNSLYL QMNSLRAEDT AVYYCARVFY DINSGYYLDG MDLWGPGTLV  120
TVSSGGGGSG GGGSSGGGSQ FVLTQSPSAS ASLGASVKLT CTLSSAHKTY TIDWYQQQPE  180
KGPRYLMQVK SDGSYTKGTG VPDRFSGSSS GADRYLTISS LQSEDEADYY CGADDNGGYV  240
FGGGTQLTVL                                                          250

SEQ ID NO: 108          moltype = AA  length = 250
FEATURE                 Location/Qualifiers
REGION                  1..250
                        note = scFv
REGION                  1..250
                        note = CAR14
source                  1..250
                        mol_type = protein
                        organism = synthetic construct
SEQUENCE: 108
QVQLQESGPG LVKPSETLSL TCAVSGYSIS RHALTWIRQP PGKGLEWIGA IDNAGTTYYA  60
SWAKSRVTIS VDTSKNQFSL KLSSVTAADT AVYYCARVFY DINSGYYLDG MDLWGPGTLV  120
TVSSGGGGSG GGGSSGGGSQ FVLTQSPSAS ASLGASVKLT CTLSSAHKTY TIDWYQQQPE  180
KGPRYLMQVK SDGSYTKGTG VPDRFSGSSS GADRYLTISS LQSEDEADYY CGADDNGGYV  240
FGGGTQLTVL                                                          250

SEQ ID NO: 109          moltype = AA  length = 250
FEATURE                 Location/Qualifiers
REGION                  1..250
                        note = scFv
REGION                  1..250
```

```
                        note = CAR25
source                  1..250
                        mol_type = protein
                        organism = synthetic construct
SEQUENCE: 109
QVQLQESGPG LVKPSETLSL TCAVSGYSIS RHALTWIRQP PGKGLEWIGA IDNAGTTYYA  60
SWAKSRVTIS VDTSKNQFSL KLSSVTAADT AVYYCARVFY DINSGYYLDG MDLWGPGTLV  120
TVSSGGGGSG GGGSSGGGSQ LVLTQSPSAS ASLGASVKLT CTLSSAHKTY TIDWYQQQPE  180
KGPRYLMQVK SDGSYTKGTG VPDRFSGSSS GADRYLTISS LQSEDEADYY CGADDNGGYV  240
FGGGTQLTVL                                                        250

SEQ ID NO: 110          moltype = AA  length = 250
FEATURE                 Location/Qualifiers
REGION                  1..250
                        note = scFv
REGION                  1..250
                        note = CAR29
source                  1..250
                        mol_type = protein
                        organism = synthetic construct
SEQUENCE: 110
EVQLVESGGG LVQPGGSLRL SCAASGFTFS RHALTWVRQA PGKGLEWVSA IDNAGTTYYA  60
SWAKSRFTIS RDNAKNSLYL QMNSLRAEDT AVYYCARVFY DINSGYYLDG MDLWGPGTLV  120
TVSSGGGGSG GGGSSGGGSQ LVLTQSPSAS ASLGASVKLT CTLSSAHKTY TIDWYQQQPE  180
KGPRYLMQVK SDGSYTKGTG VPDRFSGSSS GADRYLTISS LQSEDEADYY CGADDNGGYV  240
FGGGTQLTVL                                                        250

SEQ ID NO: 111          moltype = DNA  length = 9088
FEATURE                 Location/Qualifiers
misc_feature            1..9088
                        note = CAR
misc_feature            1..9088
                        note = pTRPE-C10-gs-BBz
source                  1..9088
                        mol_type = other DNA
                        organism = synthetic construct
SEQUENCE: 111
gtgcacgagt gggttacatc gaactggatc tcaacagcgg taagatcctt gagagttttc  60
gccccgaaga acgttttcca atgatgagca cttttaaagt tctgctatgt ggcgcggtat  120
tatcccgtat tgacgccggg caagagcaac tcggtcgccg catacactat tctcagaatg  180
acttggttga gtactcacca gtcacagaaa agcatcttac ggatggcatg acagtaagag  240
aattatgcag tgctgccata accatgagtg ataacactgc ggccaactta cttctgacaa  300
cgatcggagg accgaaggag ctaaccgctt ttttgcacaa catgggggat catgtaactc  360
gccttgatcg ttgggaaccg gagctgaatg aagccatacc aaacgacgag cgtgacacca  420
cgatgcctgt agcaatggca acaacgttgc gcaaactatt aactggcgaa ctacttactc  480
tagcttcccg gcaacaatta atagactgga tggaggcgga taaagttgca ggaccacttc  540
tgcgctcggc ccttccggct ggctggttta ttgctgataa atctggagcc ggtgagcgtg  600
ggtctcgcgg tatcattgca gcactggggc cagatggtaa gccctcccgt atcgtagtta  660
tctacacgac ggggagtcag gcaactatgg atgaacgaaa tagacagatc gctgagatag  720
gtgcctcact gattaagcat tggtaactgt cagaccaagt ttactcatat atactttaga  780
ttgatttaaa acttcatttt taatttaaaa ggatctaggt gaagatcctt tttgataatc  840
tcatgaccaa aatcccttaa cgtgagtttt cgttccactg agcgtcagac cccgtagaaa  900
agatcaaagg atcttcttga gatccttttt ttctgcgcgt aatctgctgc ttgcaaacaa  960
aaaaaccacc gctaccagcg gtggtttgtt tgccggatca agagctacca actctttttc  1020
cgaaggtaac tggcttcagc agagcgcaga taccaaatac tgttcttcta gtgtagccgt  1080
agttaggcca ccacttcaag aactctgtag caccgcctac atacctcgct ctgctaatcc  1140
tgttaccagt ggctgctgcc agtggcgata agtcgtgtct taccgggttg gactcaagac  1200
gatagttacc ggataaggcg cagcggtcgg gctgaacggg gggttcgtgc acacagccca  1260
gcttggagcg aacgacctac accgaactga gatacctaca gcgtgagcta tgagaaagcg  1320
ccacgcttcc cgaagggaga aaggcggaca ggtatccggt aagcggcagg gtcggaacag  1380
gagagcgcac gagggagctt ccagggggaa acgcctggta tctttatagt cctgtcgggt  1440
ttcgccacct ctgacttgag cgtcgatttt tgtgatgctc gtcagggggg cggagcctat  1500
ggaaaaacgc cagcaacgcg gcctttttac ggttcctggc cttttgctgg ccttttgctc  1560
acatgttctt tcctgcgtta tcccctgatt ctgtggataa ccgtattacc gcctttgagt  1620
gagctgatac cgctcgccgc agccgaacga ccgagcgcag cgagtcagtg agcgaggaag  1680
cggaagagcg cccaatacgc aaaccgcctc tccccgcgcg ttggccgatt cattaatgca  1740
gctggcacga caggtttccc gactggaaag cgggcagtga gcgcaacgca attaatgtga  1800
gttagctcac tcattaggca ccccaggctt tacactttat gcttccggct cgtatgttgt  1860
gtggaattgt gagcggataa caatttcaca caggaaacag ctatgaccat gattacgcca  1920
agcgcgcaat taaccctcac taaagggaac aaaagctgga gctgcaagct taatgtagtc  1980
ttatgcaata ctcttgtagt cttgcaacat ggtaacgatg agttagcaac atgccttaca  2040
aggagagaaa aagcaccgtg catgccgatt ggtggaagta aggtggtacg atcgtgcctt  2100
attaggaagg caacagacgg gtctgacatg gattggacga accactgaat tgccgcattg  2160
cagagatatt gtatttaagt gcctagctcg atacataaac gggtctctct ggttagacca  2220
gatctgagcc tgggagctct ctggctaact agggaaccca ctgcttaagc ctcaataaag  2280
cttgccttga gtgcttcaag tagtgtgtgc ccgtctgttg tgtgactctg gtaactagag  2340
atccctcaga cccttttagt cagtgtggaa aatctctagc agtggcgccc gaacagggac  2400
ttgaaagcga aagggaaacc agaggagctc tctcgacgca ggactcggct tgctgaagcg  2460
cgcacggcaa gaggcgaggg gcggcgactg gtgagtacgc caaaaatttt gactagcgga  2520
```

-continued

```
ggctagaagg agagagatgg gtgcgagagc gtcagtatta agcgggggag aattagatcg  2580
cgatgggaaa aaattcggtt aaggccaggg ggaaagaaaa aatataaatt aaaacatata  2640
gtatgggcaa gcagggagct agaacgattc gcagttaatc ctggcctgtt agaaacatca  2700
gaaggctgta gacaaatact gggacagcta caaccatccc ttcagacagg atcagaagaa  2760
cttagatcat tatataatac agtagcaacc ctctattgtg tgcatcaaag gatagagata  2820
aaagacacca aggaagcttt agacaagata gaggaagagc aaaacaaaag taagaccacc  2880
gcacagcaag cggccgctga tcttcagacc tggaggagga gatatgaggg acaattggag  2940
aagtgaatta tataaatata aagtagtaaa aattgaacca ttaggagtag cacccaccaa  3000
ggcaaagaga agagtggtgc agagagaaaa aagagcagtg ggaataggag ctttgttcct  3060
tgggttcttg ggagcagcag gaagcactat gggcgcagcg tcaatgacgc tgacggtaca  3120
ggccagacaa ttattgtctg gtatagtgca gcagcagaac aatttgctga gggctattga  3180
ggcgcaacag catctgttgc aactcacagt ctggggcatc aagcagctcc aggcaagaat  3240
cctggctgtg gaaagatacc taaaggatca acagctcctg gggatttggg gttgctctgg  3300
aaaactcatt tgcaccactg ctgtgccttg gaatgctagt tggagtaata aatctctgga  3360
acagatttgg aatcacacga cctggatgga gtgggacaga gaaattaaca attacacaag  3420
cttaatacac tccttaattg aagaatcgca aaaccagcaa gaaaagaatg aacaagaatt  3480
attggaatta gataaatggg caagtttgtg gaattggttt aacataacaa attggctgtg  3540
gtatataaaa ttattcataa tgatagtagg aggcttggta ggtttaagaa tagtttttgc  3600
tgtactttct atagtgaata gagttaggca gggatattca ccattatcgt ttcagaccca  3660
cctcccaacc ccgaggggac ccgacaggcc cgaaggaata gaagaagaag gtggagagag  3720
agacagagac agatccattc gattagtgaa cggatctcga cggtatcgat tagactgtag  3780
cccaggaata tggcagctag attgtacaca tttagaagga aaagttatct tggtagcagt  3840
tcatgtagcc agtggatata tagaagcaga agtaattcca gcagagacag ggcaagaaac  3900
agcatacttc ctcttaaaat tagcaggaag atggccagta aaaacagtac atacagacaa  3960
tggcagcaat ttcaccagta ctacagttaa ggccgcctgt tggtgggcgg ggatcaagca  4020
ggaatttggc attccctaca atccccaaag tcaaggagta atagaatcta tgaataaaga  4080
attaaagaaa attataggac aggtaagaga tcaggctgaa catcttaaga cagcagtaca  4140
aatggcagta ttcatccaca attttaaaag aaaagggggg attggggggt acagtgcagg  4200
ggaaagaata gtagacataa tagcaacaga catacaaact aaagaattac aaaaacaaat  4260
tacaaaaatt caaaattttc gggtttatta cagggacagc agagatccag tttggctgca  4320
tacgcgtcgt gaggctccgg tgcccgtcag tgggcagagc gcacatcgcc cacagtcccc  4380
gagaagttgg ggggaggggt cggcaattga accggtgcct agagaaggtg gcgcggggta  4440
aactgggaaa gtgatgtcgt gtactggctc cgcctttttc ccgagggtgg gggagaaccg  4500
tatataagtg cagtagtcgc cgtgaacgtt ctttttcgca acgggtttgc cgccagaaca  4560
caggtaagtg ccgtgtgtgg ttcccgcggg cctggcctct ttacgggtta tggcccttgc  4620
gtgccttgaa ttacttccac ctggctgcag tacgtgattc ttgatcccga gcttcgggtt  4680
ggaagtgggt gggagagttc gaggccttgc gcttaaggag ccccttcgcc tcgtgcttga  4740
gttgaggcct ggcctgggcg ctggggccgc cgcgtgcgaa tctggtggca ccttcgcgcc  4800
tgtctcgctg ctttcgataa gtctctagcc atttaaaatt tttgatgacc tgctgcgacg  4860
ctttttttct ggcaagatag tcttgtaaat gcgggccaag atctgcacac tggtatttcg  4920
gtttttgggg ccgcgggcgg cgacggggcc cgtgcgtccc agcgcacatg ttcggcgagg  4980
cggggcctgc gagcgcggcc accgagaatc ggacgggggt agtctcaagc tggccggcct  5040
gctctggtgc ctggcctcgc gccgccgtgt atcgccccgc cctgggcggc aaggctggcc  5100
cggtcggcac cagttgcgtg agcggaaaga tggccgcttc ccggccctgc tgcagggagc  5160
tcaaaatgga ggacgcggcg ctcgggagag cgggcgggtg agtcacccac acaaaggaaa  5220
agggcctttc cgtcctcagc cgtcgcttca tgtgactcca ctgagtaccg ggcgccgtcc  5280
aggcacctcg attagttctc gtgcttttgg agtacgtcgt ctttaggttg gggggagggg  5340
ttttatgcga tggagtttcc ccacactgag tgggtggaga ctgaagttag gccagcttgg  5400
cacttgatgt aattctcctt ggaatttgcc ctttttgagt ttggatcttg gttcattctc  5460
aagcctcaga cagtggttca aagttttttt cttccatttc aggtgtcgtg agctagagcc  5520
accatggagt ttgggctgag ctggcttttt cttgtggcta ttttaaaagg tgtccagtgc  5580
ggatccgagg tgcagctggt ggagtctgga ggaggactgg tgcaacccgg tggctcttta  5640
agactgagct gcgccgcctc tggcttcacc ttttctcgtc acgctttaac atgggtgaga  5700
caagctcccg gaaagggact ggagtgggtg tccgccatcg acaacgccgg caccacctac  5760
tacgccagct gggccaagag cagattcacc atctctcgtg acaacgccaa gaactcttta  5820
tatttacaga tgaactcttt aagggccgag gacaccgccg tgtactactg cgctcgtgtg  5880
ttctacgaca tcaactccgg ctactattta gacggcatgg atttatgggg acccggtaca  5940
ctggtcacag tgagctctgg aggcggaggt agcggaggcg gaggaagcag cggtggaggc  6000
agccagtttg tgctgacaca gtccccttcc gcttccgcct ctttaggagc ctccgtgaag  6060
ctgacttgta ctttaagcag cgcccacaaa acctacacca tcgactggta ccagcagcag  6120
cccgagaagg gcccacgtta tttaatgcaa gttaagtccg acggctccta caccaagggc  6180
accggcgtgc ccgatagatt cagcggctcc agcagcggcg ccgataggta tttaaccatc  6240
tcctctttac agagcgagga cgaggccgac tactactgtg gcgccgacga caacggcggc  6300
tacgtgtttg gaggcggcac ccagctgacc gtgctggcta gcggtggcgg aggttctgga  6360
ggtggaggtt cctccggaat ctacatctgg gcgcccttgg ccgggacttg tggggtcctt  6420
ctcctgtcac tggttatcac cctttactgc aaacggggca gaaagaaact cctgtatata  6480
ttcaaacaac catttatgag accagtacaa actactcaag aggaagatgg ctgtagctgc  6540
cgatttccag aagaagaaga aggaggatgt gaactgagag tgaagttcag caggagcgca  6600
gacgcccccg cgtaccagca gggccagaac cagctctata acgagctcaa tctaggacga  6660
agagaggagt acgatgtttt ggacaagaga cgtggccggg accctgagat ggggggaaag  6720
ccgagaagga agaaccctca ggaaggcctg tacaatgaac tgcagaaaga taagatggcg  6780
gaggcctaca gtgagattgg gatgaaaggc gagcgccgga ggggcaaggg gcacgatggc  6840
ctttaccagg gtctcagtac agccaccaag gacacctacg acgcccttca catgcaggcc  6900
ctgccccctc gctaagtcga caatcaacct ctggattaca aaatttgtga aagattgact  6960
ggtattctta actatgttgc tccttttacg ctatgtggat acgctgcttt aatgcctttg  7020
tatcatgcta ttgcttcccg tatggctttc attttctcct ccttgtataa atcctggttg  7080
ctgtctcttt atgaggagtt gtggcccgtt gtcaggcaac gtggcgtggt gtgcactgtg  7140
tttgctgacg caacccccac tggttggggc attgccacca cctgtcagct cctttccggg  7200
actttcgctt tccccctccc tattgccacg gcggaactca tcgccgcctg ccttgcccgc  7260
```

-continued

```
tgctggacag gggctcggct gttgggcact gacaattccg tggtgttgtc ggggaagctg  7320
acgtcctttc cttggctgct cgcctgtgtt gccacctgga ttctgcgcgg gacgtccttc  7380
tgctacgtcc cttcggccct caatccagcg gaccttcctt cccgcggcct gctgccggct  7440
ctgcggcctc ttccgcgtct tcgccttcgc cctcagacga gtcggatctc cctttgggcc  7500
gcctccccgc ctggaattcg agctcggtac ctttaagacc aatgacttac aaggcagctg  7560
tagatcttag ccacttttta aaagaaaagg ggggactgga agggctaatt cactcccaac  7620
gaagacaaga tctgcttttt gcttgtactg ggtctctctg gttagaccag atctgagcct  7680
gggagctctc tggctaacta gggaacccac tgcttaagcc tcaataaagc ttgccttgag  7740
tgcttcaagt agtgtgtgcc cgtctgttgt gtgactctgg taactagaga tccctcagac  7800
ccttttagtc agtgtggaaa atctctagca gtagtagttc atgtcatctt attattcagt  7860
atttataact tgcaaagaaa tgaatatcag agagtgagag gaacttgttt attgcagctt  7920
ataatggtta caaataaagc aatagcatca caaatttcac aaataaagca tttttttcac  7980
tgcattctag ttgtggtttg tccaaactca tcaatgtatc ttatcatgtc tggctctagc  8040
tatcccgccc ctaactccgc ccagttccgc ccattctccg ccccatggct gactaatttt  8100
ttttatttat gcagaggccg aggccgcctc ggcctctgag ctattccaga agtagtgagg  8160
aggctttttt ggaggcctag ctagggacgt acccaattcg ccctatagtg agtcgtatta  8220
cgcgcgctca ctggccgtcg ttttacaacg tcgtgactgg gaaaaccctg gcgttaccca  8280
acttaatcgc cttgcagcac atcccccttt cgccagctgg cgtaatagcg aagaggcccg  8340
caccgatcgc ccttcccaac agttgcgcag cctgaatggc gaatgggacg cgccctgtag  8400
cggcgcatta agcgcggcgg gtgtggtggt tacgcgcagc gtgaccgcta cacttgccag  8460
cgccctagcg cccgctcctt tcgctttctt cccttccttt ctcgccacgt tcgccggctt  8520
tccccgtcaa gctctaaatc gggggctccc tttagggttc cgatttagtg ctttacggca  8580
cctcgacccc aaaaaacttg attagggtga tggttcacgt agtgggccat cgccctgata  8640
gacggttttt cgccctttga cgttggagtc cacgttcttt aatagtggac tcttgttcca  8700
aactggaaca acactcaacc ctatctcggt ctattctttt gatttataag ggattttgcc  8760
gatttcggcc tattggttaa aaaatgagct gatttaacaa aaatttaacg cgaattttaa  8820
caaaatatta acgcttacaa tttaggtggc acttttcggg gaaatgtgcg cggaacccct  8880
atttgtttat ttttctaaat acattcaaat atgtatccgc tcatgagaca ataaccctga  8940
taaatgcttc aataatattg aaaaaggaag agtatgagta ttcaacattt ccgtgtcgcc  9000
cttattccct tttttgcggc attttgcctt cctgtttttg ctcacccaga aacgctggtg  9060
aaagtaaaag atgctgaaga tcagttgg                                    9088

SEQ ID NO: 112          moltype = DNA  length = 9088
FEATURE                 Location/Qualifiers
misc_feature            1..9088
                        note = CAR
misc_feature            1..9088
                        note = pTRPE-C14-gs-BBz
source                  1..9088
                        mol_type = other DNA
                        organism = synthetic construct
SEQUENCE: 112
gtgcacgagt gggttacatc gaactggatc tcaacagcgg taagatcctt gagagttttc  60
gccccgaaga acgttttcca atgatgagca cttttaaagt tctgctatgt ggcgcggtat  120
tatcccgtat tgacgccggg caagagcaac tcggtcgccg catacactat tctcagaatg  180
acttggttga gtactcacca gtcacagaaa agcatcttac ggatggcatg acagtaagag  240
aattatgcag tgctgccata accatgagtg ataacactgc ggccaactta cttctgacaa  300
cgatcggagg accgaaggag ctaaccgctt ttttgcacaa catgggggat catgtaactc  360
gccttgatcg ttgggaaccg gagctgaatg aagccatacc aaacgacgag cgtgacacca  420
cgatgcctgt agcaatggca acaacgttgc gcaaactatt aactggcgaa ctacttactc  480
tagcttcccg gcaacaatta atagactgga tggaggcgga taaagttgca ggaccacttc  540
tgcgctcggc ccttccggct ggctggttta ttgctgataa atctggagcc ggtgagcgtg  600
ggtctcgcgg tatcattgca gcactggggc cagatggtaa gccctcccgt atcgtagtta  660
tctacacgac ggggagtcag gcaactatgg atgaacgaaa tagacagatc gctgagatag  720
gtgcctcact gattaagcat tggtaactgt cagaccaagt ttactcatat atactttaga  780
ttgatttaaa acttcatttt taatttaaaa ggatctaggt gaagatcctt tttgataatc  840
tcatgaccaa aatcccttaa cgtgagtttt cgttccactg agcgtcagac cccgtagaaa  900
agatcaaagg atcttcttga gatccttttt ttctgcgcgt aatctgctgc ttgcaaacaa  960
aaaaaccacc gctaccagcg gtggtttgtt tgccggatca agagctacca actctttttc  1020
cgaaggtaac tggcttcagc agagcgcaga taccaaatac tgttcttcta gtgtagccgt  1080
agttaggcca ccacttcaag aactctgtag caccgcctac atacctcgct ctgctaatcc  1140
tgttaccagt ggctgctgcc agtggcgata agtcgtgtct taccgggttg gactcaagac  1200
gatagttacc ggataaggcg cagcggtcgg gctgaacggg gggttcgtgc acacagccca  1260
gcttggagcg aacgacctac accgaactga gatacctaca gcgtgagcta tgagaaagcg  1320
ccacgcttcc cgaagggaga aaggcggaca ggtatccggt aagcggcagg gtcggaacag  1380
gagagcgcac gagggagctt ccagggggaa acgcctggta tctttatagt cctgtcgggt  1440
ttcgccacct ctgacttgag cgtcgatttt tgtgatgctc gtcagggggg cggagcctat  1500
ggaaaaacgc cagcaacgcg gcctttttac ggttcctggc cttttgctgg ccttttgctc  1560
acatgttctt tcctgcgtta tcccctgatt ctgtggataa ccgtattacc gcctttgagt  1620
gagctgatac cgctcgccgc agccgaacga ccgagcgcag cgagtcagtg agcgaggaag  1680
cggaagagcg cccaatacgc aaaccgcctc tccccgcgcg ttggccgatt cattaatgca  1740
gctggcacga caggtttccc gactggaaag cgggcagtga gcgcaacgca attaatgtga  1800
gttagctcac tcattaggca ccccaggctt tacactttat gcttccggct cgtatgttgt  1860
gtggaattgt gagcggataa caatttcaca caggaaacag ctatgaccat gattacgcca  1920
agcgcgcaat taaccctcac taaagggaac aaaagctgga gctgcaagct taatgtagtc  1980
ttatgcaata ctcttgtagt cttgcaacat ggtaacgatg agttagcaac atgccttaca  2040
aggagagaaa aagcaccgtg catgccgatt ggtggaagta aggtggtacg atcgtgcctt  2100
attaggaagg caacagacgg gtctgacatg gattggacga accactgaat tgccgcattg  2160
cagagatatt gtatttaagt gcctagctcg atacataaac gggtctctct ggttagacca  2220
```

```
gatctgagcc tgggagctct ctggctaact agggaaccca ctgcttaagc ctcaataaag  2280
cttgccttga gtgcttcaag tagtgtgtgc ccgtctgttg tgtgactctg gtaactagag  2340
atccctcaga cccttttagt cagtgtggaa aatctctagc agtggcgccc gaacagggac  2400
ttgaaagcga aagggaaacc agaggagctc tctcgacgca ggactcggct tgctgaagcg  2460
cgcacggcaa gaggcgaggg gcggcgactg gtgagtacgc caaaaatttt gactagcgga  2520
ggctagaagg agagagatgg gtgcgagagc gtcagtatta agcgggggag aattagatcg  2580
cgatgggaaa aaattcggtt aaggccaggg ggaaagaaaa aatataaatt aaaacatata  2640
gtatgggcaa gcagggagct agaacgattc gcagttaatc ctggcctgtt agaaacatca  2700
gaaggctgta gacaaatact gggacagcta caaccatccc ttcagacagg atcagaagaa  2760
cttagatcat tatataatac agtagcaacc ctctattgtg tgcatcaaag gatagagata  2820
aaagacacca aggaagcttt agacaagata gaggaagagc aaaacaaaag taagaccacc  2880
gcacagcaag cggccgctga tcttcagacc tggaggagga gatatgaggg acaattggag  2940
aagtgaatta tataaatata aagtagtaaa aattgaacca ttaggagtag cacccaccaa  3000
ggcaaagaga agagtggtgc agagagaaaa aagagcagtg ggaataggag ctttgttcct  3060
tgggttcttg ggagcagcag gaagcactat gggcgcagcg tcaatgacgc tgacggtaca  3120
ggccagacaa ttattgtctg gtatagtgca gcagcagaac aatttgctga gggctattga  3180
ggcgcaacag catctgttgc aactcacagt ctggggcatc aagcagctcc aggcaagaat  3240
cctggctgtg gaaagatacc taaaggatca acagctcctg gggatttggg gttgctctgg  3300
aaaactcatt tgcaccactg ctgtgccttg gaatgctagt tggagtaata aatctctgga  3360
acagatttgg aatcacacga cctggatgga gtgggacaga gaaattaaca attacacaag  3420
cttaatacac tccttaattg aagaatcgca aaaccagcaa gaaaagaatg aacaagaatt  3480
attggaatta gataaatggg caagtttgtg gaattggttt aacataacaa attggctgtg  3540
gtatataaaa ttattcataa tgatagtagg aggcttggta ggtttaagaa tagtttttgc  3600
tgtactttct atagtgaata gagttaggca gggatattca ccattatcgt ttcagaccca  3660
cctcccaacc ccgaggggac ccgacaggcc cgaaggaata gaagaagaag gtggagagag  3720
agacagagac agatccattc gattagtgaa cggatctcga cggtatcgat tagactgtag  3780
cccaggaata tggcagctag attgtacaca tttagaagga aaagttatct tggtagcagt  3840
tcatgtagcc agtggatata tagaagcaga agtaattcca gcagagacag ggcaagaaac  3900
agcatacttc ctcttaaaat tagcaggaag atggccagta aaaacagtac atacagacaa  3960
tggcagcaat ttcaccagta ctacagttaa ggccgcctgt tggtgggcgg ggatcaagca  4020
ggaatttggc attccctaca atccccaaag tcaaggagta atagaatcta tgaataaaga  4080
attaaagaaa attataggac aggtaagaga tcaggctgaa catcttaaga cagcagtaca  4140
aatggcagta ttcatccaca attttaaaag aaaagggggg attggggggt acagtgcagg  4200
ggaaagaata gtagacataa tagcaacaga catacaaact aaagaattac aaaaacaaat  4260
tacaaaaatt caaaattttc gggtttatta cagggacagc agagatccag tttggctgca  4320
tacgcgtcgt gaggctccgg tgcccgtcag tgggcagagc gcacatcgcc cacagtcccc  4380
gagaagttgg ggggaggggt cggcaattga accggtgcct agagaaggtg gcgcggggta  4440
aactgggaaa gtgatgtcgt gtactggctc cgcctttttc ccgagggtgg gggagaaccg  4500
tatataagtg cagtagtcgc cgtgaacgtt ctttttcgca acgggtttgc cgccagaaca  4560
caggtaagtg ccgtgtgtgg ttcccgcggg cctggcctct ttacgggtta tggcccttgc  4620
gtgccttgaa ttacttccac ctggctgcag tacgtgattc ttgatcccga gcttcgggtt  4680
ggaagtgggt gggagagttc gaggccttgc gcttaaggag ccccttcgcc tcgtgcttga  4740
gttgaggcct ggcctgggcg ctggggccgc cgcgtgcgaa tctggtggca ccttcgcgcc  4800
tgtctcgctg ctttcgataa gtctctagcc atttaaaatt tttgatgacc tgctgcgacg  4860
ctttttttct ggcaagatag tcttgtaaat gcgggccaag atctgcacac tggtatttcg  4920
gtttttgggg ccgcgggcgg cgacggggcc cgtgcgtccc agcgcacatg ttcggcgagg  4980
cggggcctgc gagcgcggcc accgagaatc ggacgggggt agtctcaagc tggccggcct  5040
gctctggtgc ctggcctcgc gccgccgtgt atcgccccgc cctgggcggc aaggctggcc  5100
cggtcggcac cagttgcgtg agcggaaaga tggccgcttc ccggccctgc tgcagggagc  5160
tcaaaatgga ggacgcggcg ctcgggagag cgggcgggtg agtcacccac acaaaggaaa  5220
agggcctttc cgtcctcagc cgtcgcttca tgtgactcca ctgagtaccg ggcgccgtcc  5280
aggcacctcg attagttctc gtgcttttgg agtacgtcgt ctttaggttg gggggagggg  5340
ttttatgcga tggagtttcc ccacactgag tgggtggaga ctgaagttag gccagcttgg  5400
cacttgatgt aattctcctt ggaatttgcc ctttttgagt ttggatcttg gttcattctc  5460
aagcctcaga cagtggttca aagttttttt cttccatttc aggtgtcgtg agctagagcc  5520
accatggagt ttgggctgag ctggcttttt cttgtggcta ttttaaaagg tgtccagtgc  5580
ggatcccaag ttcagctgca agaaagcgga cccggtttag tgaaaccctc cgagacttta  5640
tctttaacat gcgccgtgag cggctacagc atctctcgtc atgctttaac ttggattcgt  5700
cagcctcccg gaaagggttt agagtggatc ggcgccatcg acaacgccgg caccacctat  5760
tacgccagct gggccaagtc tcgtgtgacc atcagcgtgg acaccagcaa gaaccagttc  5820
tctttaaagc tgtccagcgt gaccgctgcc gacacagccg tgtactactg cgctcgtgtg  5880
ttctacgaca tcaacagcgg ctactattta gacggaatgg atctgtgggg ccccggaact  5940
ttagtgacag tcagcagcgg aggcggagga agcggaggag gaggaagctc cggaggcggt  6000
tctcaattcg tgctgacaca gagccctagc gcctctgcct ctttaggagc ctccgtgaag  6060
ctgacttgta ctttaagcag cgcccacaag acctacacca tcgactggta ccagcagcag  6120
cccgagaagg gccctagata tttaatgcaa gttaagagcg acggcagcta caccaaaggc  6180
actggtgtgc ccgatcgttt tagcggcagc agcagcggcg ccgataggta tttaaccatc  6240
agctctttac agagcgagga cgaggccgac tactactgtg gcgccgacga caacggcggc  6300
tacgtgtttg gcggcggcac acagctgacc gttttagcta gcggtggcgg aggttctgga  6360
ggtggaggtt cctccggaat ctacatctgg gcgcccttgg ccgggacttg tggggtcctt  6420
ctcctgtcac tggttatcac cctttactgc aaacggggca gaaagaaact cctgtatata  6480
ttcaaacaac catttatgag accagtacaa actactcaag aggaagatgg ctgtagctgc  6540
cgatttccag aagaagaaga aggaggatgt gaactgagag tgaagttcag caggagcgca  6600
gacgcccccg cgtaccagca gggccagaac cagctctata acgagctcaa tctaggacga  6660
agagaggagt acgatgtttt ggacaagaga cgtggccggg accctgagat ggggggaaag  6720
ccgagaagga agaaccctca ggaaggcctg tacaatgaac tgcagaaaga taagatggcg  6780
gaggcctaca gtgagattgg gatgaaaggc gagcgccgga ggggcaaggg gcacgatggc  6840
ctttaccagg gtctcagtac agccaccaag gacacctacg acgcccttca catgcaggcc  6900
ctgccccctc gctaagtcga caatcaacct ctggattaca aaatttgtga aagattgact  6960
```

```
ggtattctta actatgttgc tccttttacg ctatgtggat acgctgcttt aatgcctttg  7020
tatcatgcta ttgcttcccg tatggctttc attttctcct ccttgtataa atcctggttg  7080
ctgtctcttt atgaggagtt gtggcccgtt gtcaggcaac gtggcgtggt gtgcactgtg  7140
tttgctgacg caacccccac tggttggggc attgccacca cctgtcagct cctttccggg  7200
actttcgctt tccccctccc tattgccacg gcggaactca tcgccgcctg ccttgcccgc  7260
tgctggacag gggctcggct gttgggcact gacaattccg tggtgttgtc ggggaagctg  7320
acgtcctttc cttggctgct cgcctgtgtt gccacctgga ttctgcgcgg gacgtccttc  7380
tgctacgtcc cttcggccct caatccagcg gaccttcctt cccgcggcct gctgccggct  7440
ctgcggcctc ttccgcgtct tcgccttcgc cctcagacga gtcggatctc cctttgggcc  7500
gcctccccgc ctggaattcg agctcggtac ctttaagacc aatgacttac aaggcagctg  7560
tagatcttag ccacttttta aaagaaaagg ggggactgga agggctaatt cactcccaac  7620
gaagacaaga tctgcttttt gcttgtactg ggtctctctg gttagaccag atctgagcct  7680
gggagctctc tggctaacta gggaacccac tgcttaagcc tcaataaagc ttgccttgag  7740
tgcttcaagt agtgtgtgcc cgtctgttgt gtgactctgg taactagaga tccctcagac  7800
ccttttagtc agtgtggaaa atctctagca gtagtagttc atgtcatctt attattcagt  7860
atttataact tgcaaagaaa tgaatatcag agagtgagag gaacttgttt attgcagctt  7920
ataatggtta caaataaagc aatagcatca caaatttcac aaataaagca tttttttcac  7980
tgcattctag ttgtggtttg tccaaactca tcaatgtatc ttatcatgtc tggctctagc  8040
tatcccgccc ctaactccgc ccagttccgc ccattctccg ccccatggct gactaatttt  8100
ttttatttat gcagaggccg aggccgcctc ggcctctgag ctattccaga agtagtgagg  8160
aggctttttt ggaggcctag ctagggacgt acccaattcg ccctatagtg agtcgtatta  8220
cgcgcgctca ctggccgtcg ttttacaacg tcgtgactgg gaaaaccctg gcgttaccca  8280
acttaatcgc cttgcagcac atcccccttt cgccagctgg cgtaatagcg aagaggcccg  8340
caccgatcgc ccttcccaac agttgcgcag cctgaatggc gaatgggacg cgccctgtag  8400
cggcgcatta agcgcggcgg gtgtggtggt tacgcgcagc gtgaccgcta cacttgccag  8460
cgccctagcg cccgctcctt tcgctttctt cccttccttt ctcgccacgt tcgccggctt  8520
tccccgtcaa gctctaaatc gggggctccc tttagggttc cgatttagtg ctttacggca  8580
cctcgacccc aaaaaacttg attagggtga tggttcacgt agtgggccat cgccctgata  8640
gacggttttt cgccctttga cgttggagtc cacgttcttt aatagtggac tcttgttcca  8700
aactggaaca acactcaacc ctatctcggt ctattctttt gatttataag ggattttgcc  8760
gatttcggcc tattggttaa aaaatgagct gatttaacaa aaatttaacg cgaattttaa  8820
caaaatatta acgcttacaa tttaggtggc acttttcggg gaaatgtgcg cggaacccct  8880
atttgtttat ttttctaaat acattcaaat atgtatccgc tcatgagaca ataaccctga  8940
taaatgcttc aataatattg aaaaaggaag agtatgagta ttcaacattt ccgtgtcgcc  9000
cttattccct tttttgcggc attttgcctt cctgtttttg ctcacccaga aacgctggtg  9060
aaagtaaaag atgctgaaga tcagttgg                                     9088
```

```
SEQ ID NO: 113          moltype = DNA  length = 9088
FEATURE                 Location/Qualifiers
misc_feature            1..9088
                        note = CAR
misc_feature            1..9088
                        note = pTRPE-C25-gs-BBz
source                  1..9088
                        mol_type = other DNA
                        organism = synthetic construct
SEQUENCE: 113
gtgcacgagt gggttacatc gaactggatc tcaacagcgg taagatcctt gagagttttc  60
gccccgaaga acgttttcca atgatgagca cttttaaagt tctgctatgt ggcgcggtat  120
tatcccgtat tgacgccggg caagagcaac tcggtcgccg catacactat tctcagaatg  180
acttggttga gtactcacca gtcacagaaa agcatcttac ggatggcatg acagtaagag  240
aattatgcag tgctgccata accatgagtg ataacactgc ggccaactta cttctgacaa  300
cgatcggagg accgaaggag ctaaccgctt ttttgcacaa catgggggat catgtaactc  360
gccttgatcg ttgggaaccg gagctgaatg aagccatacc aaacgacgag cgtgacacca  420
cgatgcctgt agcaatggca acaacgttgc gcaaactatt aactggcgaa ctacttactc  480
tagcttcccg gcaacaatta atagactgga tggaggcgga taaagttgca ggaccacttc  540
tgcgctcggc ccttccggct ggctggttta ttgctgataa atctggagcc ggtgagcgtg  600
ggtctcgcgg tatcattgca gcactggggc cagatggtaa gccctcccgt atcgtagtta  660
tctacacgac ggggagtcag gcaactatgg atgaacgaaa tagacagatc gctgagatag  720
gtgcctcact gattaagcat tggtaactgt cagaccaagt ttactcatat atactttaga  780
ttgatttaaa acttcatttt taatttaaaa ggatctaggt gaagatcctt tttgataatc  840
tcatgaccaa aatcccttaa cgtgagtttt cgttccactg agcgtcagac cccgtagaaa  900
agatcaaagg atcttcttga gatccttttt ttctgcgcgt aatctgctgc ttgcaaacaa  960
aaaaaccacc gctaccagcg gtggtttgtt tgccggatca agagctacca actctttttc  1020
cgaaggtaac tggcttcagc agagcgcaga taccaaatac tgttcttcta gtgtagccgt  1080
agttaggcca ccacttcaag aactctgtag caccgcctac atacctcgct ctgctaatcc  1140
tgttaccagt ggctgctgcc agtggcgata agtcgtgtct taccgggttg gactcaagac  1200
gatagttacc ggataaggcg cagcggtcgg gctgaacggg gggttcgtgc acacagccca  1260
gcttggagcg aacgacctac accgaactga gatacctaca gcgtgagcta tgagaaagcg  1320
ccacgcttcc cgaagggaga aaggcggaca ggtatccggt aagcggcagg gtcggaacag  1380
gagagcgcac gagggagctt ccagggggaa acgcctggta tctttatagt cctgtcgggt  1440
ttcgccacct ctgacttgag cgtcgatttt tgtgatgctc gtcagggggg cggagcctat  1500
ggaaaaacgc cagcaacgcg gcctttttac ggttcctggc cttttgctgg ccttttgctc  1560
acatgttctt tcctgcgtta tcccctgatt ctgtggataa ccgtattacc gcctttgagt  1620
gagctgatac cgctcgccgc agccgaacga ccgagcgcag cgagtcagtg agcgaggaag  1680
cggaagagcg cccaatacgc aaaccgcctc tccccgcgcg ttggccgatt cattaatgca  1740
gctggcacga caggtttccc gactggaaag cgggcagtga gcgcaacgca attaatgtga  1800
gttagctcac tcattaggca ccccaggctt tacactttat gcttccggct cgtatgttgt  1860
gtggaattgt gagcggataa caatttcaca caggaaacag ctatgaccat gattacgcca  1920
```

-continued

```
agcgcgcaat taaccctcac taaagggaac aaaagctgga gctgcaagct taatgtagtc  1980
ttatgcaata ctcttgtagt cttgcaacat ggtaacgatg agttagcaac atgccttaca  2040
aggagagaaa aagcaccgtg catgccgatt ggtggaagta aggtggtacg atcgtgcctt  2100
attaggaagg caacagacgg gtctgacatg gattggacga accactgaat tgccgcattg  2160
cagagatatt gtatttaagt gcctagctcg atacataaac gggtctctct ggttagacca  2220
gatctgagcc tgggagctct ctggctaact agggaaccca ctgcttaagc ctcaataaag  2280
cttgccttga gtgcttcaag tagtgtgtgc ccgtctgttg tgtgactctg gtaactagag  2340
atccctcaga cccttttagt cagtgtggaa aatctctagc agtggcgccc gaacagggac  2400
ttgaaagcga aagggaaacc agaggagctc tctcgacgca ggactcggct tgctgaagcg  2460
cgcacggcaa gaggcgaggg gcggcgactg gtgagtacgc caaaaatttt gactagcgga  2520
ggctagaagg agagagatgg gtgcgagagc gtcagtatta agcgggggag aattagatcg  2580
cgatgggaaa aaattcggtt aaggccaggg ggaaagaaaa aatataaatt aaaacatata  2640
gtatgggcaa gcagggagct agaacgattc gcagttaatc ctggcctgtt agaaacatca  2700
gaaggctgta gacaaatact gggacagcta caaccatccc ttcagacagg atcagaagaa  2760
cttagatcat tatataatac agtagcaacc ctctattgtg tgcatcaaag gatagagata  2820
aaagacacca aggaagcttt agacaagata gaggaagagc aaaacaaaag taagaccacc  2880
gcacagcaag cggccgctga tcttcagacc tggaggagga gatatgaggg acaattggag  2940
aagtgaatta tataaatata aagtagtaaa aattgaacca ttaggagtag cacccaccaa  3000
ggcaaagaga agagtggtgc agagagaaaa aagagcagtg ggaataggag ctttgttcct  3060
tgggttcttg ggagcagcag gaagcactat gggcgcagcg tcaatgacgc tgacggtaca  3120
ggccagacaa ttattgtctg gtatagtgca gcagcagaac aatttgctga gggctattga  3180
ggcgcaacag catctgttgc aactcacagt ctggggcatc aagcagctcc aggcaagaat  3240
cctggctgtg gaaagatacc taaaggatca acagctcctg gggatttggg gttgctctgg  3300
aaaactcatt tgcaccactg ctgtgccttg gaatgctagt tggagtaata aatctctgga  3360
acagatttgg aatcacacga cctggatgga gtgggacaga gaaattaaca attacacaag  3420
cttaatacac tccttaattg aagaatcgca aaaccagcaa gaaaagaatg aacaagaatt  3480
attggaatta gataaatggg caagtttgtg gaattggttt aacataacaa attggctgtg  3540
gtatataaaa ttattcataa tgatagtagg aggcttggta ggtttaagaa tagtttttgc  3600
tgtactttct atagtgaata gagttaggca gggatattca ccattatcgt ttcagaccca  3660
cctcccaacc ccgaggggac ccgacaggcc cgaaggaata gaagaagaag gtggagagag  3720
agacagagac agatccattc gattagtgaa cggatctcga cggtatcgat tagactgtag  3780
cccaggaata tggcagctag attgtacaca tttagaagga aaagttatct tggtagcagt  3840
tcatgtagcc agtggatata tagaagcaga agtaattcca gcagagacag ggcaagaaac  3900
agcatacttc ctcttaaaat tagcaggaag atggccagta aaaacagtac atacagacaa  3960
tggcagcaat ttcaccagta ctacagttaa ggccgcctgt tggtgggcgg ggatcaagca  4020
ggaatttggc attccctaca atccccaaag tcaaggagta atagaatcta tgaataaaga  4080
attaaagaaa attataggac aggtaagaga tcaggctgaa catcttaaga cagcagtaca  4140
aatggcagta ttcatccaca attttaaaag aaaagggggg attggggggt acagtgcagg  4200
ggaaagaata gtagacataa tagcaacaga catacaaact aaagaattac aaaaacaaat  4260
tacaaaaatt caaaattttc gggtttatta cagggacagc agagatccag tttggctgca  4320
tacgcgtcgt gaggctccgg tgcccgtcag tgggcagagc gcacatcgcc cacagtcccc  4380
gagaagttgg ggggaggggt cggcaattga accggtgcct agagaaggtg gcgcggggta  4440
aactgggaaa gtgatgtcgt gtactggctc cgcctttttc ccgagggtgg gggagaaccg  4500
tatataagtg cagtagtcgc cgtgaacgtt ctttttcgca acgggtttgc cgccagaaca  4560
caggtaagtg ccgtgtgtgg ttcccgcggg cctggcctct ttacgggtta tggcccttgc  4620
gtgccttgaa ttacttccac ctggctgcag tacgtgattc ttgatcccga gcttcgggtt  4680
ggaagtgggt gggagagttc gaggccttgc gcttaaggag ccccttcgcc tcgtgcttga  4740
gttgaggcct ggcctgggcg ctggggccgc cgcgtgcgaa tctggtggca ccttcgcgcc  4800
tgtctcgctg ctttcgataa gtctctagcc atttaaaatt tttgatgacc tgctgcgacg  4860
cttttttttct ggcaagatag tcttgtaaat gcgggccaag atctgcacac tggtatttcg  4920
gtttttgggg ccgcgggcgg cgacggggcc cgtgcgtccc agcgcacatg ttcggcgagg  4980
cggggcctgc gagcgcggcc accgagaatc ggacgggggt agtctcaagc tggccggcct  5040
gctctggtgc ctggcctcgc gccgccgtgt atcgccccgc cctgggcggc aaggctggcc  5100
cggtcggcac cagttgcgtg agcggaaaga tggccgcttc ccggccctgc tgcagggagc  5160
tcaaaatgga ggacgcggcg ctcgggagag cgggcgggtg agtcacccac acaaaggaaa  5220
agggcctttc cgtcctcagc cgtcgcttca tgtgactcca ctgagtaccg ggcgccgtcc  5280
aggcacctcg attagttctc gtgcttttgg agtacgtcgt ctttaggttg gggggagggg  5340
ttttatgcga tggagtttcc ccacactgag tgggtggaga ctgaagttag gccagcttgg  5400
cacttgatgt aattctcctt ggaatttgcc ctttttgagt ttggatcttg gttcattctc  5460
aagcctcaga cagtggttca aagttttttt cttccatttc aggtgtcgtg agctagagcc  5520
accatggagt ttgggctgag ctggcttttt cttgtggcta ttttaaaagg tgtccagtgc  5580
ggatcccaag ttcagctgca agaaagcgga cccggtttag tgaaaccctc cgagacttta  5640
tctttaacat gcgccgtgag cggctacagc atctctcgtc atgctttaac ttggattcgt  5700
cagcctcccg gaaagggttt agagtggatc ggcgccatcg acaacgccgg caccacctat  5760
tacgccagct gggccaagtc tcgtgtgacc atcagcgtgg acaccagcaa gaaccagttc  5820
tctttaaagc tgtccagcgt gaccgctgcc gacacagccg tgtactactg cgctcgtgtg  5880
ttctacgaca tcaacagcgg ctactattta gacggaatgg atctgtgggg ccccggaact  5940
ttagtgacag tcagcagcgg aggcggagga agcggaggag gaggaagctc cggaggcggt  6000
tctcaactgg tgctgacaca gagccctagc gcctctgcct ctttaggagc ctccgtgaag  6060
ctgacttgta ctttaagcag cgcccacaag acctacacca tcgactggta ccagcagcag  6120
cccgagaagg gccctagata tttaatgcaa gttaagagcg acggcagcta caccaaaggc  6180
actggtgtgc ccgatcgttt tagcggcagc agcagcggcg ccgataggta tttaaccatc  6240
agctctttac agagcgagga cgaggccgac tactactgtg gcgccgacga caacggcggc  6300
tacgtgtttg gcggcggcac acagctgacc gttttagcta gcggtggcgg aggttctgga  6360
ggtggaggtt cctccggaat ctacatctgg gcgcccttgg ccgggacttg tggggtcctt  6420
ctcctgtcac tggttatcac cctttactgc aaacggggca gaaagaaact cctgtatata  6480
ttcaaacaac catttatgag accagtacaa actactcaag aggaagatgg ctgtagctgc  6540
cgatttccag aagaagaaga aggaggatgt gaactgagag tgaagttcag caggagcgca  6600
gacgcccccg cgtaccagca gggccagaac cagctctata acgagctcaa tctaggacga  6660
```

```
agagaggagt acgatgtttt ggacaagaga cgtggccggg accctgagat gggggggaaag  6720
ccgagaagga agaaccctca ggaaggcctg tacaatgaac tgcagaaaga taagatggcg  6780
gaggcctaca gtgagattgg gatgaaaggc gagcgccgga ggggcaaggg gcacgatggc  6840
ctttaccagg gtctcagtac agccaccaag gacacctacg acgcccttca catgcaggcc  6900
ctgccccctc gctaagtcga caatcaacct ctggattaca aaatttgtga aagattgact  6960
ggtattctta actatgttgc tccttttacg ctatgtggat acgctgcttt aatgcctttg  7020
tatcatgcta ttgcttcccg tatggctttc attttctcct ccttgtataa atcctggttg  7080
ctgtctcttt atgaggagtt gtggcccgtt gtcaggcaac gtggcgtggt gtgcactgtg  7140
tttgctgacg caacccccac tggttggggc attgccacca cctgtcagct cctttccggg  7200
actttcgctt tccccctccc tattgccacg gcggaactca tcgccgcctg ccttgcccgc  7260
tgctggacag gggctcggct gttgggcact gacaattccg tggtgttgtc ggggaagctg  7320
acgtcctttc cttggctgct cgcctgtgtt gccacctgga ttctgcgcgg gacgtccttc  7380
tgctacgtcc cttcggccct caatccagcg gaccttcctt cccgcggcct gctgccggct  7440
ctgcggcctc ttccgcgtct tcgccttcgc cctcagacga gtcggatctc cctttgggcc  7500
gcctccccgc ctggaattcg agctcggtac ctttaagacc aatgacttac aaggcagctg  7560
tagatcttag ccacttttta aaagaaaagg ggggactgga agggctaatt cactcccaac  7620
gaagacaaga tctgcttttt gcttgtactg ggtctctctg gttagaccag atctgagcct  7680
gggagctctc tggctaacta gggaacccac tgcttaagcc tcaataaagc ttgccttgag  7740
tgcttcaagt agtgtgtgcc cgtctgttgt gtgactctgg taactagaga tccctcagac  7800
ccttttagtc agtgtggaaa atctctagca gtagtagttc atgtcatctt attattcagt  7860
atttataact tgcaaagaaa tgaatatcag agagtgagag gaacttgttt attgcagctt  7920
ataatggtta caaataaagc aatagcatca caaatttcac aaataaagca tttttttcac  7980
tgcattctag ttgtggtttg tccaaactca tcaatgtatc ttatcatgtc tggctctagc  8040
tatcccgccc ctaactccgc ccagttccgc ccattctccg ccccatggct gactaatttt  8100
ttttatttat gcagaggccg aggccgcctc ggcctctgag ctattccaga agtagtgagg  8160
aggctttttt ggaggcctag ctagggacgt acccaattcg ccctatagtg agtcgtatta  8220
cgcgcgctca ctggccgtcg ttttacaacg tcgtgactgg gaaaaccctg gcgttaccca  8280
acttaatcgc cttgcagcac atcccccttt cgccagctgg cgtaatagcg aagaggcccg  8340
caccgatcgc ccttcccaac agttgcgcag cctgaatggc gaatgggacg cgccctgtag  8400
cggcgcatta agcgcggcgg gtgtggtggt tacgcgcagc gtgaccgcta cacttgccag  8460
cgccctagcg cccgctcctt tcgctttctt cccttccttt ctcgccacgt tcgccggctt  8520
tccccgtcaa gctctaaatc gggggctccc tttagggttc cgatttagtg ctttacggca  8580
cctcgacccc aaaaaacttg attagggtga tggttcacgt agtgggccat cgccctgata  8640
gacggttttt cgccctttga cgttggagtc cacgttcttt aatagtggac tcttgttcca  8700
aactggaaca acactcaacc ctatctcggt ctattctttt gatttataag ggattttgcc  8760
gatttcggcc tattggttaa aaaatgagct gatttaacaa aaatttaacg cgaattttaa  8820
caaaatatta acgcttacaa tttaggtggc acttttcggg gaaatgtgcg cggaacccct  8880
atttgtttat ttttctaaat acattcaaat atgtatccgc tcatgagaca ataaccctga  8940
taaatgcttc aataatattg aaaaaggaag agtatgagta ttcaacattt ccgtgtcgcc  9000
cttattccct tttttgcggc attttgcctt cctgtttttg ctcacccaga aacgctggtg  9060
aaagtaaaag atgctgaaga tcagttgg                                    9088
```

```
SEQ ID NO: 114          moltype = DNA  length = 9088
FEATURE                 Location/Qualifiers
misc_feature            1..9088
                        note = CAR
misc_feature            1..9088
                        note = pTRPE-C29-gs-BBz
source                  1..9088
                        mol_type = other DNA
                        organism = synthetic construct
SEQUENCE: 114
gtgcacgagt gggttacatc gaactggatc tcaacagcgg taagatcctt gagagttttc  60
gccccgaaga acgttttcca atgatgagca cttttaaagt tctgctatgt ggcgcggtat  120
tatcccgtat tgacgccggg caagagcaac tcggtcgccg catacactat tctcagaatg  180
acttggttga gtactcacca gtcacagaaa agcatcttac ggatggcatg acagtaagag  240
aattatgcag tgctgccata accatgagtg ataacactgc ggccaactta cttctgacaa  300
cgatcggagg accgaaggag ctaaccgctt ttttgcacaa catgggggat catgtaactc  360
gccttgatcg ttgggaaccg gagctgaatg aagccatacc aaacgacgag cgtgacacca  420
cgatgcctgt agcaatggca acaacgttgc gcaaactatt aactggcgaa ctacttactc  480
tagcttcccg gcaacaatta atagactgga tggaggcgga taaagttgca ggaccacttc  540
tgcgctcggc ccttccggct ggctggttta ttgctgataa atctggagcc ggtgagcgtg  600
ggtctcgcgg tatcattgca gcactggggc cagatggtaa gccctcccgt atcgtagtta  660
tctacacgac ggggagtcag gcaactatgg atgaacgaaa tagacagatc gctgagatag  720
gtgcctcact gattaagcat tggtaactgt cagaccaagt ttactcatat atactttaga  780
ttgatttaaa acttcatttt taatttaaaa ggatctaggt gaagatcctt tttgataatc  840
tcatgaccaa aatcccttaa cgtgagtttt cgttccactg agcgtcagac cccgtagaaa  900
agatcaaagg atcttcttga gatccttttt ttctgcgcgt aatctgctgc ttgcaaacaa  960
aaaaaccacc gctaccagcg gtggtttgtt tgccggatca agagctacca actctttttc  1020
cgaaggtaac tggcttcagc agagcgcaga taccaaatac tgttcttcta gtgtagccgt  1080
agttaggcca ccacttcaag aactctgtag caccgcctac atacctcgct ctgctaatcc  1140
tgttaccagt ggctgctgcc agtggcgata agtcgtgtct taccgggttg gactcaagac  1200
gatagttacc ggataaggcg cagcggtcgg gctgaacggg gggttcgtgc acacagccca  1260
gcttggagcg aacgacctac accgaactga gatacctaca gcgtgagcta tgagaaagcg  1320
ccacgcttcc cgaagggaga aaggcggaca ggtatccggt aagcggcagg gtcggaacag  1380
gagagcgcac gagggagctt ccagggggaa acgcctggta tctttatagt cctgtcgggt  1440
ttcgccacct ctgacttgag cgtcgatttt tgtgatgctc gtcagggggg cggagcctat  1500
ggaaaaacgc cagcaacgcg gcctttttac ggttcctggc ctttgctggc cttttgctc  1560
acatgttctt tcctgcgtta tcccctgatt ctgtggataa ccgtattacc gcctttgagt  1620
```

-continued

```
gagctgatac cgctcgccgc agccgaacga ccgagcgcag cgagtcagtg agcgaggaag  1680
cggaagagcg cccaatacgc aaaccgcctc tccccgcgcg ttggccgatt cattaatgca  1740
gctggcacga caggtttccc gactggaaag cgggcagtga gcgcaacgca attaatgtga  1800
gttagctcac tcattaggca ccccaggctt tacactttat gcttccggct cgtatgttgt  1860
gtggaattgt gagcggataa caatttcaca caggaaacag ctatgaccat gattacgcca  1920
agcgcgcaat taaccctcac taaagggaac aaaagctgga gctgcaagct taatgtagtc  1980
ttatgcaata ctcttgtagt cttgcaacat ggtaacgatg agttagcaac atgccttaca  2040
aggagagaaa aagcaccgtg catgccgatt ggtggaagta aggtggtacg atcgtgcctt  2100
attaggaagg caacagacgg gtctgacatg gattggacga accactgaat tgccgcattg  2160
cagagatatt gtatttaagt gcctagctcg atacataaac gggtctctct ggttagacca  2220
gatctgagcc tgggagctct ctggctaact agggaaccca ctgcttaagc ctcaataaag  2280
cttgccttga gtgcttcaag tagtgtgtgc ccgtctgttg tgtgactctg gtaactagag  2340
atccctcaga cccttttagt cagtgtggaa aatctctagc agtggcgccc gaacagggac  2400
ttgaaagcga aagggaaacc agaggagctc tctcgacgca ggactcggct tgctgaagcg  2460
cgcacggcaa gaggcgaggg gcggcgactg gtgagtacgc caaaaatttt gactagcgga  2520
ggctagaagg agagagatgg gtgcgagagc gtcagtatta agcgggggag aattagatcg  2580
cgatgggaaa aaattcggtt aaggccaggg ggaaagaaaa aatataaatt aaaacatata  2640
gtatgggcaa gcagggagct agaacgattc gcagttaatc ctggcctgtt agaaacatca  2700
gaaggctgta gacaaatact gggacagcta caaccatccc ttcagacagg atcagaagaa  2760
cttagatcat tatataatac agtagcaacc ctctattgtg tgcatcaaag gatagagata  2820
aaagacacca aggaagcttt agacaagata gaggaagagc aaaacaaaag taagaccacc  2880
gcacagcaag cggccgctga tcttcagacc tggaggagga gatatgaggg acaattggag  2940
aagtgaatta tataaatata aagtagtaaa aattgaacca ttaggagtag cacccaccaa  3000
ggcaaagaga agagtggtgc agagagaaaa aagagcagtg ggaataggag ctttgttcct  3060
tgggttcttg ggagcagcag gaagcactat gggcgcagcg tcaatgacgc tgacggtaca  3120
ggccagacaa ttattgtctg gtatagtgca gcagcagaac aatttgctga gggctattga  3180
ggcgcaacag catctgttgc aactcacagt ctggggcatc aagcagctcc aggcaagaat  3240
cctggctgtg gaaagatacc taaaggatca acagctcctg gggatttggg gttgctctgg  3300
aaaactcatt tgcaccactg ctgtgccttg gaatgctagt tggagtaata aatctctgga  3360
acagatttgg aatcacacga cctggatgga gtgggacaga gaaattaaca attacacaag  3420
cttaatacac tccttaattg aagaatcgca aaaccagcaa gaaaagaatg aacaagaatt  3480
attggaatta gataaatggg caagtttgtg gaattggttt aacataacaa attggctgtg  3540
gtatataaaa ttattcataa tgatagtagg aggcttggta ggtttaagaa tagtttttgc  3600
tgtactttct atagtgaata gagttaggca gggatattca ccattatcgt ttcagaccca  3660
cctcccaacc ccgaggggac ccgacaggcc cgaaggaata gaagaagaag gtggagagag  3720
agacagagac agatccattc gattagtgaa cggatctcga cggtatcgat tagactgtag  3780
cccaggaata tggcagctag attgtacaca tttagaagga aaagttatct tggtagcagt  3840
tcatgtagcc agtggatata tagaagcaga agtaattcca gcagagacag ggcaagaaac  3900
agcatacttc ctcttaaaat tagcaggaag atggccagta aaaacagtac atacagacaa  3960
tggcagcaat ttcaccagta ctacagttaa ggccgcctgt tggtgggcgg ggatcaagca  4020
ggaatttggc attccctaca atccccaaag tcaaggagta atagaatcta tgaataaaga  4080
attaaagaaa attataggac aggtaagaga tcaggctgaa catcttaaga cagcagtaca  4140
aatggcagta ttcatccaca attttaaaag aaaagggggg attggggggt acagtgcagg  4200
ggaaagaata gtagacataa tagcaacaga catacaaact aaagaattac aaaaacaaat  4260
tacaaaaatt caaaattttc gggtttatta cagggacagc agagatccag tttggctgca  4320
tacgcgtcgt gaggctccgg tgcccgtcag tgggcagagc gcacatcgcc cacagtcccc  4380
gagaagttgg ggggaggggt cggcaattga accggtgcct agagaaggtg gcgcggggta  4440
aactgggaaa gtgatgtcgt gtactggctc cgcctttttc ccgagggtgg gggagaaccg  4500
tatataagtg cagtagtcgc cgtgaacgtt ctttttcgca acgggtttgc cgccagaaca  4560
caggtaagtg ccgtgtgtgg ttcccgcggg cctggcctct ttacgggtta tggcccttgc  4620
gtgccttgaa ttacttccac ctggctgcag tacgtgattc ttgatcccga gcttcgggtt  4680
ggaagtgggt gggagagttc gaggccttgc gcttaaggag ccccttcgcc tcgtgcttga  4740
gttgaggcct ggcctgggcg ctggggccgc cgcgtgcgaa tctggtggca ccttcgcgcc  4800
tgtctcgctg ctttcgataa gtctctagcc atttaaaatt tttgatgacc tgctgcgacg  4860
cttttttttct ggcaagatag tcttgtaaat gcgggccaag atctgcacac tggtatttcg  4920
gtttttgggg ccgcgggcgg cgacggggcc cgtgcgtccc agcgcacatg ttcggcgagg  4980
cggggcctgc gagcgcggcc accgagaatc ggacgggggt agtctcaagc tggccggcct  5040
gctctggtgc ctggcctcgc gccgccgtgt atcgccccgc cctgggcggc aaggctggcc  5100
cggtcggcac cagttgcgtg agcggaaaga tggccgcttc ccggccctgc tgcagggagc  5160
tcaaaatgga ggacgcggcg ctcgggagag cgggcgggtg agtcacccac acaaaggaaa  5220
agggcctttc cgtcctcagc cgtcgcttca tgtgactcca ctgagtaccg ggcgccgtcc  5280
aggcacctcg attagttctc gtgcttttgg agtacgtcgt ctttaggttg gggggagggg  5340
ttttatgcga tggagtttcc ccacactgag tgggtggaga ctgaagttag gccagcttgg  5400
cacttgatgt aattctcctt ggaatttgcc ctttttgagt ttggatcttg gttcattctc  5460
aagcctcaga cagtggttca aagttttttt cttccatttc aggtgtcgtg agctagagcc  5520
accatggagt ttgggctgag ctggcttttt cttgtggcta ttttaaaagg tgtccagtgc  5580
ggatccgagg tgcagctggt ggagtctgga ggaggactgg tgcaacccgg tggctcttta  5640
agactgagct gcgccgcctc tggcttcacc ttttctcgtc acgctttaac atgggtgaga  5700
caagctcccg gaaagggact ggagtgggtg tccgccatcg acaacgccgg caccacctac  5760
tacgccagct gggccaagag cagattcacc atctctcgtg acaacgccaa gaactcttta  5820
tatttacaga tgaactcttt aagggccgag gacaccgccg tgtactactg cgctcgtgtg  5880
ttctacgaca tcaactccgg ctactattta gacggcatgg atttatgggg acccggtaca  5940
ctggtcacag tgagctctgg aggcggaggt agcggaggcg gaggaagcag cggtggaggc  6000
agccagctgg tgctgacaca gtccccttcc gcttccgcct ctttaggagc ctccgtgaag  6060
ctgacttgta ctttaagcag cgcccacaaa acctacacca tcgactggta ccagcagcag  6120
cccgagaagg gcccacgtta tttaatgcaa gttaagtccg acggctccta caccaagggc  6180
accggcgtgc ccgatagatt cagcggctcc agcagcggcg ccgataggta tttaaccatc  6240
tcctctttac agagcgagga cgaggccgac tactactgtg gcgccgacga caacggcggc  6300
tacgtgtttg gaggcggcac ccagctgacc gtgctggcta gcggtggcgg aggttctgga  6360
```

-continued

```
ggtggaggtt cctccggaat ctacatctgg gcgcccttgg ccgggacttg tggggtcctt  6420
ctcctgtcac tggttatcac cctttactgc aaacggggca gaaagaaact cctgtatata  6480
ttcaaacaac catttatgag accagtacaa actactcaag aggaagatgg ctgtagctgc  6540
cgatttccag aagaagaaga aggaggatgt gaactgagag tgaagttcag caggagcgca  6600
gacgcccccg cgtaccagca gggccagaac cagctctata acgagctcaa tctaggacga  6660
agagaggagt acgatgtttt ggacaagaga cgtggccggg accctgagat gggggggaaag  6720
ccgagaagga agaaccctca ggaaggcctg tacaatgaac tgcagaaaga taagatggcg  6780
gaggcctaca gtgagattgg gatgaaaggc gagcgccgga ggggcaaggg gcacgatggc  6840
ctttaccagg gtctcagtac agccaccaag gacacctacg acgcccttca catgcaggcc  6900
ctgccccctc gctaagtcga caatcaacct ctggattaca aaatttgtga aagattgact  6960
ggtattctta actatgttgc tccttttacg ctatgtggat acgctgcttt aatgcctttg  7020
tatcatgcta ttgcttcccg tatggctttc attttctcct ccttgtataa atcctggttg  7080
ctgtctcttt atgaggagtt gtggcccgtt gtcaggcaac gtggcgtggt gtgcactgtg  7140
tttgctgacg caacccccac tggttggggc attgccacca cctgtcagct cctttccggg  7200
actttcgctt tccccctccc tattgccacg gcggaactca tcgccgcctg ccttgcccgc  7260
tgctggacag gggctcggct gttgggcact gacaattccg tggtgttgtc ggggaagctg  7320
acgtcctttc cttggctgct cgcctgtgtt gccacctgga ttctgcgcgg gacgtccttc  7380
tgctacgtcc cttcggccct caatccagcg gaccttcctt cccgcggcct gctgccggct  7440
ctgcggcctc ttccgcgtct tcgccttcgc cctcagacga gtcggatctc cctttgggcc  7500
gcctccccgc ctggaattcg agctcggtac ctttaagacc aatgacttac aaggcagctg  7560
tagatcttag ccacttttta aaagaaaagg ggggactgga agggctaatt cactcccaac  7620
gaagacaaga tctgcttttt gcttgtactg ggtctctctg gttagaccag atctgagcct  7680
gggagctctc tggctaacta gggaacccac tgcttaagcc tcaataaagc ttgccttgag  7740
tgcttcaagt agtgtgtgcc cgtctgttgt gtgactctgg taactagaga tccctcagac  7800
ccttttagtc agtgtggaaa atctctagca gtagtagttc atgtcatctt attattcagt  7860
atttataact tgcaaagaaa tgaatatcag agagtgagag gaacttgttt attgcagctt  7920
ataatggtta caaataaagc aatagcatca caaatttcac aaataaagca tttttttcac  7980
tgcattctag ttgtggtttg tccaaactca tcaatgtatc ttatcatgtc tggctctagc  8040
tatcccgccc ctaactccgc ccagttccgc ccattctccg ccccatggct gactaatttt  8100
ttttatttat gcagaggccg aggccgcctc ggcctctgag ctattccaga agtagtgagg  8160
aggctttttt ggaggcctag ctagggacgt acccaattcg ccctatagtg agtcgtatta  8220
cgcgcgctca ctggccgtcg ttttacaacg tcgtgactgg gaaaaccctg gcgttaccca  8280
acttaatcgc cttgcagcac atcccccttt cgccagctgg cgtaatagcg aagaggcccg  8340
caccgatcgc ccttcccaac agttgcgcag cctgaatggc gaatgggacg cgccctgtag  8400
cggcgcatta agcgcggcgg gtgtggtggt tacgcgcagc gtgaccgcta cacttgccag  8460
cgccctagcg cccgctcctt tcgctttctt cccttccttt ctcgccacgt tcgccggctt  8520
tccccgtcaa gctctaaatc gggggctccc tttagggttc cgatttagtg ctttacggca  8580
cctcgacccc aaaaaacttg attagggtga tggttcacgt agtgggccat cgccctgata  8640
gacggttttt cgccctttga cgttggagtc cacgttcttt aatagtggac tcttgttcca  8700
aactggaaca acactcaacc ctatctcggt ctattctttt gatttataag ggattttgcc  8760
gatttcggcc tattggttaa aaaatgagct gatttaacaa aaatttaacg cgaattttaa  8820
caaaatatta acgcttacaa tttaggtggc acttttcggg gaaatgtgcg cggaacccct  8880
atttgtttat ttttctaaat acattcaaat atgtatccgc tcatgagaca ataaccctga  8940
taaatgcttc aataatattg aaaaaggaag agtatgagta ttcaacattt ccgtgtcgcc  9000
cttattccct tttttgcggc attttgcctt cctgtttttg ctcacccaga aacgctggtg  9060
aaagtaaaag atgctgaaga tcagttgg                                    9088

SEQ ID NO: 115         moltype = DNA  length = 1398
FEATURE                Location/Qualifiers
misc_feature           1..1398
                       note = Antigen
misc_feature           1..1398
                       note = GFRa1
source                 1..1398
                       mol_type = other DNA
                       organism = synthetic construct
SEQUENCE: 115
atgttcctgg ccaccctgta cttcgccctg cctctgctgg acctgctgct gagcgccgaa  60
gtgagcggag gagacagact ggactgcgtg aaggccagcg accaatgtct gaaggagcaa  120
tcctgctcca ccaagtacag gacactcagg cagtgcgtgg ccggaaagga aaccaacttc  180
agcctggcca gcggcctcga agctaaggac gaatgcagga gcgccatgga ggccctgaaa  240
cagaagagcc tgtacaactg caggtgcaag aggggcatga agaaggagaa aaactgcctg  300
aggatctact ggagcatgta tcagagcctc cagggcaacg atctgctgga ggacagcccc  360
tacgagcctg tcaacagcag gctgtccgat atcttcaggg tggtgccttt cattagcgac  420
gtgttccagc aggtggagca catccccaaa ggcaacaatt gtctggacgc tgccaaagct  480
tgcaacctcg atgacatctg taagaaatac aggagcgcct acatcacccc ctgcaccaca  540
tccgtgagca atgacgtgtg taacaggagg aagtgccaca aagctctgag gcagttcttc  600
gacaaggtgc ctgccaagca cagctacgga atgctctttt gcagctgcag agacatcgcc  660
tgtaccgaga ggaggagaca aaccatcgtg cccgtgtgct cctatgaaga gagggagaaa  720
cccaactgcc tgaatctgca ggacagctgc aagaccaact acatctgcag gagcaggctg  780
gccgacttct tcaccaattg tcagcccgaa tccagatccg tgagctcctg cctgaaagag  840
aattatgccg actgcctgct ggcttacagc ggactgatcg gcacagtcat gacacccaac  900
tacatcgaca gctcctccct gtccgtggcc ccttggtgcg attgctccaa ctccggcaac  960
gacctggagg agtgtctgaa gttcctgaac ttcttcaagg acaatacctg cctcaagaac  1020
gccatccagg ctttcggaaa cggcagcgac gtgaccgtgt ggcagcccgc ctttcccgtg  1080
cagaccacca cagctaccac aaccaccgcc ctgagggtga agaataagcc tctgggcccc  1140
gccggcagcg agaatgagat ccccacacac gtgctgcctc cttgtgccaa tctccaggcc  1200
cagaagctga agtccaacgt gagcggcaat acccacctct gcatctccaa tggcaactac  1260
gagaaggagg gactgggagc cagcagccac attaccacca aatccatggc tgcccctccc  1320
```

```
agctgtggac tgagccctct cctcgtgctg gtggtcaccg ccctgtccac actgctgtcc  1380
ctcaccgaga ccagctga                                                1398

SEQ ID NO: 116          moltype = DNA  length = 1395
FEATURE                 Location/Qualifiers
misc_feature            1..1395
                        note = Antigen
misc_feature            1..1395
                        note = GFRa2
source                  1..1395
                        mol_type = other DNA
                        organism = synthetic construct
SEQUENCE: 116
atgatcctcg ccaacgtgtt ctgcctgttc tttttcctgg acgagaccct gagaagcctg  60
gctagcccct ccagcctcca gggacctgaa ctgcacggct ggaggccccc tgtggattgc  120
gtgagagcca acgagctgtg cgccgccgag agcaactgtt ccagcagata caggaccctc  180
agacagtgcc tggccggcag agacagaaac accatgctgg ccaacaagga gtgtcaggcc  240
gccctggaag tgctgcaaga gtcccctctg tacgattgta ggtgcaagag gggcatgaag  300
aaggaactgc agtgcctgca gatctattgg agcatccatc tgggcctcac cgagggcgaa  360
gaattttatg aggccagccc ctacgagccc gtgacctcca gactcagcga catcttcagg  420
ctcgcttcca tcttcagcgg cacaggcgcc gatcctgtgg tgagcgccaa gagcaaccat  480
tgcctggacg ctgccaaggc ctgcaacctc aacgacaact gcaagaagct caggagctcc  540
tatatcagca tttgcaacag ggagatttcc cccaccgaga ggtgtaacag gagaaagtgc  600
cacaaggccc tgagacagtt cttcgacaga gtgccttccg agtacaccta caggatgctc  660
ttctgcagct gccaggacca agcctgcgct gagagaagga ggcagaccat cctgccctcc  720
tgcagctacg aagacaagga gaagcctaac tgcctggatc tcaggggcgt ctgcagaacc  780
gaccacctct gtaggtccag actggccgac ttccacgcca attgcagggc cagctaccaa  840
accgtgacca gctgccccgc cgacaactat caggcctgcc tgggcagcta cgccggcatg  900
attggcttcg acatgacccc caattacgtt gatagctccc ccacaggcat cgtggtgagc  960
ccttggtgca gctgcagggg cagcggcaac atggaggaag agtgcgagaa gttcctgagg  1020
gacttcaccg agaatccctg cctgagaaac gccatccagg ccttcggcaa cggcacagac  1080
gtgaacgtgt cccccaaagg ccccagcttt caggccaccc aagctcccag ggtcgagaaa  1140
acccccttccc tgcccgacga cctgagcgat tccacatccc tcggcacctc cgtgatcacc  1200
acctgcacat ccgtgcagga acagggcctg aaggccaata actccaagga gctgagcatg  1260
tgcttcacag agctgaccac caacattatc cccggcagca acaaggtgat caagcccaat  1320
tccggaccta gcagagccag acccagcgcc gctctgacag tgctgtccgt gctgatgctg  1380
aaactggccc tgtga                                                   1395

SEQ ID NO: 117          moltype = DNA  length = 1203
FEATURE                 Location/Qualifiers
misc_feature            1..1203
                        note = Antigen
misc_feature            1..1203
                        note = GFRa3
source                  1..1203
                        mol_type = other DNA
                        organism = synthetic construct
SEQUENCE: 117
atggtgaggc ctctgaatcc cagacccctg cctcccgtgg tgctgatgct gctgctgctg  60
ctccctccct cccctctgcc cctggccgct ggagatcctc tgcccacaga gagcagactc  120
atgaacagct gcctccaggc caggagaaag tgccaggccg accctacctg ttccgccgcc  180
taccaccacc tggactcctg caccagcagc atcagcaccc ctctgcccag cgaagaaccc  240
tccgtccccg ctgattgcct ggaagccgcc cagcagctga gaaatagcag cctgatcggc  300
tgcatgtgcc acagaaggat gaagaaccag gtggcctgcc tggatattta ctggaccgtc  360
cacagggcca gaagcctggg aaattacgaa ctggacgtgt cccccctacga ggacacagtg  420
acaagcaagc cctggaagat gaacctcagc aagctgaaca tgctcaagcc cgacagcgac  480
ctgtgcctca aattcgccat gctgtgcacc ctgaacgaca agtgcgacag gctgaggaaa  540
gcctacggag aagcctgtag cggcccccat tgccagaggc acgtgtgcct gagacagctg  600
ctgaccttct tcgagaaggc cgctgagcct cacgcccaag gactgctcct gtgcccttgc  660
gcccccaatg ataggggctg cggcgagagg agaagaaaca ccatcgctcc caactgcgcc  720
ctgcccccctg tggcccctaa ttgcctcgag ctgagaagac tgtgcttctc cgaccctctg  780
tgcaggagca gactggtgga tttccagacc cactgtcacc ccatggacat cctcggaacc  840
tgcgccaccg agcagagcag gtgtctcaga gcctacctgg gcctgatcgg caccgccatg  900
acccccaatt ttgtgagcaa cgtgaacacc tccgtggccc tgtcctgtac ctgcagggga  960
agcggcaacc tccaggagga gtgcgagatg ctcgagggct tcttctccca caatccctgc  1020
ctgaccgagg ccatcgccgc caagatgagg ttccacagcc agctgttctc ccaggattgg  1080
ccccaccccca ccttcgctgt gatggcccac cagaacgaaa accccgctgt gagaccccag  1140
ccttgggtgc cctccctgtt cagctgcacc ctgcctctca tcctgctgct gagcctgtgg  1200
tga                                                                1203

SEQ ID NO: 118          moltype = AA  length = 465
FEATURE                 Location/Qualifiers
REGION                  1..465
                        note = Antigen
REGION                  1..465
                        note = GFRa4 isoform a
source                  1..465
                        mol_type = protein
                        organism = synthetic construct
```

```
SEQUENCE: 118
NRCVDAAEAC TADARCQRLR SEYVAQCLGR AAQGGCPRAR CRRALRRFFA RGPPALTHAL  60
LFCPCAGPAC AERRRQTFVP SCAFSGPGPA PPSCLEPLNF CERSRVCRPR LLAFQVSCTP  120
APSAPDGCLL DQGARCLRAY AGLVGTAVTP NYVDNVSARV APWCDCGASG NRREDCEAFR  180
GLFTRNRCLD GAIQAFASGW PPVLLDQLNP QGDPEHSLLQ VSIEGRMDPK SCDKTHTCPP  240
CPAPEAEGAP SVFLFPPKPK DTLMISRTPE VTCVVVDVSH EDPEVKFNWY VDGVEVHNAK  300
TKPREEQYNS TYRVVSVLTV LHQDWLNGKE YKCKVSNKAL PAPIEKTISK AKGQPREPQV  360
YTLPPSRDEL TKNQVSLTCL VKGFYPSDIA VEWESNGQPE NNYKATPPVL DSDGSFFLYS  420
KLTVDKSRWQ QGNVFSCSVM HEALHNHYTQ KSLSLSPGKH HHHHH                  465

SEQ ID NO: 119          moltype = AA  length = 497
FEATURE                 Location/Qualifiers
REGION                  1..497
                        note = Antigen
REGION                  1..497
                        note = GFRa4 isoform b
source                  1..497
                        mol_type = protein
                        organism = synthetic construct
SEQUENCE: 119
NRCVDAAEAC TADARCQRLR SEYVAQCLGR AAQGGCPRAR CRRALRRFFA RGPPALTHAL  60
LFCPCAGPAC AERRRQTFVP SCAFSGPGPA PPSCLEPLNF CERSRVCRCA RAAAGPWRGW  120
GRGLSPAHRP PAAQASPPGL SGLVHPSAQR PRRLPAGPGR PLPARLRGPR GVPAGTAVTP  180
NYVDNVSARV APWCDCGASG NRREDCEAFR GLFTRNRCLD GAIQAFASGW PPVLLDQLNP  240
QGDPEHSLLQ VGGGENLYFQ GGGGGAGGGG DKTHTCPPCP APELLGGPSV FLFPPKPKDT  300
LMISRTPEVT CVVVDVSHED PEVKFNWYVD GVEVHNAKTK PREEQYNSTY RVVSVLTVLH  360
QDWLNGKEYK CKVSNKALPA PIEKTISKAK GQPREPQVYT LPPSRDELTK NQVSLTCLVK  420
GFYPSDIAVE WESNGQPENN YKTTPPVLDS DGSFFLYSKL TVDKSRWQQG NVFSCSVMHE  480
ALHNHYTQKS LSLSPGK                                                 497

SEQ ID NO: 120          moltype = AA  length = 94
FEATURE                 Location/Qualifiers
REGION                  1..94
                        note = Heavy Chain
REGION                  1..94
                        note = Fig2A
source                  1..94
                        mol_type = protein
                        organism = synthetic construct
SEQUENCE: 120
VKESEGGLFK PTDTLTLTCT VSGFSLSRHA LTWVRQAPGN GLEWIGAIDN AGTTYYASWA  60
KSRSTITRNT DLHTVTLKMT SLTASDTATY FCAR                              94

SEQ ID NO: 121          moltype = AA  length = 94
FEATURE                 Location/Qualifiers
REGION                  1..94
                        note = Heavy Chain
REGION                  1..94
                        note = IGHV4-38-2*02
source                  1..94
                        mol_type = protein
                        organism = synthetic construct
SEQUENCE: 121
LQESGPGLVK PSETLSLTCT VSGYSISSGY YWGVIQAPGN KLEWIGSIYH SGSTYYNPSL  60
KSRVTISVDT SKNQFSLKLS SVTAADTAVY YCAR                              94

SEQ ID NO: 122          moltype = AA  length = 92
FEATURE                 Location/Qualifiers
REGION                  1..92
                        note = Heavy Chain
REGION                  1..92
                        note = IGHV4-59*05
source                  1..92
                        mol_type = protein
                        organism = synthetic construct
SEQUENCE: 122
LQESGPGLVK PSETLSLTCT VSGGSISSYY WSVIQAPGNK LEWIGRIYYS GSTYYNPSLK  60
SRVTISVDTS KNQFSLKLSS VTAADTAVYY CA                                92

SEQ ID NO: 123          moltype = AA  length = 93
FEATURE                 Location/Qualifiers
REGION                  1..93
                        note = Heavy Chain
REGION                  1..93
                        note = IGHV4-59*07
source                  1..93
                        mol_type = protein
                        organism = synthetic construct
SEQUENCE: 123
```

```
LQESGPGLVK PSDTLSLTCT VSGGSISSYY WSVIQAPGNK LEWIGYIYYS GSTSYNPALK  60
SRVTISVDTS KNQFSLKLSS VTAADTAVYY CAR                               93

SEQ ID NO: 124          moltype = AA  length = 92
FEATURE                 Location/Qualifiers
REGION                  1..92
                        note = Light Chain
REGION                  1..92
                        note = Fig2B
source                  1..92
                        mol_type = protein
                        organism = synthetic construct
SEQUENCE: 124
QFVLTQSPSV SAALGASAKL TCTLSSAHKT YTIDWYQQQQ GEAPRYLMQV KSDGSYTKGT  60
GVPDRFSGSS SGADRYLIIP SVQADDEAGY VC                                92

SEQ ID NO: 125          moltype = AA  length = 90
FEATURE                 Location/Qualifiers
REGION                  1..90
                        note = Light Chain
REGION                  1..90
                        note = IGLV4-3*01
source                  1..90
                        mol_type = protein
                        organism = synthetic construct
SEQUENCE: 125
VLTQSPSASA LLGASIKLTC TLSSEHSTYT IEWYQQRPGR SPQYTMKVKS DGSHSKGDGI  60
PDRFMGSSSG ADRYLTFSNL QSDDEAEYHC                                   90

SEQ ID NO: 126          moltype = AA  length = 92
FEATURE                 Location/Qualifiers
REGION                  1..92
                        note = Light Chain
REGION                  1..92
                        note = IGLV4-69*01 02
source                  1..92
                        mol_type = protein
                        organism = synthetic construct
SEQUENCE: 126
QLVLTQSPSA SASLGASVKL TCTLSSGHSS YAIAWHQQQP EKGPRYLMKL NSDGSHSKGD  60
GIPDRFSGSS SGAERYLTIS SLQSEDEADY YC                                92

SEQ ID NO: 127          moltype = AA  length = 96
FEATURE                 Location/Qualifiers
REGION                  1..96
                        note = Heavy Chain
REGION                  1..96
                        note = Fig3A
source                  1..96
                        mol_type = protein
                        organism = synthetic construct
SEQUENCE: 127
QSVKESEGGL FKPTDTLTLT CTVSGFSLSR HALTWVRQAP GNGLEWIGAI DNAGTTYYAS  60
WAKSRSTITR NTDLHTVTLK MTSLTASDTA TYFCAR                            96

SEQ ID NO: 128          moltype = AA  length = 98
FEATURE                 Location/Qualifiers
REGION                  1..98
                        note = Heavy Chain
REGION                  1..98
                        note = IGHV-38-2*02
source                  1..98
                        mol_type = protein
                        organism = synthetic construct
SEQUENCE: 128
QVQLQESGPG LVKPSETLSL TCAVSGYSIS SGYYWGWIRQ PPGKGLEWIG SIYHSGSTYY  60
NPSLKSRVTI SVDTSKNQFS LKLSSVTAAD TAVYYCAR                          98

SEQ ID NO: 129          moltype = AA  length = 98
FEATURE                 Location/Qualifiers
REGION                  1..98
                        note = Heavy Chain
REGION                  1..98
                        note = IGHV-48*03
source                  1..98
                        mol_type = protein
                        organism = synthetic construct
SEQUENCE: 129
EVQLVESGGG LVQPGGSLRL SCAASGFTFS SYEMNWVRQA PGKGLEWVST ISSSGSTIYY  60
```

-continued

```
ADSVKGRFTI SRDNAKNSLY LQMNSLRAED TAVYYCAR                      98

SEQ ID NO: 130          moltype = AA  length = 100
FEATURE                 Location/Qualifiers
REGION                  1..100
                        note = Light Chain
REGION                  1..100
                        note = Fig3B
source                  1..100
                        mol_type = protein
                        organism = synthetic construct
SEQUENCE: 130
QFVLTQSPSV SAALGASAKL TCTLSSAHKT YTIDWYQQQQ GEAPRYLMQV KSDGSYTKGT  60
GVPDRFSGSS SGADRYLIIP SVQADDEAGY VCGADDNGGY                      100

SEQ ID NO: 131          moltype = AA  length = 101
FEATURE                 Location/Qualifiers
REGION                  1..101
                        note = Light Chain
REGION                  1..101
                        note = Fig3B
source                  1..101
                        mol_type = protein
                        organism = synthetic construct
SEQUENCE: 131
QFVLTQSPSV SAALGASAKL TCTLSSAHKT YTIDWYQQQQ GEAPRYLMQV KSDGSYTKGT  60
GVPDRFSGSS SGADRYLIIP SVQADDEAGY VCGADDNGGY V                    101

SEQ ID NO: 132          moltype = AA  length = 99
FEATURE                 Location/Qualifiers
REGION                  1..99
                        note = Light Chain
REGION                  1..99
                        note = IGLV4-69*01
source                  1..99
                        mol_type = protein
                        organism = synthetic construct
SEQUENCE: 132
QLVLTQSPSA SASLGASVKL TCTLSSGHSS YAIAWHQQQP EKGPRYLMKL NSDGSHSKGD  60
GIPDRFSGSS SGAERYLTIS SLQSEDEADY YCQTWGTGI                       99

SEQ ID NO: 133          moltype = AA  length = 98
FEATURE                 Location/Qualifiers
REGION                  1..98
                        note = Light Chain
REGION                  1..98
                        note = IGLV1-44*01
source                  1..98
                        mol_type = protein
                        organism = synthetic construct
SEQUENCE: 133
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYCA AWDDSLNG                        98

SEQ ID NO: 134          moltype = AA  length = 99
FEATURE                 Location/Qualifiers
REGION                  1..99
                        note = Light Chain
REGION                  1..99
                        note = IGLV2-14*01
source                  1..99
                        mol_type = protein
                        organism = synthetic construct
SEQUENCE: 134
QSALTQPASV SGSPGQSITI SCTGTSSDVG GYNYVSWYQQ HPGKAPKLMI YEVSNRPSGV  60
SNRFSGSKSG NTASLTISGL QAEDEADYYC SSYTSSSTL                       99

SEQ ID NO: 135          moltype = AA  length = 101
FEATURE                 Location/Qualifiers
REGION                  1..101
                        note = Light Chain
REGION                  1..101
                        note = IGLV4-3*01
source                  1..101
                        mol_type = protein
                        organism = synthetic construct
SEQUENCE: 135
VLTQPPSASA LLGASIKLTC TLSSEHSTYT IEWYQQRPGR SPQYIMKVKS DGSHSKGDGI  60
PDRFMGSSSG ADRYLTFSNL QSDDEAEYHC GESHTIDGQV G                    101
```

```
SEQ ID NO: 136          moltype = AA  length = 97
FEATURE                 Location/Qualifiers
REGION                  1..97
                        note = Heavy Chain
REGION                  1..97
                        note = H1
source                  1..97
                        mol_type = protein
                        organism = synthetic construct
SEQUENCE: 136
QVQLQESGPG LVKPSETLSL TCAVSGYSIS RHALTWIRQP PGKGLEWIGA IDNAGTTYYA  60
SWAKSRVTIS VDTSKNQFSL KLSSVTAADT AVYYCAR                           97

SEQ ID NO: 137          moltype = AA  length = 97
FEATURE                 Location/Qualifiers
REGION                  1..97
                        note = Heavy Chain
REGION                  1..97
                        note = H1m3
source                  1..97
                        mol_type = protein
                        organism = synthetic construct
SEQUENCE: 137
QVQLQESGPG LVKPSETLSL TCAVSGFSLS RHALTWIRQP PGKGLEWIGA IDNAGTTYYA  60
SWAKSRVTIS VDTSKNQFSL KLSSVTAADT AVYYCAR                           97

SEQ ID NO: 138          moltype = AA  length = 97
FEATURE                 Location/Qualifiers
REGION                  1..97
                        note = Heavy Chain
REGION                  1..97
                        note = H1m2
source                  1..97
                        mol_type = protein
                        organism = synthetic construct
SEQUENCE: 138
QQSVKESGPG LVKPSETLSL TCAVSGFSLS RHALTWIRQP PGKGLEWIGA IDNAGTTYYA  60
SWAKSRVTIS VDTSKNQFSL KLSSVTAADT AVYYCAR                           97

SEQ ID NO: 139          moltype = AA  length = 97
FEATURE                 Location/Qualifiers
REGION                  1..97
                        note = Heavy Chain
REGION                  1..97
                        note = H1m1
source                  1..97
                        mol_type = protein
                        organism = synthetic construct
SEQUENCE: 139
QQSVKESGPG LVKPSETLSL TCAVSGFSLS RHALTWVRQP PGKGLEWIGA IDNAGTTYYA  60
SWAKSRVTIS RNTDLHTVSL KLSSVTAADT AVYFCAR                           97

SEQ ID NO: 140          moltype = AA  length = 98
FEATURE                 Location/Qualifiers
REGION                  1..98
                        note = Heavy Chain
REGION                  1..98
                        note = IGHV3-48*03
source                  1..98
                        mol_type = protein
                        organism = synthetic construct
SEQUENCE: 140
EVQLVESGGG LVQPGGSLRL SCAASGFTFS SYEMNWVRQA PGKGLEWVSY ISSSGSTIYY  60
ADSVKGRFTI SRDNAKNSLY LQMNSLRAED TAVYYCAR                          98

SEQ ID NO: 141          moltype = AA  length = 97
FEATURE                 Location/Qualifiers
REGION                  1..97
                        note = Heavy Chain
REGION                  1..97
                        note = H2
source                  1..97
                        mol_type = protein
                        organism = synthetic construct
SEQUENCE: 141
EVQLVESGGG LVQPGGSLRL SCAASGFTFS RHALTWVRQA PGKGLEWVSA IDNAGTTYYA  60
SWAKSRFTIS RDNAKNSLYL QMNSLRAEDT AVYYCAR                           97
```

-continued

```
SEQ ID NO: 142         moltype = AA  length = 97
FEATURE                Location/Qualifiers
REGION                 1..97
                       note = Heavy Chain
REGION                 1..97
                       note = H2m1
source                 1..97
                       mol_type = protein
                       organism = synthetic construct
SEQUENCE: 142
EQSVKESGGG LVQPGGSLRL SCAASGFTLS RHALTWVRQA PGKGLEWIGA IDNAGTTYYA  60
SWAKSRFTIS RNTDLHTVYL QMNSLRAEDT AVYFCAR                           97

SEQ ID NO: 143         moltype = AA  length = 101
FEATURE                Location/Qualifiers
REGION                 1..101
                       note = Light Chain
REGION                 1..101
                       note = L1
source                 1..101
                       mol_type = protein
                       organism = synthetic construct
SEQUENCE: 143
QLVLTQSPSA SASLGASVKL TCTLSSAHKT YTIAWHQQQP EKGPRYLMKV KSDGSYSKGD  60
GIPDRFSGSS SGAERYLTIS SLQSEDEADY YCGADDNGGY V                      101

SEQ ID NO: 144         moltype = AA  length = 101
FEATURE                Location/Qualifiers
REGION                 1..101
                       note = Light Chain
REGION                 1..101
                       note = L1m2
source                 1..101
                       mol_type = protein
                       organism = synthetic construct
SEQUENCE: 144
QFVLTQSPSA SASLGASVKL TCTLSSAHKT YTIDWHQQQP EKGPRYLMQV KSDGSYTKGT  60
GIPDRFSGSS SGAERYLTIS SLQSEDEADY YCGADDNGGY V                      101

SEQ ID NO: 145         moltype = AA  length = 101
FEATURE                Location/Qualifiers
REGION                 1..101
                       note = Light Chain
REGION                 1..101
                       note = L1m4
source                 1..101
                       mol_type = protein
                       organism = synthetic construct
SEQUENCE: 145
QLVLTQSPSA SASLGASVKL TCTLSSAHKT YTIAWHQQQP EKGPRYLMQV KSDGSYTKGT  60
GVPDRFSGSS SGADRYLTIS SLQSEDEADY YCGADDNGGY V                      101

SEQ ID NO: 146         moltype = AA  length = 101
FEATURE                Location/Qualifiers
REGION                 1..101
                       note = Light Chain
REGION                 1..101
                       note = L1m3
source                 1..101
                       mol_type = protein
                       organism = synthetic construct
SEQUENCE: 146
QLVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY V                      101

SEQ ID NO: 147         moltype = AA  length = 101
FEATURE                Location/Qualifiers
REGION                 1..101
                       note = Light Chain
REGION                 1..101
                       note = L1m1
source                 1..101
                       mol_type = protein
                       organism = synthetic construct
SEQUENCE: 147
QFVLTQSPSA SASLGASVKL TCTLSSAHKT YTIDWYQQQP EKGPRYLMQV KSDGSYTKGT  60
GVPDRFSGSS SGADRYLTIS SLQSEDEADY YCGADDNGGY V                      101

SEQ ID NO: 148         moltype = AA  length = 101
```

```
FEATURE                Location/Qualifiers
REGION                 1..101
                       note = Light Chain
REGION                 1..101
                       note = L2
source                 1..101
                       mol_type = protein
                       organism = synthetic construct
SEQUENCE: 148
QSVLTQPPSA SGTPGQRVTI SCTLSSAHKT YTIDWYQQLP GTAPKLLIYV KSDGSYTKGT  60
GVPDRFSGSK SGTSASLAIS GLQSEDEADY YCGADDNGGY V                     101

SEQ ID NO: 149         moltype = AA  length = 101
FEATURE                Location/Qualifiers
REGION                 1..101
                       note = Light Chain
REGION                 1..101
                       note = L2m3
source                 1..101
                       mol_type = protein
                       organism = synthetic construct
SEQUENCE: 149
QSVLTQPPSA SGTPGQRVTI SCTLSSAHKT YTIDWYQQLP GTAPKLLIYV KSDGSYTKGT  60
GVPDRFSGSK SGTSASLAIS GLQSEDEADY YCGADDNGGY V                     101

SEQ ID NO: 150         moltype = AA  length = 101
FEATURE                Location/Qualifiers
REGION                 1..101
                       note = Light Chain
REGION                 1..101
                       note = L2m2
source                 1..101
                       mol_type = protein
                       organism = synthetic construct
SEQUENCE: 150
QFVLTQPPSA SGTPGQRVTI SCTLSSAHKT YTIDWYQQLP GTAPKLLIYV KSDGSYTKGT  60
GVPDRFSGSS SGADASLAIS GLQSEDEADY YCGADDNGGY V                     101

SEQ ID NO: 151         moltype = AA  length = 101
FEATURE                Location/Qualifiers
REGION                 1..101
                       note = Light Chain
REGION                 1..101
                       note = L2m1
source                 1..101
                       mol_type = protein
                       organism = synthetic construct
SEQUENCE: 151
QFVLTQPPSA SGTPGQRVTI SCTLSSAHKT YTIDWYQQLP GTAPKLLIYV KSDGSYTKGT  60
GVPDRFSGSS SGADRYLAIS GLQSEDEADY YCGADDNGGY V                     101

SEQ ID NO: 152         moltype = AA  length = 101
FEATURE                Location/Qualifiers
REGION                 1..101
                       note = Light Chain
REGION                 1..101
                       note = L3
source                 1..101
                       mol_type = protein
                       organism = synthetic construct
SEQUENCE: 152
QSALTQPASV SGSPGQSITI SCTGTSAHKT YTVSWYQQHP GKAPKLMIYV KSDGSYNRPS  60
GVSNRFSGSK SGNTASLTIS GLQAEDEADY YCGADDNGGY V                     101

SEQ ID NO: 153         moltype = AA  length = 101
FEATURE                Location/Qualifiers
REGION                 1..101
                       note = Light Chain
REGION                 1..101
                       note = L3m3
source                 1..101
                       mol_type = protein
                       organism = synthetic construct
SEQUENCE: 153
QSALTQPASV SGSPGQSITI SCTGTSAHKT YTIDWYQQHP GKAPKLMIYV KSDGSYTKGT  60
GVSNRFSGSK SGNTASLTIS GLQAEDEADY YCGADDNGGY V                     101

SEQ ID NO: 154         moltype = AA  length = 101
FEATURE                Location/Qualifiers
```

```
REGION                1..101
                      note = Light Chain
REGION                1..101
                      note = L3m5
source                1..101
                      mol_type = protein
                      organism = synthetic construct
SEQUENCE: 154
QSALTQPASV SGSPGQSITI SCTGTSAHKT YTVSWYQQHP GKAPKLMIYV KSDGSYTKGT  60
GVPNRFSGSS SGADRYLTIS GLQAEDEADY YCGADDNGGY V                     101

SEQ ID NO: 155        moltype = AA  length = 101
FEATURE               Location/Qualifiers
REGION                1..101
                      note = Light Chain
REGION                1..101
                      note = L3m4
source                1..101
                      mol_type = protein
                      organism = synthetic construct
SEQUENCE: 155
QSALTQPASV SGSPGQSITI SCTGTSAHKT YTVSWYQQHP GKAPKYLMQV KSDGSYTKGT  60
GVPNRFSGSS SGADRYLTIS GLQAEDEADY YCGADDNGGY V                     101

SEQ ID NO: 156        moltype = AA  length = 101
FEATURE               Location/Qualifiers
REGION                1..101
                      note = Light Chain
REGION                1..101
                      note = L3m2
source                1..101
                      mol_type = protein
                      organism = synthetic construct
SEQUENCE: 156
QFVLTQPASV SGSPGQSITI SCTLSSAHKT YTIDWYQQHP GKAPKLMIQV KSDGSYTKGT  60
GVSNRFSGSS SGADRYLTIS GLQAEDEADY YCGADDNGGY V                     101

SEQ ID NO: 157        moltype = AA  length = 101
FEATURE               Location/Qualifiers
REGION                1..101
                      note = Light Chain
REGION                1..101
                      note = L3m1
source                1..101
                      mol_type = protein
                      organism = synthetic construct
SEQUENCE: 157
QFVLTQPASV SGSPGQSITI SCTLSSAHKT YTIDWYQQHP GKAPKYLMQV KSDGSYTKGT  60
GVPNRFSGSS SGADRYLTIS GLQAEDEADY VCGADDNGGY V                     101

SEQ ID NO: 158        moltype = AA  length = 254
FEATURE               Location/Qualifiers
REGION                1..254
                      note = CAR
REGION                1..254
                      note = CAR10
source                1..254
                      mol_type = protein
                      organism = synthetic construct
SEQUENCE: 158
GSEVQLVESG GGLVQPGGSL RLSCAASGFT FSRHALTWVR QAPGKGLEWV SAIDNAGTTY  60
YASWAKSRFT ISRDNAKNSL YLQMNSLRAE DTAVYYCARV FYDINSGYYL DGMDLWGPGT  120
LVTVSSGGGG SGGGGSSGGG SQFVLTQSPS ASASLGASVK LTCTLSSAHK TYTIDWYQQQ  180
PEKGPRYLMQ VKSDGSYTKG TGVPDRFSGS SSGADRYLTI SSLQSEDEAD YYCGADDNGG  240
YVFGGGTQLT VLAS                                                   254

SEQ ID NO: 159        moltype = AA  length = 254
FEATURE               Location/Qualifiers
REGION                1..254
                      note = CAR
REGION                1..254
                      note = CAR14
source                1..254
                      mol_type = protein
                      organism = synthetic construct
SEQUENCE: 159
GSQVQLQESG PGLVKPSETL SLTCAVSGYS ISRHALTWIR QPPGKGLEWI GAIDNAGTTY  60
YASWAKSRVT ISVDTSKNQF SLKLSSVTAA DTAVYYCARV FYDINSGYYL DGMDLWGPGT  120
LVTVSSGGGG SGGGGSSGGG SQFVLTQSPS ASASLGASVK LTCTLSSAHK TYTIDWYQQQ  180
```

```
PEKGPRYLMQ VKSDGSYTKG TGVPDRFSGS SSGADRYLTI SSLQSEDEAD YYCGADDNGG  240
YVFGGGTQLT VLAS                                                   254

SEQ ID NO: 160         moltype = AA  length = 254
FEATURE                Location/Qualifiers
REGION                 1..254
                       note = CAR
REGION                 1..254
                       note = CAR25
source                 1..254
                       mol_type = protein
                       organism = synthetic construct
SEQUENCE: 160
GSQVQLQESG PGLVKPSETL SLTCAVSGYS ISRHALTWIR QPPGKGLEWI GAIDNAGTTY  60
YASWAKSRVT ISVDTSKNQF SLKLSSVTAA DTAVYYCARV FYDINSGYYL DGMDLWGPGT  120
LVTVSSGGGG SGGGGSSGGG SQLVLTQSPS ASASLGASVK LTCTLSSAHK TYTIDWYQQQ  180
PEKGPRYLMQ VKSDGSYTKG TGVPDRFSGS SSGADRYLTI SSLQSEDEAD YYCGADDNGG  240
YVFGGGTQLT VLAS                                                   254

SEQ ID NO: 161         moltype = AA  length = 254
FEATURE                Location/Qualifiers
REGION                 1..254
                       note = CAR
REGION                 1..254
                       note = CAR29
source                 1..254
                       mol_type = protein
                       organism = synthetic construct
SEQUENCE: 161
GSEVQLVESG GGLVQPGGSL RLSCAASGFT FSRHALTWVR QAPGKGLEWV SAIDNAGTTY  60
YASWAKSRFT ISRDNAKNSL YLQMNSLRAE DTAVYYCARV FYDINSGYYL DGMDLWGPGT  120
LVTVSSGGGG SGGGGSSGGG SQLVLTQSPS ASASLGASVK LTCTLSSAHK TYTIDWYQQQ  180
PEKGPRYLMQ VKSDGSYTKG TGVPDRFSGS SSGADRYLTI SSLQSEDEAD YYCGADDNGG  240
YVFGGGTQLT VLAS                                                   254

SEQ ID NO: 162         moltype = AA  length = 5
FEATURE                Location/Qualifiers
REGION                 1..5
                       note = CDR
REGION                 1..5
                       note = HCDR1
source                 1..5
                       mol_type = protein
                       organism = synthetic construct
SEQUENCE: 162
RHALT                                                             5

SEQ ID NO: 163         moltype = AA  length = 16
FEATURE                Location/Qualifiers
REGION                 1..16
                       note = CDR
REGION                 1..16
                       note = HCDR2
source                 1..16
                       mol_type = protein
                       organism = synthetic construct
SEQUENCE: 163
AIDNAGTTYY ASWAKS                                                 16

SEQ ID NO: 164         moltype = AA  length = 16
FEATURE                Location/Qualifiers
REGION                 1..16
                       note = CDR
REGION                 1..16
                       note = HCDR3
source                 1..16
                       mol_type = protein
                       organism = synthetic construct
SEQUENCE: 164
VFYDINSGYY LDGMDL                                                 16

SEQ ID NO: 165         moltype = AA  length = 7
FEATURE                Location/Qualifiers
REGION                 1..7
                       note = CDR
REGION                 1..7
                       note = LCDR1
source                 1..7
                       mol_type = protein
```

-continued

```
                        organism = synthetic construct
SEQUENCE: 165
SAHKTYT                                                           7

SEQ ID NO: 166          moltype = AA  length = 7
FEATURE                 Location/Qualifiers
REGION                  1..7
                        note = CDR
REGION                  1..7
                        note = LCDR2
source                  1..7
                        mol_type = protein
                        organism = synthetic construct
SEQUENCE: 166
VKSDGSY                                                           7

SEQ ID NO: 167          moltype = AA  length = 9
FEATURE                 Location/Qualifiers
REGION                  1..9
                        note = CDR
REGION                  1..9
                        note = LCDR3
source                  1..9
                        mol_type = protein
                        organism = synthetic construct
SEQUENCE: 167
GADDNGGYV                                                         9

SEQ ID NO: 168          moltype = AA  length = 10
FEATURE                 Location/Qualifiers
REGION                  1..10
                        note = Hinge
REGION                  1..10
                        note = GS-linker
source                  1..10
                        mol_type = protein
                        organism = synthetic construct
SEQUENCE: 168
GGGGSGGGGS                                                        10

SEQ ID NO: 169          moltype = AA  length = 18
FEATURE                 Location/Qualifiers
REGION                  1..18
                        note = Hinge
REGION                  1..18
                        note = GS-linker
source                  1..18
                        mol_type = protein
                        organism = synthetic construct
SEQUENCE: 169
GGSSRSSSSG GGGSGGGG                                               18
```